United States Patent
Naidu et al.

(10) Patent No.: US 9,273,067 B2
(45) Date of Patent: Mar. 1, 2016

(54) PYRAZOLOPYRIMIDINE MACROCYCLES AS INHIBITORS OF HUMAN IMMUNODEFICIENCY VIRUS REPLICATION

(71) Applicant: BRISTOL-MYERS SQUIBB COMPANY, Princeton, NJ (US)

(72) Inventors: B. Narasimhulu Naidu, Durham, CO (US); Michael A. Walker, Durham, CO (US); Margaret E. Sorenson, Meriden, CO (US); Manoj Patel, Berlin, CO (US); Zhizhen Barbara Zheng, Cheshire, CO (US); John F. Kadow, Wallingford, CO (US); Bin Zheng, Kendall Park, NJ (US); Martin D. Eastgate, Titusville, NJ (US); Ke Chen, East Brunswick, NJ (US); Francisco Gonzalez-Bobes, New Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/619,728

(22) Filed: Feb. 11, 2015

(65) Prior Publication Data
US 2015/0232481 A1     Aug. 20, 2015

Related U.S. Application Data

(60) Provisional application No. 61/941,931, filed on Feb. 19, 2014.

(51) Int. Cl.
*C07D 498/22*     (2006.01)
*C07D 211/48*     (2006.01)

(52) U.S. Cl.
CPC ............ *C07D 498/22* (2013.01); *C07D 211/48* (2013.01)

(58) Field of Classification Search
CPC .................................................. C07D 498/22
See application file for complete search history.

(56) References Cited

U.S. PATENT DOCUMENTS

2002/0055631 A1    5/2002    Augeri et al.

FOREIGN PATENT DOCUMENTS

| | | |
|---|---|---|
| WO | WO 2007/131350 | 11/2007 |
| WO | WO 2008/015271 | 2/2008 |
| WO | WO 2009/062285 | 5/2009 |
| WO | WO 2009/062288 | 5/2009 |
| WO | WO 2009/062289 | 5/2009 |
| WO | WO 2009/062308 | 5/2009 |
| WO | WO 2010/130842 | 11/2010 |
| WO | WO 2011/076765 | 6/2011 |
| WO | WO 2012/003497 | 1/2012 |
| WO | WO 2012/003498 | 1/2012 |
| WO | WO 2012/033735 | 3/2012 |
| WO | WO 2012/065963 | 5/2012 |
| WO | WO 2012/066442 | 5/2012 |
| WO | WO 2013/012649 | 1/2013 |
| WO | WO 2013/025584 | 2/2013 |
| WO | WO 2013/043553 | 3/2013 |
| WO | WO 2013/062028 | 5/2013 |
| WO | WO 2013/073875 | 5/2013 |
| WO | WO 2013/134113 | 9/2013 |
| WO | WO 2013/134142 | 9/2013 |
| WO | WO 2014/028384 | 2/2014 |
| WO | WO 2014/159076 | 10/2014 |
| WO | WO 2014/164428 | 10/2014 |

OTHER PUBLICATIONS

Naidu et al., caplus an 2014:273130.*
Toda et al., caplus an 2001:618024.*
Johnson, V.A. et al., Chapter 4: "Quantitative Assays for Virus Infectivity", Techniques in HIV Research, pp. 71-76, Aldovini, A. et al., eds., Stockton Press, publ. (1990).
Palella, Jr., F.J. et al., "Declining Morbidity and Mortality Among Patients with Advanced Human Immunodeficiency Virus Infection", The New England Journal of Medicine, vol. 338, No. 13, pp. 853-860 (1998).

* cited by examiner

*Primary Examiner* — Sun Jae Yoo
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for making and using these compounds in the treatment of HIV infection.

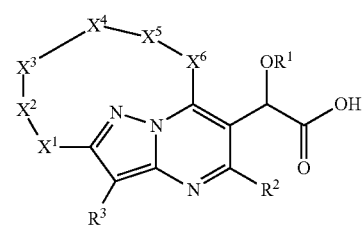

17 Claims, No Drawings

PYRAZOLOPYRIMIDINE MACROCYCLES AS INHIBITORS OF HUMAN IMMUNODEFICIENCY VIRUS REPLICATION

CROSS-REFERENCE TO RELATED APPLICATIONS

This application claims priority to Provisional Patent Application U.S. Ser. No. 61/941,931 filed Feb. 19, 2014, hereby incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130842, WO2011076765, WO2012003497, WO2012003498, WO2012033735, WO2012065963, WO2012066442, WO2013012649, WO2013043553, WO2013062028, WO2013073875, WO2013134113, WO2013134142, WO2014021867, WO20140028384, and WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, methods for making the compounds and their use in inhibiting HIV integrase and treating those infected with HIV or AIDS.

One aspect of the invention is a compound of Formula I

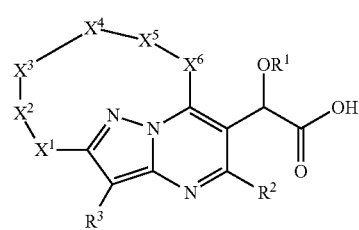

I where:
$R^1$ is alkyl or haloalkyl;
$R^2$ is hydrogen or alkyl;
$R^3$ is hydrogen, alkyl or halo;
$R^4$ is hydrogen, alkyl, or cycloalkyl;
$R^5$ is hydrogen, alkyl, or $(Ar^4)$alkyl;
$Ar^1$ is phenyl or naphthyl substituted with 0-3 substituents selected from cyano, halo, alkyl, haloalkyl, alkoxy, or haloalkoxy;
$Ar^2$ is pyrrolyl, pyrazolyl, or triazolyl substituted with 0-2 alkyl substituents;
$Ar^3$ is phenyl substituted with 0-3 substituents selected from cyano, halo, alkyl, haloalkyl, alkoxy, or haloalkoxy;
$Ar^4$ is phenyl substituted with 0-3 substituents selected from cyano, halo, alkyl, haloalkyl, alkoxy, or haloalkoxy;
$X^1$ is alkylene, alkenylene, —$CH_2O$—, —$CH_2OCH_2$—, —$CH_2N(R^4)CH_2$—, or —$CH_2CON(R^4)$—;
$X^2$ is —O—, —$Ar^1$—, —$Ar^2$—, —$CON(R^5)$—, —$(Ar^3)$CH—, -((benzyloxy)$CH_2$)CH—,)—, —O($Ar^3$)CH—, —$CH_2CON(R^5)$—, or —$N(R^5)COCON(R^5)$—;

$X^3$ is absent, —O—, alkyloxy, cycloalkyloxy, cycloalkyl, $Ar^3$, $(Ar^3)O$—, $((Ar^3)alkyl)O$—;
$X^4$ is alkylene, alkenylene, alkyleneoxy, or alkenyleneoxy;
$X^5$ is absent or —O—; and
$X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

Another aspect of the invention is a compound of formula I
where:
$R^1$ is alkyl or haloalkyl;
$R^2$ is hydrogen or alkyl;
$R^3$ is hydrogen, alkyl or halo;
$R^4$ is hydrogen or alkyl;
$R^5$ is $(Ar^4)$alkyl;
$Ar^1$ is phenyl substituted with 0-3 substituents selected from cyano, halo, alkyl, haloalkyl, alkoxy, or haloalkoxy;
$Ar^2$ is pyrrolyl, pyrazolyl, or triazolyl substituted with 0-2 alkyl substituents;
$Ar^3$ is phenyl substituted with 0-3 substituents selected from cyano, halo, alkyl, haloalkyl, alkoxy, or haloalkoxy;
$Ar^4$ is phenyl substituted with 0-3 substituents selected from cyano, halo, alkyl, haloalkyl, alkoxy, or haloalkoxy;
$X^1$ is alkylene, alkenylene, —O—, —$CH_2O$—, —$CH_2OCH_2$—, —$CON(R^4)$—, or —$CH_2CON(R^4)$—;
$X^2$ is $Ar^1$, $Ar^2$, or —$CON(R^5)$—;
$X^3$ is absent, —O—, alkyloxy, cycloalkyloxy, cycloalkyl, $Ar^3$, $(Ar^3)O$—, $((Ar^3)alkyl)O$—;
$X^4$ is alkylene, alkenylene, alkyleneoxy, or alkenyleneoxy;
$X^5$ is absent or —O—; and
$X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or $X^6$ is phenyl or chromanyl, and is substituted with 0-3 substituents selected from halo, alkyl, haloalkyl, alkoxy, and haloalkoxy;
or a pharmaceutically acceptable salt thereof.

Another aspect of the invention is a compound of formula I where $R^1$ is alkyl or haloalkyl; $R^2$ is hydrogen or alkyl; $R^3$ is hydrogen, alkyl or halo; $R^4$ is hydrogen, alkyl, or cycloalkyl; $R^5$ is hydrogen, alkyl, or $(Ar^4)$alkyl; $Ar^1$ is phenyl substituted with 0-3 substituents selected from cyano, halo, alkyl, haloalkyl, alkoxy, or haloalkoxy; $Ar^3$ is phenyl substituted with 0-3 substituents selected from cyano, halo, alkyl, haloalkyl, alkoxy, or haloalkoxy; $Ar^4$ is phenyl substituted with 0-3 substituents selected from cyano, halo, alkyl, haloalkyl, alkoxy, or haloalkoxy; $X^1$ is alkylene, alkenylene, —$CH_2O$—, —$CH_2OCH_2$—, —$CH_2N(R^4)CH_2$—, or —$CH_2CON(R^4)$—; $X^2$ is —O—, —$Ar^1$—, —$CON(R^5)$—, —$(Ar^3)CH$—, -((benzyloxy)$CH_2$)CH—,)—, —$O(Ar^3)CH$—, —$CH_2CON(R^5)$—, or —$N(R^5)COCON(R^5)$—; $X^3$ is absent, —O—, alkyloxy, cycloalkyloxy, cycloalkyl, $Ar^3$, $(Ar^3)O$—, $((Ar^3)alkyl)O$—; $X^4$ is alkylene, alkenylene, alkyleneoxy, or alkenyleneoxy; $X^5$ is absent or —O—; and $X^6$ is piperidinyl substituted with 0-3 halo or alkyl substituents; or a pharmaceutically acceptable salt thereof.

Another aspect of the invention is a compound of formula I where $R^1$ is alkyl, $R^2$ is alkyl, and $R^3$ is hydrogen.

Another aspect of the invention is a compound of formula I where $Ar^1$ is phenyl substituted with 0-3 substituents selected from cyano, halo, alkyl, haloalkyl, alkoxy, or haloalkoxy.

Another aspect of the invention is a compound of formula I where $Ar^2$ is triazolyl substituted with 0-2 alkyl substituents.

Another aspect of the invention is a compound of formula I where $X^1$ is —$CON(R^4)$—, $X^2$ is —$CON(R^5)$—, and $X^3$ is absent.

Another aspect of the invention is a compound of formula I where $X^2$ is $Ar^1$.

Another aspect of the invention is a compound of formula I where $X^2$ is $Ar^1$ and $X^3$ is absent, —O—, or alkyloxy.

Another aspect of the invention is a compound of formula I where $X^2$ is $Ar^2$ and $X^3$ is alkyloxy, cycloalkyloxy, $(Ar^3)O$—, or $((Ar^3)alkyl)O$—.

Another aspect of the invention is a compound of formula I where $X^3$ is absent or —O—; $X^4$ is alkylene or alkenylene; and $X^5$ is —O—.

Another aspect of the invention is a compound of formula I where $X^6$ is piperidinyl substituted with 0-3 halo or alkyl substituents.

Another aspect of the invention is a compound of formula II where $R^1$ is hydrogen or alkyl; $R^2$ is hydrogen, arylalkyl, allyloxycarbonyl, alkoxycarbonyl, aryloxycarbonyl, arylalkoxycarbonyl, trialkylsilyl, alkyl(aryl)$_2$silyl, or (alkyl)$_2$arylsilyl; $R^3$ is alkyl or haloalkyl; $R^4$ is hydrogen, alkyl, arylalkyl, alkoxycarbonyl, aryloxycarbonyl, or arylalkoxycarbonyl:

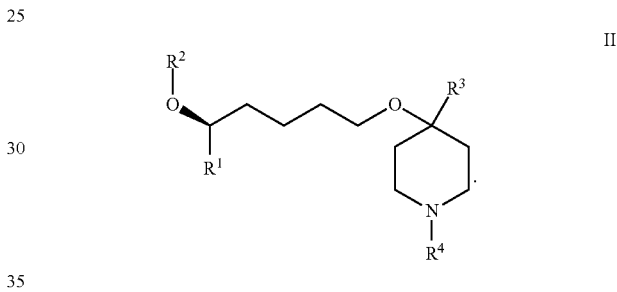

Another aspect of the invention is a compound of formula II where $R^1$ is alkyl; $R^2$ is hydrogen, benzyl, or t-butyldiphenylsilyl; $R^3$ is methyl or iodomethyl; $R^4$ is hydrogen, t-butoxycarbonyl, or benzyloxycarbonyl.

Another aspect of the invention is a method for a preparing a compound of formula II where $R^1$ is alkyl, $R^2$ is hydrogen, $R^3$ is methyl, and $R^4$ is hydrogen; comprising the hydrogenolysis of a compound of formula II where $R^1$ is alkyl, $R^2$ is benzyl, $R^3$ is iodomethyl, and $R^4$ is benzyloxycarbonyl

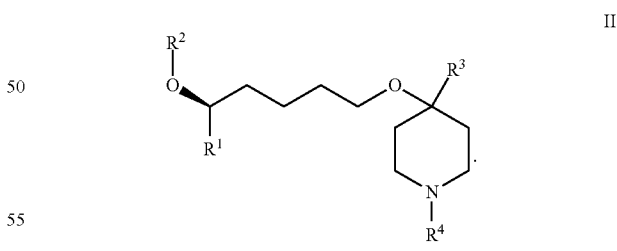

Another aspect of the invention is a method for a preparing a compound of formula II further comprising where the compound of formula II where $R^1$ is alkyl, $R^2$ is benzyl, $R^3$ is iodomethyl, and $R^4$ is benzyloxycarbonyl is prepared from N-benzyloxycarbonyl-4-methylenepiperidine and 5-alkyl-5-benzyloxypentane-1-ol.

Another aspect of the invention is a method for a preparing a compound of formula II where $R^1$ is alkyl, $R^2$ is trialkylsilyl, alkyl(aryl)$_2$silyl, or (alkyl)$_2$arylsilyl, $R^3$ is methyl, and $R^4$ is hydrogen; comprising protonolysis of a compound of formula II where $R^1$ is alkyl, $R^2$ is trialkylsilyl, alkyl(aryl)$_2$silyl, or (alkyl)$_2$arylsilyl, $R^3$ is methyl, and $R^4$ is t-butoxycarbonyl.

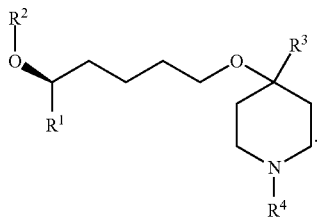

II

Another aspect of the invention is a method for a preparing a compound of formula II further comprising where the compound of formula II where $R^1$ is alkyl, $R^2$ is trialkylsilyl, alkyl(aryl)$_2$silyl, or (alkyl)$_2$arylsilyl, $R^3$ is methyl, and $R^4$ is t-butoxycarbonyl is hydrogenolyzed from compound of formula II where $R^1$ is alkyl, $R^2$ is trialkylsilyl, alkyl(aryl)$_2$silyl, or (alkyl)$_2$arylsilyl, $R^3$ is iodomethyl, and $R^4$ is t-butoxycarbonyl.

Another aspect of the invention is a method for a preparing a compound of formula II further comprising where the compound of formula II where $R^1$ is alkyl, $R^2$ is trialkylsilyl, alkyl(aryl)$_2$silyl, or (alkyl)$_2$arylsilyl, $R^3$ is iodomethyl, and $R^4$ is t-butoxycarbonyl is prepared from N-benzyloxycarbonyl-4-methylenepiperidine and 5-alkyl-5-(trialkylsilyloxy, alkyl (aryl)$_2$silyloxy, or (alkyl)$_2$arylsilyloxy)pentane-1-ol.

Another aspect of the invention is a method for a preparing a compound of formula III where $R^1$ is alkoxy substituted with 0-1 benzyloxy, trialkylsiloxy, alkyl(aryl)$_2$siloxy, or (alkyl)$_2$arylsiloxy substituents, $R^3$ is methyl, and $R^4$ is benzyloxycarbonyl or alkoxycarbonyl, comprising iodo-etherification of a compound of formula III where $R^3$ and $R^4$ together are methylene with an alcohol substituted with 0-1 benzyloxy, trialkylsiloxy, alkyl(aryl)$_2$siloxy, or (alkyl)$_2$arylsiloxy substituents, followed by hydrogenolysis

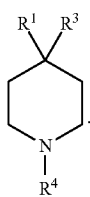

III

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Alkynylene" means a straight or branched divalent alkyne group composed of 2 to 6 carbons with at least one triple bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —CH$_2$CH$_2$CH$_2$O—. "Alkenyleneoxy" means a straight or branched divalent alkeneoxy group composed of 2 to 6 carbons with at least one double bond, for example, —CH═CHCH$_2$O—. "Alkynyleneoxy" means a straight or branched divalent alkyneoxy group composed of 2 to 6 carbons with at least one double bond, for example, —CC—CH$_2$O—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the Renilla Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC 18 at the PvuII site. The NL-RLuc virus was prepared by transfection of 293T cells with the plasmid pNLR-Luc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}\ \mu M$ |
|---|---|
| 1 | 2.486 |
| 2 | 2.689 |
| 3 | 0.253 |
| 4 | 0.249 |
| 5 | 0.045 |
| 6 | 0.080 |
| 7 | 0.134 |
| 8 | 0.111 |
| 9 | 0.093 |
| 10 | 0.251 |
| 11 | 0.204 |
| 12 | 0.136 |
| 13 | 0.124 |
| 14 | 0.045 |
| 15 | 0.120 |
| 16 | 0.021 |
| 17 | 0.024 |
| 18 | 0.122 |
| 19 | 0.034 |
| 20 | 0.105 |
| 21 | 0.646 |
| 22 | 0.141 |
| 23 | 0.011 |
| 24 | 0.003 |
| 25 | 0.031 |
| 26 | 0.032 |
| 27 | 0.037 |
| 28 | 0.005 |
| 29 | 0.006 |
| 30 | 0.064 |
| 31 | 0.012 |
| 32 | 0.003 |
| 33 | 0.006 |
| 34 | 0.005 |
| 35 | 0.002 |
| 36 | 3.689 |
| 37 | 0.004 |
| 38 | 0.002 |
| 39 | 0.005 |
| 40 | 0.031 |
| 41 | 0.010 |
| 42 | 0.002 |
| 43 | 0.001 |
| 44 | 0.005 |
| 45 | 0.035 |
| 46 | 0.735 |
| 47 | 1.586 |
| 48 | 0.111 |
| 49 | 0.005 |
| 50 | 0.019 |
| 51 | 0.018 |
| 52 | 0.060 |
| 53 | 0.002 |
| 54 | 0.007 |
| 55 | 0.007 |
| 56 | 0.008 |
| 57 | 0.034 |
| 58 | 0.062 |
| 59 | 0.016 |
| 60 | 0.013 |
| 61 | 0.005 |
| 62 | 0.041 |
| 63 | 0.016 |
| 64 | 0.012 |
| 65 | 0.002 |
| 66 | 0.004 |
| 67 | 0.005 |
| 68 | 0.001 |
| 69 | 0.012 |
| 70 | 0.043 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I. Compounds I-1 and I-2 are commercially available or synthesized by reactions known in the art. Reacting I-1 with I-2 in the presence of catalytic TsOH in refluxing xylenes provide the intermediate I-3. Treatment of I-3 with POCl$_3$ provide intermediate I-4 which can be converted to intermediate I-5 by Davis oxidation. Intermediate I-5 can be oxidized to ketoester I-6 by treating with Dess-Martin reagent. Intermediate I-6 can be reduced to chiral alcohol I-7 with catecholborane in the presence of catalytic chiral Lewis acid. Treatment of chiral alcohol I-7 with tertiary-butyl acetate and perchloric acid can provide tertiary butyl ether I-8. Amine can be coupled with I-8 in the presence of organic bases such as Hunig's base to provide intermediate I-9. Treatment of diester I-9 with hydroxide in ethanol can provide the mono-carboxylic acid intermediate I-10 which was can be converted to primary alcohol I-11 via mixed anhydride. Reaction of primary alcohol I-11 with diphenyl phosphorazidate can provide the azide intermediate I-12. Treatment of azide I-12 with appropriate alkyne in the presence of CuI can furnish the triazole intermediate I-13 which can be converted to macrocyclic carboxylic acids I-14 by ring closing metathesis reaction followed by hydrolysis. Hydrogenolysis of I-14 in the presence of 10% Pd/C can provide the saturated compound I-15.

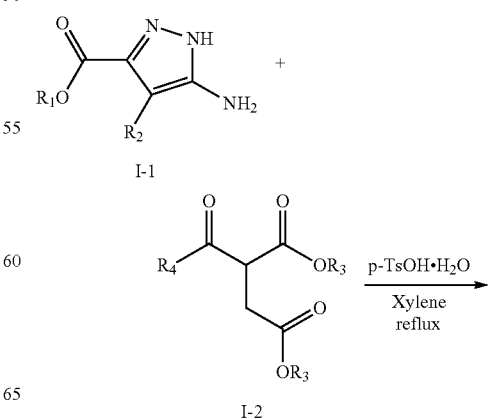

Scheme I.

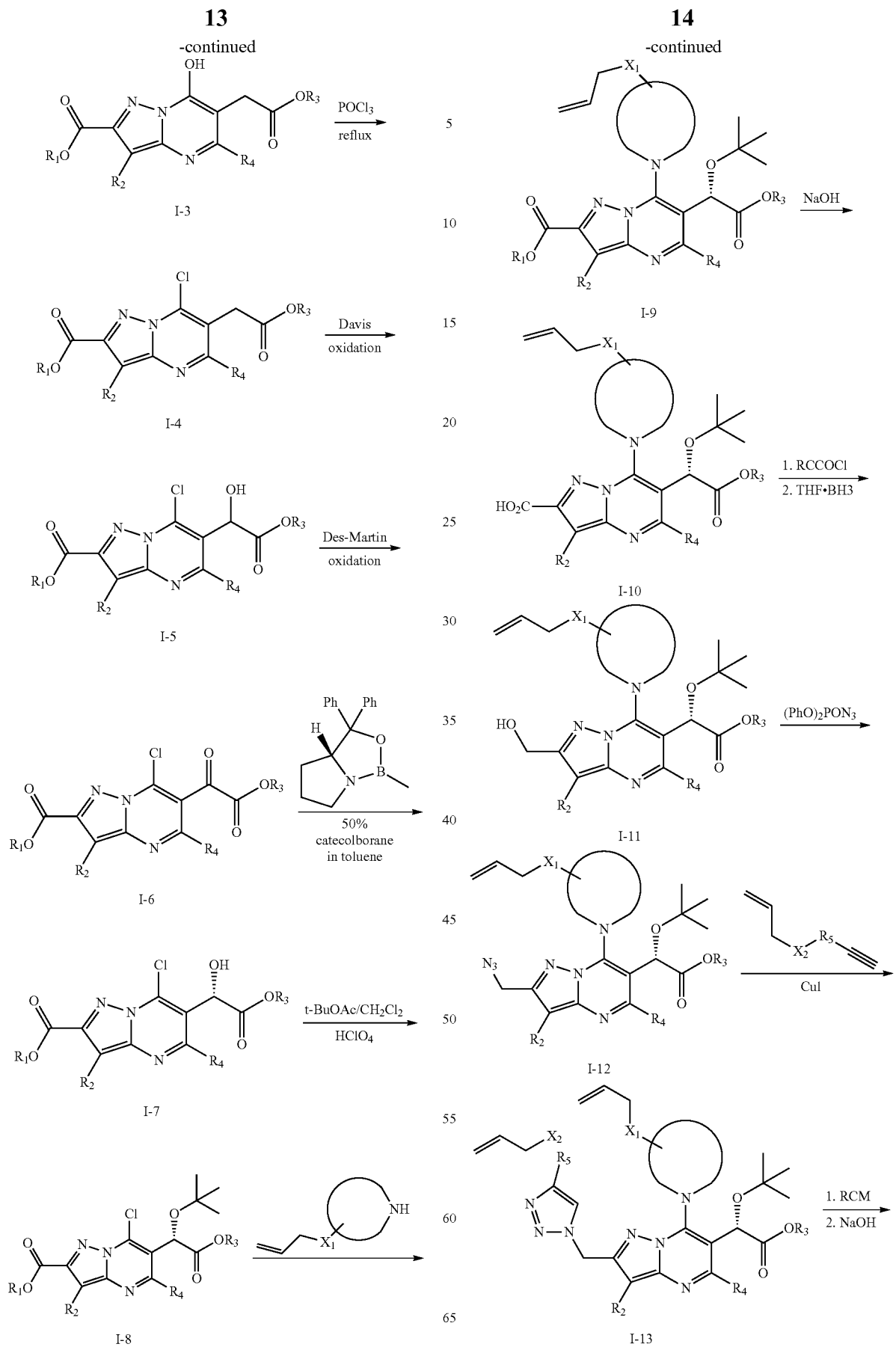

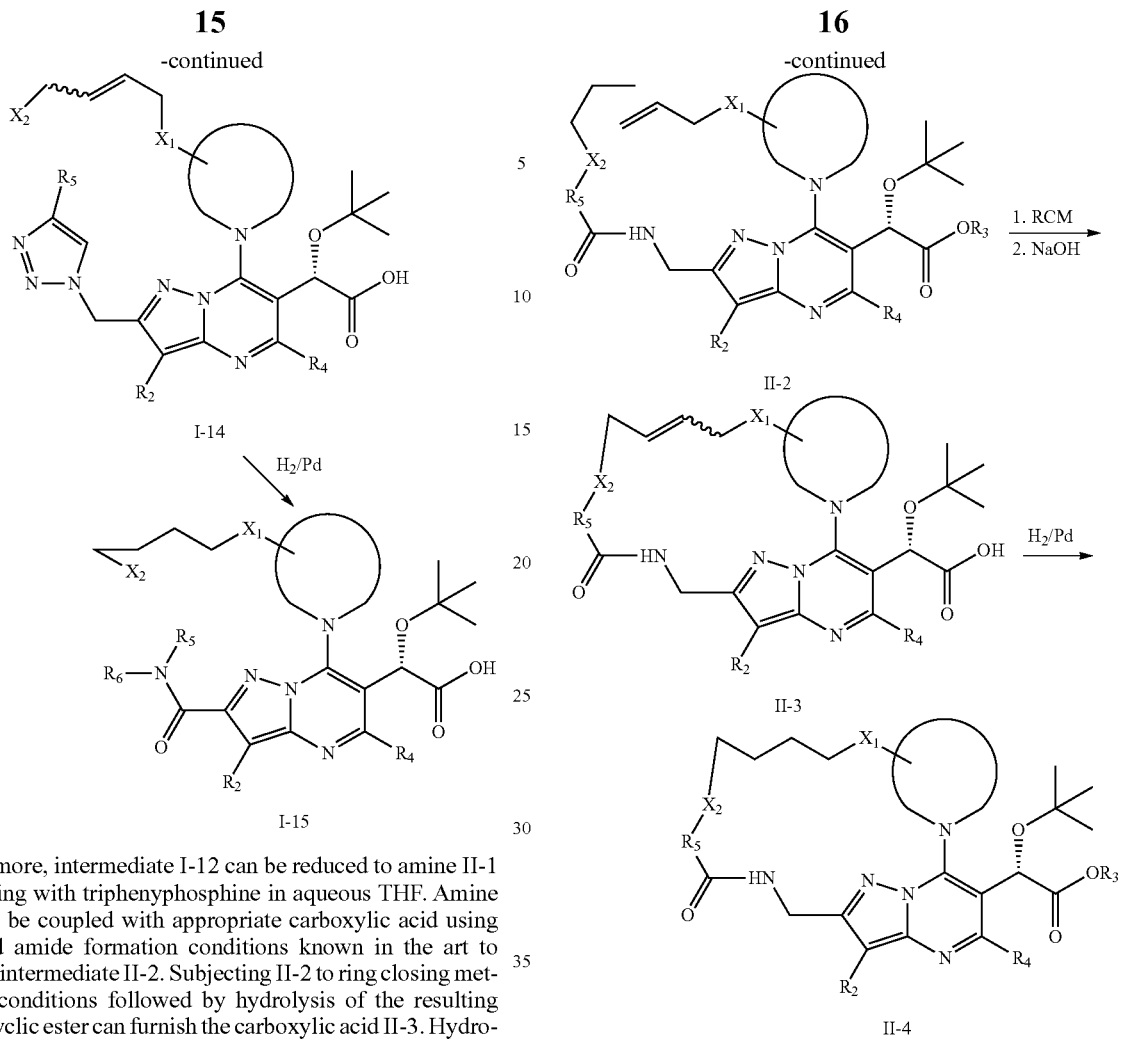

Furthermore, intermediate I-12 can be reduced to amine II-1 by treating with triphenyphosphine in aqueous THF. Amine II-1 can be coupled with appropriate carboxylic acid using standard amide formation conditions known in the art to provide intermediate II-2. Subjecting II-2 to ring closing metathesis conditions followed by hydrolysis of the resulting macrocyclic ester can furnish the carboxylic acid II-3. Hydrogenolysis of unsaturated carboxylic acid II-3 can provide the saturated carboxylic acid II-4.

Intermediate I-11 can be transformed to final compounds III-2 and III-3 by methods known in the art as outlined in Scheme III.

Scheme II

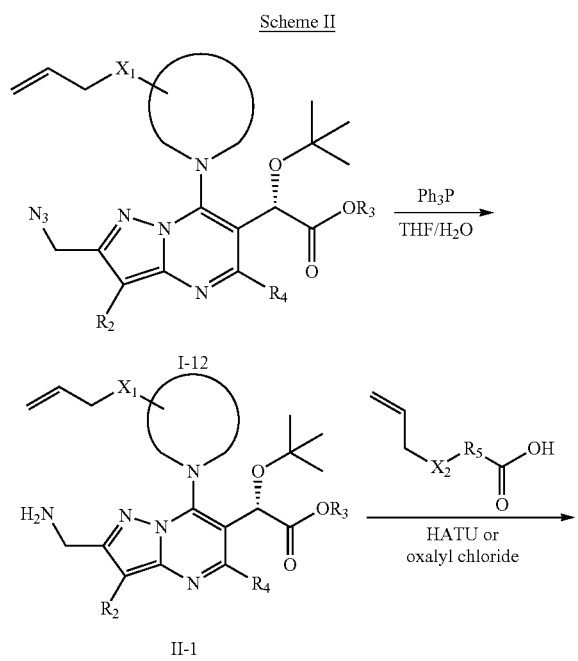

Scheme III

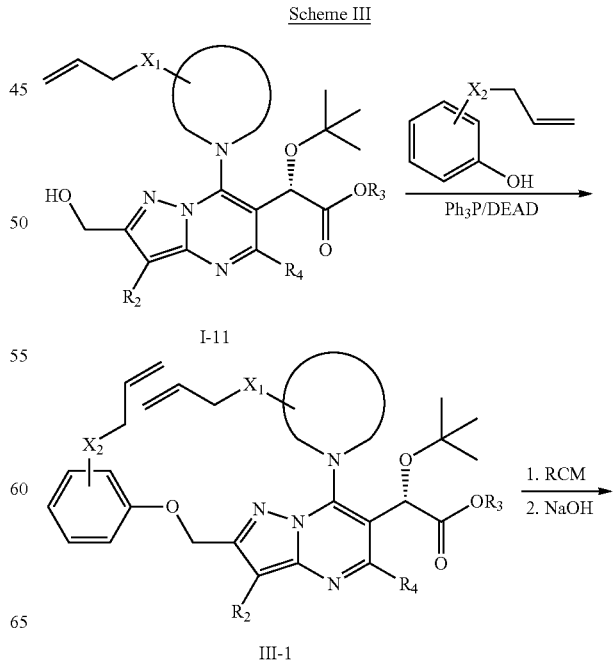

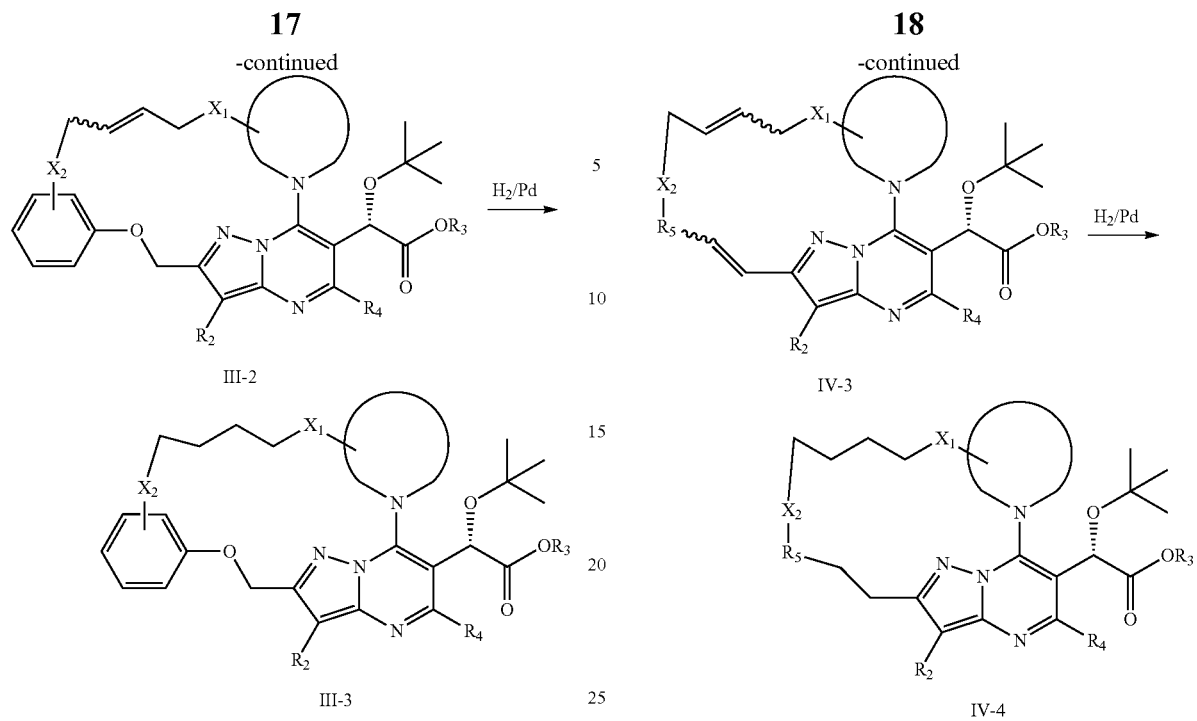
Intermediate I-11 can be transformed to final compounds IV-3 and IV-4 by methods known in the art as outlined in Scheme IV.
Intermediate I-11 can be transformed to final compounds V-3 and V-3 by methods known in the art as outlined in Scheme V.
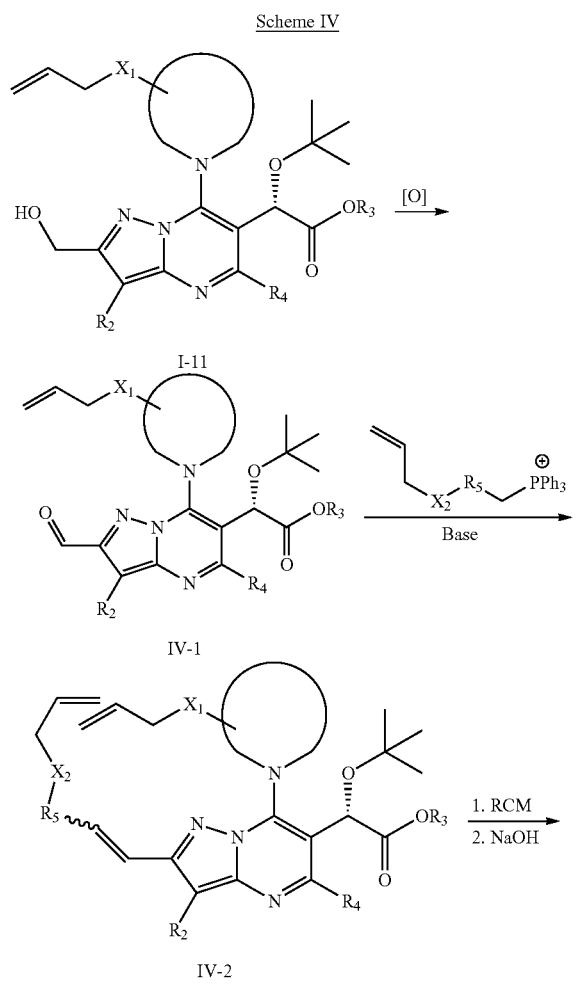
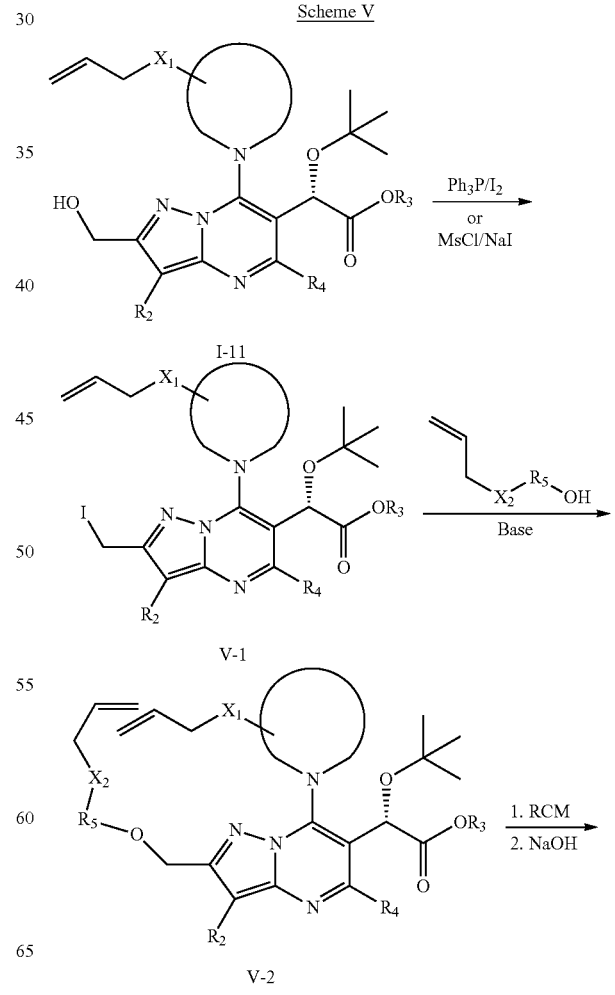

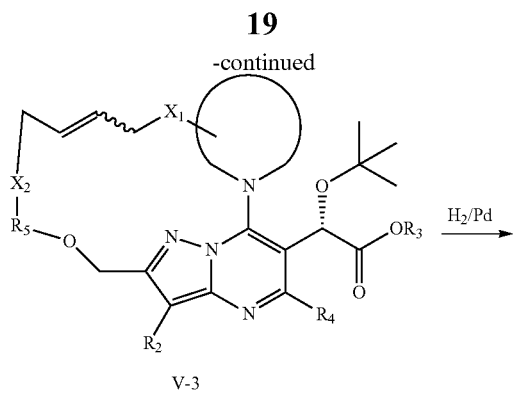
V-3
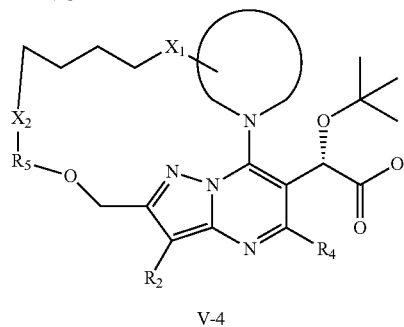
V-4
Intermediate I-11 can be transformed to final compounds VI-2 and VI-3 by methods known in the art as outlined in Scheme VI.
Scheme VI
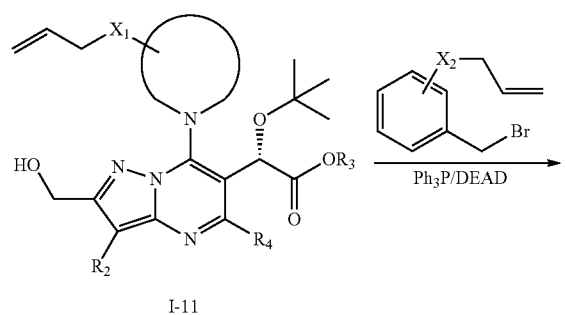
I-11
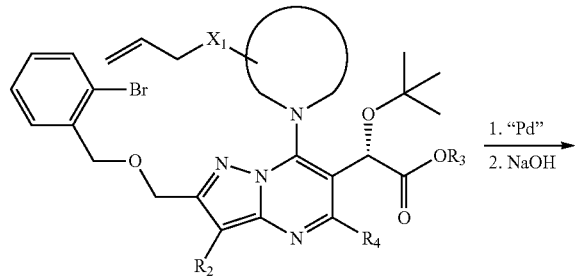
VI-1
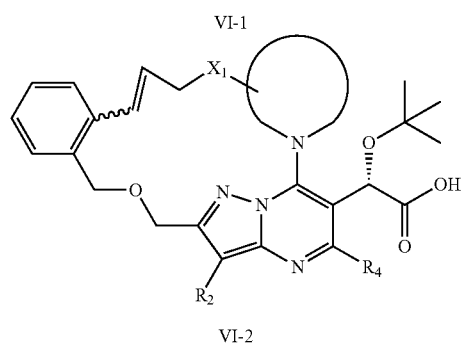
VI-2
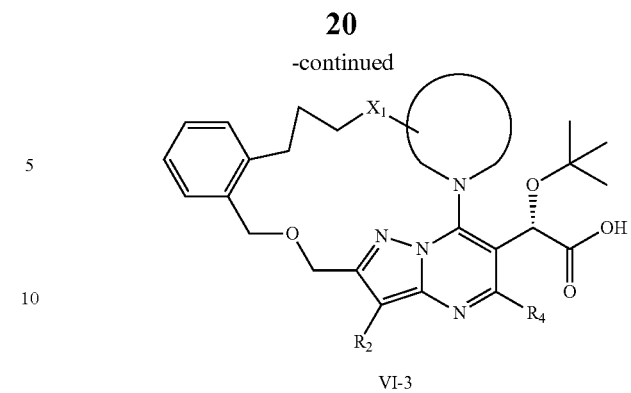
VI-3
Intermediate IV-1 can be transformed to final compounds VII-2 and VII-3 by methods known in the art as outlined in Scheme VII.
Scheme VII
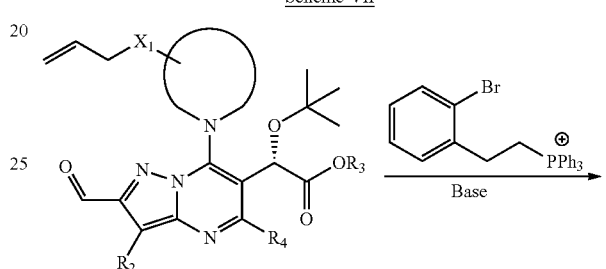
IV-1
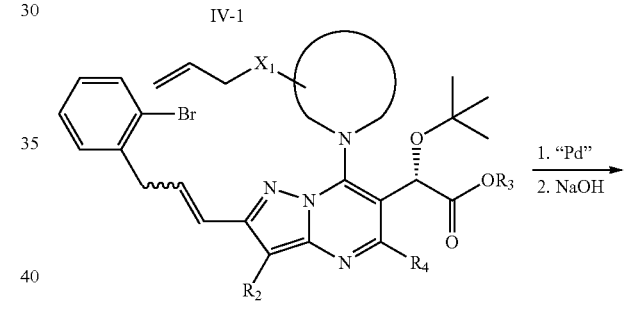
VII-1
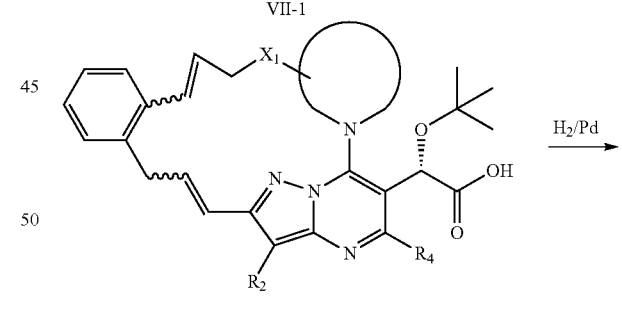
VII-2
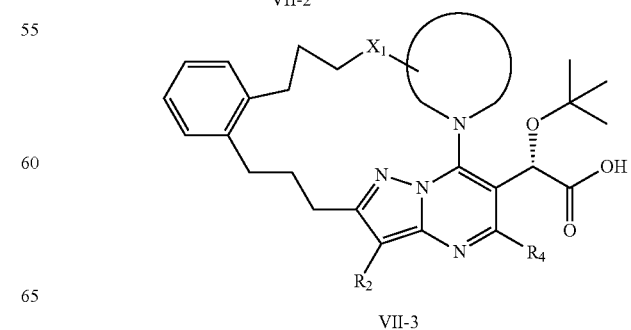
VII-3

Scheme VIII

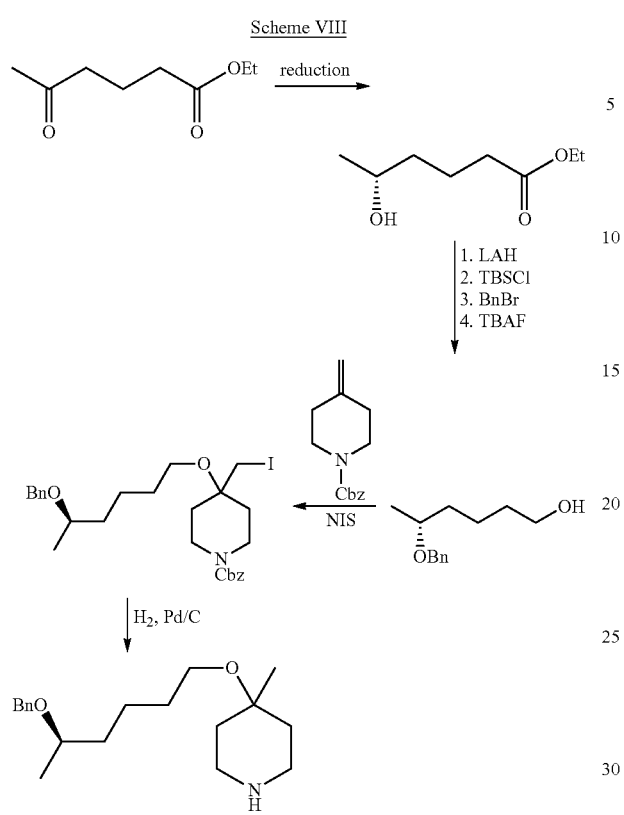

Scheme IX

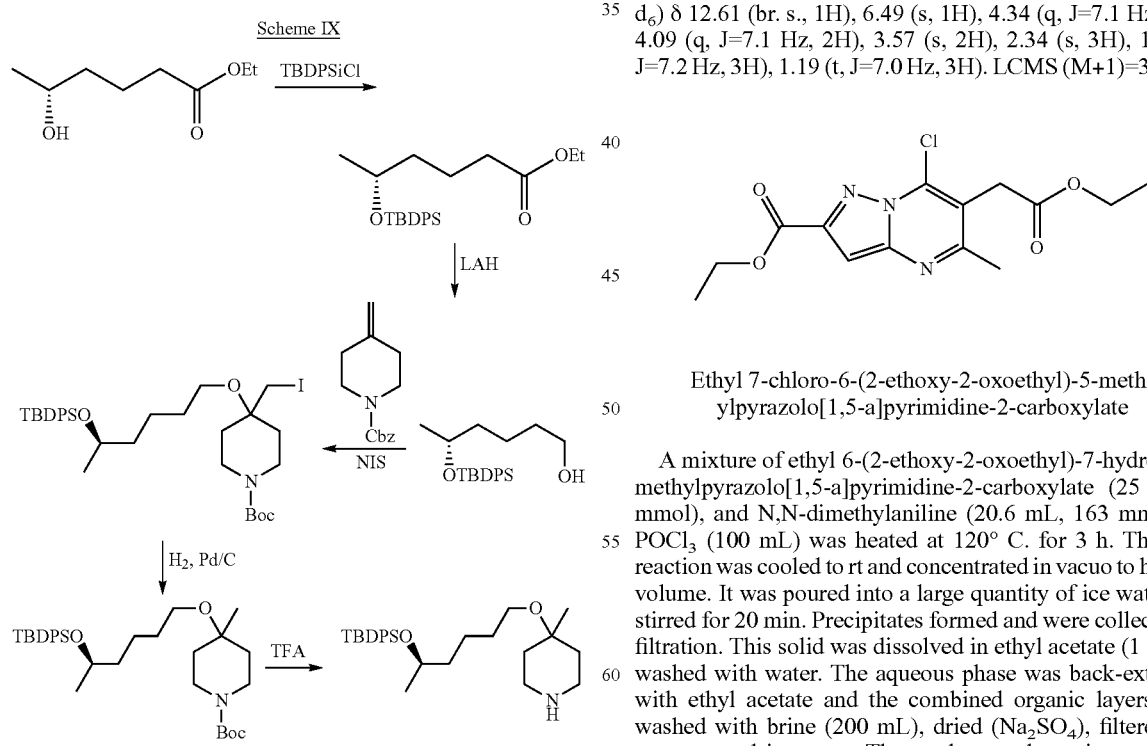

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A:9:1 H$_2$O/acetonitrile with 10 mM NH$_4$OAc and mobile phase B:A:9:1 acetonitrile/H$_2$O with: 10 mM NH$_4$OAc or mobile phase A:95:5 H$_2$O/MeOH with 20 mM NH$_4$OAc and mobile phase B:95:5 MeOH/H$_2$O with 20 mM NH$_4$OAc.

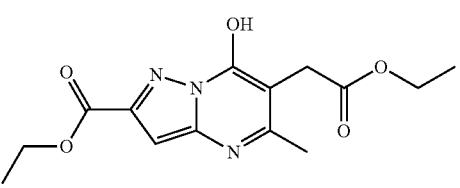 [SMILES: CCOC(=O)Cc1c(C)nc2cc(C(=O)OCC)nn2c1O]

Ethyl 6-(2-ethoxy-2-oxoethyl)-7-hydroxy-5-methylpyrazolo[1,5-a]pyrimidine-2-carboxylate A suspension of ethyl 5-amino-1H-pyrazole-3-carboxylate (35.5 g, 229 mmol, prepared according to WO 2008015271), diethyl 2-acetylsuccinate (51.2 mL, 275 mmol) and TsOH.H$_2$O (0.218 g, 1.144 mmol) in o-xylene (500 mL) was refluxed using a Dean-Stork condenser for 5 h. (Note: The suspension turned into a clear homogeneous solution and then in about 15 min a yellow solid started precipitated out of solution). Then, the reaction mixture was cooled, diluted with hexanes (250 mL), filtered, washed with hexanes and dried to afford ethyl 6-(2-ethoxy-2-oxoethyl)-7-hydroxy-5-methylpyrazolo[1,5-a]pyrimidine-2-carboxylate (53 g, 75% yield) as light yellow solid. $^1$H NMR (500 MHz, DMSO-d$_6$) δ 12.61 (br. s., 1H), 6.49 (s, 1H), 4.34 (q, J=7.1 Hz, 2H), 4.09 (q, J=7.1 Hz, 2H), 3.57 (s, 2H), 2.34 (s, 3H), 1.33 (t, J=7.2 Hz, 3H), 1.19 (t, J=7.0 Hz, 3H). LCMS (M+1)=308.04.

Ethyl 7-chloro-6-(2-ethoxy-2-oxoethyl)-5-methylpyrazolo[1,5-a]pyrimidine-2-carboxylate A mixture of ethyl 6-(2-ethoxy-2-oxoethyl)-7-hydroxy-5-methylpyrazolo[1,5-a]pyrimidine-2-carboxylate (25 g, 81 mmol), and N,N-dimethylaniline (20.6 mL, 163 mmol) in POCl$_3$ (100 mL) was heated at 120° C. for 3 h. Then the reaction was cooled to rt and concentrated in vacuo to half the volume. It was poured into a large quantity of ice water and stirred for 20 min. Precipitates formed and were collected by filtration. This solid was dissolved in ethyl acetate (1 L) and washed with water. The aqueous phase was back-extracted with ethyl acetate and the combined organic layers were washed with brine (200 mL), dried (Na$_2$SO$_4$), filtered and concentrated in vacuo. The crude was then triturated with EtOAc/hexane to afford ethyl 7-chloro-6-(2-ethoxy-2-oxoethyl)-5-methylpyrazolo[1,5-a]pyrimidine-2-carboxylate (22 g, 67.5 mmol, 83% yield) as light yellow solid. $^1$H NMR (500 MHz, CDCl$_3$) δ 7.21 (s, 1H), 4.52 (q, J=7.2 Hz, 2H), 4.24 (q, J=7.2 Hz, 2H), 3.94 (s, 2H), 2.66 (s, 3H), 1.48 (t, J=7.0 Hz, 3H), 1.30 (t, J=7.2 Hz, 3H). LCMS (M+1)=326.2.

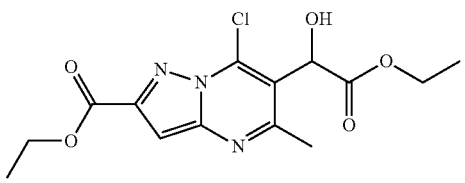 [SMILES: CCOC(=O)c1cc2nc(C)c(C(O)C(=O)OCC)c(Cl)n2n1]

Ethyl 7-chloro-6-(2-ethoxy-1-hydroxy-2-oxoethyl)-5-methylpyrazolo[1,5-a]pyrimidine-2-carboxylate To a stirred solution of 0.9M KHMDS (40.9 mL, 36.8 mmol) in THF (100 mL) at −78° C. was added a THF (50 mL) solution of ethyl 7-chloro-6-(2-ethoxy-2-oxoethyl)-5-methylpyrazolo[1,5-a]pyrimidine-2-carboxylate (10 g, 30.7 mmol, for synthesis see WO2013025584) was added over the course of 20 min. After 30 min, a THF (15 mL) solution of 3-phenyl-2-(phenylsulfonyl)-1,2-oxaziridine (10.43 g, 39.9 mmol) was added to the red reaction mixture and stirring was continued for an additional 30 min at −78° C. Then, the resulting orange reaction mixture was quenched with sat. aq. NH₄Cl (50 mL), diluted with EtOAc (200 mL), washed with water (100 mL), brine (100 mL), dried (Na₂SO₄), filtered and concentrated in vacuo to give a solid. This solid was triturated with small amount of ethyl acetate and solids were filtered, washed with hexanes and dried under high vacuum to afford ethyl 7-chloro-6-(2-ethoxy-1-hydroxy-2-oxoethyl)-5-methylpyrazolo[1,5-a]pyrimidine-2-carboxylate (5 g, 16.85 mmol, 43% yield, 90% pure) as light yellow solid. $^1$H NMR (400 MHz, CDCl₃) δ 7.21 (s, 1H), 5.76 (s, 1H), 4.58-4.49 (m, 2H), 4.33 (dtt, J=10.7, 7.1, 3.7 Hz, 2H), 2.71-2.64 (s, 3H), 1.48 (t, J=7.2 Hz, 3H), 1.29-1.24 (m, 3H). LCMS (M+1)=342.16.

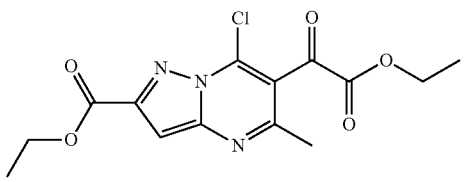 [SMILES: CCOC(=O)C(=O)c1c(C)nc2cc(C(=O)OCC)nn2c1Cl]

Ethyl 6-(2-ethoxy-2-oxoacetyl)-7-chloro-5-methylpyrazolo[1,5-a]pyrimidine-2-carboxylate To a mixture of 7-chloro-6-(2-ethoxy-1-hydroxy-2-oxoethyl)-5-methylpyrazolo[1,5-a]pyrimidine-2-carboxylate (5.9 g 13.81 mmol) in CH₂Cl₂ (100 mL) was added Dess-Martin (5.86 g, 13.81 mmol) and the resulting mixture was stirred at rt for 1 h. The reaction mixture was diluted with ethyl acetate (100 mL) and washed with sat. aq. NaHCO₃ solution (30 mL), dried (Na₂SO₄), filtered, and concentrated in vacuo. The residue was purified by silica gel chromatography (5-70% EtOAc/hexane) to afford the desired ethyl 7-chloro-6-(2-ethoxy-2-oxoacetyl)-5-methylpyrazolo[1,5-a]pyrimidine-2-carboxylate (3.5 g, 9.27 mmol, 67.1% yield) as an off-white solid. $^1$H NMR (400 MHz, CDCl₃) δ 7.24 (s, 1H), 4.56-4.43 (m, 4H), 2.63 (s, 3H), 1.50-1.41 (m, 6H). LCMS (M+1)=340.13.

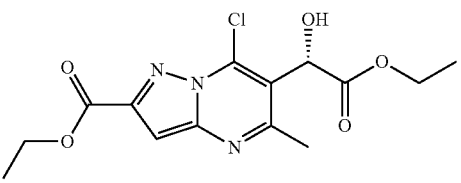 [SMILES: CCOC(=O)c1cc2nc(C)c([C@H](O)C(=O)OCC)c(Cl)n2n1]

(S)-Ethyl 7-chloro-6-(2-ethoxy-1-hydroxy-2-oxoethyl)-5-methylpyrazolo[1,5-a]pyrimidine-2-carboxylate To a stirred yellow solution of ethyl 6-(2-ethoxy-2-oxoacetyl)-7-chloro-5-methylpyrazolo[1,5-a]pyrimidine-2-carboxylate (264 mg, 0.777 mmol) in anhydrous toluene (5 mL) was added 1.0M (R)-1-methyl-3,3-diphenylhexahydro-pyrrolo[1,2-c][1,3,2]oxazaborole/toluene (0.311 mL, 0.311 mmol). The mixture was cooled to −35° C. and a solution of 50% catechoborane/toluene (0.272 mL, 1.088 mmol) was added over the course of 10 min. After 30 min, the reaction mixture was slowly warmed to −15° C. and stirred for additional 2 h, then diluted with EtOAc (30 mL) and sat.aq. Na₂CO₃ (5 mL). The mixture was stirred vigorously for 30 min, and the organic phase was washed with sat. aq. Na₂CO₃ (2×5 mL), dried (Na₂SO₄), filtered, concentrated. The residue was purified by silica gel chromatography (5-100% EtOAc/hexane) to afford the desired (S)-ethyl 7-chloro-6-(2-ethoxy-1-hydroxy-2-oxoethyl)-5-methylpyrazolo[1,5-a]pyrimidine-2-carboxylate (200 mg, 0.585 mmol, 75% yield) as an off-white solid. $^1$H NMR (400 MHz, CDCl₃) δ 7.21 (s, 1H), 5.77 (d, J=2.7 Hz, 1H), 4.53 (d, J=7.1 Hz, 2H), 4.33 (dd, J=7.1, 5.5 Hz, 2H), 3.61 (br. s., 1H), 2.68 (s, 3H), 1.50-1.46 (t, J=7.09 Hz, 3H), 1.28 (t, J=7.09 Hz, 3H). LCMS (M+1)=342.13.

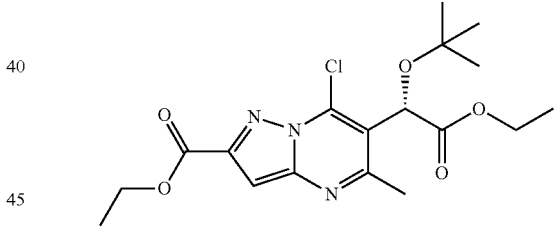

(S)-Ethyl 6-(1-(tert-butoxy)-2-ethoxy-2-oxoethyl)-7-chloro-5-methylpyrazolo[1,5-a]pyrimidine-2-carboxylate To a stirred solution of (S)-ethyl 7-chloro-6-(2-ethoxy-1-hydroxy-2-oxoethyl)-5-methylpyrazolo[1,5-a]pyrimidine-2-carboxylate (200 mg, 0.585 mmol) in CH₂Cl₂ (6 mL) and t-butyl acetate (4 mL) at rt was added perchloric acid (0.151 mL, 1.756 mmol). The reaction flask was sealed. After stirring for 3 h, the reaction mixture was diluted with CH₂Cl₂ (50 mL), carefully quenched with sat. aq. NaHCO₃ (5 mL). The organic layer was separated and washed with brine (5 mL), dried (Na₂SO₄), filtered and concentrated in vacuo to give a yellow liquid. This crude product was purified by flash column chromatography on a silica gel column using (10-50% EtOAc/Hex as eluant) to afford the desired (S)-ethyl 6-(1-(tert-butoxy)-2-ethoxy-2-oxoethyl)-7-chloro-5-methylpyrazolo[1,5-a]pyrimidine-2-carboxylate (200 mg, 0.503 mmol, 86% yield) as viscous oil. $^1$H NMR (400 MHz, CDCl₃) δ 7.19

(s, 1H), 5.66 (s, 1H), 4.52 (q, J=7.2 Hz, 2H), 4.25-4.19 (m, 2H), 2.72 (s, 3H), 1.51-1.45 (m, 3H), 1.28 (s, 9H), 1.26-1.21 (m, 3H). LCMS (M+1)=398.25.

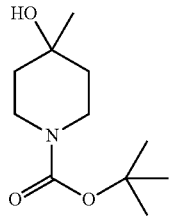

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. ¹H NMR (400 MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

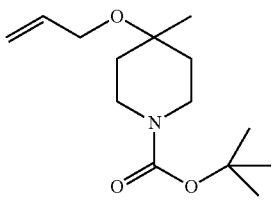 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO₄, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. ¹H NMR (500 MHz, CDCl₃) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

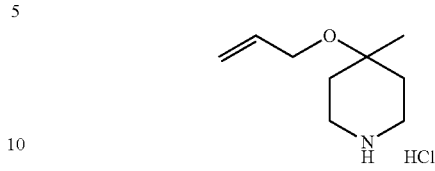

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. ¹H NMR (500 MHz, CD₃OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H). Free amine is obtained by stirring DCM solution of amine.HCl salt with aqueous Na₂CO₃.

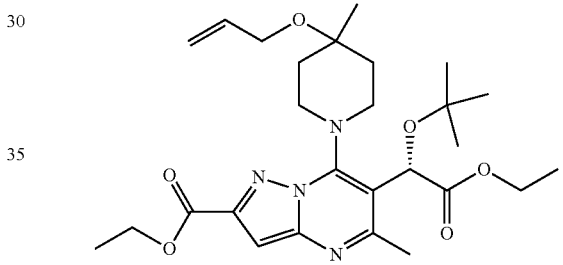

(S)-Ethyl 7-(4-(allyloxy)-4-methylpiperidin-1-yl)-6-(1-tert-butoxy-2-ethoxy-2-oxoethyl)-5-methylpyrazolo[1,5-a]pyrimidine-2-carboxylate A mixture of (S)-ethyl 6-(1-(tert-butoxy)-2-ethoxy-2-oxoethyl)-7-chloro-5-methylpyrazolo[1,5-a]pyrimidine-2-carboxylate (21.4 g, 53.8 mmol), 4-(allyloxy)-4-methylpiperidine, HCl (11.34 g, 59.2 mmol) and DIEA (10.33 ml, 59.2 mmol) in DMF (100 mL) was stirred at 60° C. (oil bath temp) for 22 h. Note: LCMS of the reaction mixture was identical at 2 and 22 h, indicating that there may not be enough amine for the reaction to complete. The amineHCl salt was free flowing liquid, possible due to the absorbtion of lot of water. So, additional amine HCl (7.85 g, 41 mmol) and DIEA (5 mL) were added and continued stirring at 60° C. for 4 h. Then, cooled, diluted with Et₂O (300 mL), washed with water (3×50 mL), brine (50 mL), dried (MgSO₄), filtered and concentrated to give brown viscous oil. Flash chromatography using 4:1 Hex/EtOAc afforded (S)-ethyl 7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylate (25.9 g, 50.1 mmol, 93% yield) as yellow paste. ¹H NMR (400 MHz, CDCl₃) δ 7.03 (s, 1H), 6.11-6.01 (m, 1H), 5.86 (br. s., 1H), 5.45 (d, J=17.8 Hz, 1H), 5.22 (dd, J=10.4, 1.6 Hz, 1H), 4.50-4.43 (m, 2H), 4.29-4.18 (m, 2H), 4.06-4.01 (m, 2H), 3.90-3.25 (br. s, 4H), 2.63 (s, 3H), 2.05-1.90 (m, 2H), 1.80-

1.69 (m, 1H), 1.66-1.59 (m, 1H), 1.45 (t, J=7.1 Hz, 3H), 1.37 (s, 3H), 1.25-1.21 (m, 12H). LCMS (M+H)=517.5.

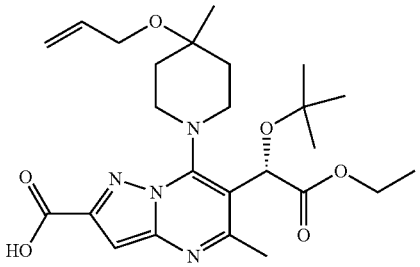 [SMILES: C=CCOC1(C)CCN(c2c([C@H](OC(C)(C)C)C(=O)OCC)c(C)nc3cc(C(=O)O)nn23)CC1]

(S)-7-(4-(Allyloxy)-4-methylpiperidin-1-yl)-6-(1-tert-butoxy-2-ethoxy-2-oxoethyl)-5-methylpyrazolo[1,5-a]pyrimidine-2-carboxylic acid To a stirred solution of (S)-ethyl 7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylate (25.9 g, 50.1 mmol) in EtOH (150 mL) was slowly added 1M NaOH (53 ml, 53.0 mmol) at rt over 5 min. Note: the reaction mixture was warm to touch at the end of NaOH addition. LCMS after 43 h showed presence of unhydrolyzed di-ester. So, added additional 1M NaOH (10 mL) and continued stirring at rt for additional 26 h. LCMS at this point also showed presence of unreacted diester. So, heated at 45° C. for 6 h. Then, concentrated and pale yellow mixture was diluted with water (100 mL), extracted with Et$_2$O (2×100 mL) to remove unreacted di-ester. The combine ether layers dried (MgSO$_4$), filtered and concentrated give unreacted (S)-ethyl 7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylate (7.7 g, 30%) as pale yellow paste. The aq. layer was carefully acidified with slow addition of 1M HCl (70 mL) and extracted with Et$_2$O (3×100 mL). The combined ether layers dried (MgSO$_4$), filtered and concentrated give (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (16.51 g, 33.8 mmol, 67.4% yield) as white solid. $^1$H NMR (500 MHz, CDCl$_3$) δ 7.15 (s, 1H), 6.01-6.10 (m, 1H), 5.89 (br. s., 1H), 5.46 (d, J=17.2 Hz, 1H), 5.25 (d, J=10.3 Hz, 1H), 4.16-4.30 (m, 2H), 4.03 (dd, J=1.0, 5.04 Hz, 2H), 2.66 (s, 3H), 1.94-2.07 (m, 3H), 1.73 (t, J=9.7 Hz, 1H), 1.37 (s, 3H), 1.24-1.28 (m, 12H). 4Hs of piperidine are missing in HNMR. LCMS (M+H)=489.4.

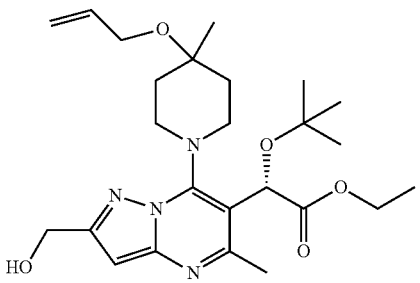 [SMILES: C=CCOC1(C)CCN(c2c([C@H](OC(C)(C)C)C(=O)OCC)c(C)nc3cc(CO)nn23)CC1]

(S)-Ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate To a stirred solution of (S)-7-(4-(allyloxy)-4-methylpiperidin-1-yl)-6-(1-(tert-butoxy)-2-ethoxy-2-oxoethyl)-5-methylpyrazolo[1,5-a]pyrimidine-2-carboxylic acid (2.443 g, 5 mmol) and Et$_3$N (0.836 ml, 6.00 mmol) in THF (100 mL) was added 1M isopropyl chloroformate/toluene (6.00 ml, 6.00 mmol) at 0° C. After 1 h, a solution of NaBH$_4$ (0.567 g, 15.00 mmol) in cold water (20 mL) was added at once and stirred for at 0° C. LCMS after 1 h showed formation of desired product and presence of unreacted mixed unhydride intermediate. So, added additional NaBH$_4$ (0.284 g, 7.5 mmol) and continued stirring for 3 h while allowing reaction mixture to slowly warm to 10° C. LCMS at this point showed still remaining about 10% unreacted material. So, added additional NaBH$_4$ (0.189 g) and stirred for 1 h at 10° C. Then the reaction was quenched with AcOH (1 mL), diluted with Et$_2$O (200 mL), washed with water (2×50 mL) and brine (25 mL). The organic layer dried (MgSO$_4$), filtered and concentrated to give (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (2.7 g, 5.12 mmol, 102% yield, 90% purity) as pale yellow paste which was used in next step without purification. LCMS (M+H)=475.2.

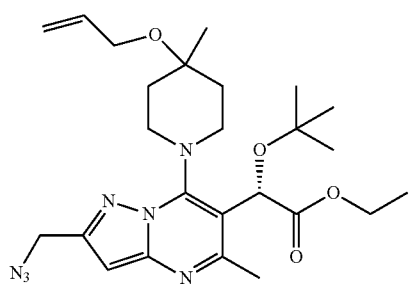 [SMILES: C=CCOC1(C)CCN(c2c([C@H](OC(C)(C)C)C(=O)OCC)c(C)nc3cc(CN=[N+]=[N-])nn23)CC1]

(S)-Ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate To a stirred solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.70 g, 1.475 mmol) and diphenyl phosphorazidate (0.381 ml, 1.770 mmol) in toluene (10 mL) was added DBU (0.222 ml, 1.475 mmol) at 0° C. After 2 h, cold bath was removed, stirred for 22 h at rt. LCMS at 8 and 22 h is same and incomplete. So, added THF (10 mL) to the turbid reaction mixture and heated at 55° C. for 5 h. Then diluted with Et$_2$O (100 mL), washed with water (2×10 mL), brine (10 mL), dried (MgSO$_4$), filtered, concentrated and purified by flash chromatography using 15 and 20% EtOAc/Hex to provide (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.5038 g, 1.008 mmol, 68.4% yield) as colorless viscous oil. $^1$H NMR (500 MHz, CDCl$_3$) δ 6.51 (s, 1H), 6.00-6.09 (m, 1H), 5.92 (br. s., 1H), 5.46 (d, J=16.6 Hz, 1H), 5.23 (dd, J=1.4, 10.4 Hz, 1H), 4.46-4.53 (m, 2H), 4.15-4.29 (m, 2H), 4.00-4.04 (m, 2H), 2.63 (s, 3H), 1.90-2.04 (m, 3H), 1.67-1.76 (m, 1H), 1.36 (s, 3H), 1.23-1.27 (m, 12H). 4H of piperidine are missing. LCMS (M+H)=500.5.

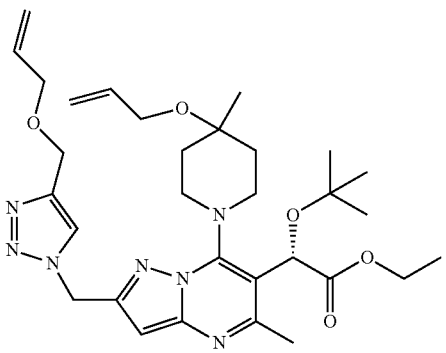 [SMILES: C=CCOCc1cn(Cc2cc3nc(C)c([C@H](OC(C)(C)C)C(=O)OCC)c(N4CCC(C)(OCC=C)CC4)n3n2)nn1]

(S)-Ethyl 2-(7-(4-(allyloxy)-4-methylpiperidin-1-yl)-
2-((4-((allyloxy)methyl)-1H-1,2,3-triazol-1-yl)me-
thyl)-5-methylpyrazolo[1,5-a]pyrimidin-6-yl)-2-
(tert-butoxy)acetate To a stirred colorless clear solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.049 g, 0.098 mmol), propargyl alcohol (0.029 ml, 0.490 mmol) and DIEA (0.086 ml, 0.490 mmol) in THF (2 mL) was added CuI (0.037 g, 0.196 mmol) at rt. The resulting turbid yellow reaction mixture stirred for 22 h and diluted with Et$_2$O (50 mL), washed with 1% aq NH$_4$OH (2×10 mL), brine (10 mL), dried (MgSO4), filtered and concentrated to afford (S)-ethyl 2-(7-(4-(allyloxy)-4-methylpiperidin-1-yl)-2-((4-(hydroxymethyl)-1H-1,2,3-triazol-1-yl)methyl)-5-methylpyrazolo[1,5-a]pyrimidin-6-yl)-2-(tert-butoxy)acetate as pale yellow paste which was used in the next step without purification.

To a stirred colorless solution of (S)-ethyl 2-(7-(4-(allyloxy)-4-methylpiperidin-1-yl)-2-((4-(hydroxymethyl)-1H-1,2,3-triazol-1-yl)methyl)-5-methylpyrazolo[1,5-a]pyrimidin-6-yl)-2-(tert-butoxy)acetate in DMF (2 mL) was added at once 60% NaH (10 mg, 0.250 mmol) at 0° C. After 5 min, allyl bromide (0.085 ml, 0.981 mmol) was added to the brown reaction mixture and stirred for 30 min at 0° C. and 1 h at rt. Then, quenched with EtOH and purified by prep-HPLC to give (S)-ethyl 2-(7-(4-(allyloxy)-4-methylpiperidin-1-yl)-2-((4-((allyloxy)methyl)-1H-1,2,3-triazol-1-yl)methyl)-5-methylpyrazolo[1,5-a]pyrimidin-6-yl)-2-(tert-butoxy)acetate (0.0334 g, 0.056 mmol, 57.2% yield) as brown paste. $^1$H NMR (500 MHz, CDCl$_3$) δ 7.67 (s, 1H), 6.45 (s, 1H), 5.98-6.08 (m, 1H), 5.83-5.97 (m, 2H), 5.73 (s, 2H), 5.40-5.53 (m, 1H), 5.30 (qd, J=1.6, 17.2 Hz, 1H), 5.17-5.24 (m, 2H), 4.64 (d, J=0.5 Hz, 2H), 4.13-4.28 (m, 2H), 4.06 (td, J=1.4, 5.7 Hz, 2H), 4.00-4.03 (m, 2H), 2.60 (s, 3H), 1.87-2.03 (m, 3H), 1.64-1.75 (m, 1H), 1.34 (s, 3H), 1.20-1.26 (m, 12H). LCMS (M+H)=596.6.

Example 1

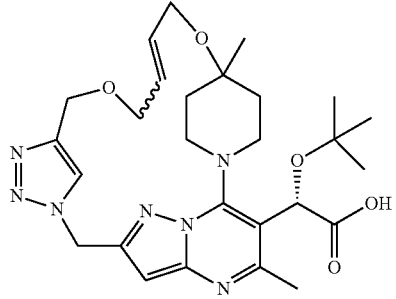 [SMILES: Cc1nc2cc3nn2c(c1[C@H](OC(C)(C)C)C(=O)O)N1CCC(C)(CC1)OCC=CCOCc1cn(nn1)C3]

(2S)-2-(tert-Butoxy)-2-[4,22-dimethyl-16,21-dioxa-
1,5,7,8,11,12,13-heptaazapentacyclo[20.2.2.
1$^{6,9}$.1$^{11,14}$.0$^{2,7}$]octacosa-2,4,6(28),8,12,14(27),18-
heptaen-3-yl]acetic acid To a stirred solution of (S)-ethyl 2-(7-(4-(allyloxy)-4-methylpiperidin-1-yl)-2-((4-((allyloxy)methyl)-1H-1,2,3-triazol-1-yl)methyl)-5-methylpyrazolo[1,5-a]pyrimidin-6-yl)-2-(tert-butoxy)acetate (0.033 g, 0.055 mmol) in 1,2-dichloroethane (15 mL) was added Hoveyda-Grubbs catalyst 2nd generation (1.736 mg, 2.77 μmol) at 70° C. and the resulting mixture was refluxed for 2 h. The, cooled, concentrated and filtered through a plug of silica gel (2×1) using 3:1 EtOAc/Hex and EtOAc to removed catalyst. The fractions containing the product were concentrated to give the macrocycle ester.

A solution of above macrcycle ester and 1M NaOH (0.166 ml, 0.166 mmol) in MeOH (2 mL) refluxed for 4 h. Then, cooled and purified by prep-HPLC to afford desired macrocycle carboxylic acid product (0.0195 g, 0.036 mmol, 65.2% yield) as white solid, contaminated with other olefin isomers (~10%). $^1$H NMR (500 MHz, CDCl$_3$) δ 8.24 (s, 1H), 6.62 (s, 1H), 5.98-6.05 (m, 1H), 5.97 (br. s., 1H), 5.84-5.91 (m, 1H), 5.82 (d, J$_{AB}$=15.5 Hz, 1H), 5.67 (d, J$_{AB}$=15.5 Hz, 1H), 4.74-4.82 (m, 2H), 4.52 (dt, J=2.1, 12.4 Hz, 1H), 4.11-4.19 (m, 2H), 3.97-4.06 (m, 2H), 3.75 (dt, J=1.9, 12.2 Hz, 1H), 3.33 (d, J=11.7 Hz, 1H), 2.86 (d, J=11.8 Hz, 1H), 2.63 (s, 3H), 1.98-2.04 (m, 2H), 1.63-1.75 (m, 2H), 1.32 (s, 3H), 1.30 (s, 9H). LCMS (M+H)=540.5. Additional 11 mg (36.8%) of desired product obtained as a mixture of three isomers.

Example 2

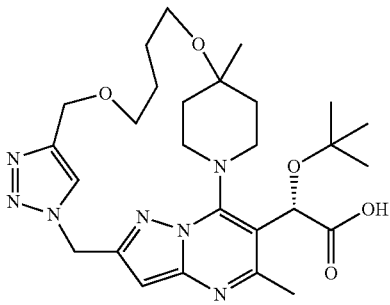 [SMILES: Cc1nc2cc3nn2c(c1[C@H](OC(C)(C)C)C(=O)O)N1CCC(C)(CC1)OCCCCOCc1cn(nn1)C3]

(2S)-2-(tert-Butoxy)-2-{4,22-dimethyl-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27)-hexaen-3-yl}acetic acid To a stirred solution of mixture of three isomers (0.011 g, 0.020 mmol) in 2:1 EtOAc/MeOH (5 mL) was added 10% Pd/C (2.169 mg, 2.038 µmol) and evacuated and left under balloon hydrogen pressure for 4 h. Then, filtered, concentrated and purified by prep-HPLC to afford desired product (0.0061 g, 0.011 mmol, 55.2% yield) as white solid. $^1$H NMR (500 MHz, CDCl$_3$) δ 8.10 (s, 1H), 6.60 (s, 1H), 5.90 (br. s., 1H), 5.79 (d, J$_{AB}$=15.6 Hz, 1H), 5.74 (d, J$_{AB}$=15.6 Hz, 1H), 4.70-4.77 (m, 2H), 4.27 (dt, J=2.3, 12.41 Hz, 1H), 3.71-3.78 (m, 1H), 3.65 (t, J=5.6 Hz, 2H), 3.44-3.50 (m, 1H), 3.35-3.40 (m, 2H), 2.86 (d, J=12.0 Hz, 1H), 2.62 (s, 3H), 1.93-2.00 (m, 2H), 1.74-1.80 (m, 3H), 1.64-1.72 (m, 2H), 1.55-1.62 (m, 1H), 1.28 (s, 9H), 1.26 (s, 3H). LCMS (M+H)=542.5.

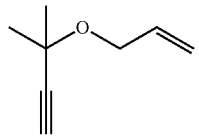

3-(Allyloxy)-3-methylbut-1-yne

To stirred solution of 2-methylbut-3-yn-2-ol (7.33 ml, 75 mmol) in DMF (100 mL) was added 60% NaH (3.00 g, 75 mmol) at 0° C. After 30 min, the cold bath was removed stirred for 1 h at rt. To this was added allyl bromide (9.74 ml, 113 mmol) over 5 min and continued stirring for 16 h. Then, diluted with Et2O (250 mL), washed with water (5×50 mL), brine (50 mL), dried (MgSO4), filtered and concentrated to give yellow liquid (5.64 g). HNMR of this indicated it is 2:1 mixture of product and unreacted alcohol. This was used without purification. $^1$H NMR (500 MHz, CDCl$_3$) δ 5.93-6.02 (m, 1H), 5.32 (qd, J=1.7, 17.2 Hz, 1H), 5.18 (qd, J=1.5, 10.4 Hz, 1H), 4.13 (td, J=1.4, 5.6 Hz, 2H), 2.45 (s, 1H), 1.52 (s, 6H).

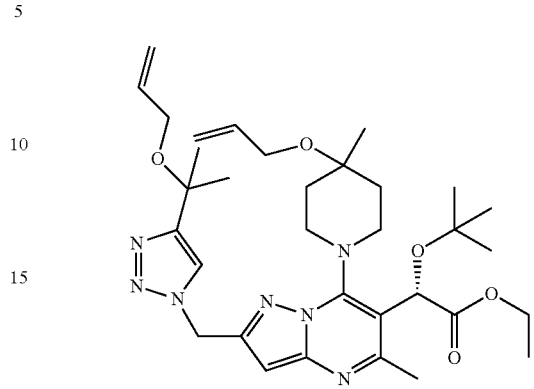

(S)-Ethyl 2-(7-(4-(allyloxy)-4-methylpiperidin-1-yl)-2-((4-(2-(allyloxy)propan-2-yl)-1H-1,2,3-triazol-1-yl)methyl)-5-methylpyrazolo[1,5-a]pyrimidin-6-yl)-2-(tert-butoxy)acetate To a stirred clear colorless solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.075 g, 0.150 mmol), mixture of 3-(allyloxy)-3-methylbut-1-yne (0.106 g, 0.854 mmol) and 2-methylbut-3-yn-2-ol (0.035 g, 0.416 mmol) and DIEA (0.131 ml, 0.751 mmol) in THF (3 mL) was added CuI (0.057 g, 0.300 mmol) at rt. The resulting turbid reaction mixture was stirred for 5 h at rt and diluted with Et$_2$O (50 mL), washed with water (10 mL), brine (10 mL), dried (MgSO$_4$), filtered, concentrated and purified by prep-HPLC to give two compounds.

(S)-Ethyl 2-(7-(4-(allyloxy)-4-methylpiperidin-1-yl)-2-((4-(2-hydroxypropan-2-yl)-1H-1,2,3-triazol-1-yl)methyl)-5-methylpyrazolo[1,5-a]pyrimidin-6-yl)-2-(tert-butoxy)acetate (0.0256 g, 0.044 mmol, 29.2% yield), yellow paste; $^1$H NMR (500 MHz, CDCl$_3$) δ 7.59 (s, 1H), 6.45 (s, 1H), 5.98-6.08 (m, 1H), 5.84-5.93 (br. s., 1H), 5.72 (s, 2H), 5.46 (d, J=16.7 Hz, 1H), 5.21 (dd, J=1.7, 10.4 Hz, 1H), 4.14-4.28 (m, 2H), 4.00-4.04 (m, 2H), 3.00-3.99 (br.m., 4H), 2.61 (s, 3H), 2.54 (br. s., 1H), 1.88-2.04 (m, 2H), 1.66-1.83 (m, 2H), 1.63 (s, 6H), 1.35 (s, 3H), 1.22-1.26 (m, 12H). LCMS (M+H)=584.5.

(S)-Ethyl 2-(7-(4-(allyloxy)-4-methylpiperidin-1-yl)-2-((4-(2-(allyloxy)propan-2-yl)-1H-1,2,3-triazol-1-yl)methyl)-5-methylpyrazolo[1,5-a]pyrimidin-6-yl)-2-(tert-butoxy)acetate (0.0342 g, 0.055 mmol, 36.5% yield), yellow paste; $^1$H NMR (500 MHz, CDCl$_3$) δ 7.58 (s, 1H), 6.43 (s, 1H), 5.98-6.08 (m, 1H), 5.78-5.94 (m, 2H), 5.72 (s, 2H), 5.47 (d, J=16.2 Hz, 1H), 5.16-5.24 (m, 2H), 5.06 (d, J=10.4 Hz, 1H), 4.13-4.28 (m, 2H), 4.01 (d, J=4.4 Hz, 2H), 3.82 (d, J=5.4 Hz, 2H), 3.00-4.50 (br. m., 4H), 2.61 (s, 3H), 1.90-2.02 (m, 2H), 1.66-1.83 (m, 2H), 1.63 (s, 6H), 1.35 (s, 3H), 1.18-1.29 (m, 12H). LCMS (M+H)=624.6.

Examples 3 and 4

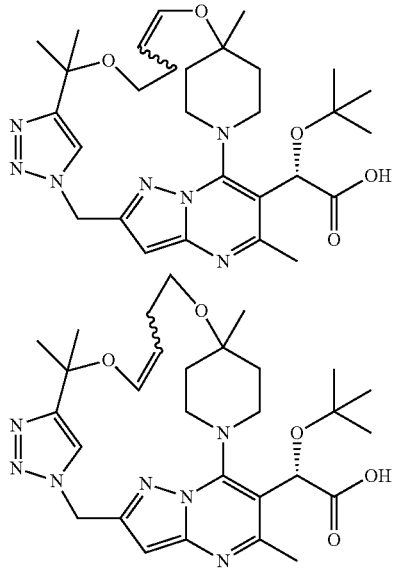

(2S)-2-(tert-Butoxy)-2-[4,15,15,22-tetramethyl-16,
21-dioxa-1,5,7,8,11,12,13-heptaazapentacyclo
[20.2.2.1$^{6,9}$.1$^{11,14}$.0$^{2,7}$]octacosa-2,4,6(28),8,12,14
(27),17-heptaen-3-yl]acetic acid To a stirred solution of (S)-ethyl 2-(7-(4-(allyloxy)-4-methylpiperidin-1-yl)-2-((4-(2-(allyloxy)propan-2-yl)-1H-1,2,3-triazol-1-yl)methyl)-5-methylpyrazolo[1,5-a]pyrimidin-6-yl)-2-(tert-butoxy)acetate (0.034 g, 0.055 mmol) in 1,2-dichloroethane (15 mL) was added Hoveyda-Grubbs catalyst 2nd generation (1.708 mg, 2.73 μmol) at 70 C and refluxed for 2 h. Then, cooled, concentrated and the resulting residue was used in the next step without purification.

A solution of above residue and 1M NaOH (0.164 ml, 0.164 mmol) in MeOH (3 mL) was refluxed for h. The, cooled and purified by prep-HPLC to afford two products.

(2S)-2-(tert-Butoxy)-2-[4,15,15,22-tetramethyl-16,
21-dioxa-1,5,7,8,11,12,13-heptaazapentacyclo
[20.2.2.1$^{6,9}$.1$^{11,14}$.0$^{2,7}$]octacosa-2,4,6(28),8,12,14
(27),19-heptaen-3-yl]acetic acid White solid: $^1$H NMR (500 MHz, CDCl$_3$) δ 7.89 (s, 1H), 6.61 (s, 1H), 6.24 (d, J=6.3 Hz, 1H), 5.83 (s, 1H), 5.67-5.79 (m, 2H), 4.46-4.53 (m, 1H), 4.25 (dt, J=2.4, 12.7 Hz, 1H), 3.51-3.60 (m, 2H), 3.41 (t, J=7.7 Hz, 2H), 3.03 (d, J=12.1 Hz, 1H), 2.59 (s, 3H), 2.45-2.54 (m, 1H), 2.38 (qd, J=7.1, 14.1 Hz, 1H), 1.97-2.07 (m, 3H), 1.62-1.69 (m, 2H), 1.65 (s, 3H), 1.61 (s, 3H), 1.35 (s, 3H), 1.27 (s, 9H). LCMS (M+H)=568.6.

(2S)-2-(tert-Butoxy)-2-[4,15,15,22-tetramethyl-16,
21-dioxa-1,5,7,8,11,12,13-heptaazapentacyclo
[20.2.2.1$^{6,9}$.1$^{11,14}$.0$^{2,7}$]octacosa-2,4,6(28),8,12,14
(27),17-heptaen-3-yl]acetic acid $^1$H NMR (500 MHz, CDCl$_3$) δ 8.24 (s, 1H), 6.61 (s, 1H), 6.35 (d, J=6.2 Hz, 1H), 5.94 (br. s., 1H), 5.65-5.78 (m, 2H), 4.51-4.58 (m, 1H), 4.40 (t, J=11.7 Hz, 1H), 3.77 (t, J=11.7 Hz, 1H), 3.42-3.48 (m, 1H), 3.35 (q, J=7.8 Hz, 2H), 2.85 (d, J=11.66 Hz, 1H), 2.60 (s, 3H), 2.53-2.59 (m, 1H), 2.40-2.49 (m, 1H), 2.01 (d, J=13.9 Hz, 3H), 1.70 (s, 3H), 1.66 (s, 3H), 1.63 (t, J=6.6 Hz, 2H), 1.29 (s, 3H), 1.28 (s, 9H). LCMS (M+H)=568.6.

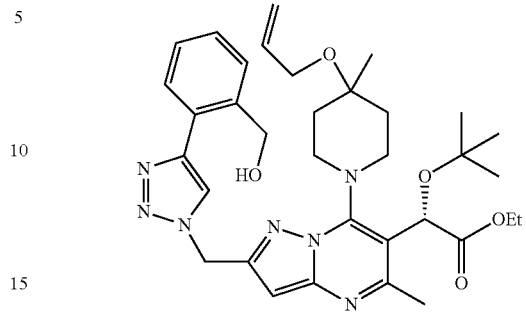

(S)-Ethyl 2-(7-(4-(allyloxy)-4-methylpiperidin-1-yl)-
2-((4-(2-(hydroxymethyl)phenyl)-1H-1,2,3-triazol-1-
yl)methyl)-5-methylpyrazolo[1,5-a]pyrimidin-6-yl)-
2-(tert-butoxy)acetate To a stirred clear solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.0946 g, 0.189 mmol), (2-ethynylphenyl)methanol (0.125 g, 0.947 mmol) and DIEA (0.165 ml, 0.947 mmol) in THF (5 mL) was added CuI (0.072 g, 0.379 mmol) at rt. After 48 h, the reaction mixture was diluted with Et$_2$O (50 mL), washed with 1% NH$_4$OH (2×10 mL), brine (10 mL), dried (MgSO$_4$), filtered and concentrated to give yellow solid which was purified by prep-HPLC to afford (S)-ethyl 2-(7-(4-(allyloxy)-4-methylpiperidin-1-yl)-2-((4-(2-(hydroxymethyl)phenyl)-1H-1,2,3-triazol-1-yl)methyl)-5-methylpyrazolo[1,5-a]pyrimidin-6-yl)-2-(tert-butoxy)acetate (0.0521 g, 0.082 mmol, 43.6% yield) as off-white solid. $^1$H NMR (500 MHz, CDCl$_3$) δ 8.02 (s, 1H), 7.51-7.55 (m, 1H), 7.45-7.49 (m, 1H), 7.33-7.38 (m, 2H), 6.54 (s, 1H), 5.96-6.05 (m, 1H), 5.89 (br. s., 1H), 5.82 (s, 2H), 5.45 (d, J=16.87 Hz, 1H), 5.26-5.38 (m, 1H), 5.18 (qd, J=1.58, 10.40 Hz, 1H), 4.64 (s, 2H), 4.13-4.28 (m, 2H), 4.00 (d, J=5.2 Hz, 2H), 2.62 (s, 3H), 1.83-2.04 (m, 3H), 1.65-1.73 (m, 1H), 1.31 (s, 3H), 1.22-1.26 (m, 12H). LCMS (M+H)=632.7.

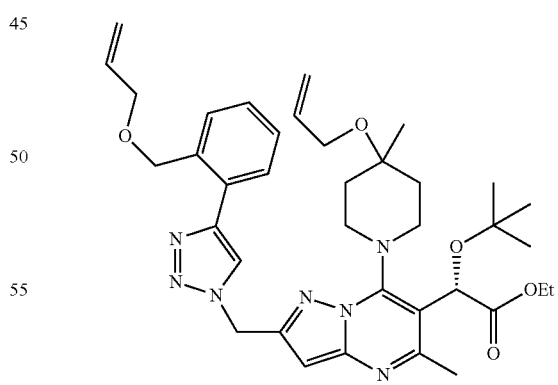

(S)-Ethyl 2-(7-(4-(allyloxy)-4-methylpiperidin-1-yl)-
2-((4-(2-((allyloxy)methyl)phenyl)-1H-1,2,3-triazol-
1-yl)methyl)-5-methylpyrazolo[1,5-a]pyrimidin-6-
yl)-2-(tert-butoxy)acetate To a stirred solution of (S)-ethyl 2-(7-(4-(allyloxy)-4-methylpiperidin-1-yl)-2-((4-(2-(hydroxymethyl)phenyl)-1H-1, 2,3-triazol-1-yl)methyl)-5-methylpyrazolo[1,5-a]pyrimidin-6-yl)-2-(tert-butoxy)acetate (0.052 g, 0.082 mmol) in DMF (3 mL) was added 60% NaH (8.23 mg, 0.206 mmol) at 0° C. After 10 min allyl bromide (0.071 ml, 0.823 mmol) was added at once and stirred for 30 min at 0° C. and 1 h at rt. Then, quenched with EtOH, diluted with ether (50 mL), washed with water (3×5 mL), brine (5 mL), dried (MgSO$_4$), filtered and concentrated to give (S)-ethyl 2-(7-(4-(allyloxy)-4-methylpiperidin-1-yl)-2-((4-(2-((allyloxy)methyl)phenyl)-1H-1,2,3-triazol-1-yl)methyl)-5-methylpyrazolo[1,5-a]pyrimidin-6-yl)-2-(tert-butoxy)acetate as yellow paste which was used in the next step without purification. LCMS (M+H)=672.7.

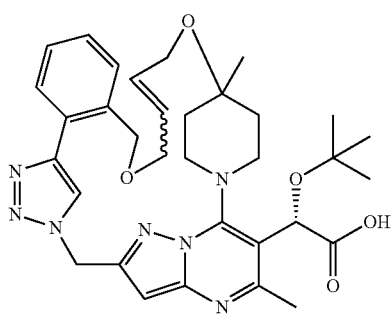 [SMILES: Cc1nc2cc3nn2c(c1[C@H](OC(C)(C)C)C(=O)O)N1CCC(C)(CC1)OCC=CCOCc1ccccc1-c1cn(nn1)C3]

Ethyl (2S)-2-(tert-butoxy)-2-[4,28-dimethyl-22,27-dioxa-1,5,7,8,11,12,13-heptaazahexacyclo[26.2.2.1$^{6,9}$.1$^{11,14}$.0$^{2,7}$.0$^{15,20}$]tetratriaconta-2,4,6(34),8,12,14(33),15(20),16,18,24-decaen-3-yl]acetate To a stirred solution of (S)-ethyl 2-(7-(4-(allyloxy)-4-methylpiperidin-1-yl)-2-((4-(2-((allyloxy)methyl)phenyl)-1H-1,2,3-triazol-1-yl)methyl)-5-methylpyrazolo[1,5-a]pyrimidin-6-yl)-2-(tert-butoxy)acetate (0.055 g, 0.082 mmol) in 1,2-dichloroethane (20 mL) was added at once Hoveyda-Grubbs catalyst 2nd generation (2.56 mg, 4.09 µmol) at 70° C. and refluxed for 5 h. Then, cooled, concentrated and purified by prep-HPLC to afford a mixture of products and one major isomer. Trans-isomer (0.0089 g, 0.014 mmol, 16.89% yield), off-white solid. $^1$H NMR (500 MHz, CDCl$_3$) δ 8.37 (s, 1H), 7.94 (dd, J=1.1, 7.7 Hz, 1H), 7.39-7.46 (m, 2H), 7.32-7.36 (m, 1H), 6.73 (s, 1H), 6.00-6.13 (m, 2H), 5.98 (s, 1H), 5.89 (d, J$_{AB}$=14.3 Hz, 1H), 5.65 (d, J$_{AB}$=14.3 Hz, 1H), 4.58 (dt, J=2.3, 12.4 Hz, 1H), 4.49 (d, J$_{AB}$=10.5 Hz, 1H), 4.40 (d, J$_{AB}$=10.5 Hz, 1H), 4.08-4.22 (m, 4H), 3.95-4.05 (m, 2H), 3.75-3.82 (m, 1H), 3.03 (td, J=2.0, 11.5 Hz, 1H), 2.73-2.79 (m, 1H), 2.61 (s, 3H), 2.00 (dd, J=2.4, 13.6 Hz, 1H), 1.90 (dd, J=2.1, 13.7 Hz, 1H), 1.67-1.74 (m, 2H), 1.31 (s, 3H), 1.24 (s, 9H), 1.18 (t, J=7.1 Hz, 3H). LCMS (M+H)=644.6. This is contaminated with minor isomer.

Example 5

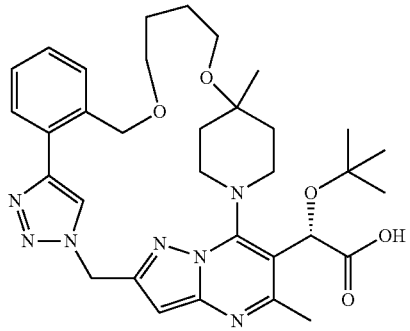 [SMILES: Cc1nc2cc3nn2c(c1[C@H](OC(C)(C)C)C(=O)O)N1CCC(C)(CC1)OCCCCOCc1ccccc1-c1cn(nn1)C3]

(2S)-2-(tert-Butoxy)-2-{4,28-dimethyl-22,27-dioxa-1,5,7,8,11,12,13-heptaazahexacyclo[26.2.2.1$^{6,9}$.1$^{11,14}$.0$^{2,7}$.0$^{15,20}$]tetratriaconta-2,4,6(34),8,12,14(33),15(20),16,18-nonaen-3-yl}acetic acid A mixture of mixture of isomers/unreacted sm (0.0285 g, 0.044 mmol) and 10% Pd/C (4.71 mg, 4.43 µmol) in 1:1 MeOH/EtOAc (10 mL) was left under balloon hydrogen pressure for 6 h. Then, filtered and concentrated to give yellow paste which was used in the next step without purification.

A solution of above material and 1M NaOH (0.2 mL) in MeOH (2 mL) refluxed for 2 h. Then, cooled and purified by prep-HPLC to afford carboxylic acid (0.0098 g, 0.015 mmol, 34.0% yield) as white solid. $^1$H NMR (500 MHz, CDCl$_3$) δ 8.32 (s, 1H), 7.98 (dd, J=1.0, 7.8 Hz, 1H), 7.42 (dt, J=1.6, 7.5 Hz, 1H), 7.37-7.40 (m, 1H), 7.31-7.35 (m, 1H), 6.73 (s, 1H), 5.91 (br. s., 1H), 5.87 (d, J$_{AB}$=14.3 Hz, 1H), 5.66 (d, J$_{AB}$=14.3 Hz, 1H), 4.54-4.61 (m, 1H), 4.43 (d, J$_{AB}$=10.2 Hz, 1H), 4.36 (d, J$_{AB}$=10.2 Hz, 1H), 3.82 (t, J=11.4 Hz, 1H), 3.59-3.71 (m, 2H), 3.49 (td, J=5.3, 8.7 Hz, 1H), 3.34-3.40 (m, 1H), 3.22 (d, J=10.1 Hz, 1H), 2.73 (d, J=11.2 Hz, 1H), 2.60 (s, 3H), 1.90-1.99 (m, 3H), 1.73-1.82 (m, 3H), 1.58-1.67 (m, 2H), 1.26 (s, 12H). LCMS (M+H)=618.6.

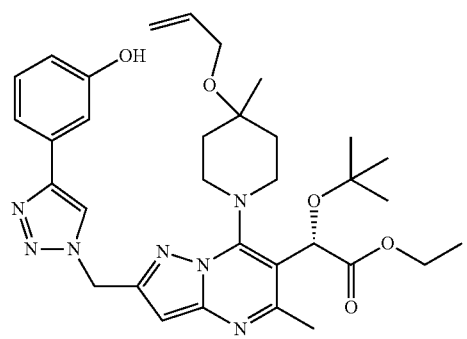 [SMILES: C=CCOC1(C)CCN(c2c([C@H](OC(C)(C)C)C(=O)OCC)c(C)nc3cc(Cn4cc(-c5cccc(O)c5)nn4)nn23)CC1]

(S)-Ethyl 2-(7-(4-(allyloxy)-4-methylpiperidin-1-yl)-2-((4-(3-hydroxyphenyl)-1H-1,2,3-triazol-1-yl)methyl)-5-methylpyrazolo[1,5-a]pyrimidin-6-yl)-2-(tert-butoxy)acetate To a stirred clear yellow solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.070 g, 0.140 mmol), 3-ethynylphenol (0.083 g, 0.701 mmol) and DIEA (0.122 ml, 0.701 mmol) in THF (5 mL) was added CuI (0.053 g, 0.280 mmol) at rt. After 28 h, the reaction mixture was diluted with Et$_2$O (50 mL), washed with water (2×10 mL), brine (10 mL), dried (MgSO$_4$), filtered and concentrated to give yellow oil which was purified by prep-HPLC to afford (S)-ethyl 2-(7-(4-(allyloxy)-4-methylpiperidin-1-yl)-2-((4-(3-hydroxyphenyl)-1H-1,2,3-triazol-1-yl)methyl)-5-methylpyrazolo[1,5-a]pyrimidin-6-yl)-2-(tert-butoxy)acetate (0.0528 g, 0.085 mmol, 61.0% yield) as off-white solid. $^1$H NMR (500 MHz, CDCl$_3$) δ 7.75-7.99 (m, 2H), 7.52 (t, J=1.8 Hz, 1H), 7.22-7.30 (m, 2H), 6.84-6.89 (m, 1H), 6.51 (s, 1H), 5.97-6.07 (m, 1H), 5.86 (br. s., 1H), 5.78 (s, 2H), 5.44 (d, J=16.7 Hz, 1H), 5.19 (dd, J=1.6, 10.4 Hz, 1H), 4.14-4.29 (m, 2H), 4.00 (d, J=4.7 Hz, 2H), 2.62 (s, 3H), 1.82-2.03 (m, 3H), 1.65-1.73 (m, 1H), 1.31 (s, 3H), 1.24 (t, J=7.1 Hz, 3H), 1.23 (s, 9H). LCMS (M+H)=618.6.

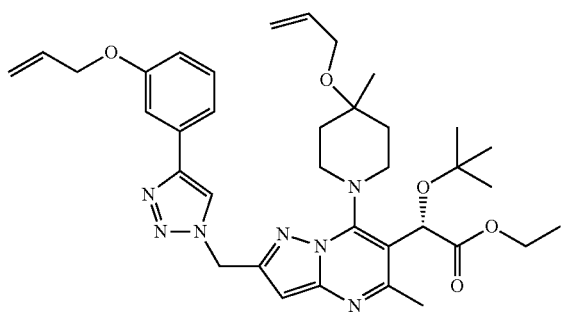 [SMILES: C=CCOc1cccc(-c2cn(Cc3cc4nc(C)c([C@H](OC(C)(C)C)C(=O)OCC)c(N5CCC(C)(OCC=C)CC5)n4n3)nn2)c1]

(S)-Ethyl 2-(7-(4-(allyloxy)-4-methylpiperidin-1-yl)-2-((4-(3-(allyloxy)phenyl)-1H-1,2,3-triazol-1-yl)methyl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-((4-(3-hydroxyphenyl)-1H-1,2,3-triazol-1-yl)methyl)-5-methylpyrazolo[1,5-a]pyrimidin-6-yl)-2-(tert-butoxy)acetate (0.0525 g, 0.085 mmol), K$_2$CO$_3$ (0.047 g, 0.340 mmol) and allyl bromide (0.074 ml, 0.850 mmol) in DMF (3 mL) was heated at 60° C. for 24 h. Then, cooled and purified prep-HPLC to afford (S)-ethyl 2-(7-(4-(allyloxy)-4-methylpiperidin-1-yl)-2-((4-(3-(allyloxy)phenyl)-1H-1,2,3-triazol-1-yl)methyl)-5-methylpyrazolo[1,5-a]pyrimidin-6-yl)-2-(tert-butoxy)acetate (0.0184 g, 0.028 mmol, 32.9% yield) as colorless paste. $^1$H NMR (500 MHz, CDCl$_3$) δ 7.90 (s, 1H), 7.46 (dd, J=1.5, 2.4 Hz, 1H), 7.35-7.38 (m, 1H), 7.29-7.34 (m, 1H), 6.90 (ddd, J=1.0, 2.6, 8.1 Hz, 1H), 6.51 (s, 1H), 5.98-6.14 (m, 2H), 5.88 (br. s., 1H), 5.79 (s, 2H), 5.45 (qd, J=1.6, 17.2 Hz, 2H), 5.31 (qd, J=1.4, 10.4 Hz, 1H), 5.20 (qd, J=1.6, 10.4 Hz, 1H), 4.62 (td, J=1.5, 5.3 Hz, 2H), 4.14-4.28 (m, 2H), 4.00 (d, J=5.0 Hz, 2H), 2.70-3.90 (m, 2H), 2.61 (s, 3H), 1.85-2.03 (m, 3H), 1.64-1.74 (m, 2H), 1.31 (s, 3H), 1.25 (t, J=7.1 Hz, 3H), 1.24 (s, 9H). LCMS (M+H)=658.6.

Example 6

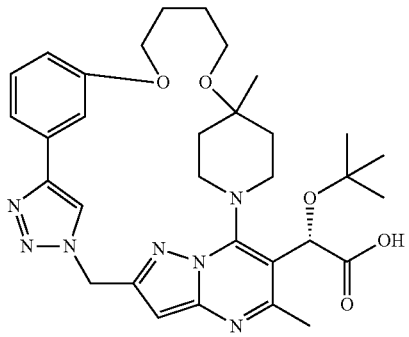 [SMILES: Cc1nc2cc3nn2c(c1[C@H](OC(C)(C)C)C(=O)O)N1CCC(C)(CC1)OCCCCOc1cccc(c1)-c1cn(nn1)C3]

(2S)-2-(tert-Butoxy)-2-{4,26-dimethyl-20,25-dioxa-1,5,7,8,11,12,13-heptaazahexacyclo[24.2.2. 1$^{6,9}$.1$^{11,14}$.1$^{15,19}$.0$^{2,7}$]tritriaconta-2,4,6(33),8,12, 14(32),15(31),16,18-nonaen-3-yl}acetic acid To a stirred solution of (S)-ethyl 2-(7-(4-(allyloxy)-4-methylpiperidin-1-yl)-2-((4-(3-(allyloxy)phenyl)-1H-1,2,3-triazol-1-yl)methyl)-5-methylpyrazolo[1,5-a]pyrimidin-6-yl)-2-(tert-butoxy)acetate (0.018 g, 0.027 mmol) in 1,2-dichloroethane (15 mL) was added at once Hoveyda-Grubbs catalyst 2nd generation (0.857 mg, 1.368 µmol) at 70° C. and refluxed for 2 h. Then, cooled, 10% Pd/C (2.91 mg, 2.74 µmol) was added and stirred under balloon H2 atmosphere for 5 h. Then, filtered, concentrated and the dark residue was refluxed with NaOH (0.137 ml, 0.137 mmol) in MeOH (2 mL) for 6 h. Then, cooled and purified by pre-HPLC to afford desired product (0.0064 g, 10.18 µmol, 37.2% yield) as white solid. $^1$H NMR (500 MHz, CDCl$_3$) δ 8.44 (s, 1H), 7.77 (d, J=7.6 Hz, 1H), 7.38 (t, J=8.0 Hz, 1H), 7.16-7.20 (m, 1H), 6.90-6.95 (m, 1H), 6.61 (s, 1H), 5.73-5.87 (m, 3H), 4.24-4.37 (m, 2H), 4.16-4.23 (m, 1H), 3.73 (t, J=11.4 Hz, 1H), 3.49-3.59 (m, 3H), 3.03 (d, J=11.8 Hz, 1H), 2.59 (s, 3H), 1.88-2.04 (m, 4H), 1.74-1.82 (m, 2H), 1.52-1.72 (m, 2H), 1.26 (s, 3H), 1.25 (s, 9H). LCMS (M+H)=604.6.

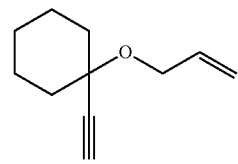

1-(Allyloxy)-1-ethynylcyclohexane

A solution of 1-ethynylcyclohexanol (2.28 g, 18.36 mmol) in DMF (25 ml) was cooled (0° C. ice bath) and treated with 60% NaH (0.890 g, 22.25 mmol). The reaction was stirred for 30 min, then warmed to room temperature and stirred for 1 hr. To this was added allyl bromide (4.8 ml, 55.5 mmol) over 5 min and continued stirring for 16 h. The reaction was diluted with Et$_2$O (75 mL), washed with water (4×50 mL), brine (50 mL), dried (MgSO$_4$), filtered and concentrated to give the product, 1-(allyloxy)-1-ethynylcyclohexane (2.873 g, 12.24 mmol, 66.7% yield) as a pale yellow mobile oil. ¹H NMR consistent with expected product, consists of approx 3:1 product/SM. Used as-is without further purification ¹H NMR (CDCl3) δ: 5.94-6.04 (m, 1H), 5.33 (dq, J=17.2, 1.7 Hz, 1H), 5.17 (dq, J=10.3, 1.5 Hz, 1H), 4.15 (dt, J=5.6, 1.5 Hz, 2H), 2.50 (s, 1H), 2.49 (s, 1H), 1.91-1.98 (m, 3H), 1.49-1.77 (m, 12H), 1.24-1.38 (m, 3H).

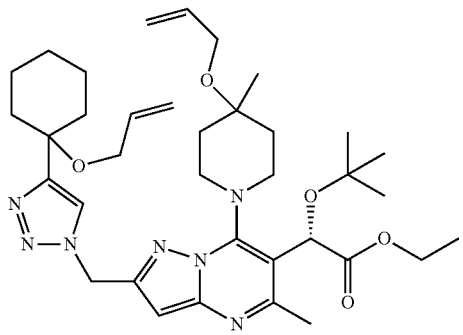 [SMILES: C=CCOC1(C)CCN(c2c([C@H](OC(C)(C)C)C(=O)OCC)c(C)nc3cc(Cn4cc(C5(OCC=C)CCCCC5)nn4)nn23)CC1]

(S)-Ethyl 2-(7-(4-(allyloxy)-4-methylpiperidin-1-yl)-2-((4-(1-(allyloxy)cyclohexyl)-1H-1,2,3-triazol-1-yl)methyl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.06 g, 0.120 mmol), 1-(allyloxy)-1-ethynylcyclohexane (0.039 g, 0.240 mmol), Cu(II) SO₄.5H₂O (3.00 mg, 0.012 mmol) and (+)-sodium L-ascorbate (0.024 g, 0.120 mmol) in MeOH (2 mL) was stirred for 16 h at rt. Then, purified by prep-HPLC to afford (S)-ethyl 2-(7-(4-(allyloxy)-4-methylpiperidin-1-yl)-2-((4-(1-(allyloxy)cyclohexyl)-1H-1,2,3-triazol-1-yl)methyl)-5-methylpyrazolo[1,5-a]pyrimidin-6-yl)-2-(tert-butoxy)acetate (0.0287 g, 0.043 mmol, 36.0% yield) as pale yellow paste. ¹H NMR (500 MHz, CDCl₃) δ 7.56 (s, 1H), 6.41 (s, 1H), 5.99-6.08 (m, 1H), 5.90 (br. s., 1H), 5.82 (tdd, J=5.3, 10.5, 17.2 Hz, 1H), 5.73 (s, 2H), 5.47 (d, J=16.4 Hz, 1H), 5.17-5.23 (m, 2H), 5.01-5.06 (m, 1H), 4.12-4.28 (m, 2H), 4.00-4.03 (m, 2H), 3.74 (td, J=1.5, 5.4 Hz, 2H), 2.61 (s, 3H), 1.90-2.06 (m, 6H), 1.67-1.75 (m, 4H), 1.54-1.61 (m, 1H), 1.44-1.52 (m, 2H), 1.35 (s, 3H), 1.23-1.25 (m, 12H). LCMS (M+H)=664.7.

Example 7

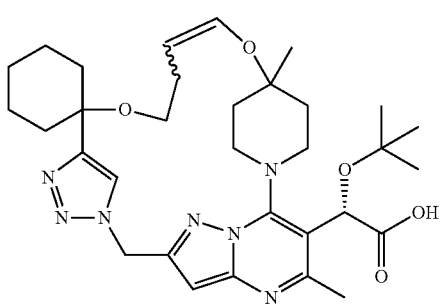 [SMILES: Cc1nc2cc3nn2c(c1[C@H](OC(C)(C)C)C(=O)O)N1CCC(C)(CC1)OCCCCOC1(CCCCC1)c1cn(nn1)C3]

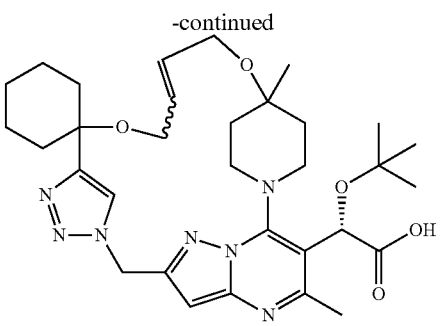

(2S)-2-(tert-Butoxy)-2-[4',22'-dimethyl-16',21'-dioxa-1',5',7',8',11',12',13'-heptaazaspiro[cyclohexane-1,15'-pentacyclo[20.2.2.1⁶,⁹.1¹¹,¹⁴.0²,⁷]octacosane]-2',4',6'(28'),8',12',14'(27'),18'-heptaen-3-yl]acetic acid To a stirred solution of (S)-ethyl 2-(7-(4-(allyloxy)-4-methylpiperidin-1-yl)-2-((4-(1-(allyloxy)cyclohexyl)-1H-1,2,3-triazol-1-yl)methyl)-5-methylpyrazolo[1,5-a]pyrimidin-6-yl)-2-(tert-butoxy)acetate (0.0285 g, 0.043 mmol) in 1,2-dichloroethane (10 mL) was added Hoveyda-Grubbs catalyst 2nd generation (1.345 mg, 2.147 μmol) at 70° C. and refluxed for 2 h. Then, concentrated and the brown paste filtered through a plug of silica gel with EtOAc and concentrated to give the macrocycle ester as yellow paste which used in the next step without purification.

A solution of above crude ester and 1M NaOH (0.129 ml, 0.129 mmol) in MeOH (2 mL) was refluxed for 2 h. Then, cooled and purified by pre-HPLC to afford single product (0.0084 g, 0.013 mmol, 30.6% yield) and mixture of isomers (0.0063 g, 10.37 μmol, 24.15% yield).

(2S)-2-(tert-Butoxy)-2-[4',22'-dimethyl-16',21'-dioxa-1',5',7',8' 11',12',13'-heptaazaspiro[cyclohexane-1,15'-pentacyclo[20.2.2.1⁶,⁹.1¹¹,¹⁴.0²,⁷]octacosane]-2',4',6'(28'),8',12',14'(27'),19'-heptaen-3-yl]acetic acid Single isomer: ¹H NMR (400 MHz, CDCl₃) δ 7.80 (s, 1H), 6.60 (s, 1H), 6.20 (d, J=6.5 Hz, 1H), 5.80 (s, 1H), 5.72 (d, J=2.8 Hz, 2H), 4.47 (q, J=7.3 Hz, 1H), 4.14-4.25 (m, 1H), 3.52 (d, J=8.0 Hz, 2H), 3.27-3.35 (m, 2H), 3.02 (d, J=11.3 Hz, 1H), 2.57 (s, 3H), 2.44-2.54 (m, 1H), 2.29-2.40 (m, 1H), 1.94-2.03 (m, 6H), 1.48-1.79 (m, 8H), 1.33 (s, 3H), 1.25 (s, 9H). LCMS (M+H)=608.7.

Example 8

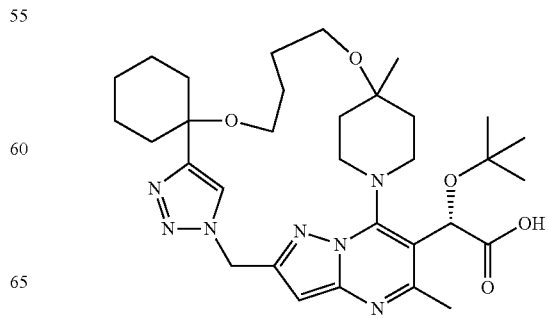

(2S)-2-(tert-Butoxy)-2-{4',22'-dimethyl-16',21'-dioxa-1',5',7',8',11',12',13'-heptaazaspiro[cyclohexane-1,15'-pentacyclo[20.2.2.1$^{6,9}$.1$^{11,14}$.0$^{2,7}$]octacosane]-2',4',6'(28'),8',12',14'(27')-hexaen-3'-yl}acetic acid A mixture of isomers (0.0063 g, 10.37 μmol) and 10% Pd/C (1.103 mg, 1.037 μmol) in EtOAc (5 mL) was evacuated and left under balloon atmosphere for 24 h. Then, filtered through a plug of celite, concentrated and purified by prep-HPLC to afford product (0.0039 g, 6.33 μmol, 61.1% yield) as solid. $^1$H NMR (500 MHz, CDCl$_3$) δ 7.86 (s, 1H), 6.64 (s, 1H), 5.97 (br. s., 1H), 5.72 (s, 2H), 4.50 (dt, J=2.2, 12.4 Hz, 1H), 3.82 (t, J=11.4 Hz, 1H), 3.54 (td, J=5.9, 8.8 Hz, 1H), 3.31-3.43 (m, 4H), 2.81 (d, J=11.7 Hz, 1H), 2.63 (s, 3H), 1.92-2.09 (m, 4H), 1.85-1.91 (m, 2H), 1.48-1.78 (m, 12H), 1.31 (s, 9H), 1.27 (s, 3H). LCMS (M+H)=610.7.

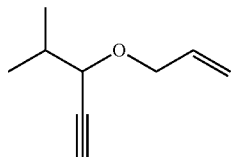

3-(Allyloxy)-4-methylpent-1-yne

A solution of 4-methylpent-1-yn-3-ol (2.00 g, 20.38 mmol) in DMF (30 ml) was cooled (0° C. ice bath) and treated with 60% NaH (0.992 g, 24.80 mmol). The reaction was stirred for 20 min, then warmed to room temperature and stirred for 1 hr. To this was added allyl bromide (5.3 ml, 61.2 mmol) over 5 min. The reaction was stirred over the weekend. The reaction was diluted with Et$_2$O (100 mL), washed with water (4×25 mL), brine (25 mL), dried (MgSO$_4$), filtered and concentrated to give the product, 3-(allyloxy)-4-methylpent-1-yne (2.401 g, 13.03 mmol, 63.9% yield) as a pale yellow mobile oil. $_1$H NMR consistent with expected product; contains approx 4:1 product/SM. Used as-is without further purification. $^1$H NMR (CDCl3) δ: 5.86-5.99 (m, 1H), 5.32 (dq, J=17.2, 1.7 Hz, 1H), 5.16-5.25 (m, 1H), 4.28 (ddt, J=12.7, 5.0, 1.6 Hz, 1H), 4.19 (td, J=5.7, 2.1 Hz, 1H), 3.98 (ddt, J=12.7, 6.3, 1.3 Hz, 1H), 3.87 (dd, J=5.8, 2.0 Hz, 1H), 2.41 (d, J=2.0 Hz, 1H), 1.92-2.03 (m, 1H), 0.98-1.06 (m, 8H).

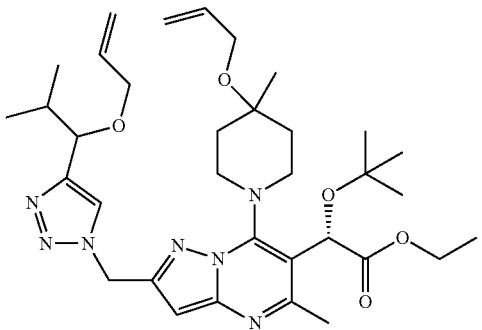 [SMILES: C=CCOC(c1cn(Cc2cc3nc(C)c([C@H](OC(C)(C)C)C(=O)OCC)c(N4CCC(C)(OCC=C)CC4)n3n2)nn1)C(C)C]

(2S)-Ethyl 2-(2-((4-(1-(allyloxy)-2-methylpropyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.15 g, 0.300 mmol), 3-(allyloxy)-4-methylpent-1-yne (0.083 g, 0.600 mmol), Cu(II) SO$_4$.5H$_2$O (7.50 mg, 0.030 mmol) and (+)-sodium L-ascorbate (0.059 g, 0.300 mmol) in MeOH (2 mL) was stirred for 1 h at rt. Then, purified by prep-HPLC to afford (2S)-ethyl 2-(2-((4-(1-(allyloxy)-2-methylpropyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate (0.0761 g, 0.119 mmol, 39.7% yield) as pale yellow paste. LCMS (M+H)=638.7.

Example 9

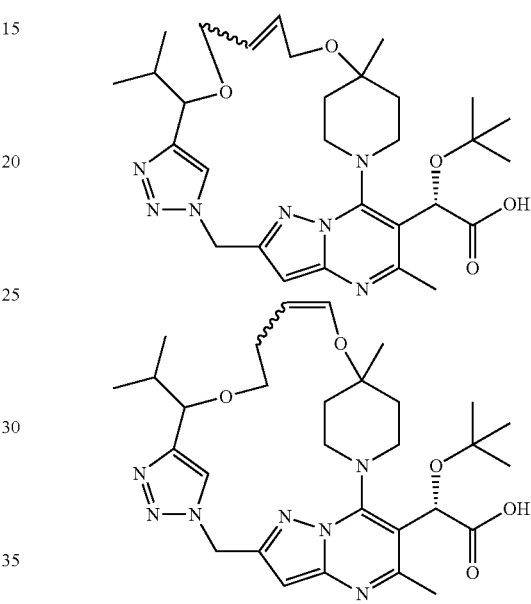

(2S)-2-(tert-Butoxy)-2-[4,22-dimethyl-15-(propan-2-yl)-16,21-dioxa-1,5,7,8,11,12,13-heptaazapentacyclo [20.2.2.1$^{6,9}$.1$^{11,14}$.0$^{2,7}$]octacosa-2,4,6(28),8,12,14 (27),18-heptaen-3-yl]acetic acid To a stirred solution of (2S)-ethyl 2-(2-((4-(1-(allyloxy)-2-methylpropyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate (0.076 g, 0.119 mmol) in 1,2-dichloroethane (30 mL) was added Hoveyda-Grubbs catalyst 2nd generation (3.73 mg, 5.96 μmol) at 70° C. and refluxed for 2.5 h. Then, concentrated and the brown paste filtered through a plug of silica gel with EtOAc and concentrated to give the macrocycle ester as yellow paste which used in the next step without purification.

A solution of above crude ester and NaOH (0.477 ml, 0.477 mmol) in MeOH (4 mL) was refluxed for 2 h. Then, cooled and purified by prep-HPLC. All the front peaks were combined and concentrated to give mixture of isomers (0.0531 g, 0.091 mmol, 77% yield) and concentration of the last peak afforded single product (0.008 g, 0.014 mmol, 11.43% yield) as white solid.

(2S)-2-(tert-Butoxy)-2-[4,22-dimethyl-15-(propan-2-yl)-16,21-dioxa-1,5,7,8,11,12,13-heptaazapentacyclo [20.2.2.1$^{6,9}$.1$^{11,14}$.0$^{2,7}$]octacosa-2,4,6(28),8,12,14 (27),19-heptaen-3-yl]acetic acid $^1$H NMR (500 MHz, CDCl$_3$) δ 7.89 (s, 1H), 6.63 (s, 1H), 6.24 (d, J=6.0 Hz, 1H), 5.82 (d, J$_{AB}$=15.5 Hz, 1H), 5.79 (br. s., 1H), 5.59 (d, $J_{AB}$=15.5 Hz, 1H), 4.50 (q, J=7.4 Hz, 1H), 4.33 (d, J=5.4 Hz, 1H), 4.26-4.32 (m, 1H), 3.47-3.55 (m, 2H), 3.32-3.43 (m, 2H), 3.06 (d, J=11.8 Hz, 1H), 2.54-2.65 (m, 1H), 2.58 (s, 3H), 2.28-2.37 (m, 1H), 2.11-2.19 (m, 1H), 2.07 (d, J=13.4 Hz, 1H), 1.97 (d, J=13.6 Hz, 1H), 1.63-1.77 (m, 2H), 1.33 (s, 3H), 1.26 (s, 9H), 0.97 (d, J=6.8 Hz, 3H), 0.95 (d, J=6.8 Hz, 3H). LCMS (M+H)=582.6.

Example 10 and 11

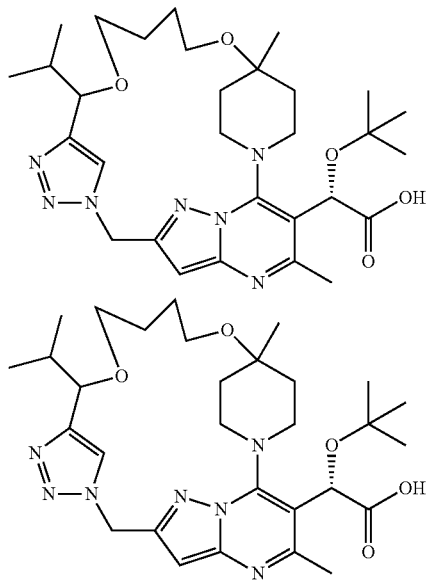

(2S)-2-(tert-Butoxy)-2-[4,22-dimethyl-15-(propan-2-yl)-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27)-hexaen-3-yl]acetic acid A mixture of isomers (0.053 g, 0.091 mmol) and 10% Pd/C (9.70 mg, 9.11 μmol) in EtOAc/MeOH (9:1, 10 mL) was evacuated and stirred under balloon $H_2$ pressure for 18 h. Then, filtered, concentrated and purified by prep-HPLC to afford two diastereomers diastereomer 1 (0.0135 g, 0.022 mmol, 24.62% yield) and diastereomer 2 (0.0168 g, 0.028 mmol, 30.6% yield) as white solids.

Diastereomer 1: $^1$H NMR (500 MHz, CDCl$_3$) δ 7.86 (s, 1H), 6.61 (s, 1H), 5.95 (br. s., 1H), 5.71-5.80 (m, 2H), 4.29-4.37 (m, 2H), 3.77 (t, J=11.9 Hz, 1H), 3.63 (t, J=7.0 Hz, 1H), 3.30-3.51 (m, 4H), 2.82 (d, J=11.7 Hz, 1H), 2.62 (s, 3H), 1.95-2.05 (m, 2H), 1.87 (d, J=13.2 Hz, 1H), 1.50-1.77 (m, 8H), 1.29 (s, 9H), 1.25 (s, 3H), 0.85-0.91 (m, 6H). LCMS (M+H)=584.6.

Diastereomer 2: $^1$H NMR (500 MHz, CDCl$_3$) δ 8.16 (s, 1H), 6.64 (s, 1H), 5.93 (br. s., 1H), 5.75-5.80 (m, 1H), 5.63-5.69 (m, 1H), 4.35-4.45 (m, 2H), 3.85 (t, J=11.6 Hz, 1H), 3.69 (dt, J=5.1, 8.6 Hz, 1H), 3.59-3.65 (m, 1H), 3.48 (dt, J=3.5, 9.0 Hz, 1H), 3.23-3.36 (m, 2H), 2.73 (d, J=11.4 Hz, 1H), 2.63 (s, 3H), 2.02-2.10 (m, 2H), 1.82-1.91 (m, 2H), 1.55-1.76 (m, 5H), 1.28 (s, 9H), 1.27 (br. s., 3H), 0.93 (d, J=6.8 Hz, 3H), 0.83 (d, J=6.8 Hz, 3H). LCMS (M+H)=584.6.

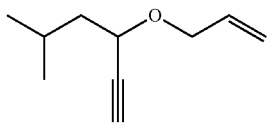

3-(Allyloxy)-5-methylhex-1-yne

A solution of 5-methylhex-1-yn-3-ol (2.11 g, 18.81 mmol) in DMF (30 ml) was cooled (0° C. ice bath) and treated with 60% NaH (0.903 g, 22.57 mmol). The reaction was stirred for 20 min, then warmed to room temperature and stirred for 1 hr. To this was added allyl bromide (4.9 ml, 56.6 mmol) over 5 min. The reaction was stirred overnight. The reaction was diluted with Et$_2$O (100 mL), washed with water (4×25 mL), brine (25 mL), dried (MgSO$_4$), filtered and concentrated to give the product, 3-(allyloxy)-5-methylhex-1-yne (2.83 g, 13.94 mmol, 74.1% yield) as a yellow mobile oil. $^1$H NMR consistent with expected product, contains ca. 4:1 product/SM. Used as-is without further purification. 1H NMR (CDCl3) δ: 5.89-6.00 (m, 1H), 5.34 (dq, J=17.2, 1.6 Hz, 1H), 5.22 (dq, J=10.3, 1.4 Hz, 1H), 4.29 (ddt, J=12.6, 5.1, 1.5 Hz, 1H), 4.14 (ddd, J=7.6, 6.7, 2.0 Hz, 1H), 3.99 (ddt, J=12.6, 6.3, 1.3 Hz, 1H), 2.44 (d, J=2.0 Hz, 1H), 1.90 (dsxt, J=13.5, 6.8 Hz, 1H), 1.64-1.80 (m, 2H), 1.56-1.64 (m, 2H), 0.95 (d, J=4.6 Hz, 3H), 0.94 (d, J=4.6 Hz, 3H).

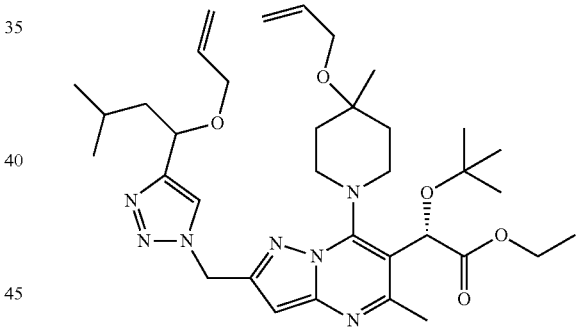

(2S)-Ethyl 2-(2-((4-(1-(allyloxy)-3-methylbutyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.179 g, 0.358 mmol), 3-(allyloxy)-5-methylhex-1-yne (0.109 g, 0.717 mmol), Cu(II)SO$_4$.5H$_2$O (8.95 mg, 0.036 mmol) and (+)-sodium L-ascorbate (0.071 g, 0.358 mmol) in MeOH (2 mL) was stirred for 1 h at rt. Then, purified by prep-HPLC to afford (2S)-ethyl 2-(2-((4-(1-(allyloxy)-3-methylbutyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate (0.0921 g, 0.141 mmol, 39.4% yield) as pale yellow paste. LCMS (M+H)=652.7.

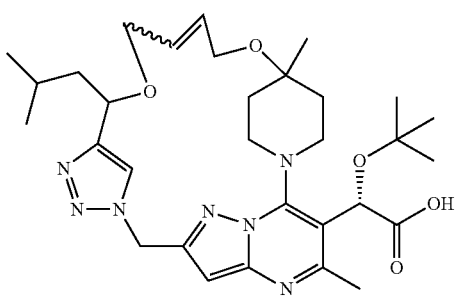 [SMILES: Cc1nc2cc3nn2c(c1[C@H](OC(C)(C)C)C(=O)O)N1CCC(C)(CC1)OCC=CCOC(CC(C)C)c1cn(nn1)C3]

(2S)-2-(tert-Butoxy)-2-[4,22-dimethyl-15-(2-methyl-propyl)-16,21-dioxa-1,5,7,8,11,12,13-heptaazapenta-cyclo[20.2.2.1$^{6,9}$.1$^{11,14}$.0$^{2,7}$]octacosa-2,4,6(28),8,12,14(27),18-heptaen-3-yl]acetic acid To a stirred solution of (2S)-ethyl 2-(2-((4-(1-(allyloxy)-3-methylbutyl)-1H-1,2,3-triazol-1-yl)methyl)-7-(4-(allyloxy)-4-methylpiperidin-1-yl)-5-methylpyrazolo[1,5-a]pyrimidin-6-yl)-2-(tert-butoxy)acetate (0.080 g, 0.123 mmol) in 1,2-dichloroethane (30 mL) was added Hoveyda-Grubbs catalyst 2nd generation (3.85 mg, 6.14 μmol) at 70° C. After 2 h at 75° C., the reaction mixture was filtered through a plug of silica gel (washed with 10 mL of EtOAC), concentrated and used in the next step without purification. A solution of above crude ester and NaOH (0.491 ml, 0.491 mmol) in MeOH (4 mL) was refluxed for 2 h. Then, cooled and purified by prep-HPLC to afford mixture of diastereomers (0.087 g, 0.146 mmol, 119% yield) as white solid. LCMS (M+H)=596.7.

Example 12 and 13

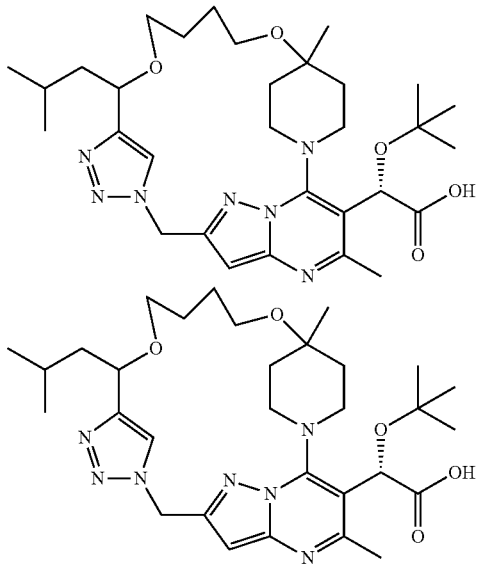

(2S)-2-(tert-Butoxy)-2-[4,22-dimethyl-15-(2-methyl-propyl)-16,21-dioxa-1,5,7,8,11,12,13-heptaazapenta-cyclo[20.2.2.1$^{6,9}$.1$^{11,14}$.0$^{2,7}$]octacosa-2,4,6(28),8,12,14(27)-hexaen-3-yl]acetic acid A mixture of above diastereomers (0.073 g, 0.123 mmol) and 10% Pd/C (0.013 g, 0.012 mmol) in EtOA/MeOH (10 mL, 9:1) was evacuated and left under balloon H$_2$ atmosphere for 15 h. Then, filtered and purified by prep-HPLC to afford diastereomer 1 (0.0157 g, 0.025 mmol, 20.50% yield) and diastereomer 2 (0.028 g, 0.046 mmol, 37.3% yield) as white solids.

Diastereomer 1: $^1$H NMR (500 MHz, CDCl$_3$) δ 7.83 (s, 1H), 6.60 (s, 1H), 5.93 (br. s., 1H), 5.79 (d, J$_{AB}$=15.5 Hz, 1H), 5.71 (d, J$_{AB}$=15.5 Hz, 1H), 4.64 (dd, J=5.0, 8.9 Hz, 1H), 4.31 (dt, J=2.1, 12.4 Hz, 1H), 3.74 (t, J=11.5 Hz, 1H), 3.64 (dt, J=3.8, 8.4 Hz, 1H), 3.51 (q, J=7.8 Hz, 1H), 3.34-3.42 (m, 3H), 2.83 (d, J=12.0 Hz, 1H), 2.61 (s, 3H), 1.97-2.02 (m, 1H), 1.88 (dd, J=2.2, 13.6 Hz, 1H), 1.71-1.83 (m, 3H), 1.53-1.69 (m, 7H), 1.28 (s, 9H), 1.24 (s, 3H), 0.94 (t, J=6.2 Hz, 6H). LCMS (M+H)=598.7.

Diastereomer 2: $^1$H NMR (500 MHz, CDCL$_3$) δ 8.06 (s, 1H), 6.63 (s, 1H), 5.91 (br. s., 1H), 5.70 (s, 2H), 4.61 (dd, J=4.9, 8.7 Hz, 1H), 4.38 (t, J=11.6 Hz, 1H), 3.75 (t, J=11.5 Hz, 1H), 3.60-3.66 (m, 1H), 3.47-3.59 (m, 2H), 3.25-3.35 (m, 2H), 2.83 (d, J=11.5 Hz, 1H), 2.61 (s, 3H), 1.99-2.05 (m, 1H), 1.88 (d, J=12.5 Hz, 1H), 1.76-1.85 (m, 2H), 1.59-1.74 (m, 7H), 1.27 (s, 9H), 1.25 (br. s., 3H), 0.95 (d, J=5.5, Hz, 3H), 0.94 (d, J=5.5, Hz, 3H). LCMS (M+H)=598.7.

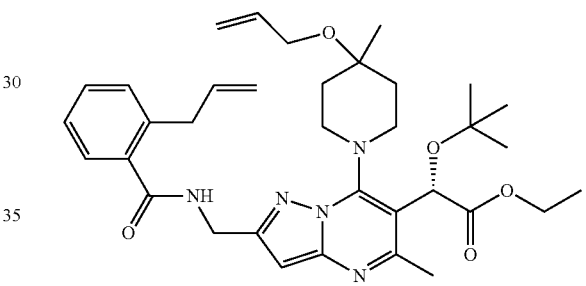

(S)-Ethyl 2-(2-((2-allylbenzamido)methyl)-7-(4-(allyloxy)-4-methylpiperidin-1-yl)-5-methylpyrazolo[1,5-a]pyrimidin-6-yl)-2-(tert-butoxy)acetate A solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.10 g, 0.200 mmol) and Ph$_3$P (0.063 g, 0.240 mmol) in 9:1 THF/H$_2$O (5 mL) stirred at rt for 1 h and at 45° C. for 4 h. Then, diluted with Et$_2$O (25 mL) and extracted with 0.5M HCl (2×5 mL). The combine aqueous layers neutralized with sat Na$_2$CO$_3$ and extracted with CH$_2$Cl$_2$ (2×20 mL). The combine CH$_2$Cl$_2$ layers dried (MgSO$_4$), filtered and concentrated to give (S)-ethyl 2-(7-(4-(allyloxy)-4-methylpiperidin-1-yl)-2-(aminomethyl)-5-methylpyrazolo[1,5-a]pyrimidin-6-yl)-2-(tert-butoxy)acetate as viscous pale yellow oil which was used in the subsequent step without purification. To a stirred solution of 2-allylbenzoic acid (0.065 g, 0.400 mmol) in CH$_2$Cl$_2$ (5 mL) containing cat. DMF was added 2M oxalyl chloride/DCM (0.400 ml, 0.801 mmol) at rt. After 1 h, concentrated and the resulting residue was re-dissolved in CH$_2$Cl$_2$ (3 mL) and added to a solution of (S)-ethyl 2-(7-(4-(allyloxy)-4-methylpiperidin-1-yl)-2-(aminomethyl)-5-methylpyrazolo[1,5-a]pyrimidin-6-yl)-2-(tert-butoxy)acetate and DIEA (0.105 ml, 0.600 mmol) in CH$_2$Cl$_2$ (2 mL) at rt. After 2 h the reaction was quenched with a drop of MeOH, concentrated and purified prep-HPLC to afford (S)-ethyl 2-(2-((2-allylbenzamido)methyl)-7-(4-(allyloxy)-4-methylpiperidin-1-yl)-5-methylpyrazolo[1,5-a]pyrimidin-6-yl)-2-(tert-butoxy)acetate (0.059 g, 0.096 mmol, 47.7% yield) as white solid. $^1$H NMR (500 MHz, CDCl$_3$) δ 7.50 (dd, J=1.2, 7.7 Hz, 1H), 7.37-7.41 (m, 1H), 7.24-7.30 (m, 3H), 6.46-6.53 (m, 1H), 6.49 (s, 1H), 5.98-6.06 (m, 1H), 5.83-5.98 (m, 2H), 5.39 (dd, J=1.6, 17.2 Hz, 1H), 5.14 (d, J=9.8 Hz, 1H), 5.06 (qd, J=1.5, 10.1 Hz, 1H), 5.01 (qd, J=1.7, 17.2 Hz, 1H), 4.84 (d, J=5.4 Hz, 2H), 4.15-4.28 (m, 2H), 3.97 (d, J=4.6 Hz, 2H), 3.64 (d, J=6.3 Hz, 2H), 2.61 (s, 3H), 1.98 (d, J=13.2 Hz, 1H), 1.84-1.94 (m, 2H), 1.70 (d, J=9.3 Hz, 1H), 1.31 (s, 3H), 1.21-1.26 (m, 12H). LCMS (M+H)=618.5.

Example 14

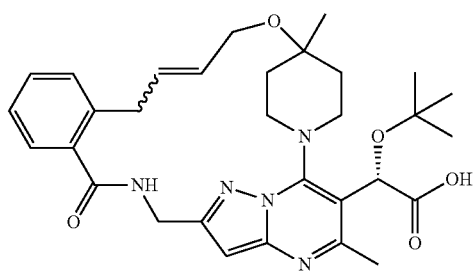 [SMILES: Cc1nc2cc3nn2c(c1[C@H](OC(C)(C)C)C(=O)O)N1CCC(C)(CC1)OCC=CCc1ccccc1C(=O)NC3]

(2S)-2-(tert-Butoxy)-2-[4,24-dimethyl-12-oxo-23-oxa-1,5,7,8,11-pentaazapentacyclo[22.2.2.1$^{6,9}$.0$^{2,7}$.0$^{13,18}$]nonacosa-2,4,6(29),8,13(18),14,16,20-octaen-3-yl]acetic acid To a stirred solution of (S)-ethyl 2-(2-((2-allylbenzamido)methyl)-7-(4-(allyloxy)-4-methylpiperidin-1-yl)-5-methylpyrazolo[1,5-a]pyrimidin-6-yl)-2-(tert-butoxy)acetate (0.058 g, 0.094 mmol) in 1,2-dichloroethane (20 mL) at 70° C. was added Hoveyda-Grubbs catalyst 2nd generation (2.94 mg, 4.69 µmol) and refluxed for 2 h. Then, cooled, concentrated and the resulting residue was purified by flash chromatography using 1:1 and 1:3 Hex/EtOAc to afford ethyl (2S)-2-(tert-butoxy)-2-[(20E)-4,24-dimethyl-12-oxo-23-oxa-1,5,7,8,11-pentaazapentacyclo[22.2.2.1$^{6,9}$.0$^{2,7}$.0$^{13,18}$]nonacosa-2,4,6(29),8,13(18),14,16,20-octaen-3-yl]acetate.

A solution of above ester and 1M NaOH (0.282 ml, 0.282 mmol) in MeOH (3 mL) was refluxed for 4 h. Then, the reaction mixture was cooled and purified by prep-HPLC to afford desired product (0.0375 g, 0.067 mmol, 71.1% yield). $^1$H NMR (500 MHz, CDCl$_3$) δ 7.53 (dd, J=1.3, 7.7 Hz, 1H), 7.37-7.41 (m, 1H), 7.27-7.31 (m, 1H), 7.25 (dd, J=0.8, 7.7 Hz, 1H), 6.83 (br. s., 1H), 6.49 (s, 1H), 6.25-6.33 (m, 1H), 5.97 (br. s., 1H), 5.57-5.65 (m, 1H), 5.04 (dd, J=4.9, 16.9 Hz, 1H), 4.87 (dd, J=3.3, 16.9 Hz, 1H), 4.51 (t, J=11.2 Hz, 1H), 3.89-3.96 (m, 3H), 3.58 (d, J=4.9 Hz, 2H), 2.97-3.11 (m, 2H), 2.71-2.94 (m, 3H), 2.65 (s, 3H), 2.58 (d, J=11.4 Hz, 1H), 1.93 (dt, J=2.2, 16.2 Hz, 2H), 1.58-1.71 (m, 1H), 1.31 (s, 9H), 1.27 (s, 3H). LCMS (M+H)=562.5.

Example 15

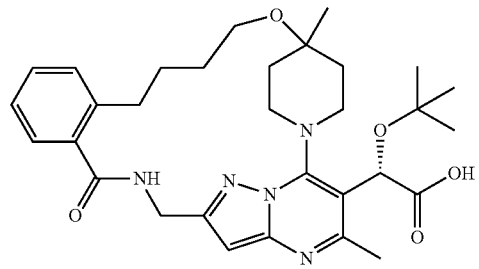 [SMILES: Cc1nc2cc3nn2c(c1[C@H](OC(C)(C)C)C(=O)O)N1CCC(C)(CC1)OCCCCc1ccccc1C(=O)NC3]

(2S)-2-(tert-Butoxy)-2-{4,24-dimethyl-12-oxo-23-oxa-1,5,7,8,11-pentaazapentacyclo[22.2.2.1$^{6,9}$.0$^{2,7}$.0$^{13,18}$]nonacosa-2,4,6(29),8,13(18),14,16-heptaen-3-yl}acetic acid To a stirred solution of olefin mixture (0.0053 g, 9.44 µmol) in MeOH/EtOAc (1:1; 5 mL) was added 10% Pd/C (5 mg, 4.70 µmol), evacuated and left under balloon hydrogen pressure for 5 h. Then, filtered, concentrated and purified by prep-HPLC to provide saturated product (0.001 g, 1.774 µmol, 18.80% yield) as white solid. $^1$H NMR (500 MHz, CDCl$_3$) δ 7.48 (dd, J=1.2, 7.5 Hz, 1H), 7.33-7.37 (m, 1H), 7.20-7.28 (m, 2H), 6.66 (br. s., 1H), 6.50 (s, 1H), 5.99 (br. s.; 1H), 4.90-5.01 (m, 2H), 4.49 (t, J=12.0 Hz, 1H), 3.82 (t, J=11.2 Hz, 1H), 3.44-3.49 (m, 1H), 3.38-3.43 (m, 1H), 3.09 (d, J=10.4 Hz, 1H), 3.00 (td, J=6.4, 13.3 Hz, 1H), 2.88 (ddd, J=6.0, 8.3, 13.8 Hz, 1H), 2.64 (s, 3H), 2.58 (d, J=11.0 Hz, 1H), 1.87-2.12 (m, 4H), 1.56-1.76 (m, 4H), 1.31 (s, 9H), 1.23 (s, 3H). LCMS (M+H)=564.5.

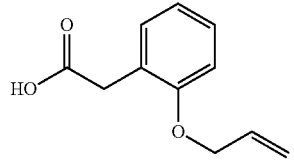

Allyl bromide (1.194 mL, 13.80 mmol) was added during 20 min to a solution of 2-(2-hydroxyphenyl)acetic acid (1 g, 6.57 mmol) and KOH (0.42 g) in MeOH (10 mL) and the mixture was boiled under reflux for 2 h. Additional KOH (0.42 g) in MeOH (8 ml) was added to the mixture which was then boiled under reflux for 1 h, poured into water, and washed with Et$_2$O. Acidification with 10M HCl and extraction with Et$_2$O gave (380 mg, 1.977 mmol, 30.1% yield) as a colorless solid. $^1$H NMR (400 MHz, DMSO-d$_6$) δ 7.16-7.25 (m, 2H), 6.95 (d, J=7.8 Hz, 1H), 6.88 (dt, J=0.9, 7.4 Hz, 1H), 6.01 (tdd, J=4.6, 10.7, 17.4 Hz, 1H), 5.41 (qd, J=1.9, 17.3 Hz, 1H), 5.22 (qd, J=1.6, 10.6 Hz, 1H), 4.55 (td, J=1.7, 4.7 Hz, 2H), 3.52 (s, 2H).

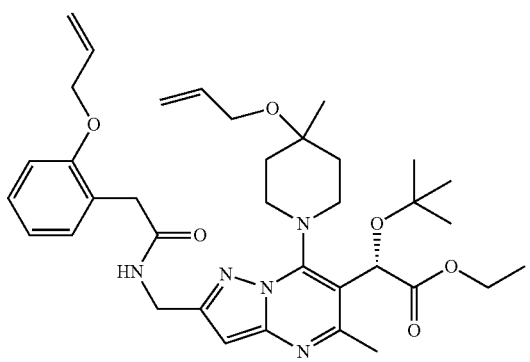 [SMILES: C=CCOc1ccccc1CC(=O)NCc1cc2nc(C)c([C@H](OC(C)(C)C)C(=O)OCC)c(N3CCC(C)(OCC=C)CC3)n2n1]

(S)-Ethyl 2-(7-(4-(allyloxy)-4-methylpiperidin-1-yl)-2-((2-(2-(allyloxy)phenyl)acetamido)methyl)-5-methylpyrazolo[1,5-a]pyrimidin-6-yl)-2-(tert-butoxy)acetate A solution of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.072 g, 0.144 mmol) and Ph₃P (0.057 g, 0.216 mmol) in 1:9 (H₂O/THF, 5 mL) was stirred at 55° C. for h. Then, cooled in ice-water bath and added DIEA (0.076 ml, 0.432 mmol) followed by freshly prepared acid chloride (To a solution of 2-(2-(allyloxy)phenyl)acetic acid (0.055 g, 0.288 mmol) in CH₂Cl₂ (5 mL) containing cat amount of DMF was added 2M oxalyl chloride (0.288 ml, 0.576 mmol) at rt. After 1 h, the reaction was concentrated and the residue was dissolved in CH₂Cl₂ (5 mL) and added to the amine). After the reaction mixture was taken up in Et₂O (50 mL), washed with water (2×10 mL), brine (10 mL), dried (MgSO₄), filtered, concentrated and the resulting yellow residue purified by prep-HPLC to afford (S)-ethyl 2-(7-(4-(allyloxy)-4-methylpiperidin-1-yl)-2-((2-(2-(allyloxy)phenyl)acetamido)methyl)-5-methylpyrazolo[1,5-a]pyrimidin-6-yl)-2-(tert-butoxy)acetate (0.0559 g, 0.086 mmol, 59.9% yield) as off-white solid. ¹H NMR (500 MHz, CDCl₃) δ 7.28-7.30 (m, 1H), 7.23-7.27 (m, 1H), 6.96 (dt, J=1.0, 7.5 Hz, 1H), 6.89 (d, J=8.2 Hz, 1H), 6.29 (s, 1H), 6.25 (t, J=5.0 Hz, 1H), 5.92-6.06 (m, 2H), 5.88 (br. s., 1H), 5.44 (d, J=17.0 Hz, 1H), 5.33 (qd, J=1.6, 17.3 Hz, 1H), 5.17-5.21 (m, 2H), 4.60 (dd, J=3.8, 5.4 Hz, 2H), 4.56 (td, J=1.6, 5.2 Hz, 2H), 4.13-4.26 (m, 2H), 4.00 (d, J=4.9 Hz, 2H), 3.68 (s, 2H), 2.59 (s, 3H), 1.82-2.01 (m, 3H), 1.64-1.72 (m, 1H), 1.34 (s, 3H), 1.21-1.25 (m, 12H). LCMS (M+H)=648.7.

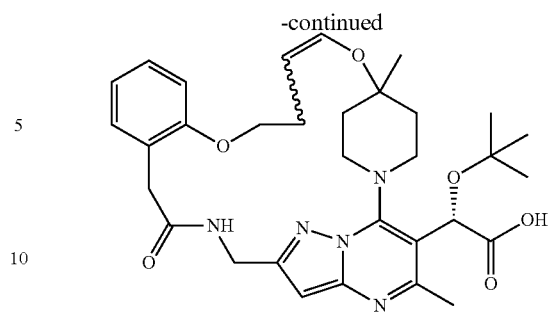

(2S)-2-(tert-Butoxy)-2-[4,26-dimethyl-12-oxo-20,25-dioxa-1,5,7,8,11-pentaazapentacyclo[24.2.2.1⁶,⁹.1²,⁷.0¹⁴,¹⁹]hentriaconta-2,4,6(31),8,14(19),15,17,22-octaen-3-yl]acetic acid To a stirred solution of (S)-ethyl 2-(7-(4-(allyloxy)-4-methylpiperidin-1-yl)-2-((2-(2-(allyloxy)phenyl)acetamido)methyl)-5-methylpyrazolo[1,5-a]pyrimidin-6-yl)-2-(tert-butoxy)acetate (0.0555 g, 0.086 mmol) in 1,2-dichloroethane (10 mL) was added Hoveyda-Grubbs catalyst 2nd generation (2.68 mg, 4.28 µmol) at 70° C. and refluxed for 4 h. Note: LCMS of the reaction mixture at 2 h and 4 h looked similar. Then, cooled, concentrated and purified by flash chromatography using 1:1 and 1:3 Hex/EtOAc. All fractions containing products and unreacted sm were combined, concentrated and used in next step. A solution of above residue and 1M NaOH (0.257 ml, 0.257 mmol) in MeOH (3 mL) was refluxed for 6 h. Then, cooled and purified by prep-HPLC. The fractions containing macrocycles were pooled and evaporated to offer as a mixture of isomers (0.016 g, 0.027 mmol, 31.6% yield); white solid and one isomer (0.0059 g, 9.97 µmol, 11.64% yield); white solid.

(2S)-2-(tert-Butoxy)-2-[4,26-dimethyl-12-oxo-20,25-dioxa-1,5,7,8,11-pentaazapentacyclo[24.2.2.1⁶,⁹.1²,⁷.0¹⁴,¹⁹]hentriaconta-2,4,6(31),8,14(19),15,17,23-octaen-3-yl]acetic acid Single isomers. ¹H NMR (500 MHz, CDCL₃) δ 7.30 (dd, J=1.3, 7.5 Hz, 1H), 7.21-7.26 (m, 1H), 6.90-6.96 (m, 2H), 6.78 (br. s., 1H), 6.44 (s, 1H), 6.36 (d, J=6.2 Hz, 1H), 5.94 (br. s., 1H), 4.47-4.66 (m, 4H), 4.11-4.17 (m, 2H), 3.79 (t, J=11.5 Hz, 1H), 3.68 (d, J_{AB}=13.7 Hz, 1H), 3.54 (d, J_{AB}=13.7 Hz, 1H), 3.33-3.41 (m, 1H), 2.91 (q, J=7.4 Hz, 2H), 2.81 (d, J=11.8 Hz, 1H), 2.60 (s, 3H), 1.95-2.09 (m, 3H), 1.69-1.83 (m, 3H), 1.43 (s, 3H), 1.29 (s, 9H). LCMS (M+H)=592.6.

Example 16

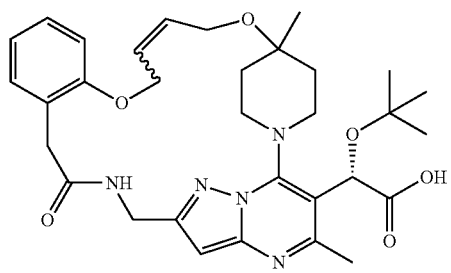 [SMILES: Cc1nc2cc3nn2c(c1[C@H](OC(C)(C)C)C(=O)O)N1CCC(C)(CC1)OCCCCOc1ccccc1CC(=O)NC3]

Example 17

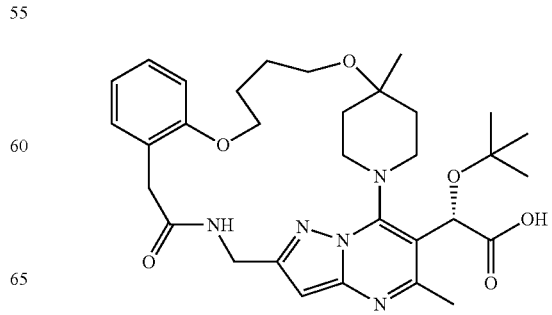

(2S)-2-(tert-Butoxy)-2-{4,26-dimethyl-12-oxo-20,25-dioxa-1,5,7,8,11-pentaazapentacyclo[24.2.2.1$^{6,9}$.1$^{2,7}$.0$^{14,19}$]hentriaconta-2,4,6(31),8,14(19),15,17-heptaen-3-yl}acetic acid A mixture of macrocycle isomers (0.016 g, 0.027 mmol) and 10% Pd/C (2.88 mg, 2.70 µmol) in 9:1 EtOAc/MeOH (10 mL) was left under balloon hydrogen atmosphere for 24 h. Then, filtered, concentrated and purified by prep-HPLC to afford product (0.0107 g, 0.018 mmol, 66.6% yield) as white solid. $^1$H NMR (500 MHz, CDCl$_3$) δ 7.34 (dd, J=1.7, 7.5 Hz, 1H), 7.24 (dt, J=1.7, 7.8 Hz, 1H), 6.95 (dt, J=1.0, 7.5 Hz, 1H), 6.91 (d, J=8.4 Hz, 1H), 6.87 (t, J=5.4 Hz, 1H), 6.48 (s, 1H), 6.00 (br. s., 1H), 4.68 (dd, J=6.5, 15.1 Hz, 1H), 4.58 (t, J=11.5 Hz, 1H), 4.44 (dd, J=4.7, 15.1 Hz, 1H), 4.10-4.16 (m, 2H), 3.85 (t, J=11.4 Hz, 1H), 3.59 (d, J=1.6 Hz, 2H), 3.54-3.58 (m, 1H), 3.48 (dt, J=4.0, 7.9 Hz, 1H), 3.27 (d, J=10.3 Hz, 1H), 2.73 (d, J=12.0 Hz, 1H), 2.62 (s, 3H), 2.23-2.32 (m, 1H), 2.08-2.17 (m, 1H), 1.98-2.05 (m, 2H), 1.50-1.93 (m, 4H), 1.31 (s, 9H), 1.29 (br. s., 3H). LCMS (M+H)=594.6.

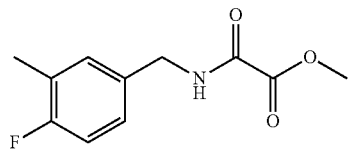 [SMILES: COC(=O)C(=O)NCc1ccc(F)c(C)c1]

Methyl 2-((4-fluoro-3-methylbenzyl)amino)-2-oxoacetate

To a stirred solution of (4-fluoro-3-methylphenyl)methanamine (6.96 g, 50 mmol) and Et$_3$N (10.45 ml, 75 mmol) was added methyl oxalyl chloride (5.10 ml, 55.0 mmol) at −18° C. (ice-salt bath) over 10 min. The reaction mixture was stirred for 2 h while warming to rt. Then, concentrated and the residue was taken up in Et$_2$O (200 mL), washed with 1M HCl (2×50 mL), brine (25 mL), dried (MgSO$_4$), filtered and concentrated to give yellow residue which solidified on standing. This solid was stirred with 5% Et$_2$O/Hex (100 mL) and filtered to give methyl 2-((4-fluoro-3-methylbenzyl)amino)-2-oxoacetate (9.22 g, 40.9 mmol, 82% yield) as white solid. $^1$H NMR (500 MHz, CDCl$_3$) δ 7.31-7.39 (m, 1H), 7.13-7.16 (m, 1H), 7.08-7.12 (m, 1H), 6.97-7.02 (m, 1H), 4.48 (d, J=6.2 Hz, 2H), 3.94 (s, 3H), 2.29 (d, J=1.9 Hz, 3H). LCMS (M+H)=226.2.

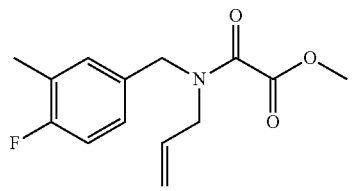 [SMILES: C=CCN(Cc1ccc(F)c(C)c1)C(=O)C(=O)OC]

2-(Allyl(4-fluoro-3-methylbenzyl)amino)-2-oxoacetic acid

To a stirred solution of methyl 2-((4-fluoro-3-methylbenzyl)amino)-2-oxoacetate (1 g, 4.44 mmol) in DMF (20 mL) was added 60% NaH (0.391 g, 9.77 mmol) at 0° C. After 30 min, cold bath was removed, stirred for 1 h at rt and allyl bromide (1.921 ml, 22.20 mmol) was added to the resulting turbid reaction mixture. LCMS after 15 h showed presence unreacted sm. So, heated at 95° C. for 48 h. Then, diluted with Et$_2$O (150 mL), washed with 1M HCl (20 mL), water (3×10 mL), brine (10 mL), dried (4), filtered and concentrated to give brown oil.

To a solution of above oil in MeOH (10 mL) was added 1M NaOH (6 ml, 6.00 mmol) and resulting slurry was stirred at rt for 24 h. Then, diluted with water (50 mL) and extracted with Et$_2$O (2×50 mL). The ether layers discarded and aq layer acidified with conc HCl and extracted with CH$_2$Cl$_2$ (2×50 mL). The combined CH$_2$Cl$_2$ layers dried (MgSO$_4$), filtered and concentrated to give brown residue which was purified by prep-HPLC to afford 2-(allyl(4-fluoro-3-methylbenzyl)amino)-2-oxoacetic acid (0.471 g, 1.875 mmol, 42.2% yield) as white solid. $^1$H NMR (500 MHz, CDCl$_3$) δ 7.04-7.11 (m, 1H), 6.85-6.99 (m, 2H), 5.56-5.82 (m, 1H), 4.99-5.16 (m, 2H), 4.34-4.45 (m, 2H), 3.68-3.85 (m, 2H), 2.20 (br. s., 3H). LCMS (M+H)=252.2.

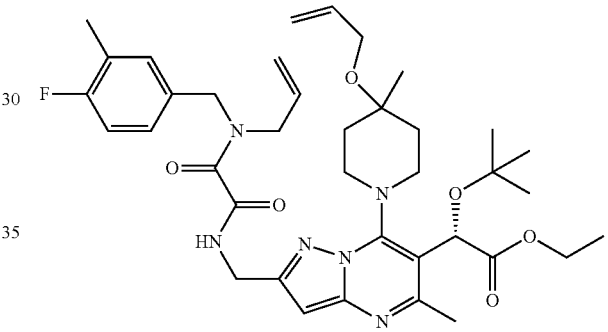

(S)-Ethyl 2-(2-((2-(allyl(4-fluoro-3-methylbenzyl)amino)-2-oxoacetamido)methyl)-7-(4-(allyloxy)-4-methylpiperidin-1-yl)-5-methylpyrazolo[1,5-a]pyrimidin-6-yl)-2-(tert-butoxy)acetate A mixture of (S)-ethyl 2-(7-(4-(allyloxy)-4-methylpiperidin-1-yl)-2-(azidomethyl)-5-methylpyrazolo[1,5-a]pyrimidin-6-yl)-2-(tert-butoxy)acetate (0.206 g, 0.412 mmol) and Ph$_3$P (0.162 g, 0.618 mmol) in 9:1 THF/H$_2$O (15 mL) was refluxed for 2 h. Then, cooled, diluted with Et$_2$O (50 mL) and extracted with 0.1M HCl (3×10 mL). The organic layer discarded and the combined aqueous. layers neutralized with sat Na$_2$CO$_3$ and extracted with CH$_2$Cl$_2$ (3×10 mL). The combined CH$_2$Cl$_2$ layers dried (MgSO$_4$), filtered and concentrated to give (S)-ethyl 2-(7-(4-(allyloxy)-4-methylpiperidin-1-yl)-2-(aminomethyl)-5-methylpyrazolo[1,5-a]pyrimidin-6-yl)-2-(tert-butoxy)acetate (0.193 g, 0.408 mmol, 99% yield) as pale yellow paste which was used in the next step without purification. To a stirred solution of (S)-ethyl 2-(7-(4-(allyloxy)-4-methylpiperidin-1-yl)-2-(aminomethyl)-5-methylpyrazolo[1,5-a]pyrimidin-6-yl)-2-(tert-butoxy)acetate (0.195 g, 0.412 mmol), 2-(allyl(4-fluoro-3-methylbenzyl)amino)-2-oxoacetic acid (0.207 g, 0.824 mmol) and DIEA (0.288 ml, 1.648 mmol) in DMF (5 mL) was added HATU (0.470 g, 1.236 mmol) at rt. After 17 h, the reaction mixture was taken up in Et₂O (100 mL), washed with 1M HCl (5 mL), water (3×10 mL), brine (10 mL), dried (MgSO₄), filtered, concentrated and purified by prep-HPLC to afford (S)-ethyl 2-(2-((2-(allyl(4-fluoro-3-methylbenzyl)amino)-2-oxoacetamido)methyl)-7-(4-(allyloxy)-4-methylpiperidin-1-yl)-5-methylpyrazolo[1,5-a]pyrimidin-6-yl)-2-(tert-butoxy)acetate (0.1145 g, 0.162 mmol, 39.3% yield) as yellow paste. ¹H NMR (400 MHz, CDCl₃) δ 7.92 (d, J=14.8 Hz, 1H), 7.03-7.16 (m, 2H), 6.91-6.99 (m, 1H), 6.42 (s, 1H), 5.69-6.07 (m, 3H), 5.43 (d, J=17.3 Hz, 1H), 5.11-5.26 (m, 3H), 5.00 (s, 1H), 4.68 (t, J=5.4 Hz, 2H), 4.54 (s, 1H), 4.38 (d, J=5.8 Hz, 1H), 4.12-4.27 (m, 3H), 3.95-4.05 (m, 3H), 3.92 (d, J=6.0 Hz, 1H), 2.59 (s, 3H), 2.26 (d, J=1.76 Hz, 3H), 1.81-2.03 (m, 3H), 1.72 (td, J=2.6, 7.0 Hz, 1H), 1.34 (s, 3H), 1.20-1.25 (m, 12H). LCMS (M+H)=707.7.

Example 18

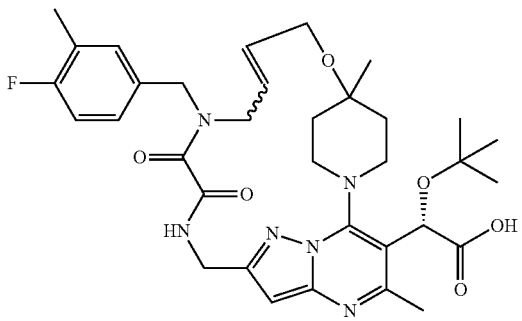 [SMILES: Cc1cc(CN2CC=CCOC3(C)CCN(CC3)c3c([C@H](OC(C)(C)C)C(=O)O)c(C)nc4cc(nn34)CNC(=O)C2=O)ccc1F]

(2S)-2-(tert-Butoxy)-2-[14-[(4-fluoro-3-methylphenyl)methyl]-4,20-dimethyl-12,13-dioxo-19-oxa-1,5,7,8,11,14-hexaazatetracyclo[18.2.2.1⁶,⁹.0²,⁷]pentacosa-2,4,6(25),8,16-pentaen-3-yl]acetic acid To a stirred solution of (S)-ethyl 2-(2-((2-(allyl(4-fluoro-3-methylbenzyl)amino)-2-oxoacetamido)methyl)-7-(4-(allyloxy)-4-methylpiperidin-1-yl)-5-methylpyrazolo[1,5-a]pyrimidin-6-yl)-2-(tert-butoxy)acetate (0.114 g, 0.161 mmol) in 1,2-dichloroethane (40 mL) was added at once Hoveyda-Grubbs catalyst 2nd generation (5.05 mg, 8.06 μmol) at 70° C. and refluxed for 2 h. Then, cooled, concentrated and dark residue was passed through a plug of silica gel using EtOAc. The filtrate was concentrated and the resulting residue was used in the next step without purification.

A solution of crude above ester and NaOH (0.484 ml, 0.484 mmol) in MeOH (5 mL) was refluxed for 2 h. Then, cooled and purified by prep-HPLC to afford desired product (0.0671 g, 0.102 mmol, 63.3% yield) as off-white solid. ¹H NMR (500 MHz, METHANOL-d₄) δ 7.22 (dd, J=1.7, 7.3 Hz, 1H), 7.14-7.19 (m, 1H), 7.00-7.05 (m, 1H), 6.48 (s, 1H), 6.26 (td, J=6.9, 15.3 Hz, 1H), 6.07 (s, 1H), 5.88 (td, J=3.0, 15.5 Hz, 1H), 4.58-4.73 (m, 3H), 4.42-4.56 (m, 1H), 3.94-4.14 (m, 4H), 3.87 (t, J=11.5 Hz, 1H), 3.35-3.39 (m, 1H), 3.27-3.31 (m, 1H), 3.14-3.20 (m, 1H), 2.71 (J=11.5 Hz, 1H), 2.64 (s, 3H), 2.29 (d, J=1.7 Hz, 3H), 1.94-2.00 (m, 2H), 1.72-1.93 (m, 3H), 1.33 (s, 3H), 1.29 (s, 9H). LCMS (M+H)=651.6.

Example 19

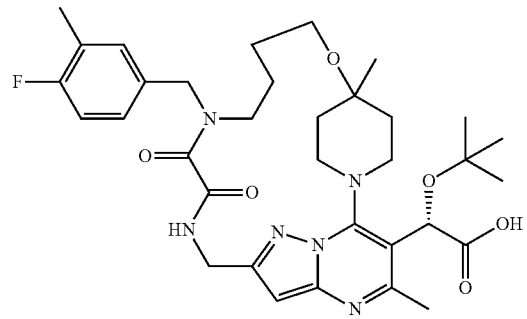 [SMILES: Cc1cc(CN2CCCCOC3(C)CCN(CC3)c3c([C@H](OC(C)(C)C)C(=O)O)c(C)nc4cc(nn34)CNC(=O)C2=O)ccc1F]

(2S)-2-(tert-Butoxy)-2-{14-[(4-fluoro-3-methylphenyl)methyl]-4,20-dimethyl-12,13-dioxo-19-oxa-1,5,7,8,11,14-hexaazatetracyclo[18.2.2.1⁶,⁹.0²,⁷]pentacosa-2,4,6(25),8-tetraen-3-yl}acetic acid A mixture of olefin (0.037 g, 0.057 mmol) and 10% Pd/C (6.05 mg, 5.69 μmol) in EtOAc (10 mL) stirred under balloon hydrogen atmosphere for 12 h. Then, filtered through a plug of celite and concentrated to afford desired product (0.0295 g, 0.044 mmol, 77% yield) as white solid. ¹H NMR (500 MHz, CDCl3) δ 7.56 (t, J=4.2 Hz, 0.3H), 7.20-7.25 (m, 1H), 7.14-7.18 (m, 0.3H), 7.11 (d, J=7.4 Hz, 0.7H), 7.07-7.09 (m, 0.7H), 6.94-6.99 (m, 1H), 6.46 (s, 0.7H), 6.42 (s, 0.3H), 5.98 (br. s., 1H), 4.87-4.97 (m, 1H), 4.35-4.80 (m, 3H), 3.65-3.96 (m, 3H), 3.32-3.48 (m, 3H), 3.11-3.28 (m, 1H), 2.63 (s, 2H), 2.62 (s, 1H), 2.60-2.66 (m, 1H), 2.28 (s, 3H), 1.88-1.93 (m, 3H), 1.57-1.80 (m, 5H), 1.31 (s, 9H), 1.29 (s, 3H). LCMS (M+H)=653.7. By HNMR this compound is 7:3 mixture of rotomers.

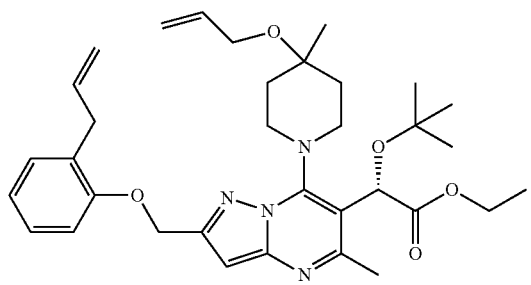 [SMILES: C=CCOC1(C)CCN(c2c([C@H](OC(C)(C)C)C(=O)OCC)c(C)nc3cc(COc4ccccc4CC=C)nn23)CC1]

(S)-Ethyl 2-(7-(4-(allyloxy)-4-methylpiperidin-1-yl)-2-((2-allylphenoxy)methyl)-5-methylpyrazolo[1,5-a]pyrimidin-6-yl)-2-(tert-butoxy)acetate To a stirred solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.190 g, 0.320 mmol), 2-allylphenol (0.084 ml, 0.641 mmol) and Ph₃P (0.126 g, 0.480 mmol) in THF (5 mL) was added DEAD (0.101 ml, 0.641 mmol) at 0° C. The reaction was slowly warming to rt over 3 h and after 1 h at rt, diluted with Et₂O (50 mL), washed with water (2×10 mL), brine (10 mL), dried (MgSO$_4$), filtered, concentrated and the resulting yellow residue purified by flash chromatography using 10 and 20% EtOAc/Hex to afford (S)-ethyl 2-(7-(4-(allyloxy)-4-methylpiperidin-1-yl)-2-((2-allylphenoxy)methyl)-5-methylpyrazolo[1,5-a]pyrimidin-6-yl)-2-(tert-butoxy)acetate (0.0374 g, 0.063 mmol, 19.77% yield) as colorless paste. $^1$H NMR (500 MHz, CDCl$_3$) δ 7.17-7.23 (m, 2H), 7.08 (d, J=7.9 Hz, 1H), 6.94 (t, J=7.4 Hz, 1H), 6.63 (s, 1H), 6.00-6.10 (m, 2H), 5.88-5.98 (m, 1H), 5.44-5.55 (m, 1H), 5.31 (s, 2H), 5.22 (dd, J=1.3, 10.4 Hz, 1H), 4.15-4.27 (m, 2H), 4.00-4.06 (m, 2H), 3.47 (d, J=6.5 Hz, 2H), 2.62 (s, 3H), 1.88-2.06 (m, 3H), 1.68-1.77 (m, 2H), 1.37 (br. s., 3H), 1.21-1.28 (m, 12H). LCMS (M+H)=591.6.

Example 20, 21 and 22

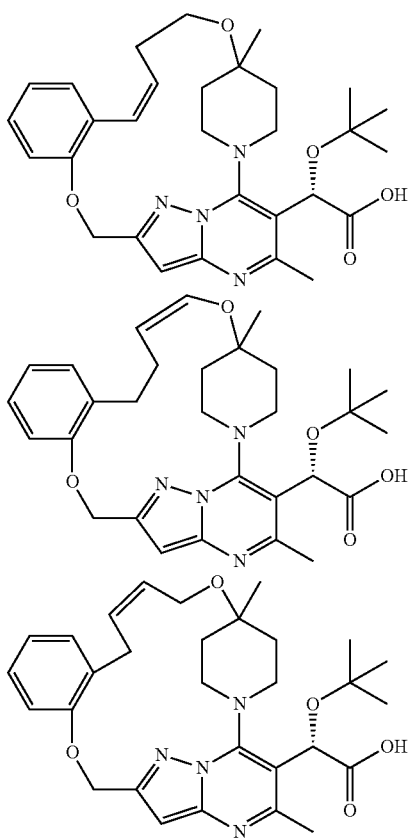

To a stirred solution of (S)-ethyl 2-(7-(4-(allyloxy)-4-methylpiperidin-1-yl)-2-((2-allylphenoxy)methyl)-5-methylpyrazolo[1,5-a]pyrimidin-6-yl)-2-(tert-butoxy)acetate (0.037 g, 0.063 mmol) in 1,2-dichloroethane (20 mL) at 70° C. was added Hoveyda-Grubbs catalyst 2nd generation (3.92 mg, 6.26 µmol) and refluxed for 2 h. Then, cooled, concentrated and the resulting residue and 1M NaOH (0.188 ml, 0.188 mmol) in MeOH (3 mL) was refluxed for 5 h. The reaction mixture cooled and purified by prep-HPLC to afford three macrocycle carboxylic acids.

(2S)-2-(tert-Butoxy)-2-[(18Z)-4,23-dimethyl-11,22-dioxa-1,5,7,8-tetraazapentacyclo[21.2.2.1$^{6,9}$.1$^{2,7}$.0$^{12,17}$]octacosa-2,4,6(28),8,12(17),13,15,18-octaen-3-yl]acetic acid (0.0045 g, 8.00 µmol, 12.77% yield), white solid, contaminated with other isomer; $^1$H NMR (500 MHz, CDCl$_3$) δ 7.32 (dd, J=1.7, 7.7 Hz, 1H), 7.12-7.16 (m, 1H), 7.03 (dd, J=0.8, 8.2 Hz, 1H), 6.89-6.93 (m, 3H), 6.48 (s, 1H), 5.93-6.05 (br. s., 1H), 5.44-5.52 (m, 2H), 4.79 (t, J=11.4 Hz, 1H), 3.99-4.06 (m, 1H), 3.61-3.66 (m, 2H), 3.00-3.06 (m, 1H), 2.63 (s, 3H), 2.54-2.62 (m, 3H), 1.93-2.00 (m, 2H), 1.65 (tt, J=5.1, 13.3 Hz, 3H), 1.31 (s, 9H), 1.29 (s, 3H). LCMS (M+H)=535.5.

(2S)-2-(tert-Butoxy)-2-[(20Z)-4,23-dimethyl-11,22-dioxa-1,5,7,8-tetraazapentacyclo[21.2.2.1$^{6,9}$.1$^{2,7}$.0$^{12,17}$]octacosa-2,4,6(28),8,12(17),13,15,20-octaen-3-yl]acetic acid (0.0043 g, 7.64 µmol, 12.20% yield), white solid, contaminated with other isomer; $^1$H NMR (500 MHz, CDCl$_3$) δ 7.19 (dd, J=1.7, 7.5 Hz, 1H), 7.03-7.07 (m, 1H), 6.90 (dt, J=1.0, 7.4 Hz, 1H), 6.72 (d, J=8.2 Hz, 1H), 6.54 (s, 1H), 6.19 (d, J=12.0 Hz, 1H), 5.84-5.96 (m, 1H), 5.48-5.53 (m, 1H), 5.39 (d, J$_{AB}$=12.9 Hz, 1H), 5.26 (d, J$_{AB}$=12.9 Hz, 1H), 4.57-4.64 (m, 1H), 4.21 (t, J=11.0 Hz, 1H), 3.10 (d, J=8.2 Hz, 1H), 2.93 (ddd, J=2.7, 10.0, 13.0 Hz, 1H), 2.74 (ddd, J=2.5, 7.7, 13.0 Hz, 1H), 2.67 (s, 3H), 2.31-2.37 (m, 2H), 1.82-1.90 (m, 2H), 1.70 (dt, J=4.8, 13.1 Hz, 2H), 1.57 (dt, J=4.6, 13.4 Hz, 2H), 1.31 (s, 9H), 1.28 (br. s., 3H). LCMS (M+H)=535.5.

(2S)-2-(tert-Butoxy)-2-[(19Z)-4,23-dimethyl-11,22-dioxa-1,5,7,8-tetraazapentacyclo[21.2.2.1$^{6,9}$.1$^{2,7}$.0$^{12,17}$]octacosa-2,4,6(28),8,12(17),13,15,19-octaen-3-yl]acetic acid (0.0161 g, 0.029 mmol, 45.7% yield), white solid; $^1$H NMR (500 MHz, CDCl$_3$) δ 7.21 (dd, J=1.7, 7.3 Hz, 1H), 7.16 (dt, J=1.7, 7.8 Hz, 1H), 6.91 (dt, J=1.0, 7.4 Hz, 1H), 6.87 (d, J=8.0 Hz, 1H), 6.52 (s, 1H), 6.18 (d, J=6.3 Hz, 1H), 5.98 (br. s., 1H), 5.36 (s, 2H), 4.62 (t, J=11.2 Hz, 1H), 4.55 (q, J=6.4 Hz, 1H), 3.98 (t, J=10.9 Hz, 1H), 3.01-3.09 (m, 1H), 2.81-2.94 (m, 2H), 2.69-2.74 (m, 1H), 2.67 (s, 3H), 2.55-2.63 (m, 2H), 2.07-2.14 (m, 2H), 1.98 (dd, J=2.2, 13.9 Hz, 1H), 1.93 (dd, J=2.3, 13.6 Hz, 1H), 1.66-1.75 (m, 2H), 1.38 (s, 3H), 1.32 (s, 9H). LCMS (M+H)=535.5.

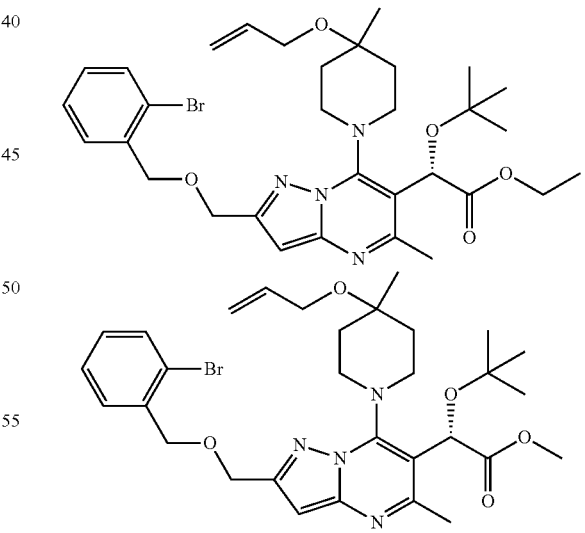

(S)-Methyl 2-(7-(4-(allyloxy)-4-methylpiperidin-1-yl)-2-(((2-bromobenzyl)oxy)methyl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.500 g, 1.054 mmol) and 1-bromo-2-(bromomethyl)benzene (0.527 g, 2.107 mmol) in DMF (2 mL) was added sodium hydride (0.126 g, 3.16 mmol) and the mixture was stirred at room temperature. After 30 min, the reaction was quenched with water and extracted with EtOAc (3×'s) to give the ethyl ester product. Combined organic extracts were dried ($Na_2SO_4$), filtered and concentrated. The residue was purified by flash chromatography (biotage; 0%-50% EtOAc/hexane, 20 CV) to give the ethyl ester title compound. $^1$H NMR (400 MHz, $CDCl_3$) δ 7.64-7.48 (m, 2H), 7.33 (td, J=7.5, 1.1 Hz, 1H), 7.16 (td, J=7.7, 1.7 Hz, 1H), 6.61 (s, 1H), 6.11-5.83 (m, 2H), 5.46 (d, J=16.9 Hz, 1H), 5.20 (dd, J=10.5, 1.7 Hz, 1H), 4.84 (s, 2H), 4.74 (s, 2H), 4.33-4.10 (m, 2H), 4.02 (d, J=4.9 Hz, 2H), 2.69-2.49 (m, 3H), 2.06-1.67 (m, 4H), 1.39-1.20 (m, 15H). 4 piperidine protons not seen. LCMS (M+H) calcd for $C_{32}H_{44}BrN_4O_5$: 645.24. found: 645.0.

The aqueous phase was acidified with concentrated HCl and extracted with EtOAc. The combined EtOAc extracts were dried ($Na_2SO_4$), filtered and concentrated to give the carboxylic acid. The carboxylic acid residue was taken up in 1 mL MeOH and treated with 2M trimethylsilyldiazomethane (0.527 mL, 1.054 mmol). After stirring at room temperature for 1 h, the mixture was concentrated and the residue was purified by flash chromatography (biotage; 0%-50% EtOAc/hexane, 20 CV) to give the methyl ester. The methyl and ethyl ester products were combined to give the title compounds (0.36 g, 0.559 mmol, 53.1% yield) as a colorless oil with the methyl ester as the predominant product. LCMS (M+H) calcd for $C_{31}H_{42}BrN_4O_5$: 630.22. found: 631.3.

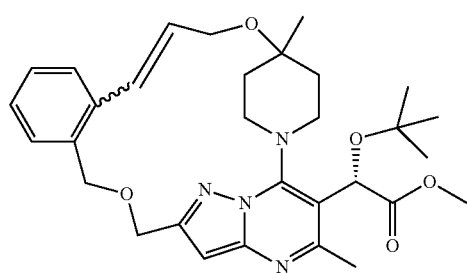 [SMILES: COC(=O)[C@@H](OC(C)(C)C)c1c(C)nc2cc3nn2c1N1CCC(C)(CC1)OCC=Cc1ccccc1COC3]

Methyl (2S)-2-(tert-butoxy)-2-[4,23-dimethyl-11,22-dioxa-1,5,7,8-tetraazapentacyclo[21.2.2.1$^{6,9}$.0$^{2,7}$.0$^{13,18}$]octacosa-2,4,6(28),8,13(18),14,16,19-octaen-3-yl]acetate To a solution of (S)-methyl 2-(7-(4-(allyloxy)-4-methylpiperidin-1-yl)-2-(((2-bromobenzyl)oxy)methyl)-5-methylpyrazolo[1,5-a]pyrimidin-6-yl)-2-(tert-butoxy)acetate (0.025 g, 0.040 mmol) in acetonitrile (1 ml) in a pressure tube were added $Et_3N$ (0.055 ml, 0.397 mmol), triphenylphosphine (3.12 mg, 0.012 mmol) and tris(dibenzylideneacetone)dipalladium (0) (3.64 mg, 3.97 μmol). The tube was sealed and the mixture was stirred at 120° C. After 18 h, the dark mixture was cooled and concentrated. The brown residue was purified by flash chromatography (Biotage; 0%-60% EtOAc/hexane; 20 CV) to afford the title compound as mixture of cis- and trans-isomers (16.9 mg, 0.031 mmol, 78% yield) as a pale yellow oil. LCMS (M+H) calcd for $C_{31}H_{41}N_4O_5$: 549.30. found: 549.4.

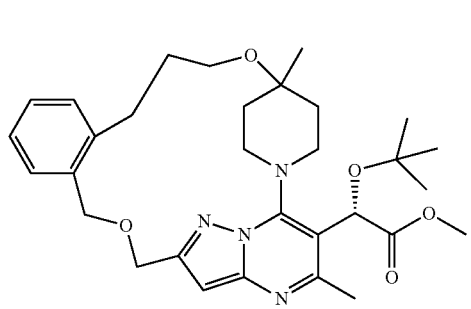 [SMILES: COC(=O)[C@@H](OC(C)(C)C)c1c(C)nc2cc3nn2c1N1CCC(C)(CC1)OCCCc1ccccc1COC3]

Methyl (2S)-2-(tert-butoxy)-2-{4,23-dimethyl-1,22-dioxa-1,5,7,8-tetraazapentacyclo[21.2.2.1$^{6,9}$.0$^{2,7}$.0$^{13,18}$]octacosa-2,4,6(28),8,13(18),14,16-heptaen-3-yl}acetate To a solution of the reactant (Intermediate 2) (16.9 mg, 0.031 mmol) in MeOH (1 mL) was added palladium on carbon (3.28 mg, 3.08 μmol). The mixture was flushed with hydrogen then stirred under a hydrogen balloon. After 1.5 h, the mixture was filtered over celite rinsing with MeOH then concentrated to give the title compound. LCMS (M+H) calcd for $C_{31}H_{42}N_4O_5$: 551.34. found: 551.4.

Example 23

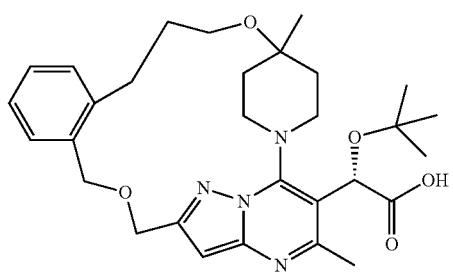 [SMILES: Cc1nc2cc3nn2c(c1[C@H](OC(C)(C)C)C(=O)O)N1CCC(C)(CC1)OCCCc1ccccc1COC3]

(2S)-2-(tert-Butoxy)-2-{4,23-dimethyl-11,22-dioxa-1,5,7,8-tetraazapentacyclo[21.2.2.1$^{6,9}$.0$^{2,7}$.0$^{13,18}$]octacosa-2,4,6(28),8,13(18),14,16-heptaen-3-yl}acetic acid To a solution of the reactant (Intermediate 3) (17.07 mg, 0.031 mmol) in dioxane (1 mL)/MeOH (1 mL) was added 10N sodium hydroxide (0.031 mL, 0.310 mmol) and the mixture was stirred at 70° C. for 1 h. The reaction was cooled and concentrated. The crude material was purified via preparative HPLC to give the title compound (0.9 mg, 5.14% yield). $^1$H NMR (400 MHz, METHANOL-$d_4$) δ 7.46 (d, J=7.0 Hz, 1H), 7.33-7.14 (m, 3H), 6.41 (s, 1H), 6.10 (s, 1H), 5.07 (s, 1H), 5.02-4.94 (m, 1H), 4.69 (s, 2H), 4.04 (t, J=10.9 Hz, 1H), 3.61 (t, J=4.8 Hz, 2H), 3.27-3.03 (m, 3H), 2.75-2.55 (m, 4H), 2.20-1.60 (m, 7H), 1.38-1.25 (m, 12H). LCMS (M+H) calcd for $C_{30}H_{41}N_4O_5$: 537.30. found: 537.3.

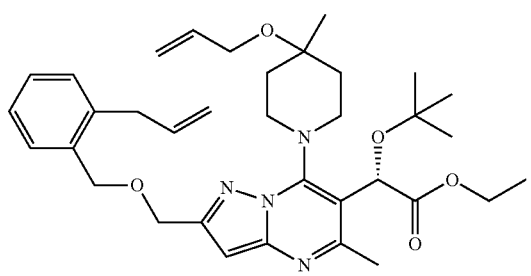

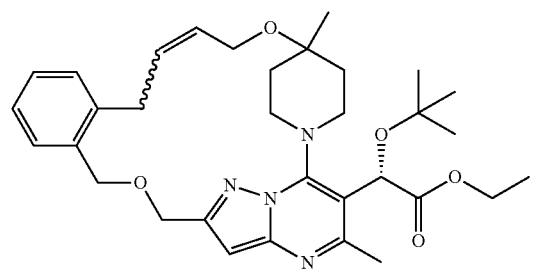 [SMILES: CCOC(=O)[C@@H](OC(C)(C)C)c1c(C)nc2cc3nn2c1N1CCC(C)(CC1)OCC=CCc1ccccc1COC3]

Ethyl (2S)-2-(tert-butoxy)-2-[4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16,20-octaen-3-yl]acetate A solution of (S)-ethyl 2-(2-(((2-allylbenzyl)oxy)methyl)-7-(4-(allyloxy)-4-methylpiperidin-1-yl)-5-methylpyrazolo[1,5-a]pyrimidin-6-yl)-2-(tert-butoxy)acetate (0.059 g, 0.098 mmol) and Copper(I) iodide (0.019 g, 0.098 mmol) in DCE (70.0 ml) was heated to 70° C. Added to this was Hoveyda-Grubbs Catalyst 2nd generation (0.012 g, 19.6 µmol) and the mixture was stirred at 70° C. for two hours then cooled to room temperature overnight. The mixture was concentrated and purified by flash chromatography (Biotage; 0%-50% EtOAc/hexane; 20 CV) to give the title compound (0.0429 g, 0.074 mmol, 76% yield) as a mixture of cis/trans isomers. LCMS (M+H) calcd for $C_{33}H_{45}N_4O_5$: 577.33. found: 577.2.

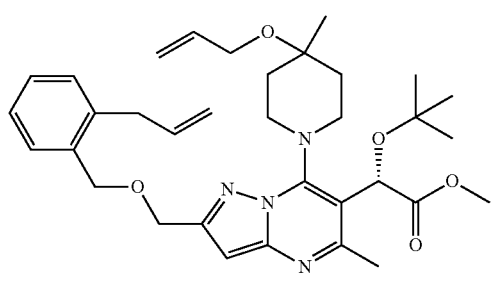

(S)-Ethyl 2-(2-(((2-allylbenzyl)oxy)methyl)-7-(4-(allyloxy)-4-methylpiperidin-1-yl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.10 g, 0.211 mmol) and 1-allyl-2-(bromomethyl)benzene (0.089 g, 0.421 mmol) in DMF (0.5 mL) was added sodium hydride (0.025 g, 0.632 mmol) and the mixture was stirred at room temperature. After 30 min, the reaction was quenched with water and extracted with EtOAc (3×'s) to give the ethyl ester product. The aqueous phase was acidified with concentrated HCl and extracted with EtOAc to give the carboxylic acid intermediate. Both organic solutions were separately dried (Na$_2$SO$_4$), filtered and concentrated. The ethyl ester residue was purified by flash chromatography (biotage; 0%-50% EtOAc/hexane, 20 CV) to give the ethyl ester title compound. The carboxylic acid residue was taken up in 1 mL MeOH and treated with trimethylsilyldiazomethane (0.105 ml, 0.211 mmol). After stirring at room temperature for 1 h, the mixture was concentrated and the residue was purified by flash chromatography (biotage; 0%-50% EtOAc/hexane, 20 CV) to give the methyl ester title compound. The methyl and ethyl ester products were combined to give the title compounds as a mixture of methyl and ethyl esters 59.1 mg (46.8% yield) with the ethyl ester predominating. For the ethyl ester: $^1$H NMR (400 MHz, CDCl$_3$) δ 7.50-7.36 (m, 1H), 7.32-7.06 (m, 3H), 6.58 (s, 1H), 6.13-5.83 (m, 3H), 5.46 (d, J=16.9 Hz, 1H), 5.20 (dd, J=10.5, 1.7 Hz, 1H), 5.09-4.93 (m, 2H), 4.76 (s, 2H), 4.67 (s, 2H), 4.32-4.11 (m, 2H), 4.02 (d, J=4.9 Hz, 2H), 3.48 (d, J=6.4 Hz, 3H), 2.62 (s, 3H), 2.04-1.60 (m, 4H), 1.43-1.28 (m, 4H), 1.26-1.18 (m, 12H). LCMS (M+H) calcd for $C_{35}H_{49}N_4O_5$: 605.37. found: 605.4. For the methyl ester: LCMS (M+H) calcd for $C_{35}H_{49}N_4O_5$: 605.37. found: 605.4.

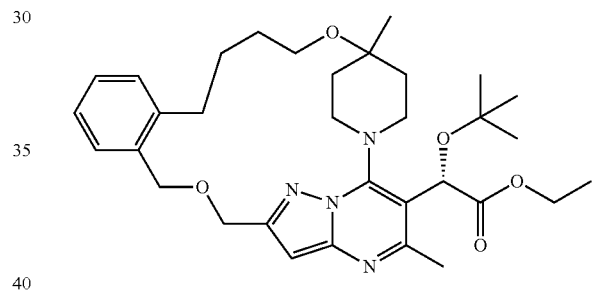

Ethyl (2S)-2-(tert-butoxy)-2-{4,24-dimethyl-1,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetate To a solution of the reactant (Intermediate 5) (19.3 mg, 0.033 mmol) in MeOH (1 mL) was added palladium on carbon (3.56 mg, 3.35 µmol). The mixture was flushed with hydrogen then stirred under a hydrogen balloon. After 1.5 h, the mixture was stirred with celite for 10 min then filtered over celite and concentrated to give the title compound. LCMS (M+H) calcd for $C_{33}H_{47}N_4O_5$: 579.35. found: 579.4.

Example 24

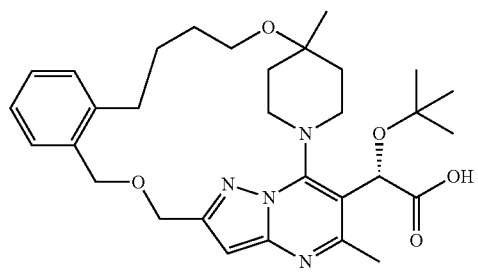 [SMILES: Cc1nc2cc3nn2c(c1[C@H](OC(C)(C)C)C(=O)O)N1CCC(C)(CC1)OCCCCc1ccccc1COC3]

(2S)-2-(tert-Butoxy)-2-{4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid To a solution of the reactant (Intermediate 6) (17.36 mg, 0.030 mmol) in dioxane (1 mL)/MeOH (1 mL) was added 10N sodium hydroxide (0.030 mL, 0.300 mmol) and the mixture was stirred at 80° C. for 1 h. The reaction was cooled and concentrated. The crude material was purified via preparative HPLC to give the title compound (6.0 mg, 10.68 μmol, 35.6% yield). $^1$H NMR (500 MHz, DMSO-d$_6$) δ 7.37 (d, J=7.3 Hz, 1H), 7.26-7.10 (m, 3H), 6.54 (s, 1H), 5.92 (s, 1H), 4.92-4.80 (m, 2H), 4.76 (d, J=12.2 Hz, 1H), 4.62 (d, J=12.5 Hz, 1H), 4.48 (t, J=13.0 Hz, 1H), 3.69 (t, J=11.1 Hz, 1H), 2.92 (d, J=9.5 Hz, 2H), 2.71-2.60 (m, 3H), 2.55 (d, J=10.4 Hz, 1H), 1.91 (s, 3H), 1.88-1.46 (m, 8H), 1.21-1.12 (m, 12H). LCMS (M+H) calcd for C$_{31}$H$_{43}$N$_4$O$_5$: 551.32. found: 551.3.

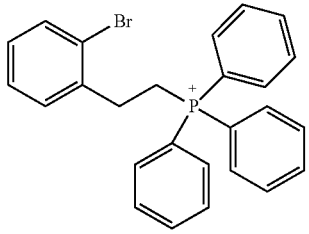

(2-Bromophenethyl)triphenylphosphonium iodide

To a solution of 1-bromo-2-(2-iodoethyl)benzene (0.3244 g, 1.043 mmol) in toluene (1.739 ml) in a pressure tube was added triphenylphosphine (0.274 g, 1.043 mmol) and the tube was sealed and stirred at 100° C. The mixture was cooled to room temperature. The product solidified and the solvent was decanted off. The solid was taken up in DCM and concentrated to give the title compound (0.4526 g, 0.790 mmol, 76% yield) as a white foam. LCMS (M+H) calcd for C$_{26}$H$_{24}$BrP: 447.07. found: 448.0.

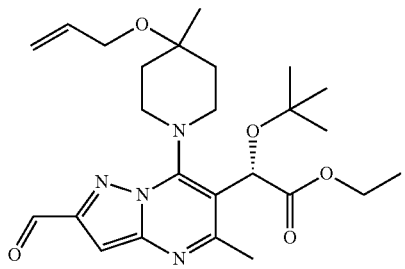 [SMILES: C=CCOC1(C)CCN(c2c([C@H](OC(C)(C)C)C(=O)OCC)c(C)nc3cc(C=O)nn23)CC1]

(S)-Ethyl 2-(7-(4-(allyloxy)-4-methylpiperidin-1-yl)-2-formyl-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.2747 g, 0.579 mmol) in wet DCM (5 mL) was added Dess-Martin periodinane (0.319 g, 0.752 mmol) and the mixture was stirred at room temperature. After 3 h, the solids were removed by filtration. The filtrate was washed with aq Na$_2$S$_2$O$_3$, dried (Na$_2$SO$_4$), filtered and concentrated. The resulting oil was purified by flash chromatography (Biotage; 0%-50% EtOAc/hexane; 10 CV) to give the title compound (0.1962 g, 0.415 mmol, 71.7% yield) as a colorless oil. $^1$H NMR (400 MHz, CDCl$_3$) δ 10.17 (s, 1H), 7.02 (s, 1H), 6.19-5.98 (m, 1H), 5.96-5.76 (m, 1H), 5.57-5.37 (m, 2H), 5.24 (dd, J=10.4, 1.6 Hz, 1H), 4.24 (dd, J=15.9, 7.1 Hz, 2H), 4.03 (d, J=4.9 Hz, 2H), 2.65 (s, 3H), 2.08-1.93 (m, 5H), 1.81-1.66 (m, 1H), 1.37 (s, 3H), 1.29-1.25 (m, 12H). 2 piperidine protons not seen by NMR. LCMS (M+H) calcd for C$_{25}$H$_{37}$N$_4$O$_5$: 473.27. found: 473.3.

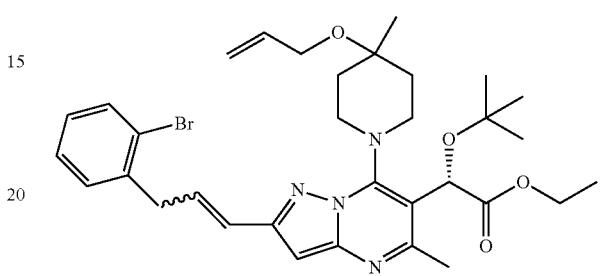

(S)-Ethyl 2-(7-(4-(allyloxy)-4-methylpiperidin-1-yl)-2-(3-(2-bromophenyl)prop-1-en-1-yl)-5-methylpyrazolo[1,5-a]pyrimidin-6-yl)-2-(tert-butoxy)acetate To a suspension of (2-bromophenethyl)triphenylphosphonium iodide (0.121 g, 0.212 mmol) in THF (1 ml) at 0° C. was added sodium hydride (8.68 mg, 0.217 mmol) and the resulting mixture was stirred at rt for 45 min. The mixture was cooled to −78° C. and (S)-ethyl 2-(7-(4-(allyloxy)-4-methylpiperidin-1-yl)-2-formyl-5-methylpyrazolo[1,5-a]pyrimidin-6-yl)-2-(tert-butoxy)acetate (0.050 g, 0.106 mmol) dissolved in THF (1 ml) was added dropwise and the mixture was stirred at −78° C. for 1 h then warmed to room temperature and stirred 2 h. The reaction was quenched with water and the product was extracted with EtOAc. The organic phase was washed with brine, dried (Na$_2$SO$_4$), filtered and concentrated. The residue was purified by flash chromatography (Biotage; 0%-50% EtOAc/hexane; 20 CV) to give the title compound (0.0386 g, 0.060 mmol, 57.0% yield) as a pale yellow oil. 1H NMR (400 MHz, CDCl$_3$) δ 7.65-7.50 (m, 1H), 7.40-7.30 (m, 1H), 7.28-7.20 (m, 1H), 7.17-7.05 (m, 1H), 6.73-6.55 (m, 1H), 6.54-6.44 (m, 1H), 6.11-5.74 (m, 3H), 5.56-4.97 (m, 2H), 4.33-4.11 (m, 4H), 4.07-3.98 (m, 1H), 3.94 (d, J=4.4 Hz, 1H), 2.62 (s, 3H), 2.01-1.79 (m, 3H), 1.77-1.64 (m, 1H), 1.29-1.19 (m, 15H), (4 piperidine protons not visible in NMR). LCMS (M+H) calcd for C$_{33}$H$_{43}$BrN$_4$O$_4$: 640.24. found: 641.4.

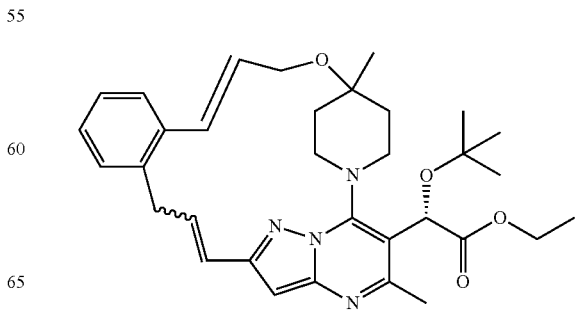

Ethyl (2S)-2-(tert-butoxy)-2-[4,23-dimethyl-22-oxa-1,5,7,8-tetraazapentacyclo[21.2.2.1$^{6,9}$.0$^{2,7}$.0$^{13,18}$]octacosa-2,4,6(28),8,10,13(18),14,16,19-nonaen-3-yl]acetate To a pressure tube flushed with N$_2$ were added (S)-ethyl 2-(7-(4-(allyloxy)-4-methylpiperidin-1-yl)-2-(3-(2-bromophenyl)prop-1-en-1-yl)-5-methylpyrazolo[1,5-a]pyrimidin-6-yl)-2-(tert-butoxy)acetate (0.09 g, 0.141 mmol), acetonitrile (4 ml) and triethylamine (0.196 ml, 1.407 mmol). Added to this solution were triphenylphosphine (0.011 g, 0.042 mmol) and tris(dibenzylideneacetone)dipalladium (0) (0.013 g, 0.014 mmol). The tube was sealed and stirred at 120° C. After stirring for 20 h, the mixture was cooled, filtered and concentrated to give a yellow residue. The residue was purified by flash chromatography (Biotage; 0%-100% EtOAc/hexane; 20 CV) to give the title compound (0.0406 g, 0.073 mmol, 51.6% yield) as a sticky yellow oil. LCMS (M+H) calcd for C$_{33}$H$_{43}$N$_4$O$_4$: 559.32. found: 559.5.

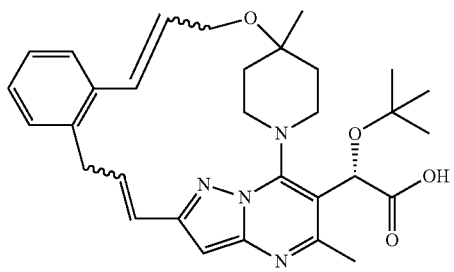 [SMILES: Cc1nc2cc3nn2c(c1[C@H](OC(C)(C)C)C(=O)O)N1CCC(C)(CC1)OCC=Cc1ccccc1CC=C3]

(2S)-2-(tert-Butoxy)-2-[4,23-dimethyl-22-oxa-1,5,7,8-tetraazapentacyclo[21.2.2.1$^{6,9}$.0$^{2,7}$.0$^{13,18}$]octacosa-2,4,6(28),8,10,13(18),14,16,19-nonaen-3-yl]acetic acid To a solution of the ethyl (2S)-2-(tert-butoxy)-2-[4,23-dimethyl-22-oxa-1,5,7,8-tetraazapentacyclo[21.2.2.1$^{6,9}$.0$^{2,7}$.0$^{13,18}$]octacosa-2,4,6(28),8,10,13(18),14,16,19-nonaen-3-yl]acetate (0.0366 g, 0.066 mmol)) in dioxane (1 mL)/MeOH (1 mL) was added 10N sodium hydroxide (0.066 mL, 0.655 mmol) and the mixture was stirred at 70° C. for 1 h. The reaction was cooled and concentrated. The crude material was purified via preparative HPLC to give the title compound as diastereomers. LCMS (M+H) calcd for C$_{31}$H$_{38}$N$_4$O$_4$: 531.29. found: 531.4.

Example 25

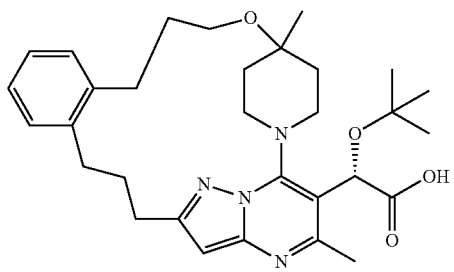 [SMILES: Cc1nc2cc3nn2c(c1[C@H](OC(C)(C)C)C(=O)O)N1CCC(C)(CC1)OCCCc1ccccc1CCC3]

(2S)-2-(tert-Butoxy)-2-{4,23-dimethyl-22-oxa-1,5,7,8-tetraazapentacyclo[21.2.2.1$^{6,9}$.0$^{2,7}$.0$^{13,18}$]octacosa-2,4,6(28),8,13(18),14,16-heptaen-3-yl}acetic acid To a solution of the (2S)-2-(tert-butoxy)-2-[4,23-dimethyl-22-oxa-1,5,7,8-tetraazapentacyclo[21.2.2.1$^{6,9}$.0$^{2,7}$.0$^{13,18}$]octacosa-2,4,6(28),8,10,13(18),14,16,19-nonaen-3-yl]acetic acid (21 mg, 0.040 mmol) and triethylamine (5.52 µl, 0.040 mmol) in MeOH (2 mL) was added palladium on carbon (0.42 mg, 3.96 µmol). The mixture was flushed with hydrogen then stirred under a hydrogen balloon. After 1 h, the mixture was filtered over celite rinsing with MeOH then concentrated. The crude material was purified via preparative HPLC to give the title compound (9.1 mg, 0.016 mmol, 41.3% yield). $^1$H NMR (500 MHz, DMSO-d$_6$) δ 7.21 (d, J=3.4 Hz, 2H), 7.14 (d, J=3.7 Hz, 2H), 6.30 (s, 1H), 5.86 (s, 1H), 4.74-4.59 (m, 1H), 3.77 (t, J=11.4 Hz, 1H), 3.52 (d, J=1.8 Hz, 3H), 3.22-2.94 (m, 5H), 2.90 (s, 3H), 2.72-2.58 (m, 2H), 2.37-2.20 (m, 1H), 2.00-1.54 (m, 7H), 1.38 (s, 1H), 1.17 (br. s., 9H). LCMS (M+H) calcd for C$_{31}$H$_{43}$N$_4$O$_4$: 535.32. found: 535.5.

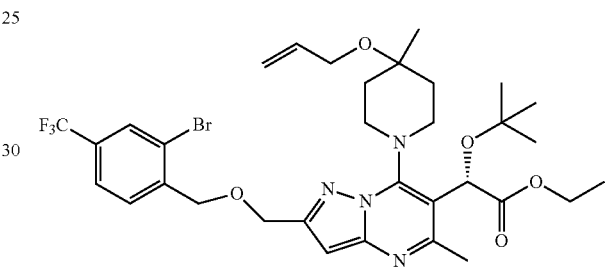

(S)-Ethyl 2-(7-(4-(allyloxy)-4-methylpiperidin-1-yl)-2-(((2-bromo-4-(trifluoromethyl)benzyl)oxy)methyl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.200 g, 0.421 mmol) and 2-bromo-1-(bromomethyl)-4-(trifluoromethyl)benzene (0.268 g, 0.843 mmol) in DMF (1 mL) was added sodium hydride (0.051 g, 1.264 mmol). The mixture was stirred at rt. After 30 min, the reaction was quenched with water and extracted with EtOAc (3×'s). The organic phases were combined and washed with brine, dried, filtered and concentrated. The residue was purified by flash chromatography (Biotage; 0%-100% EtOAc/hexane; 25 CV) to give the title compound (0.200 g, 0.281 mmol, 66.7% yield) as a colorless oil. $^1$H NMR (400 MHz, CDCl$_3$) δ 7.81 (d, J=0.7 Hz, 1H), 7.73 (d, J=8.1 Hz, 1H), 7.59 (dd, J=8.6, 1.0 Hz, 1H), 6.59 (s, 1H), 6.02 (ddt, J=17.0, 10.4, 5.1 Hz, 1H), 5.95-5.85 (m, 1H), 5.53-5.39 (m, 1H), 5.19 (dd, J=10.5, 1.7 Hz, 1H), 4.87 (s, 2H), 4.77 (s, 2H), 4.30-4.14 (m, 2H), 4.02 (d, J=5.1 Hz, 2H), 2.62 (s, 3H), 2.06-1.61 (m, 3H), 1.35 (s, 3H), 1.25 (s, 12H) 5 piperidine protons not visible. LCMS (M+H) calcd for C$_{33}$H$_{43}$BrF$_3$N$_4$O$_5$: 712.33. found: 713.4.

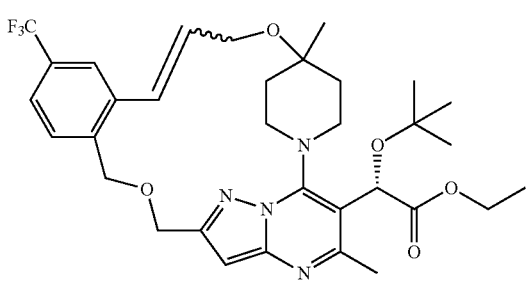 [SMILES: CCOC(=O)[C@@H](OC(C)(C)C)c1c(C)nc2cc3nn2c1N1CCC(C)(CC1)OCC=Cc1cc(C(F)(F)F)ccc1COC3]

Ethyl (2S)-2-(tert-butoxy)-2-[4,23-dimethyl-16-(trifluoromethyl)-11,22-dioxa-1,5,7,8-tetraazapentacyclo[21.2.2.1$^{6,9}$.0$^{2,7}$.0$^{13,18}$]octacosa-2,4,6(28),8,13(18),14,16,19-octaen-3-yl]acetate To a pressure tube flushed with N$_2$ were added (S)-ethyl 2-(7-(4-(allyloxy)-4-methylpiperidin-1-yl)-2-(((2-bromo-4-(trifluoromethyl)benzyl)oxy)methyl)-5-methylpyrazolo[1,5-a]pyrimidin-6-yl)-2-(tert-butoxy)acetate (0.200 g, 0.281 mmol), acetonitrile (8 ml) and triethylamine (0.392 ml, 2.81 mmol). Added to this solution were triphenylphosphine (0.022 g, 0.084 mmol) and tris(dibenzylideneacetone)dipalladium (0) (0.026 g, 0.028 mmol). The tube was sealed and stirred at 120° C. for 23 h. The mixture was cooled, filtered and concentrated to give a yellow residue that was purified by flash chromatography (Biotage; 0%-100% EtOAc/hexane; 20 CV) to give the title compound (0.1115 g, 0.177 mmol, 62.9% yield) as a yellow foam. LCMS (M+H) calcd for C$_{34}$H$_{44}$F$_3$N$_4$O$_4$: 631.31. found: 631.3.

Example 26

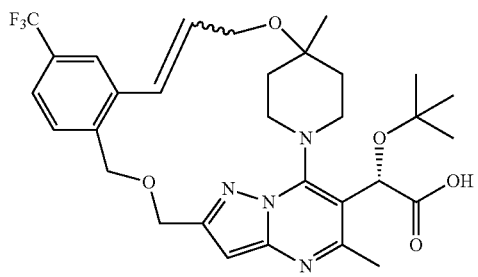 [SMILES: Cc1nc2cc3nn2c(c1[C@H](OC(C)(C)C)C(=O)O)N1CCC(C)(CC1)OCC=Cc1cc(C(F)(F)F)ccc1COC3]

(2S)-2-(tert-Butoxy)-2-[4,23-dimethyl-16-(trifluoromethyl)-11,22-dioxa-1,5,7,8-tetraazapentacyclo[21.2.2.1$^{6,9}$.0$^{2,7}$.0$^{13,18}$]octacosa-2,4,6(28),8,13(18),14,16,19-octaen-3-yl]acetic acid To a solution of the reactant (Intermediate 12) (0.1115 g, 0.177 mmol) in dioxane (2 mL)/MeOH (2 mL) was added 10N sodium hydroxide (0.177 mL, 1.77 mmol) and the mixture was stirred at 70° C. for 45 min. The reaction was cooled and concentrated. The crude material was purified via preparative HPLC to give the title compound (0.010 g, 0.0165 mmol, 9.3% yield). $^1$H NMR (500 MHz, DMSO-d$_6$) δ 7.67-7.61 (m, 1H), 7.61-7.53 (m, 2H), 6.57-6.50 (m, 1H), 6.48 (s, 1H), 5.92 (s, 1H), 4.99 (d, J=2.4 Hz, 1H), 4.83-4.57 (m, 4H), 4.00-3.92 (m, 1H), 3.85 (d, J=7.6 Hz, 1H), 3.00 (d, J=14.0 Hz, 1H), 2.61 (d, J=13.4 Hz, 1H), 2.53 (s, 3H), 1.97-1.65 (m, 4H), 1.39 (s, 3H), 1.21-1.18 (m, 9H). (Two piperidine protons not visible in NMR). LCMS (M+H) calcd for C$_{31}$H$_{38}$F$_3$N$_4$O$_5$: 603.27. found: 603.4.

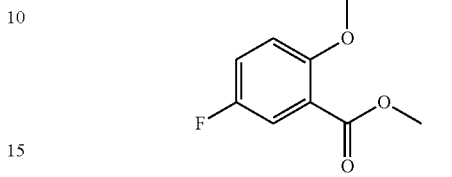

5-Fluoro-2-(pent-4-en-2-yloxy)benzoate

To a solution of methyl 5-fluoro-2-hydroxybenzoate (1.0 g, 5.88 mmol), (R)-(−)-pent-4-en-2-ol (1.210 ml, 11.76 mmol) and triphenylphosphine (2.004 g, 7.64 mmol) in THF (14 ml) was added dropwise DIAD (1.486 ml, 7.64 mmol) and the resulting solution was stirred at rt. After 20 h, the reaction was diluted with Et$_2$O and washed with 1N NaOH, water (3×'s) and brine. The organic phase was dried (Na$_2$SO$_4$), filtered and concentrated. The residue was purified by flash chromatography (Biotage; 0%-40% EtOAc/hexane; 20 CV) to give methyl 5-fluoro-2-(pent-4-en-2-yloxy)benzoate (1.1331 g, 4.76 mmol, 81% yield) as a yellow oil. $^1$H NMR (400 MHz, CDCl$_3$) δ 7.49 (dd, J=8.7, 3.3 Hz, 1H), 7.15 (ddd, J=8.9, 7.7, 3.4 Hz, 1H), 6.96 (dd, J=9.0, 4.2 Hz, 1H), 6.02-5.79 (m, 1H), 5.20-5.06 (m, 2H), 4.50-4.34 (m, 1H), 3.90 (s, 3H), 2.60-2.32 (m, 2H), 1.34 (d, J=6.1 Hz, 3H).

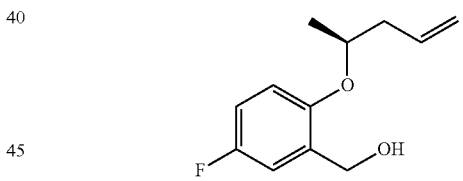

(5-Fluoro-2-(pent-4-en-2-yloxy)phenyl)methanol

To a solution of methyl 5-fluoro-2-(pent-4-en-2-yloxy)benzoate (1.00 g, 4.20 mmol) in THF (10 mL) cooled to 0° C. was added dropwise lithium aluminum hydride (5.04 ml, 5.04 mmol) over 30 min. The resulting mixture was stirred at rt for 2 h. The reaction was diluted with 2 mL THF and cooled to 0° C. and quenched by the dropwise addition of brine. The mixture was further diluted with 5 mL EtOAc and the organic phase was decanted off, dried (Na$_2$SO$_4$), filtered and concentrated to give (5-fluoro-2-(pent-4-en-2-yloxy)phenyl)methanol (0.80 g, 3.81 mmol, 91% yield) as a colorless oil. $^1$H NMR (400 MHz, CDCl$_3$) δ 7.04 (dd, J=8.7, 3.1 Hz, 1H), 6.93 (td, J=8.5, 3.1 Hz, 1H), 6.82 (dd, J=8.9, 4.3 Hz, 1H), 5.86 (ddt, J=17.1, 10.1, 7.1 Hz, 1H), 5.25-5.06 (m, 2H), 4.75-4.54 (m, 2H), 4.54-4.38 (m, 1H), 2.51 (dt, J=13.9, 6.7 Hz, 2H), 1.42-1.31 (m, 3H).

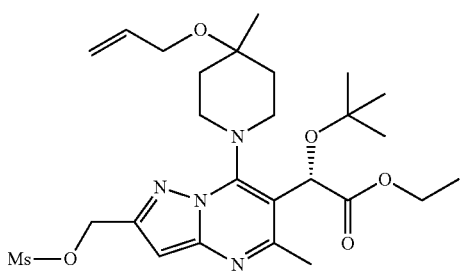 [SMILES: C=CCOC1(C)CCN(c2c([C@H](OC(C)(C)C)C(=O)OCC)c(C)nc3cc(COS(C)(=O)=O)nn23)CC1]

(S)-Ethyl 2-(7-(4-(allyloxy)-4-methylpiperidin-1-yl)-
5-methyl-2-(((methylsulfonyl)oxy)methyl)pyrazolo[,
5-a]pyrimidin-6-yl)-2-(tert-butoxy)acetate To a solution of (S)-ethyl 2-(7-(4-(allyloxy)-4-methylpiperidin-1-yl)-2-(hydroxymethyl)-5-methylpyrazolo[1,5-a]pyrimidin-6-yl)-2-(tert-butoxy)acetate (0.50 g, 1.054 mmol) in DCM (6 ml) cooled to 0° C. were added DMAP (0.013 g, 0.105 mmol) and TEA (0.294 ml, 2.107 mmol) followed by methanesulfonyl chloride (0.098 ml, 1.264 mmol) and the resulting solution was stirred at 0° C. After 45 min, the reaction was diluted with DCM and quenched with sat'd aq NaHCO$_3$. The organic phase was washed with water, dried and concentrated to give (S)-ethyl 2-(7-(4-(allyloxy)-4-methylpiperidin-1-yl)-5-methyl-2-(((methylsulfonyl)oxy)methyl)pyrazolo[1,5-a]pyrimidin-6-yl)-2-(tert-butoxy)acetate (0.62 g, 1.122 mmol, 106% yield) as a pale yellow oil. $^1$H NMR (400 MHz, CDCl$_3$) δ 6.63 (s, 1H), 6.15-5.97 (m, 1H), 5.98-5.81 (m, 1H), 5.55-5.38 (m, 3H), 5.29-5.20 (m, 1H), 4.32-4.11 (m, 2H), 4.02 (d, J=4.9 Hz, 2H), 3.06 (s, 3H), 2.63 (s, 3H), 1.93 (br. s., 4H), 1.35 (s, 3H), 1.29-1.19 (m, 12H).

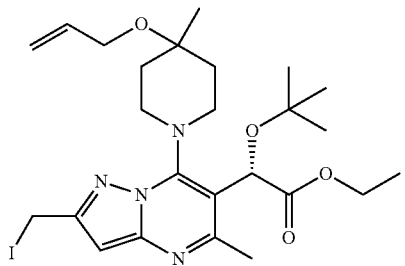 [SMILES: C=CCOC1(C)CCN(c2c([C@H](OC(C)(C)C)C(=O)OCC)c(C)nc3cc(CI)nn23)CC1]

S)-Ethyl 2-(7-(4-(allyloxy)-4-methylpiperidin-1-yl)-
2-(iodomethyl)-5-methylpyrazolo[1,5-a]pyrimidin-6-
yl)-2-(tert-butoxy)acetate To a solution of (S)-ethyl 2-(7-(4-(allyloxy)-4-methylpiperidin-1-yl)-5-methyl-2-(((methylsulfonyl)oxy)methyl)pyrazolo[1,5-a]pyrimidin-6-yl)-2-(tert-butoxy)acetate (0.62 g, 1.122 mmol) in acetone (6 ml) was added sodium iodide (0.673 g, 4.49 mmol) and the mixture was stirred at rt for 45 min. The reaction was diluted with EtOAc and washed with water. The organic phase was dried (Na$_2$SO$_4$), filtered and concentrated. The crude oil was purified by flash chromatography (Biotage; 0%-50% EtOAc/hexane; 20 CV) to give (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.5519 g, 0.944 mmol, 84% yield) as a pale yellow oil. $^1$H NMR (400 MHz, CDCl$_3$) δ 6.53 (s, 1H), 6.16-5.99 (m, 1H), 5.99-5.77 (m, 1H), 5.64-5.39 (m, 1H), 5.32-5.14 (m, 1H), 4.56 (s, 2H), 4.35-4.17 (m, 2H), 4.03 (d, J=4.9 Hz, 2H), 2.59 (s, 3H), 1.93 (br. s., 4H), 1.36 (s, 3H), 1.31-1.18 (m, 12H). 4 piperidine protons not seen. LCMS (M+H) calcd for C$_{25}$H$_{38}$IN$_4$O$_4$: 585.19. found: 585.5.

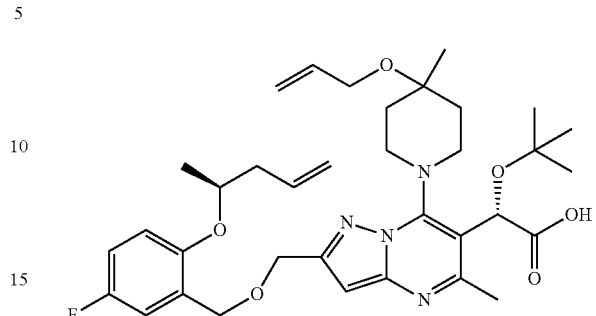

(S)-2-(7-(4-(Allyloxy)-4-methylpiperidin-1-yl)-2-
(((5-fluoro-2-((S)-pent-4-en-2-yloxy)benzyl)oxy)
methyl)-5-methylpyrazolo[1,5-a]pyrimidin-6-yl)-2-
(tert-butoxy)acetic acid To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.05 g, 0.086 mmol) and (S)-(5-fluoro-2-(pent-4-en-2-yloxy)phenyl)methanol (0.022 g, 0.103 mmol) in DMF (1 ml) was added sodium hydride (5.13 mg, 0.128 mmol) and the resulting yellow mixture was stirred at rt. After 5 h, the mixture was diluted with EtOAc and washed with 1N HCl followed by water and brine. The organic phase was dried (Na$_2$SO$_4$), filtered and concentrated. The oil was purified by flash chromatography (Biotage; 0%-10% MeOH/DCM; 10 CV) to give (S)-2-(7-(4-(allyloxy)-4-methylpiperidin-1-yl)-2-(((5-fluoro-2-((S)-pent-4-en-2-yloxy)benzyl)oxy)methyl)-5-methylpyrazolo[1,5-a]pyrimidin-6-yl)-2-(tert-butoxy)acetic acid (20 mg, 0.031 mmol, 36.6% yield) was obtained as an amber oil. $^1$H NMR (400 MHz, CDCl$_3$) δ 7.22 (dd, J=9.0, 2.9 Hz, 1H), 6.89 (dd, J=8.1, 3.2 Hz, 1H), 6.84-6.75 (m, 1H), 6.60 (s, 1H), 6.10-5.95 (m, 1H), 5.89-5.75 (m, 1H), 5.52-5.38 (m, 1H), 5.23-4.99 (m, 4H), 4.80 (s, 2H), 4.66 (s, 2H), 4.45-4.28 (m, 1H), 4.06-3.93 (m, 2H), 2.71-2.54 (m, 3H), 2.47 (d, J=5.9 Hz, 1H), 2.40-2.30 (m, 1H), 2.08-1.56 (m, 4H), 1.49-1.01 (m, 15H). LCMS (M+H) calcd for C$_{35}$H$_{48}$FN$_4$O$_6$: 639.35. found: 639.2.

Example 27

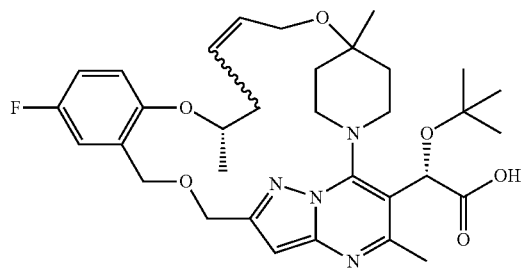 [SMILES: Cc1nc2cc3nn2c(c1[C@H](OC(C)(C)C)C(=O)O)N1CCC(C)(CC1)OCC=CC[C@H](C)Oc1ccc(F)cc1COC3]

(2S)-2-(tert-Butoxy)-2-[(20S)-15-fluoro-4,20,26-
trimethyl-11,19,25-trioxa-1,5,7,8-tetraazapentacyclo
[24.2.2.1$^{6,9}$.0$^{2,7}$.0$^{13,18}$]hentriaconta-2,4,6(31),8,13,
15,17,22-octaen-3-yl]acetic acid To a solution of (S)-2-(7-(4-(allyloxy)-4-methylpiperidin-1-yl)-2-(((5-fluoro-2-((S)-pent-4-en-2-yloxy)benzyl)oxy)

methyl)-5-methylpyrazolo[1,5-a]pyrimidin-6-yl)-2-(tert-butoxy)acetic acid (20 mg, 0.031 mmol) in DCE (75 mL) were added (1,3-dimesitylimidazolidin-2-ylidene)(2-isopropoxybenzylidene)ruthenium(VI) chloride/Hoveyda-Grubbs II (4.90 mg, 7.83 μmol) and copper(I) iodide (5.96 mg, 0.031 mmol) and the mixture was stirred at 90° C. After 3 h, the reaction was concentrated. The crude material was purified via preparative HPLC to afford (2S)-2-(tert-butoxy)-2-[(20S, 22Z)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6 (31),8,13,15,17,22-octaen-3-yl]acetic acid (9.8 mg, 0.016 mmol, 50.2% yield). $^1$H NMR (500 MHz, DMSO-d$_6$) δ 7.19-6.92 (m, 3H), 6.57-6.38 (m, 1H), 6.11-5.87 (m, 1H), 5.81-5.64 (m, 1H), 5.59-5.46 (m, 1H), 4.94-4.47 (m, 4H), 4.45-4.31 (m, 1H), 4.01-3.78 (m, 1H), 3.74-3.47 (m, 1H), 2.51 (br. s., 13H), 1.71-1.49 (m, 1H), 1.33-1.06 (m, 14H). LCMS (M+H) calcd for C$_{33}$H$_{44}$FN$_4$O$_6$: 611.32. found: 611.5.

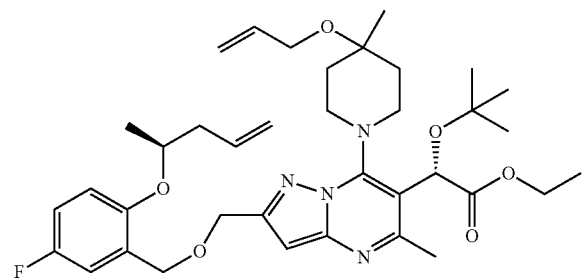 [SMILES: C=CCOC1(C)CCN(c2c([C@H](OC(C)(C)C)C(=O)OCC)c(C)nc3cc(COCc4cc(F)ccc4O[C@@H](C)CC=C)nn23)CC1]

(S)-Ethyl 2-(7-(4-(allyloxy)-4-methylpiperidin-1-yl)-2-(((5-fluoro-2-((S)-pent-4-en-2-yloxy)benzyl)oxy)methyl)-5-methylpyrazolo[1,5-a]pyrimidin-6-yl)-2-(tert-butoxy)acetate To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.50 g, 0.855 mmol) and (S)-(5-fluoro-2-(pent-4-en-2-yloxy)phenyl)methanol (0.216 g, 1.027 mmol) in DMF (10 ml) was added sodium hydride (0.051 g, 1.283 mmol) and the resulting yellow mixture was stirred at rt. After 3 h, the mixture was diluted with EtOAc and washed with 1N HCl followed by water then brine. The organic phase was dried (Na$_2$SO$_4$), filtered and concentrated. The residue was purified by flash chromatography (Biotage; 0%-100% EtOAc/hexane; 10 CV) to give (S)-ethyl 2-(7-(4-(allyloxy)-4-methylpiperidin-1-yl)-2-(((5-fluoro-2-((S)-pent-4-en-2-yloxy)benzyl)oxy)methyl)-5-methylpyrazolo[1,5-a]pyrimidin-6-yl)-2-(tert-butoxy)acetate (0.1481 g, 0.222 mmol, 26.0% yield) as a red oil. LCMS (M+H) calcd for C$_{37}$H$_{52}$FN$_4$O$_6$: 667.38. found: 667.6.

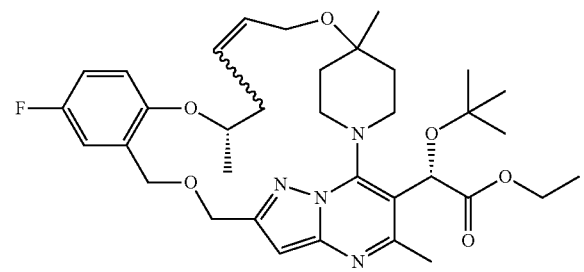 [SMILES: CCOC(=O)[C@@H](OC(C)(C)C)c1c(C)nc2cc3nn2c1N1CCC(C)(CC1)OCC=CC[C@H](C)Oc1ccc(F)cc1COC3]

Ethyl (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetate To a solution of (S)-ethyl 2-(7-(4-(allyloxy)-4-methylpiperidin-1-yl)-2-(((5-fluoro-2-((S)-pent-4-en-2-yloxy)benzyl)oxy)methyl)-5-methylpyrazolo[1,5-a]pyrimidin-6-yl)-2-(tert-butoxy)acetate (0.1481 g, 0.222 mmol) in DCE (500 mL) were added (1,3-dimesitylimidazolidin-2-ylidene)(2-isopropoxybenzylidene)ruthenium(VI) chloride (0.035 g, 0.056 mmol) and copper(I) iodide (0.042 g, 0.222 mmol) and the resulting solution was stirred at 90° C. for 3 h. The mixture was cooled to rt and concentrated. The residue was purified by flash chromatography (Biotage; 0%-100% EtOAc/hexane; 20 CV) to give ethyl (2S)-2-(tert-butoxy)-2-[(20S,22Z)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8, 13(18),14,16,22-octaen-3-yl]acetate: (0.0461 g, 0.072 mmol, 32.5% yield) as a pale brown foam. LCMS (M+H) calcd for C$_{35}$H$_{48}$FN$_4$O$_6$: 639.35. found: 639.5.

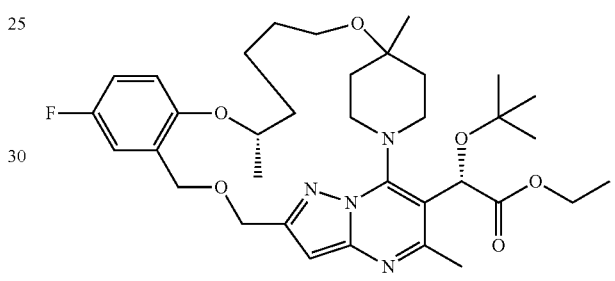

Ethyl (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetate To a solution of ethyl (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8, 13(18),14,16,22-octaen-3-yl]acetate: (46.1 mg, 0.072 mmol) in ethanol (3 mL) were added (1,3-dimesitylimidazolidin-2-ylidene)(2-isopropoxybenzylidene)ruthenium(VI) chloride (9.04 mg, 0.014 mmol) then sodium borohydride (13.65 mg, 0.361 mmol) and the mixture was stirred at rt. After 10 min, LCMS indicated completion of reaction. The reaction was quenched with water and extracted with EtOAc. The organic phase was dried (Na$_2$SO$_4$), filtered and concentrated. The crude was purified by flash chromatography (Biotage; 0%-100% EtOAc/hexane; 20 CV) to give ethyl (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetate (36.5 mg, 0.057 mmol, 79% yield) as a colorless oil. $^1$H NMR (400 MHz, CDCl$_3$) δ δ 7.15 (dd, J=9.0, 3.2 Hz, 1H), 6.89 (td, J=8.6, 3.2 Hz, 1H), 6.79 (dd, J=8.9, 4.5 Hz, 1H), 6.56 (s, 1H), 5.97 (s, 1H), 4.93 (d, J=12.2 Hz, 1H), 4.75-4.66 (m, 3H), 4.56-4.39 (m, 2H), 4.29-4.15 (m, 2H), 3.97-3.81 (m, 1H), 3.56-3.34 (m, 2H), 3.14 (d, J=11.7 Hz, 1H), 2.83 (d, J=12.2 Hz, 1H), 2.61 (s, 3H), 2.03-1.53 (m, 10H), 1.34-1.13 (m, 18H). LCMS (M+H) calcd for C$_{35}$H$_{50}$FN$_4$O$_6$: 641.37. found: 641.6.

Example 28

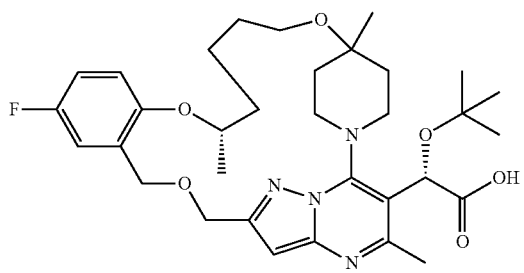 [SMILES: Cc1nc2cc3nn2c(c1[C@H](OC(C)(C)C)C(=O)O)N1CCC(C)(CC1)OCCCC[C@H](C)Oc1ccc(F)cc1COC3]

(2S)-2-(tert-Butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid To a solution of ethyl (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetate (36.5 mg, 0.057 mmol) in Methanol (3 mL) was added sodium hydroxide/1N (0.285 mL, 0.285 mmol) and the resulting solution was refluxed. After 3 h, The mixture was cooled and concentrated. The residue was purified by prep HPLC to afford (2S)-2-(tert-butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid (4.2 mg, 11.31% yield). $^1$H NMR (500 MHz, DMSO-d$_6$) δ 7.96 (s, 1H), 7.13 (dd, J=9.0, 2.8 Hz, 1H), 7.06-6.89 (m, 2H), 6.49 (s, 1H), 5.57 (s, 1H), 4.87 (d, J=12.5 Hz, 1H), 4.69-4.45 (m, 4H), 4.32 (t, J=11.6 Hz, 1H), 3.70-3.19 (m, 5H), 2.80 (br. s., 1H), 2.49-2.44 (m, 3H), 1.88 (d, J=14.3 Hz, 2H), 1.74-1.46 (m, 8H), 1.22-1.05 (m, 15H).

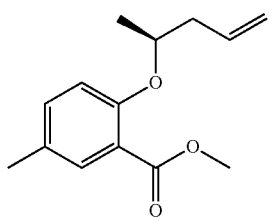 [SMILES: C=CC[C@H](C)Oc1ccc(C)cc1C(=O)OC]

(S)-Methyl 5-methyl-2-(pent-4-en-2-yloxy)benzoate

To a solution of methyl 2-hydroxy-5-methylbenzoate (1.0 g, 6.02 mmol) in THF (14 ml) were added (R)-(−)-pent-4-en-2-ol (1.037 g, 12.04 mmol) and triphenylphosphine (2.052 g, 7.82 mmol). DIAD (1.521 ml, 7.82 mmol) was added dropwise (exotherm) and the mixture was stirred at rt. After 4.5 h, the mixture was diluted with Et$_2$O and washed with 1N NaOH followed by water (3×'s) then brine, dried (Na$_2$SO$_4$), filtered and concentrated. The yellow oil was purified by flash chromatography (Biotage; 0%-100% EtOAc/hexane; 20 CV) to give (S)-methyl 5-methyl-2-(pent-4-en-2-yloxy)benzoate (1.2664 g, 5.41 mmol, 90% yield) as a yellow oil. $^1$H NMR (400 MHz, CDCl$_3$) δ 7.58 (d, J=2.2 Hz, 1H), 7.23 (dd, J=8.3, 2.0 Hz, 1H), 6.90 (d, J=8.6 Hz, 1H), 6.03-5.77 (m, 1H), 5.21-4.99 (m, 2H), 4.61-4.35 (m, 1H), 3.89 (s, 3H), 2.60-2.46 (m, 1H), 2.46-2.34 (m, 1H), 2.34-2.25 (m, 3H), 1.34 (d, J=6.1 Hz, 3H).

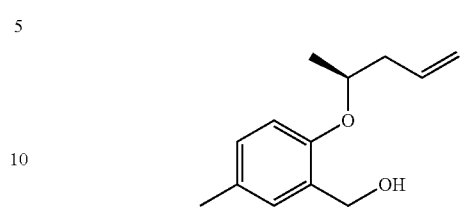

(S)-(5-Methyl-2-(pent-4-en-2-yloxy)phenyl)methanol

To a solution of (S)-methyl 5-methyl-2-(pent-4-en-2-yloxy)benzoate (1.2664 g, 5.41 mmol) in THF (15 ml) cooled to 0° C. was added dropwise lithium aluminum hydride (3.25 ml, 6.49 mmol). The mixture was stirred at rt for 2 h then cooled to 0° C. and quenched by the dropwise addition of brine. The mixture was partitioned between EtOAc and water. The organic phase was washed with brine, dried (Na$_2$SO$_4$), filtered and concentrated to give (S)-(5-methyl-2-(pent-4-en-2-yloxy)phenyl)methanol (0.8702 g, 4.22 mmol, 78% yield) as a colorless oil. $^1$H NMR (400 MHz, CDCl$_3$) δ 7.14-7.01 (m, 2H), 6.80 (d, J=8.1 Hz, 1H), 6.01-5.74 (m, 1H), 5.24-5.04 (m, 2H), 4.76-4.64 (m, 1H), 4.64-4.56 (m, 1H), 4.51 (sxt, J=6.0 Hz, 1H), 2.63-2.48 (m, 2H), 2.48-2.41 (m, 1H), 2.30 (s, 3H), 1.37 (d, J=6.1 Hz, 3H).

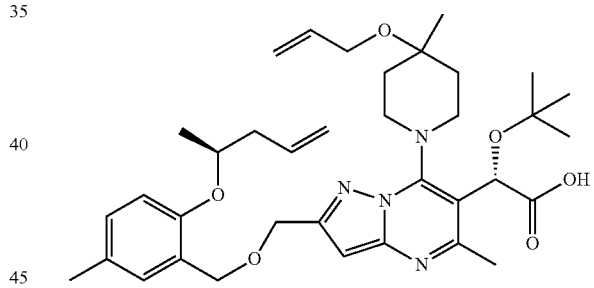

(S)-2-(7-(4-(Allyloxy)-4-methylpiperidin-1-yl)-5-methyl-2-(((5-methyl-2-((S)-pent-4-en-2-yloxy)benzyl)oxy)methyl)pyrazolo[1,5-a]pyrimidin-6-yl)-2-(tert-butoxy)acetic acid To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.20 g, 0.342 mmol) and (S)-(5-methyl-2-(pent-4-en-2-yloxy)phenyl)methanol (0.085 g, 0.411 mmol) in DMF (4 ml) was added sodium hydride (0.021 g, 0.513 mmol) and the mixture was stirred at rt. After 5 h, the reaction was diluted with EtOAc and washed with 1N HCl, water then brine. The organic phase was dried (Na$_2$SO$_4$), filtered and concentrated. The yellow residue was purified by flash chromatography (Biotage; 10% MeOH/DCM; 10 CV) to give (S)-2-(7-(4-(allyloxy)-4-methylpiperidin-1-yl)-5-methyl-2-(((5-methyl-2-((S)-pent-4-en-2-yloxy)benzyl)oxy)methyl)pyrazolo[1,5-a]pyrimidin-6-yl)-2-(tert-butoxy)acetic acid (32.7 mg, 0.052 mmol, 15.05% yield) as a pale yellow oil. LCMS (M+H) calcd for $C_{36}H_{51}N_4O_6$: 635.38. found: 635.5.

Example 29

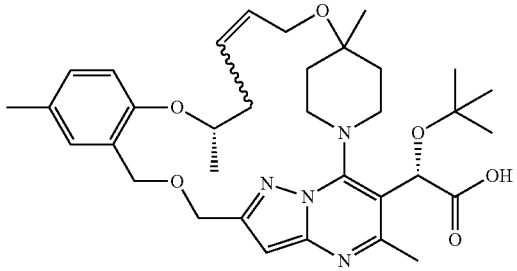 [SMILES: Cc1ccc2c(c1)COCc1cc3nc(C)c([C@H](OC(C)(C)C)C(=O)O)c(n3n1)N1CCC(C)(CC1)OCC=CC[C@H](C)O2]

(2S)-2-(tert-Butoxy)-2-[(20S)-4,15,20,26-tetramethyl-11,19,25-trioxa-1,5,7,8-tetraazapentacyclo [24.2.2.1$^{6,9}$.0$^{2,7}$.0$^{13,18}$]hentriaconta-2,4,6(31),8,13, 15,17,22-octaen-3-yl]acetic acid To a solution of (S)-2-(7-(4-(allyloxy)-4-methylpiperidin-1-yl)-5-methyl-2-(((5-methyl-2-((S)-pent-4-en-2-yloxy)benzyl)oxy)methyl)pyrazolo[1,5-a]pyrimidin-6-yl)-2-(tert-butoxy)acetic acid (32.7 mg, 0.052 mmol) in DCE (4 mL) were added Hoveyda-Grubbs catalyst 2nd generation (8.07 mg, 0.013 mmol) and copper(I) iodide (9.81 mg, 0.052 mmol) and the mixture was stirred at 90° C. After 3 h, the mixture was cooled to rt and concentrated. The crude material was purified via preparative HPLC to give (2S)-2-(tert-butoxy)-2-[(20S)-4,15,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6 (31),8,13,15,17,22-octaen-3-yl]acetic acid (2.1 mg, 5.64% yield). $^1$H NMR (500 MHz, DMSO-d$_6$) δ 7.10 (s, 1H), 7.03 (d, J=6.6 Hz, 1H), 6.88 (d, J=8.4 Hz, 1H), 6.52 (s, 1H), 6.08-5.93 (m, 1H), 5.78 (s, 1H), 5.75-5.67 (m, 1H), 4.82 (d, J=12.1 Hz, 1H), 4.71-4.56 (m, 4H), 4.56-4.39 (m, 2H), 4.01-3.79 (m, 2H), 3.73 (t, J=11.2 Hz, 1H), 3.35 (br. s., 1H), 3.17 (br. s., 1H), 2.74-2.59 (m, 1H), 2.45-2.31 (m, 2H), 2.29-2.14 (m, 5H), 1.89 (t, J=12.5 Hz, 2H), 1.68 (td, J=12.8, 4.0 Hz, 1H), 1.56 (td, J=13.0, 4.4 Hz, 1H), 1.26-1.19 (m, 6H), 1.19-1.01 (m, 9H). LCMS (M+H) calcd for $C_{14}H_{20}FN_3O_4S$: 607.35. found: 607.4.

Example 30

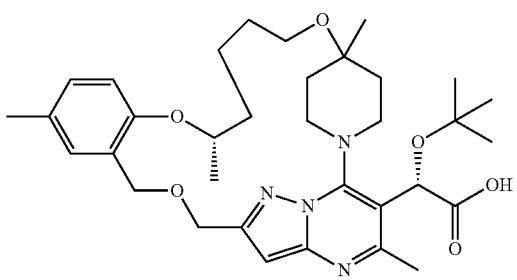 [SMILES: Cc1ccc2c(c1)COCc1cc3nc(C)c([C@H](OC(C)(C)C)C(=O)O)c(n3n1)N1CCC(C)(CC1)OCCCC[C@H](C)O2]

(2S)-2-(tert-Butoxy)-2-[(20S)-4,15,20,26-tetramethyl-11,19,25-trioxa-1,5,7,8-tetraazapentacyclo [24.2.2.1$^{6,9}$.0$^{2,7}$.0$^{13,18}$]hentriaconta-2,4,6(31),8,13, 15,17-heptaen-3-yl]acetic To a solution of (2S)-2-(tert-butoxy)-2-[(20S)-4,15,20,26-tetramethyl-11,19,25-trioxa-1,5,7,8-tetraazapentacyclo [24.2.2.1$^{6,9}$.0$^{2,7}$.0$^{13,18}$]hentriaconta-2,4,6(31),8,13,15,17, 22-octaen-3-yl]acetic acid (0.020 g, 0.033 mmol) in ethanol (1 mL) was added Hoveyda-Grubbs catalyst 2nd generation (4.13 mg, 6.59 μmol). Sodium borohydride (6.24 mg, 0.165 mmol) was added and the mixture was stirred at rt. After 45 min, the reaction was quenched by careful addition of water. The product was extracted with EtOAc, dried (Na$_2$SO$_4$), filtered and concentrated. The crude material was purified via preparative HPLC to afford (2S)-2-(tert-butoxy)-2-[(20S)-4, 15,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15, 17-heptaen-3-yl]acetic acid (2.1 mg, 9.94% yield). $^1$H NMR (500 MHz, DMSO-d$_6$) δ 7.14 (s, 1H), 7.04-6.95 (m, 1H), 6.86 (d, J=8.4 Hz, 1H), 6.42 (s, 1H), 4.83 (d, J=12.5 Hz, 1H), 4.62-4.42 (m, 3H), 4.39-4.26 (m, 1H), 3.47-3.31 (m, 3H), 2.85-2.74 (m, 1H), 2.64 (br. s., 1H), 2.42-2.33 (m, 1H), 2.23 (s, 3H), 2.02-1.30 (m, 14H), 1.28-0.96 (m, 15H). LCMS (M+H) calcd for $C_{34}H_{49}N_4O_6$: 609.36. found: 609.4.

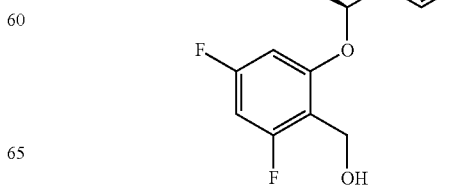

(S)-2,4-Difluoro-6-(pent-4-en-2-yloxy)benzaldehyde

To a solution of 2,4-difluoro-6-hydroxybenzaldehyde (1.0 g, 6.33 mmol) in THF (14 ml) were added (R)-(−)-pent-4-en-2-ol (1.090 g, 12.65 mmol) and triphenylphosphine (2.157 g, 8.22 mmol). To this mixture was added dropwise DIAD (1.599 ml, 8.22 mmol) (exotherm) and stirred at rt. After 20 h, the mixture was diluted with Et$_2$O and washed with 1N NaOH followed by water (3×'s) then brine, dried (Na$_2$SO$_4$), filtered and concentrated. The crude was purified by flash chromatography (Biotage; 0%-50% EtOAc/hexane; 10 CV) to give (S)-2,4-difluoro-6-(pent-4-en-2-yloxy)benzaldehyde (0.3394 g, 1.500 mmol, 23.72% yield) as a pale yellow oil. $^1$H NMR (400 MHz, CDCl$_3$) δ: 10.33 (s, 1H), 6.67-6.32 (m, 2H), 6.04-5.63 (m, 1H), 5.32-5.00 (m, 2H), 4.66-4.40 (m, 1H), 2.68-2.28 (m, 2H), 1.41 (d, J=6.1 Hz, 3H).

(S)-(2,4-Difluoro-6-(pent-4-en-2-yloxy)phenyl)methanol

To a solution of (S)-2,4-difluoro-6-(pent-4-en-2-yloxy)benzaldehyde (0.3394 g, 1.500 mmol) in THF (4 ml) at 0° C. was added dropwise, lithium aluminum hydride (0.900 ml, 1.800 mmol). The resulting mixture was stirred at rt for 2 h. The mixture was cooled to 0° C. and quenched dropwise with brine then diluted with EtOAc and water. The organic phase was washed with brine, dried ($Na_2SO_4$) and concentrated. The oil was purified by flash chromatography (Biotage; 0%-50% EtOAc/hexane; 10 CV) to give (S)-(2,4-difluoro-6-(pent-4-en-2-yloxy)phenyl)methanol (0.1344 g, 0.589 mmol, 39.2% yield) as a colorless oil. $^1$H NMR (400 MHz, $CDCl_3$) δ: 6.59-6.28 (m, 2H), 6.07-5.71 (m, 1H), 5.30-5.02 (m, 2H), 4.69 (d, J=5.6 Hz, 2H), 4.49 (sxt, J=6.0 Hz, 1H), 2.61-2.39 (m, 2H), 2.32 (t, J=6.8 Hz, 1H), 1.40 (d, J=6.1 Hz, 3H).

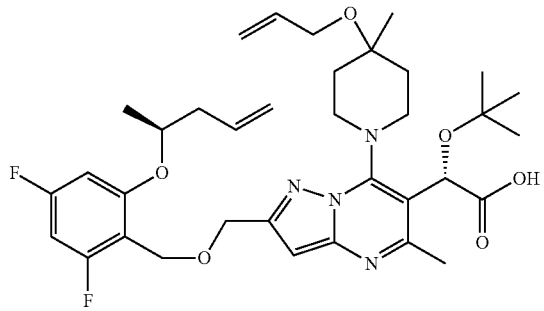 [SMILES: C=CCOC1(C)CCN(c2c([C@H](OC(C)(C)C)C(=O)O)c(C)nc3cc(COCc4c(F)cc(F)cc4O[C@@H](C)CC=C)nn23)CC1]

(S)-2-(7-(4-(Allyloxy)-4-methylpiperidin-1-yl)-2-(((2,4-difluoro-6-((S)-pent-4-en-2-yloxy)benzyl)oxy)methyl)-5-methylpyrazolo[1,5-a]pyrimidin-6-yl)-2-(tert-butoxy)acetic acid To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.2 g, 0.342 mmol) and (S)-(2,4-difluoro-6-(pent-4-en-2-yloxy)phenyl)methanol (0.094 g, 0.411 mmol) in DMF (1 mL) was added sodium hydride (0.021 g, 0.513 mmol) and the mixture was stirred at rt. After 4 h, the mixture was diluted with EtOAc and washed with water and brine. The organic phase was dried ($Na_2SO_4$), filtered and concentrated and purified by Prep HPLC: to afford (S)-2-(7-(4-(allyloxy)-4-methylpiperidin-1-yl)-2-(((2,4-difluoro-6-((S)-pent-4-en-2-yloxy)benzyl)oxy)methyl)-5-methylpyrazolo[1,5-a]pyrimidin-6-yl)-2-(tert-butoxy)acetic acid (0.030 g, 0.046 mmol, 13.35% yield) as a colorless oil. LCMS (M+H) calcd for $C_{35}H_{47}F_2N_4O_6$: 657.34. found: 657.5.

Example 31

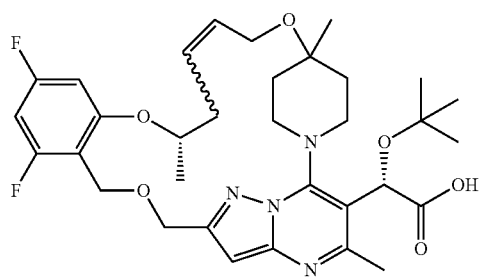 [SMILES: Cc1nc2cc3nn2c(c1[C@H](OC(C)(C)C)C(=O)O)N1CCC(C)(CC1)OCC=CC[C@H](C)Oc1cc(F)cc(F)c1COC3]

(2S)-2-(tert-Butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid To a solution of (S)-2-(7-(4-(allyloxy)-4-methylpiperidin-1-yl)-2-(((2,4-difluoro-6-((S)-pent-4-en-2-yloxy)benzyl)oxy)methyl)-5-methylpyrazolo[1,5-a]pyrimidin-6-yl)-2-(tert-butoxy)acetic acid (0.030 g, 0.046 mmol) in DCE (4 mL) were added Hoveyda-Grubbs catalyst 2nd generation (7.16 mg, 0.011 mmol) and copper(I) iodide (8.70 mg, 0.046 mmol) and the mixture was stirred at 90° C. After 1.5 h, the mixture was cooled to rt and filtered and concentrated. The crude material was purified via preparative HPLC to afford (2S)-2-(tert-butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid (2.4 mg, 5.67% yield). $^1$H NMR (500 MHz, DMSO-$d_6$) δ: 6.91 (d, J=11.7 Hz, 1H), 6.77 (t, J=9.5 Hz, 1H), 6.51 (s, 1H), 6.09-5.95 (m, 1H), 5.87 (d, J=8.1 Hz, 1H), 5.81-5.62 (m, 1H), 4.81-4.61 (m, 4H), 4.57-4.39 (m, 2H), 3.96-3.70 (m, 3H), 2.61-2.39 (m, 7H), 1.96-1.79 (m, 2H), 1.75-1.61 (m, 1H), 1.61-1.46 (m, 1H), 1.29 (s, 1H), 1.24-1.19 (m, 3H), 1.18-1.12 (m, 9H). LCMS (M+H) calcd for $C_{33}H_{43}F_2N_4O_6$: 629.31. found: 629.3.

Example 32

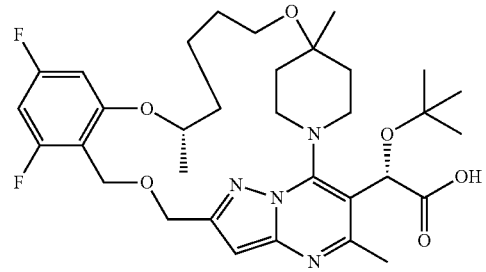 [SMILES: Cc1nc2cc3nn2c(c1[C@H](OC(C)(C)C)C(=O)O)N1CCC(C)(CC1)OCCCC[C@H](C)Oc1cc(F)cc(F)c1COC3]

(2S)-2-(tert-Butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid To a solution of (2S)-2-(tert-butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid (0.020 g, 0.032 mmol) in ethanol (0.5 mL) were added Hoveyda-Grubbs catalyst 2nd generation (3.99 mg, 6.36 μmol) and sodium borohydride (6.02 mg, 0.159 mmol) and the mixture was stirred at rt. After 30 min, the mixture was quenched with water and the product was extracted with EtOAc. The organic phase was dried ($Na_2SO_4$), filtered and concentrated. The crude material was purified via preparative HPLC to afford (2S)-2-(tert-Butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid (3.9 mg, 12.83% yield). $^1$H NMR (500 MHz, DMSO-$d_6$) δ: 6.92 (d, J=11.7 Hz, 1H), 6.77 (t, J=9.0 Hz, 1H), 6.42 (s, 1H), 4.83-4.54 (m, 4H), 4.49-4.24 (m, 2H), 3.61 (dd, J=10.5, 4.6 Hz, 2H), 3.37 (br. s., 2H), 2.59 (d, J=9.9 Hz, 1H), 2.33-1.97 (m, 4H), 1.93 (br. s., 1H), 1.88-1.41 (m, 9H), 1.31-1.06 (m, 15H). LCMS (M+H) calcd for $C_{33}H_{45}F_2N_4O_6$: 631.33. found: 631.4.

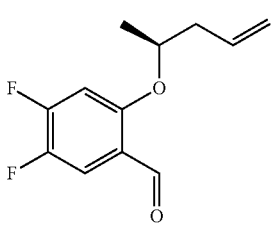

(S)-4,5-Difluoro-2-(pent-4-en-2-yloxy)benzaldehyde

To a solution of 4,5-difluoro-2-hydroxybenzaldehyde (1.0 g, 6.33 mmol) in THF (14 ml) were added (R)-(–)-pent-4-en-2-ol (1.090 g, 12.65 mmol) and triphenylphosphine (2.157 g, 8.22 mmol). DIAD (1.599 ml, 8.22 mmol) was added dropwise (exotherm) and the mixture was stirred at rt. After 1.5 h, the mixture was diluted with Et$_2$O and washed with 1N NaOH followed by water (3×'s) then brine, dried (Na$_2$SO$_4$), filtered and concentrated. The yellow oil was purified by flash chromatography (Biotage; 0%-100% EtOAc/hexane; 20 CV) to give (S)-4,5-difluoro-2-(pent-4-en-2-yloxy)benzaldehyde (0.1295 g, 0.572 mmol, 9.05% yield) as a yellow oil. $^1$H NMR (400 MHz, CDCl$_3$) δ 10.36 (d, J=3.2 Hz, 1H), 7.76-7.55 (m, 1H), 6.83 (dd, J=11.9, 6.0 Hz, 1H), 6.04-5.67 (m, 1H), 5.23-5.06 (m, 2H), 4.48 (sxt, J=6.0 Hz, 1H), 2.71-2.35 (m, 2H), 1.41 (d, J=6.1 Hz, 3H).

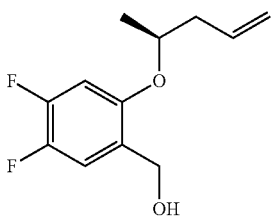 [SMILES: C=CC[C@H](C)Oc1cc(F)c(F)cc1CO]

(S)-(4,5-Difluoro-2-(pent-4-en-2-yloxy)phenyl)methanol

To a solution of (S)-4,5-difluoro-2-(pent-4-en-2-yloxy)benzaldehyde (0.1295 g, 0.572 mmol) in THF (2 ml) at 0° C. was added dropwise lithium aluminum hydride (0.343 ml, 0.687 mmol). The mixture was stirred at rt for 2 h then cooled to 0° C. and quenched by the dropwise addition of brine. The mixture was partitioned between EtOAc and water. The organic phase was washed with brine, dried (Na$_2$SO$_4$), filtered and concentrated to give (S)-(4,5-difluoro-2-(pent-4-en-2-yloxy)phenyl)methanol (0.1088 g, 0.477 mmol, 83% yield) as a yellow oil. $^1$H NMR (400 MHz, CDCl$_3$) δ 7.15 (dd, J=10.4, 9.2 Hz, 1H), 6.72 (dd, J=12.0, 6.6 Hz, 1H), 5.99-5.70 (m, 1H), 5.24-5.07 (m, 2H), 4.75-4.49 (m, 2H), 4.41 (sxt, J=6.0 Hz, 1H), 2.60-2.35 (m, 2H), 2.26 (t, J=6.5 Hz, 1H), 1.36 (d, J=6.1 Hz, 3H).

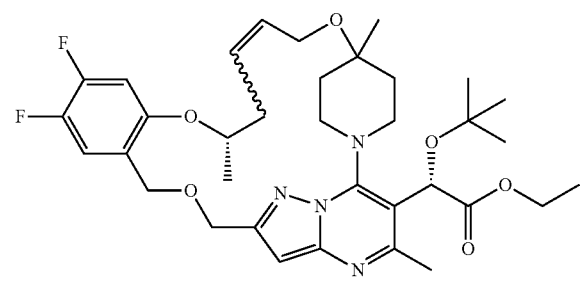 [SMILES: CCOC(=O)[C@@H](OC(C)(C)C)c1c(C)nc2cc3nn2c1N1CCC(C)(CC1)OCC=CC[C@H](C)Oc1cc(F)c(F)cc1COC3]

Ethyl (2S)-2-(tert-butoxy)-2-[(20S,22Z)-15,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetate To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.10 g, 0.171 mmol) and (S)-(4,5-difluoro-2-(pent-4-en-2-yloxy)phenyl)methanol (0.047 g, 0.205 mmol) in DMF (2 mL) was added sodium hydride (10.26 mg, 0.257 mmol) and the mixture was stirred at rt. After stirring for 4 h, the mixture was diluted with EtOAc and washed with 1N HCl followed by water and brine. The organic phase was dried (Na$_2$SO$_4$), filtered and concentrated. The amber oil was purified by flash chromatography (Biotage; 10% MeOH/DCM; 10 CV). The resulting impure amber oil (11.4 mg, 0.017 mmol) was taken up in DCE (4 mL). Hoveyda-Grubbs catalyst 2nd generation (2.72 mg, 4.34 µmol) then copper(I) iodide (3.31 mg, 0.017 mmol) were added and the mixture was stirred at 90° C. After 3 h, the mixture was cooled to rt and filtered and concentrated. The residue was purified by prep HPLC to give ethyl (2S)-2-(tert-butoxy)-2-[(20S,22Z)-15,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetate (3.0 mg, 4.57 µmol, 27% yield). LCMS (M+H) calcd for C$_{35}$H$_{47}$F$_2$N$_4$O$_6$: 657.34. found: 657.5.

Example 33

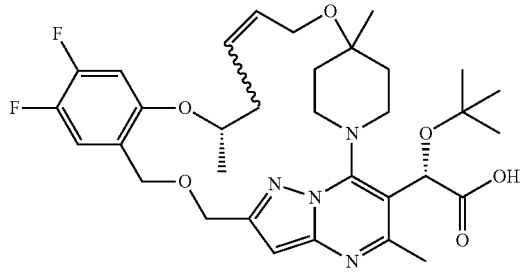 [SMILES: Cc1nc2cc3nn2c(c1[C@H](OC(C)(C)C)C(=O)O)N1CCC(C)(CC1)OCC=CC[C@H](C)Oc1cc(F)c(F)cc1COC3]

(2S)-2-(tert-Butoxy)-2-[(20S)-15,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid To a solution of Intermediate 18 (3.0 mg, 4.57 µmol) in Dioxane (0.25 mL) and MeOH (0.250 mL) was added sodium hydroxide (4.57 µl, 0.046 mmol) and the mixture was stirred at 70° C. After 45 min the mixture was cooled to rt. The crude material was purified via preparative HPLC to give (2S)-2-(tert-butoxy)-2-[(20S)-15,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid (2.9 mg, 4.57 µmol, 100% yield). $^1$H NMR (500 MHz, DMSO-d$_6$) δ 7.33 (d, J=8.4 Hz, 1H), 7.07 (s, 1H), 6.95 (d, J=8.4 Hz, 1H), 6.46 (s, 1H), 5.51 (br. s., 1H), 4.84 (d, J=12.5 Hz, 1H), 4.71-4.61 (m, 1H), 4.61-4.52 (m, 3H), 4.39-4.23 (m, 1H), 3.58 (d, J=11.4 Hz, 4H), 2.49 s, 3H), 1.77-1.42 (m, 8H), 1.21-1.15 (m, 6H), 1.13 (s, 9H). LCMS (M+H) calcd for $C_{33}H_{42}F_2N_4O_6$: 629.31. found: 629.3.

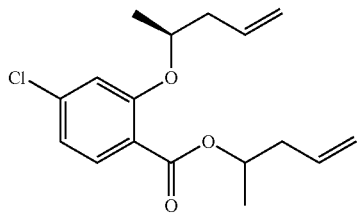 [SMILES: C=CCC(C)OC(=O)c1ccc(Cl)cc1O[C@@H](C)CC=C]

Pent-4-en-2-yl 4-chloro-2-((S)-pent-4-en-2-yloxy)benzoate

To a solution of 4-chloro-2-hydroxybenzoic acid (1.0 g, 5.79 mmol) in THF (14 ml) were added (R)-(−)-pent-4-en-2-ol (1.497 g, 17.38 mmol) and triphenylphosphine (3.95 g, 15.07 mmol). After cooling to 0° C., DIAD (2.93 ml, 15.07 mmol) was added dropwise (exotherm) and the mixture was stirred at rt. After 20 h, the mixture was diluted with $Et_2O$ and washed with 1N NaOH followed by water (3×'s) then brine, dried ($Na_2SO_4$), filtered and concentrated. The crude was purified by flash chromatography (Biotage; 0%-50% EtOAc/hexane; 10 CV) to give pent-4-en-2-yl 4-chloro-2-((S)-pent-4-en-2-yloxy)benzoate (1.3681 g, 4.43 mmol, 76% yield) as a yellow oil. $^1$H NMR (400 MHz, $CDCl_3$) δ 7.69 (d, J=8.6 Hz, 1H), 7.02-6.87 (m, 2H), 6.01-5.76 (m, 2H), 5.37-5.04 (m, 5H), 4.49 (sxt, J=6.0 Hz, 1H), 2.71-2.28 (m, 4H), 1.42-1.32 (m, 6H).

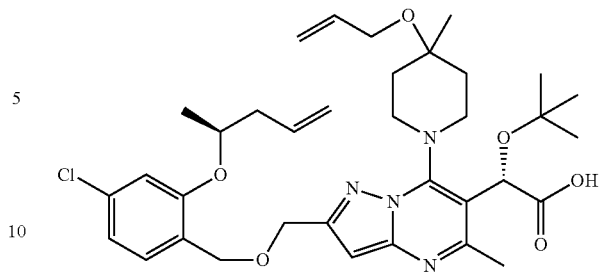

(S)-2-(7-(4-(Allyloxy)-4-methylpiperidin-1-yl)-2-(((4-chloro-2-((S)-pent-4-en-2-yloxy)benzyl)oxy)methyl)-5-methylpyrazolo[1,5-a]pyrimidin-6-yl)-2-(tert-butoxy)acetic acid To a solution of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.200 g, 0.342 mmol) and (S)-(4-chloro-2-(pent-4-en-2-yloxy)phenyl)methanol (0.093 g, 0.411 mmol) in DMF (1 mL) was added sodium hydride (0.021 g, 0.513 mmol) and the mixture was stirred at rt. After 2 h, the mixture was diluted with EtOAc and washed with water and brine. The organic phase was concentrated and purified by prep-HPLC to afford (S)-2-(7-(4-(allyloxy)-4-methylpiperidin-1-yl)-2-(((4-chloro-2-((S)-pent-4-en-2-yloxy)benzyl)oxy)methyl)-5-methylpyrazolo[1,5-a]pyrimidin-6-yl)-2-(tert-butoxy)acetic acid (41.4 mg, 0.063 mmol, 18.47% yield) as an amber glass. LCMS (M+H) calcd for $C_{35}H_{48}ClN_4O_6$: 655.32. found: 655.5.

Example 34

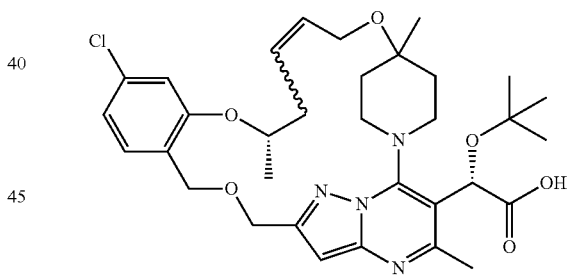

(S)-(4-Chloro-2-(pent-4-en-2-yloxy)phenyl)methanol

To a solution of pent-4-en-2-yl 4-chloro-2-((S)-pent-4-en-2-yloxy)benzoate (1.36 g, 4.40 mmol) in THF (15 ml) that was cooled to 0° C. was added dropwise over 30 min lithium aluminum hydride (2.64 ml, 5.28 mmol) and the resulting mixture was stirred at rt. After 3 h, the mixture was cooled to 0° C. and quenched by dropwise addition of brine. The mixture was diluted with EtOAc and the organic phase was washed with brine, dried ($Na_2SO_4$), filtered and concentrated. The oil was purified by flash chromatography (Biotage; 0%-50% EtOAc/hexane; 10 CV) to give (S)-(4-chloro-2-(pent-4-en-2-yloxy)phenyl)methanol (0.9554 g, 4.21 mmol, 96% yield) as a colorless oil. $^1$H NMR (400 MHz, $CDCl_3$) δ 7.21 (d, J=7.8 Hz, 1H), 6.98-6.88 (m, 1H), 6.88 (d, J=1.7 Hz, 1H), 5.86 (ddt, J=17.1, 10.1, 7.1 Hz, 1H), 5.25-5.06 (m, 2H), 4.75-4.62 (m, 1H), 4.62-4.43 (m, 2H), 2.61-2.40 (m, 2H), 2.34 (t, J=6.5 Hz, 1H), 1.38 (d, J=6.1 Hz, 3H).

(2S)-2-(tert-Butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid To a solution of (S)-2-(7-(4-(allyloxy)-4-methylpiperidin-1-yl)-2-(((4-chloro-2-((S)-pent-4-en-2-yloxy)benzyl)oxy)methyl)-5-methylpyrazolo[1,5-a]pyrimidin-6-yl)-2-(tert-butoxy)acetic acid (41.4 mg, 0.063 mmol) in DCE (2 mL) were added Hoveyda-Grubbs catalyst 2nd generation (9.90 mg, 0.016 mmol) and copper(I) iodide (12.03 mg, 0.063 mmol) and the mixture was stirred at 90° C. After 1.5 h, the mixture was cooled to rt and filtered and concentrated. The crude material was purified via preparative HPLC to afford (2S)-2-(tert-butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid (2.9 mg, 4.62 µmol, 7.32% yield). $^1$H NMR (500 MHz, DMSO-$d_6$) δ 7.31 (d, J=8.1 Hz, 1H), 7.10 (s, 1H), 6.94 (d, J=7.0 Hz, 1H), 6.48 (s, 1H), 6.34 (d, J=5.9 Hz, 1H), 5.65 (br. s., 1H), 4.75 (d, J=11.7 Hz, 1H), 4.67-4.47 (m, 5H), 4.34-4.22 (m, 1H), 3.64 (d, J=12.8 Hz, 1H), 3.39-3.27 (m, 6H), 2.49 (s, 3H), 2.41 (d, J=3.3 Hz, 1H), 2.27-2.15 (m, 1H), 1.82 (d, J=5.5 Hz, 3H), 1.68-1.55 (m, 1H), 1.32 (s, 3H), 1.20 (s, 12H). LCMS (M+H) calcd for $C_{33}H_{44}ClN_4O_6$: 627.29. found: 627.5.

Example 35

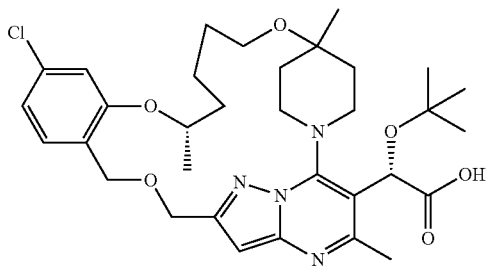 [SMILES: Cc1nc2cc3nn2c(c1[C@H](OC(C)(C)C)C(=O)O)N1CCC(C)(CC1)OCCCC[C@H](C)Oc1cc(Cl)ccc1COC3]

(2S)-2-(tert-Butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid To a solution of (2S)-2-(tert-butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid (0.020 g, 0.032 mmol) in ethanol (1 mL) was added Hoveyda-Grubbs catalyst 2nd generation (4.00 mg, 6.38 µmol). Sodium borohydride (6.03 mg, 0.159 mmol) was added and the mixture was stirred at rt. After 30 min, the reaction was quenched by careful addition of water. The product was extracted with EtOAc, dried (Na$_2$SO$_4$), filtered and concentrated. The crude material was purified via preparative HPLC to afford (2S)-2-(tert-butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid (6.1 mg, 9.70 µmol, 30.4% yield). $^1$H NMR (500 MHz, DMSO-$d_6$) δ 7.32 (d, J=8.1 Hz, 1H), 7.06 (s, 1H), 6.94 (d, J=8.1 Hz, 1H), 6.48 (s, 1H), 5.63 (br. S., 1H), 4.84 (d, J=12.5 Hz, 1H), 4.69-4.48 (m, 4H), 4.32 (t, J=11.9 Hz, 1H), 3.65 (br. S., 1H), 3.35-3.22 (m, 4H), 2.74 (s, 3H), 2.02-1.40 (m, 10H), 1.26-0.95 (m, 15H). LCMS (M+H) calcd for $C_{33}H_{46}ClN_4O_6$: 629.31. found: 629.4.

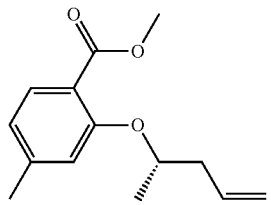 [SMILES: C=CC[C@H](C)Oc1cc(C)ccc1C(=O)OC]

(S)-Methyl 4-methyl-2-(pent-4-en-2-yloxy)benzoate

Methyl 2-hydroxy-4-methylbenzoate (5.0 g, 30.1 mmol) was dissolved in 100 mL toluene. To this was added triphenylphosphine (23.68 g, 90 mmol) and (R)-pent-4-en-2-ol (6.19 mL, 60.2 mmol). After cooling to 0° C. diisopropyl azodicarboxylate (17.77 mL, 90 mmol) was added dropwise and the reaction stirred overnight. The solvent was removed under vacuum and the product purified by silica gel chromatography using a Biotage apparatus (300 gm SiO$_2$, eluent 95:5-90:10 hexanes/ethyl acetate) to provide 1.17 grams of the title compound as an oil. $^1$H NMR (400 MHz, DMSO) δ 1.23 (3H, d), 2.33 (3H, s) 2.39 (2H, m), 3.75 (3H, s), 4.57 (1H, m), 5.12 (2H, m). 5.82 (1H, m) 6.61 (1H, d), 6.99 (1H, s), 7.54 (1H, d).

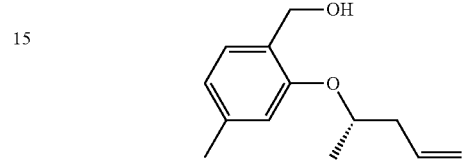

(S)-(4-Methyl-2-(pent-4-en-2-yloxy)phenyl)methanol (S)-Methyl 4-methyl-2-(pent-4-en-2-yloxy)benzoate (1 g, 4.27 mmol) was dissolved in THF and cooled to 0° C. To this was added lithium aluminum hydride (0.162 g, 4.27 mmol) and the reaction stirred 5 h at room temp. The mixture was cooled to 0° C. and ethyl acetate added, after which it was stirred for 15 min. Sat'd NH$_4$Cl was added and the ice bath removed. Stirring was continued for 0.5 h then the mixture was transferred to a separatory funnel. The solution was extracted with ethyl acetate then dried over Na$_2$SO$_4$. After filtration the solvent was removed under vacuum. The crude product was purified by silica gel chromatography using a Biotage apparatus to provided 915 mg of the title compound as an oil. $^1$H NMR (400 MHz, DMSO) δ 1.22 (3H, d), 2.28 (3H, s), 2.37 (2H, m), 4.44 (2H, d), 4.50 (1H, m), 5.09 (2H, m), 5.86 (1H, m), 6.72 (1H, d0, 6.77 (1H, s), 7.24 (1H, d).

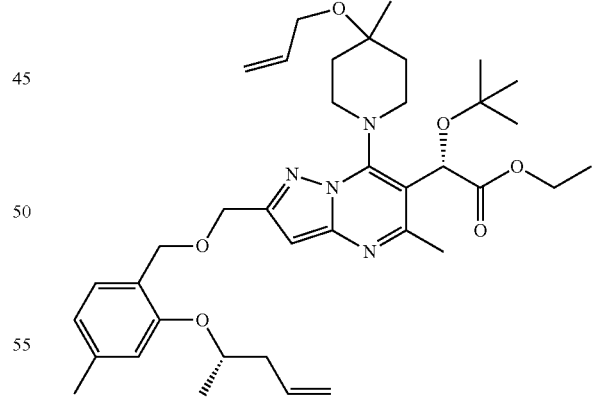

(S)-Ethyl 2-(7-(4-(allyloxy)-4-methylpiperidin-1-yl)-5-methyl-2-(((5-methyl-2-((S)-pent-4-en-2-yloxy)benzyl)oxy)methyl)pyrazolo[1,5-a]pyrimidin-6-yl)-2-(tert-butoxy)acetate (S)-Ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (0.45 g, 0.770 mmol) was dissolved in 1 mL DMF to this was added (S)-(5-methyl-2-(pent-4-en-2-yloxy)phenyl)methanol (0.191 g, 0.924 mmol) as a solution in 1 mL DMF. NaH-60% wt/wt in oil (47 mg, 1.16 mmol) was added and the reaction mixture was stirred for 5 hours. The reaction was quenched with 1N HCl then transferred to a separatory funnel where the product was extracted with ethyl acetate. The organic solution was dried over $Na_2SO_4$. After filtration the solvent was removed under vacuum and the product purified by silica gel chromatography using a Biotage apparatus to isolate the title compound as an oil (114 mg). $^1$H NMR (400 MHz, CDCl$_3$) δ 1.21-1.24 (15H, overlapping s and m), 1.32 (3H, d), 1.65-1.8 (4H, br m), 2.35 (3H, s), 2.50 (2H, m), 2.61 (3H, s), 3.0-3.5 (4H, very broad m), 3.75 (2H, s), 4.21 (2H, m), 4.45 (1H, m), 4.66 (2H, br s), 4.77 (2H, s), 5.06-5.22 (4H, overlapping m), 5.32 (1H, s), 5.85-6.2 (2H, overlapping m), 6.59 (1H, s), 6.71 (1H, s), 6.77 (1H, d), 7.34 (1H, d).

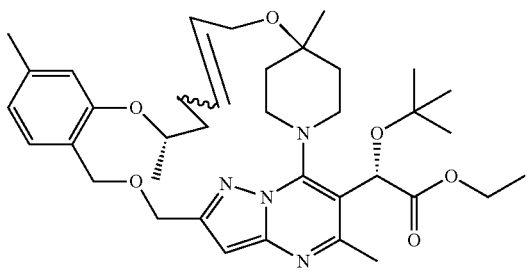 [SMILES: CCOC(=O)[C@@H](OC(C)(C)C)c1c(C)nc2cc3nn2c1N1CCC(C)(CC1)OCC=CCC[C@H](C)Oc1cc(C)ccc1COC3]

Ethyl (2S)-2-(tert-butoxy)-2-[(20S,23E/Z)-4,16,20,27-tetramethyl-11,19,26-trioxa-1,5,7,8-tetraazapentacyclo[25.2.2.1$^{6,9}$.0$^{2,7}$.0$^{13,18}$]dotriaconta-2,4,6(32),8,13(18),14,16,23-octaen-3-yl]acetate To (S)-ethyl 2-(7-(4-(allyloxy)-4-methylpiperidin-1-yl)-5-methyl-2-(((4-methyl-2-((S)-pent-4-en-2-yloxy)benzyl)oxy)methyl)pyrazolo[1,5-a]pyrimidin-6-yl)-2-(tert-butoxy)acetate (51 mg, 0.077 mmol) dissolved in ClCH$_2$CH$_2$Cl (10 mL) was added (1,3 dimesitylimidazolidin-2-yldene) (2-isopropoxybenylidene)Ruthenium(IV) chloride (12.05 mg, 0.019 mmol) followed by copper(I) iodide (14.65 mg, 0.077 mmol). The reaction was heated to 90-100° C. (oil bath temperature) and stirred for 2.5 hours. The mixture was cooled to room temperature and the solvent removed under vacuum. The crude product was purified by silica gel chromatography using a Biotage apparatus (12 gm SiO$_2$, eluent 70:30 hexanes/ethyl acetate) to provide 56 mg of the title product as an oil. LCMS MW calcd for C36H50N4O6, 634.4; observed mw (m+1),635.2.

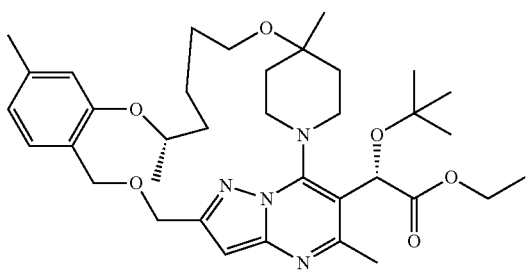 [SMILES: CCOC(=O)[C@@H](OC(C)(C)C)c1c(C)nc2cc3nn2c1N1CCC(C)(CC1)OCCCC[C@H](C)Oc1cc(C)ccc1COC3]

Ethyl (2S)-2-(tert-butoxy)-2-[(20S)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetate Ethyl (2S)-2-(tert-butoxy)-2-[(20S,23E/Z)-4,16,20,27-tetramethyl-11,19,26-trioxa-1,5,7,8-tetraazapentacyclo[25.2.2.1$^{6,9}$.0$^{2,7}$.0$^{13,18}$]dotriaconta-2,4,6(32),8,13(18),14,16,23-octaen-3-yl]acetate (17 mg, 0.027 mmol) was dissolved in MeOH to this was added (1,3-dimesitylimidazolidin-2-ylidene)(2-isopropoxybenzylidene)ruthenium (VI) chloride (3.36 mg, 5.36 µmol) followed by sodium borohydride (5.07 mg, 0.134 mmol). The reaction was stirred then quenched with water. The mixture was transferred to separatory funnel and extracted with ethyl acetate. The organic solution was dried over $Na_2SO_4$. After filtration the solvent was removed under vacuum to yield crude product as an oil. The reaction was repeated using 26 mg of ethyl (2S)-2-(tert-butoxy)-2-[(20S,23E/Z)-4,16,20,27-tetramethyl-11,19,26-trioxa-1,5,7,8-tetraazapentacyclo[25.2.2.1$^{6,9}$.0$^{2,7}$.0$^{13,18}$]dotriaconta-2,4,6(32),8,13(18),14,16,23-octaen-3-yl]acetate, 5.13 mg of (1,3-dimesitylimidazolidin-2-ylidene)(2-isopropoxybenzylidene)ruthenium (VI) chloride and 7.75 mg sodium borohydride. The crude reaction products combined and purified by silica gel chromatography using a Biotage apparatus (12 gm SiO$_2$, eluent 70:30 hexanes/ethyl acetate) to provide 22 mg of the title compound as an oil. LCMS MW calcd for $C_{36}H_{52}N_4O_6$, 636.4; observed mw (m+1), 637.2. $^1$H NMR (400 MHz, CDCl$_3$) δ 1.17-1.27 (15H, overlapping s and m), 1.31 (3H, d), 1.56-1.99 (10H, overlapping m), 2.35 (3H, s), 2.62 (3H, s), 2.75 (1H, m), 3.09 (1H, m), 3.46 (2H, m), 4.14 (2H, m), 4.21 (2H, m), 4.5-4.8 (5H, overlapping m), 6.03 (1H, s) 6.56 (1H, s), 6.72, (1H, s), 6.75 (1H, d), 7.26 (1H, d).

Example 36 and 37

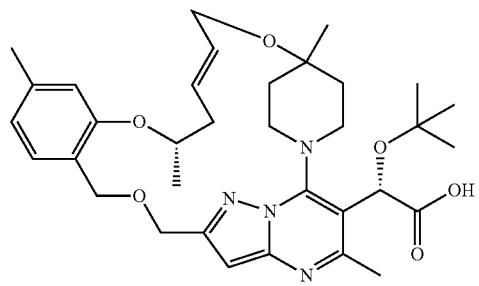

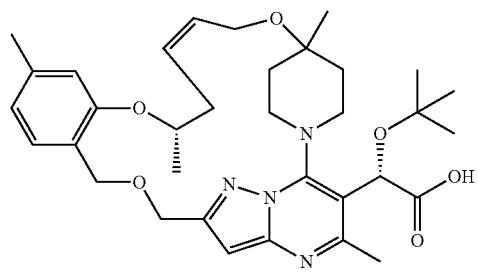

(2S)-2-(tert-Butoxy)-2-[(20S,22Z)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid and (2S)-2-(tert-Butoxy)-2-[(20S,22E)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid Ethyl (2S)-2-(tert-butoxy)-2-[(20S,23E/Z)-4,16,20,27-tetramethyl-11,19,26-trioxa-1,5,7,8-tetraazapentacyclo[25.2.2.1$^{6,9}$.0$^{2,7}$.0$^{13,18}$]dotriaconta-2,4,6(32),8,13(18),14,16,23-octaen-3-yl]acetate (56 mg, 0.00 mmol) was dissolved in 2 mL MeOH. 1N NaOH (0.35 mL, 0.35 mmol) was added and the mixture heated to 60° C. (oil bath temperature). After 3 h, the reaction was allowed to return to room temperature then quenched with 1N HCl. Ethyl acetate was added and the mixture transferred to a separatory funnel. The organic layer was isolated and dried over Na$_2$SO$_4$. After filtration the solvent was removed under vacuum to yield 41 mg of crude product as a solid. The crude material was purified twice by to compounds.

(2S)-2-(tert-Butoxy)-2-[(20S,22Z)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid $^1$H NMR (500 MHz, DMSO) δ 1.16 (9H, s), 1.21 (3H, s), 1.24 (3H, d), 1.57 (1H, m), 1.66 (1H, m), 1.88 (2H, m), 2.29 (3H, s), 2.40 (1H, m), 2.65 (1H, m), 2.74 (3H, s), 3.18-3.40 (2H, overlapping m), 3.71-3.91 (2H, overlapping m), 4.44-4.62 (6H, overlapping m), 5.72 (1H, m), 5.76 (1H, s), 6.01 (1H, m), 6.50 (1H, s), 6.70 (1H, d), 5.62 (1H, s), 7.15 (1H, d), 7.96 (1H, s). LCMS (M+H)=607.4.

(2S)-2-(tert-Butoxy)-2-[(20S,22E)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid $^1$H NMR (500 MHz, DMSO) δ 1.10 (3H, m), 1.16 (12H, overlapping m and s), 1.29 (2H, m), 1.39 (2H, m), 2.27 (5H, overlapping m and s), 2.39 (3H, s), 3.26-3.57 (4H, overlapping m), 4.21 (1H, d), 4.36 (3H, overlapping m), 4.53 (1H, d), 4.74 (1H, d), 5.33 (2H, m), 5.81 (1H, s), 6.10 (1H, s), 6.73 (1H, d), 6.76 (1H, s0, 7.24 (1H, d).

Example 38

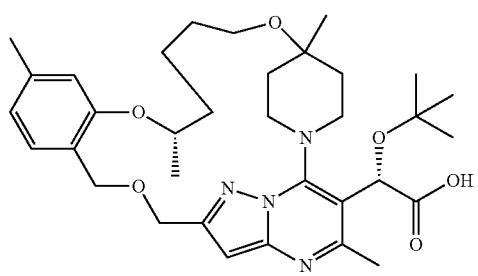 [SMILES: Cc1ccc2c(c1)O[C@@H](C)CCCCOC1(C)CCN(CC1)c1c([C@H](OC(C)(C)C)C(=O)O)c(C)nc3cc(nn13)COC2]

(2S)-2-(tert-Butoxy)-2-[(20S)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid (2S)-2-(tert-Butoxy)-2-[(20S)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetate (22 mg, 0.035 mmol) was dissolved in MeOH (1 mL). To this was added 1N sodium hydroxide (0.138 mL, 0.138 mmol) and the mixture heated to 60° C. (oil bath temperature). After stirring for 3 hrs the mixture was transferred to a separatory funnel and acidified with 1N HCl. The solution was then extracted with ethyl acetate and the organic layer dried over Na$_2$SO$_4$. After filtration the solvent was removed to under vacuum to provide 24 mg of the title compound as a powder. LCMS (M+H)=609.2.

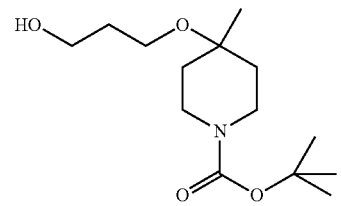 [SMILES: CC(C)(C)OC(=O)N1CCC(C)(OCCCO)CC1]

tert-Butyl 4-(3-hydroxypropoxy)-4-methylpiperidine-1-carboxylate

To a solution of tert-butyl 4-(allyloxy)-4-methylpiperidine-1-carboxylate (8.4 g, 32.9 mmol) in THF (200 mL) at room temp was added 0.5 M solution of 9-BBN (132 mL, 65.8 mmol) and the resulting mixture was stirred at room temp for 16 h. Mixture was then cooled in an ice bath and 1N NaOH (164 mL, 164 mmol) followed by 30% H$_2$O$_2$ (30.2 mL, 296 mmol) were added and the mixture was stirred for 1 h. Mixture was then extracted with ethyl acetate (250 mL), washed with water (100 mL), brine (100 mL), dried (Na$_2$SO$_4$), filtered and concentrated. The residue was then purified by Biotage (5-80% EtOAc/Hexane) to afford tert-butyl 4-(3-hydroxypropoxy)-4-methylpiperidine-1-carboxylate (6.4 g, 23.41 mmol, 71.2% yield) as colorless oil. $^1$H NMR (500 MHz, CDCl$_3$) δ 3.84-3.79 (m, 2H), 3.74 (dt, J=13.4, 3.7 Hz, 2H), 3.57 (t, J=5.6 Hz, 2H), 3.19-3.06 (m, 2H), 1.85 (quin, J=5.6 Hz, 2H), 1.75 (d, J=13.1 Hz, 2H), 1.48 (s, 9H), 1.47-1.41 (m, 2H), 1.21 (s, 3H). LCMS (M+Na)=296.7.

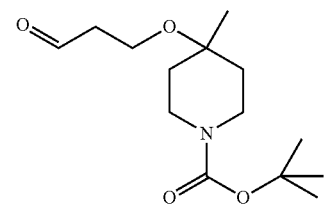 [SMILES: CC(C)(C)OC(=O)N1CCC(C)(OCCC=O)CC1]

tert-Butyl 4-methyl-4-(3-oxopropoxy)piperidine-1-carboxylate

To a solution of tert-butyl 4-(3-hydroxypropoxy)-4-methylpiperidine-1-carboxylate (6.4 g, 23.41 mmol) in CH$_2$Cl$_2$ (300 mL) was added Dess-Martin Periodinane (10.43 g, 24.58 mmol) and the resulting mixture was stirred at room temp for 3 h. Sat. NaHCO$_3$ solution was then added and the mixture was extracted with dichloromethane, dried (Na$_2$SO$_4$), filtered and concentrated. The residue was then purified by Biotage (5-50% EtOAc/hexane) to afford tert-butyl 4-methyl-4-(3-oxopropoxy)piperidine-1-carboxylate (1.3 g, 4.79 mmol, 82% yield) as colorless oil. $^1$H NMR (400 MHz, CDCl$_3$) δ 9.82 (s, 1H), 3.84-3.57 (m, 4H), 3.13-3.02 (m, 2H), 2.66 (td, J=6.0, 1.8 Hz, 2H), 1.74 (d, J=12.8 Hz, 3H), 1.47 (s, 9H), 1.46-1.38 (m, 2H), 1.20 (s, 3H).

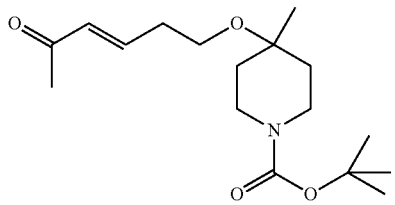 [SMILES: CC(=O)/C=C/CCOC1(C)CCN(C(=O)OC(C)(C)C)CC1]

(E)-tert-Butyl 4-methyl-4-((5-oxohex-3-en-1-yl)oxy) piperidine-1-carboxylate

To a solution of tert-butyl 4-methyl-4-(3-oxopropoxy)piperidine-1-carboxylate (5.7 g, 21.01 mmol) in CH$_2$Cl$_2$ (150 mL) was added 1-(triphenylphosphoranylidene)propan-2-one (8.69 g, 27.3 mmol) and the resulting mixture was stirred at room temp for 16 h. Water was then added and the mixture was extracted with dichloromethane, dried (Na$_2$SO$_4$), filtered and concentrated. The residue was then purified by Biotage (5-40% EtOAc/hexane) to afford (E)-tert-butyl 4-methyl-4-((5-oxohex-3-en-1-yl)oxy)piperidine-1-carboxylate (5.25 g, 16.86 mmol, 80% yield) as colorless oil. $^1$H NMR (500 MHz, CDCl$_3$) δ 6.85 (dt, J=16.1, 6.9 Hz, 1H), 6.15 (dt, J=16.0, 1.4 Hz, 1H), 3.79-3.66 (m, 2H), 3.47 (t, J=6.4 Hz, 2H), 3.12 (t, J=11.6 Hz, 2H), 2.49 (qd, J=6.5, 1.5 Hz, 2H), 2.29-2.26 (m, 3H), 1.73 (d, J=13.2 Hz, 2H), 1.47 (s, 9H), 1.46-1.39 (m, 2H), 1.18 (s, 3H). LCMS (M+Na)=334.3.

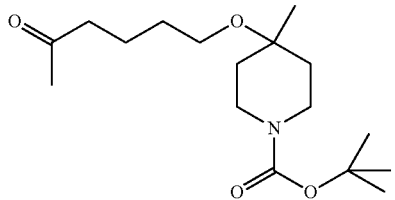 [SMILES: CC(=O)CCCCOC1(C)CCN(C(=O)OC(C)(C)C)CC1]

tert-Butyl 4-methyl-4-((5-oxohexyl)oxy)piperidine-1-carboxylate

To a solution of (E)-tert-butyl 4-methyl-4-((5-oxohex-3-en-1-yl)oxy)piperidine-1-carboxylate (6.2 g, 19.91 mmol) in MeOH (100 mL) was added 10% Pd/C (2.119 g, 1.991 mmol) and the flask was three times evacuated and released to H$_2$, then left under balloon H$_2$ atmosphere for 5 h. Then, filtered and concentrated to give tert-butyl 4-methyl-4-((5-oxohexyl) oxy)piperidine-1-carboxylate (5.8 g, 18.50 mmol, 93% yield) as colorless oil. $^1$H NMR (500 MHz, CDCl$_3$) δ 3.77-3.70 (m, 2H), 3.32 (t, J=6.3 Hz, 2H), 3.13 (t, J=11.2 Hz, 2H), 2.48 (t, J=7.3 Hz, 2H), 2.16 (s, 3H), 1.77-1.62 (m, 4H), 1.59-1.53 (m, 2H), 1.48 (s, 9H), 1.45-1.37 (m, 2H), 1.16 (s, 3H). LCMS (M+Na)=336.4.

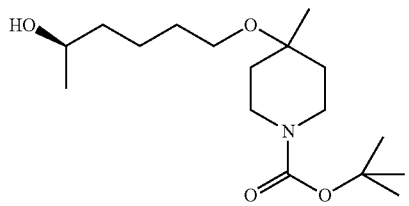 [SMILES: C[C@@H](O)CCCCOC1(C)CCN(C(=O)OC(C)(C)C)CC1]

(R)-tert-Butyl 4-((5-hydroxyhexyl)oxy)-4-methylpiperidine-1-carboxylate

To a stirred yellow solution of tert-butyl 4-methyl-4-((5-oxohexyl)oxy)piperidine-1-carboxylate (5.8 g, 18.50 mmol) in anhydrous toluene (100 mL) was added (S)-1-methyl-3,3-diphenylhexahydropyrrolo[1,2-c][1,3,2]oxazaborole (2.052 g, 7.40 mmol). The mixture was cooled to −35° C. and a solution of 50% catechoborane (6.35 mL, 25.9 mmol) in toluene was added over 5 min. After 30 min, the reaction mixture was slowly warmed to −15° C. and stirred for additional 2 h. At his point LCMS indicated completion of reaction. Mixture was then diluted with EtOAc (200 mL) and sat. Na$_2$CO$_3$ (100 mL). The mixture was stirred vigorously for 30 min, and the organic phase washed with sat Na$_2$CO$_3$ (2×50 mL), dried (Na$_2$SO$_4$), filtered, concentrated and the residue was purified by silica gel chromatography (5-70% EtOAc/hexane) to afford desired (R)-tert-butyl 4-((5-hydroxyhexyl) oxy)-4-methylpiperidine-1-carboxylate (4.6 g, 14.58 mmol, 79% yield) as colorless oil. $^1$H NMR (500 MHz, CDCl$_3$) δ 3.90-3.80 (m, 1H), 3.78-3.64 (m, 2H), 3.33 (t, J=6.4 Hz, 2H), 3.14 (t, J=11.4 Hz, 2H), 1.74 (d, J=13.2 Hz, 2H), 1.66-1.54 (m, 3H), 1.53-1.46 (m, 12H), 1.46-1.38 (m, 3H), 1.22 (d, J=6.3 Hz, 3H), 1.17 (s, 3H). LCMS (M+Na)=338.4.

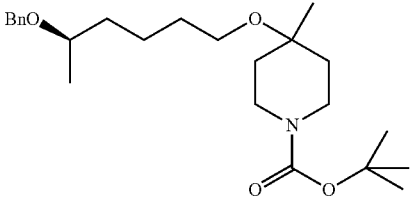 [SMILES: C[C@H](CCCCOC1(C)CCN(C(=O)OC(C)(C)C)CC1)OCc1ccccc1]

(R)-tert-Butyl 4-((5-(benzyloxy)hexyl)oxy)-4-methylpiperidine-1-carboxylate

To a solution of (R)-tert-butyl 4-((5-hydroxyhexyl)oxy)-4-methylpiperidine-1-carboxylate (4.5 g, 14.27 mmol) in DMF (50 mL) at 0° C. was added 60% NaH (0.685 g, 17.12 mmol) and the resulting mixture was stirred at room temp for 1 h. Benzyl bromide (2.55 mL, 21.40 mmol) was then added and the mixture was stirred for 16 h. Water (20 mL) was then added and the mixture was extracted with ether (100 mL), washed with brine (25 ml), dried (Na$_2$SO$_4$), filtered and concentrated. The residue was then purified by Biotage (0-20% EtOAc/hexane) to afford (R)-tert-butyl 4-((5-(benzyloxy) hexyl)oxy)-4-methylpiperidine-1-carboxylate (3.5 g, 8.63 mmol, 60.5% yield) as light yellow oil. $^1$H NMR (500 MHz, CDCl$_3$) δ 7.38-7.35 (m, 4H), 7.31-7.25 (m, 1H), 4.60 (d, J=11.8 Hz, 1H), 4.48 (d, J=11.8 Hz, 1H), 3.86-3.62 (m, 3H), 3.58-3.50 (m, 1H), 3.31 (t, J=6.3 Hz, 2H), 3.14 (br. s., 2H), 1.74 (d, J=12.9 Hz, 2H), 1.59-1.51 (m, 3H), 1.47 (s, 9H), 1.46-1.37 (m, 4H), 1.22 (d, J=6.1 Hz, 3H), 1.17 (s, 3H). LCMS (M+H)=406.3.

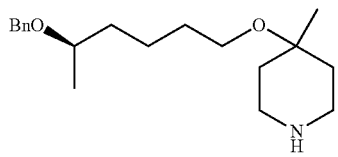 [SMILES: C[C@H](CCCCOC1(C)CCNCC1)OCc1ccccc1]

(R)-4-((5-(Benzyloxy)hexyl)oxy)-4-methylpiperidine, HCl

A solution of (R)-tert-butyl 4-((5-(benzyloxy)hexyl)oxy)-4-methylpiperidine-1-carboxylate (3.3 g, 8.14 mmol) and 4M HCl in dioxane (8.14 ml, 32.5 mmol) was stirred at room temp for 1 h. At this point LCMS indicated completion of reaction. Mixture was then concentrated and dried under high vacuum to afford (R)-4-((5-(benzyloxy)hexyl)oxy)-4-methylpiperidine, HCl (2.7 g, 7.90 mmol, 97% yield) as viscous oil. $^1$H NMR (500 MHz, CDCl$_3$) δ 9.27 (br. s., 1H), 7.40-7.30 (m, 5H), 4.60 (d, J=11.8 Hz, 1H), 4.47 (d, J=11.8 Hz, 1H), 3.50 (q, J=7.1 Hz, 1H), 3.33-3.11 (m, 5H), 1.93 (br. s., 1H), 1.88 (d, J=4.3 Hz, 1H), 1.72 (br. s., 4H), 1.58-1.39 (m, 5H), 1.24-1.20 (m, 6H). LCMS (M+H)=306.4.

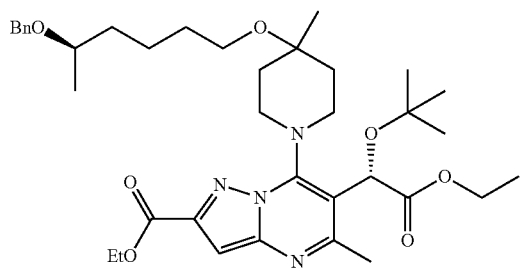 [SMILES: CCOC(=O)c1cc2nc(C)c([C@H](OC(C)(C)C)C(=O)OCC)c(N3CCC(C)(OCCCC[C@@H](C)OCc4ccccc4)CC3)n2n1]

Ethyl 7-(4-(((R)-5-(benzyloxy)hexyl)oxy)-4-methylpiperidin-1-yl)-6-((S)-1-(tert-butoxy)-2-ethoxy-2-oxoethyl)-5-methylpyrazolo[1,5-a]pyrimidine-2-carboxylate A mixture of (S)-ethyl 6-(1-(tert-butoxy)-2-ethoxy-2-oxoethyl)-7-chloro-5-methylpyrazolo[1,5-a]pyrimidine-2-carboxylate (2.2 g, 5.53 mmol) in DMF (40 ml) was treated with (R)-4-((5-(benzyloxy)hexyl)oxy)-4-methylpiperidine, HCl (2.65 g, 7.74 mmol) and Hunig's Base (2.90 ml, 16.59 mmol), and the mixture was heated (60° C. oil bath) for 16 h. At this point LCMS indicated completion of reaction. Mixture was then cooled, diluted with Et$_2$O and washed with water (3×50 mL) and brine (50 mL), then dried (Na$_2$SO$_4$), filtered, and concentrated under reduced pressure. The residue was then purified by Biotage (5-50% EtOAc/hexane) to afford ethyl 7-(4-(((R)-5-(benzyloxy)hexyl)oxy)-4-methylpiperidin-1-yl)-6-((S)-1-(tert-butoxy)-2-ethoxy-2-oxoethyl)-5-methylpyrazolo[1,5-a]pyrimidine-2-carboxylate (1.6 g, 2.399 mmol, 43.4% yield) as viscous oil. $^1$H NMR (500 MHz, CDCl$_3$) δ 7.39-7.32 (m, 4H), 7.29-7.26 (m, 1H), 7.02-7.01 (m, 1H), 5.85 (br. s., 1H), 4.63-4.54 (m, 1H), 4.51-4.39 (m, 3H), 4.29-4.16 (m, 2H), 3.61-3.53 (m, 1H), 3.47-3.38 (m, 2H), 2.63 (s, 3H), 2.01-1.85 (m, 3H), 1.75-1.64 (m, 6H), 1.59-1.49 (m, 3H), 1.44 (t, J=7.1 Hz, 3H), 1.33 (s, 3H), 1.26-1.24 (m, 2H), 1.24 (s, 9H), 1.22 (d, J=2.0 Hz, 3H). 4 missing piperidine hydrogens. LCMS (M+H)=667.6.

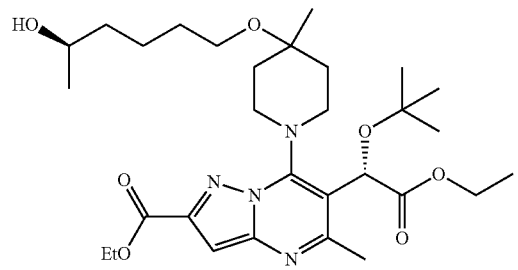 [SMILES: CCOC(=O)c1cc2nc(C)c([C@H](OC(C)(C)C)C(=O)OCC)c(N3CCC(C)(OCCCC[C@@H](C)O)CC3)n2n1]

Ethyl 6-((S)-1-(tert-butoxy)-2-ethoxy-2-oxoethyl)-7-(4-(((R)-5-hydroxyhexyl)oxy)-4-methylpiperidin-1-yl)-5-methylpyrazolo[1,5-a]pyrimidine-2-carboxylate To a solution of ethyl 7-(4-(((R)-5-(benzyloxy)hexyl)oxy)-4-methylpiperidin-1-yl)-6-((S)-1-(tert-butoxy)-2-ethoxy-2-oxoethyl)-5-methylpyrazolo[1,5-a]pyrimidine-2-carboxylate (1.7 g, 2.55 mmol) in EtOH (25 mL) was added 10% Pd/C (0.271 g, 0.255 mmol) and the resulting mixture was stirred under balloon hydrogen atmosphere for 5 h. Mixture was then filtered and concentrated to afford ethyl 6-((S)-1-(tert-butoxy)-2-ethoxy-2-oxoethyl)-7-(4-(((R)-5-hydroxyhexyl)oxy)-4-methylpiperidin-1-yl)-5-methylpyrazolo[1,5-a]pyrimidine-2-carboxylate (1.2 g, 2.081 mmol, 82% yield) as viscous oil. LCMS (M+H)=577.3. Used as is in the next step without further purification.

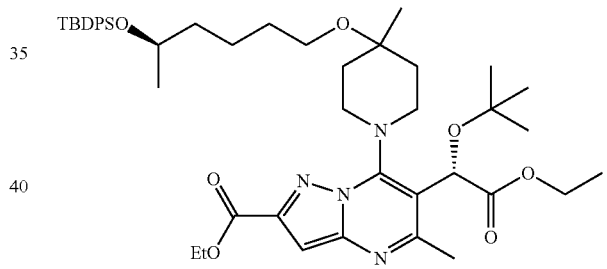

Ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate To a solution of ethyl 6-((S)-1-(tert-butoxy)-2-ethoxy-2-oxoethyl)-7-(4-(((R)-5-hydroxyhexyl)oxy)-4-methylpiperidin-1-yl)-5-methylpyrazolo[1,5-a]pyrimidine-2-carboxylate (800 mg, 1.387 mmol) in DMF (10 mL) at 0° C. was added imidazole (142 mg, 2.081 mmol) followed by tert-butylchlorodiphenylsilane (0.533 mL, 2.081 mmol) and the resulting mixture was stirred at room temp for 16 h. Water (20 mL) was then added and the mixture was extracted with ether (2×25 mL). Ether layer was then washed with brine (25 mL), dried (Na$_2$SO$_4$), filtered and concentrated. The residue was purified via Biotage (0-10% EtOAc/hexane) to afford ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate (1 g, 1.227 mmol, 88% yield) as viscous liquid. $^1$H NMR (400 MHz, CDCl$_3$) δ 7.69 (dd, J=8.0, 1.5 Hz, 4H), 7.47-7.28 (m, 6H), 7.01 (s, 1H), 5.82 (br. s., 1H), 4.50-4.38 (m, 2H), 4.31-4.07

(m, 2H), 3.94-3.77 (m, 1H), 3.41-3.24 (m, 3H), 2.61 (s, 3H), 1.88 (br. s., 2H), 1.67 (br. s., 1H), 1.54 (br. s., 1H), 1.51-1.39 (m, 5H), 1.30 (s, 3H), 1.26-1.23 (m, 6H), 1.22 (s, 9H), 1.08 (s, 3H), 1.06 (s, 9H). 4 missing piperidine hydrogens. LCMS (M+H)=816.4.

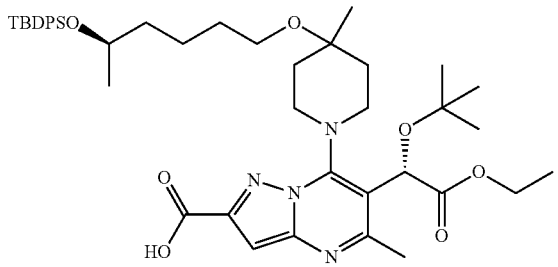

6-((S)-1-(tert-Butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid To a solution of ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate (1, 1.227 mmol) in Ethanol (12 mL) was added 1N NaOH (1.227 mL, 1.227 mmol) and the resulting mixture was stirred at room temp for 4 h. Mixture was then concentrated and the residue was diluted with water (10 mL) and extracted with ether (50 mL). The aqueous layer was then acidified with 1N HCl and extracted with ether (50 mL), washed with brine (10 mL), dried (Na$_2$SO$_4$), filtered and concentrated to afford 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid (920 mg, 1.169 mmol, 95% yield) as white solid. $^1$H NMR (500 MHz, CDCl$_3$) δ 7.73-7.68 (m, 4H), 7.47-7.35 (m, 6H), 7.13 (s, 1H), 5.85 (br.s, 1H), 4.30-4.16 (m, 2H), 3.94-3.84 (m, 1H), 3.35 (q, J=6.3 Hz, 2H), 2.65 (s, 3H), 1.92 (d, J=10.7 Hz, 2H), 1.67-1.39 (m, 12H), 1.30 (s, 3H), 1.28-1.25 (m, 3H), 1.24 (s, 9H), 1.11-1.08 (m, 3H), 1.07 (s, 9H). LCMS (M+H)=787.4.

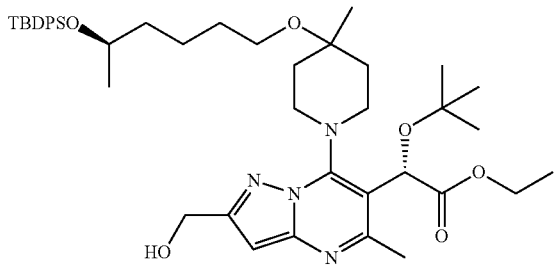

(S)-Ethyl 2-(tert-butoxy)-2-(7-(4-(((R)-5-((tert-butyl-diphenylsilyl)oxy)hexyl)oxy)-4-methylpiperidin-1-yl)-2-(hydroxymethyl)-5-methylpyrazolo[1,5-a]pyrimidin-6-yl)acetate To a stirred solution of 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid (900 mg, 1.143 mmol) and Et$_3$N (0.207 mL, 1.487 mmol) in THF (20 mL) was added 1M isopropyl chloroformate/toluene (1.487 mL, 1.487 mmol) at 0° C. After 1 h, a solution of NaBH$_4$ (216 mg, 5.72 mmol) in cold water (20 mL) was added at once and stirred for additional 1 h at 0° C. Then the reaction was quenched with MeOH (1 mL), diluted with Et$_2$O (100 mL), washed with water (2×50 mL) and brine (25 mL). The organic layer dried (Na$_2$SO$_4$), filtered and concentrate. The residue was then purified by Biotage (5-30% EtOAc/hexane) to afford (S)-ethyl 2-(tert-butoxy)-2-(7-(4-(((R)-5-((tert-butyldiphenylsilyl)oxy)hexyl)oxy)-4-methylpiperidin-1-yl)-2-(hydroxymethyl)-5-methylpyrazolo[1,5-a]pyrimidin-6-yl)acetate (580 mg, 0.750 mmol, 65.6% yield) as viscous oil. $^1$H NMR (500 MHz, CDCl$_3$) δ 7.74-7.70 (m, 4H), 7.46-7.35 (m, 6H), 6.48 (s, 1H), 5.90 (br. s., 1H), 4.91-4.83 (m, 2H), 4.29-4.11 (m, 2H), 3.94-3.84 (m, 1H), 3.41-3.29 (m, 3H), 2.61 (s, 3H), 2.17 (q, J=5.8 Hz, 1H), 1.94-1.87 (m, 2H), 1.87 (br. s., 1H), 1.66 (br. s., 1H), 1.59 (s, 3H), 1.58-1.40 (m, 5H), 1.33-1.26 (m, 3H), 1.26-1.21 (m, 12H), 1.09 (d, J=6.1 Hz, 3H), 1.07 (s, 9H). LCMS (M+H)=773.4.

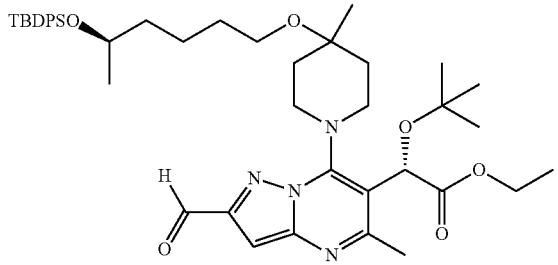

(S)-Ethyl 2-(tert-butoxy)-2-(7-(4-(((R)-5-((tert-butyl-diphenylsilyl)oxy)hexyl)oxy)-4-methylpiperidin-1-yl)-2-formyl-5-methylpyrazolo[1,5-a]pyrimidin-6-yl) acetate To a solution of (S)-ethyl 2-(tert-butoxy)-2-(7-(4-(((R)-5-((tert-butyldiphenylsilyl)oxy)hexyl)oxy)-4-methylpiperidin-1-yl)-2-(hydroxymethyl)-5-methylpyrazolo[1,5-a]pyrimidin-6-yl)acetate (540 mg, 0.698 mmol) in CH$_2$Cl$_2$ (10 mL) was added Dess-Martin Periodinane (356 mg, 0.838 mmol) and the resulting mixture was stirred at room temp for 3 h. Sat. NaHCO3 solution was then added and the mixture was extracted with dichloromethane (50 mL), dried (Na2SO4), filtered and concentrated. The residue was then purified by Biotage (5-30% EtOAc/hexane) to afford (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (490 mg, 0.635 mmol, 91% yield) as viscous oil. $^1$H NMR (500 MHz, CDCl$_3$) δ 10.15 (d, J=5.4 Hz, 1H), 7.74-7.66 (m, 4H), 7.47-7.34 (m, 6H), 7.02 (s, 1H), 5.88 (br. s., 1H), 4.30-4.18 (m, 2H), 3.94-3.81 (m, 1H), 3.40-3.28 (m, 3H), 2.64 (s, 3H), 2.02-1.85 (m, 3H), 1.68 (br. s., 1H), 1.57-1.52 (m, 2H), 1.50-1.39 (m, 3H), 1.31 (s, 3H), 1.28-1.25 (m, 3H), 1.25 (s, 9H), 1.09 (d, J=6.1 Hz, 3H), 1.07 (s, 9H). 4 missing piperidine hydrogens. LCMS (M+H)=772.3.

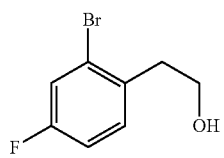 [SMILES: OCCc1ccc(F)cc1Br]

2-(2-Bromo-4-fluorophenyl)ethanol

To a solution of 2-(2-bromo-4-fluorophenyl)acetic acid (2.3 g, 9.87 mmol) in THF (20 mL) at 0° C. was added 1M $BH_3$.THF complex (14.80 mL, 14.80 mmol) in THF and the resulting mixture was stirred at room temp for 3 h. 1N HCl (50 mL) was then added and the mixture was extracted with ethyl acetate (200 mL), washed with brine (50 mL), dried ($Na_2SO_4$), filtered and concentrated to afford 2-(2-bromo-4-fluorophenyl)ethanol (2.0 g, 9.13 mmol, 93% yield) as colorless oil. $^1$H NMR (500 MHz, $CDCl_3$) δ 7.33 (dd, J=8.4, 2.7 Hz, 1H), 7.30-7.24 (m, 1H), 7.01 (td, J=8.2, 2.6 Hz, 1H), 3.89 (q, J=6.6 Hz, 2H), 3.02 (t, J=6.6 Hz, 2H), 1.43 (t, J=5.8 Hz, 1H).

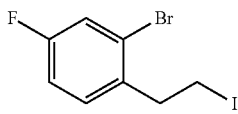

2-Bromo-4-fluoro-1-(2-iodoethyl)benzene

A solution of $Ph_3P$ (2.57 g, 9.81 mmol) and imidazole (0.668 g, 9.81 mmol) in DCM (50 mL) was cooled to 0° C. Added to this was iodine (2.489 g, 9.81 mmol) and the resulting mixture was stirred at 0° C. for 30 min. 2-(2-Bromo-4-fluorophenyl)ethanol (1.79 g, 8.17 mmol) was added portionwise over several minutes and the resulting mixture was stirred at room temp. After 16 h, the mixture was filtered washing the solids with DCM. The filtrate was washed with aq $Na_2S_2O_3$ and the organic phase was dried ($Na_2SO_4$), filtered and concentrated. The residue was purified by flash chromatography (Biotage; 0%-100% EtOAc/hexane; 20 CV) to give 2-bromo-4-fluoro-1-(2-iodoethyl)benzene (2.4 g, 7.30 mmol, 89% yield) as a colorless oil. $^1$H NMR (500 MHz, $CDCl_3$) δ 7.33 (dd, J=8.2, 2.7 Hz, 1H), 7.25 (dd, J=8.5, 5.8 Hz, 1H), 7.02 (td, J=8.2, 2.6 Hz, 1H), 3.41-3.35 (m, 2H), 3.32-3.26 (m, 2H).

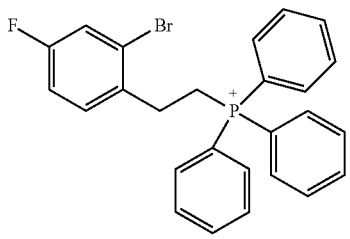

(2-Bromo-4-fluorophenethyl)triphenylphosphonium, iodide salt

To a solution of 2-bromo-4-fluoro-1-(2-iodoethyl)benzene (2.23 g, 6.78 mmol) in toluene (15 ml) was added $Ph_3P$ (1.778 g, 6.78 mmol) and the mixture was heated at 100° C. for 16 h. The mixture was cooled to rt, solids were filtered and washed with toluene and ether, dried under high vac to afford (2-bromo-4-fluorophenethyl)triphenylphosphonium, iodide salt (3 g, 5.07 mmol, 74.8% yield) as white solid. $^1$H NMR (500 MHz, DMSO-$d_6$) δ 8.01-7.87 (m, 9H), 7.85-7.77 (m, 6H), 7.66-7.51 (m, 1H), 7.35-7.24 (m, 1H), 7.20-7.07 (m, 1H), 3.93-3.80 (m, 2H), 3.07-2.86 (m, 2H).

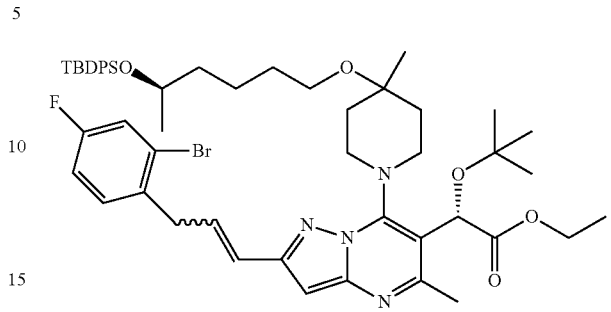

(S)-Ethyl 2-(2-(3-(2-bromo-4-fluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate To a suspension of (2-bromo-4-fluorophenethyl)triphenylphosphonium, iodide salt (705 mg, 1.193 mmol) in THF (8 ml) at 0° C. was added NaH (48.9 mg, 1.223 mmol) and the resulting mixture was stirred at rt for 45 min. The mixture was cooled to −78° C. and (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (460 mg, 0.597 mmol) dissolved in THF (8 ml) was added dropwise and the mixture was stirred at −78° C. for 1 h then warmed to rt and stirred 1 h. The reaction was quenched with water and the product was extracted with EtOAc. The organic phase was washed with brine, dried ($Na_2SO_4$), filtered and concentrated. The residue was purified by flash chromatography (Biotage; 0%-30% EtOAc/hexane) to afford (S)-ethyl 2-(2-(3-(2-bromo-4-fluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (500 mg, 0.523 mmol, 88% yield) as inseparable mixture of E and Z isomers. LCMS (M+2H)=957.2.

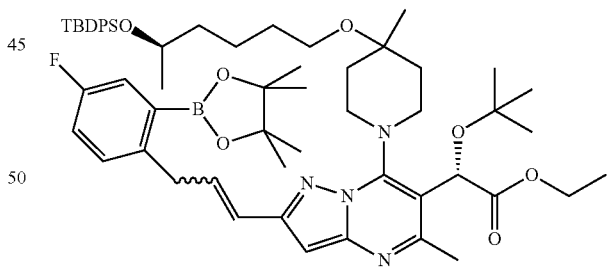

(S)-Ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-(4,4,5,5-tetramethyl-1,3,2-dioxaborolan-2-yl)phenyl)prop-1-en-1-yl)-5-methylpyrazolo[1,5-a]pyrimidin-6-yl)acetate To a solution of (S)-ethyl 2-(2-(3-(2-bromo-4-fluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (500 mg, 0.523 mmol) in anhydrous 1,4-dioxane (10 mL) was added bis(pinacolato)diborane (159 mg, 0.628 mmol) and potassium acetate (154 mg, 1.569 mmol), and the mixture was degassed for 15 min. To the degassed solution was added PdCl2(dppf)-CH$_2$Cl$_2$ adduct (42.7 mg, 0.052 mmol) and degassing continued for a further 5 min, after which the reaction was heated at 90° C. for 16 r. At this point LCMS indicated completion of reaction and appearance of desired product. After cooling to room temp, water (5 mL) was added and the mixture was extracted with ethyl ether (25 mL), washed with brine (10 mL), dried (Na$_2$SO$_4$), filtered and concentrated. Crude was then purified by Biotage using 0-20% EtOAc/hexane to afford inseparable mixture of E and Z isomers(S)-ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-(4,4,5,5-tetramethyl-1,3,2-dioxaborolan-2-yl)phenyl)prop-1-en-1-yl)-5-methylpyrazolo[1,5-a]pyrimidin-6-yl)acetate (450 mg, 0.449 mmol, 86% yield) as thick paste. product is a mixture of isomers. Used as is in the next step without further purification. LCMS (M+H)=1003.30.

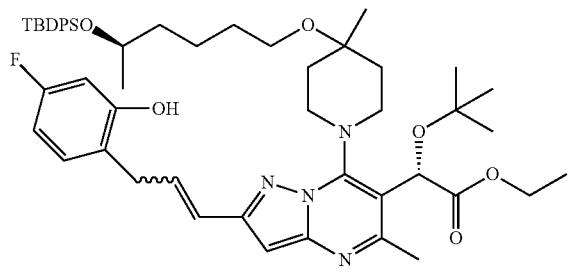

(S)-Ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-hydroxyphenyl)prop-1-en-1-yl)-5-methylpyrazolo[1,5-a]pyrimidin-6-yl)acetate To a solution of (S)-ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-(4,4,5,5-tetramethyl-1,3,2-dioxaborolan-2-yl)phenyl)prop-1-en-1-yl)-5-methylpyrazolo[1,5-a]pyrimidin-6-yl)acetate (450 mg, 0.449 mmol) in Acetone (6 mL) was added solution of oxone (276 mg, 0.449 mmol) in water (6 mL) and the resulting mixture was stirred at room temp for 1 h. Sat. sodium thiosulfate was then added and the mixture was extracted with ethyl acetate, dried (Na$_2$SO$_4$), filtered and concentrated to afford (S)-ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-hydroxyphenyl)prop-1-en-1-yl)-5-methylpyrazolo[1,5-a]pyrimidin-6-yl)acetate (370 mg, 0.414 mmol, 92% yield) as viscous oil. Product is a mixture of isomers LCMS (M+H)=893.4. Used as is in the next reaction without further purification.

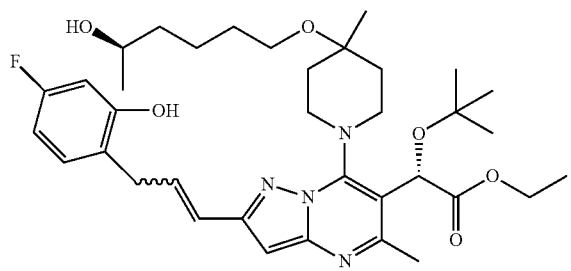 [SMILES: CCOC(=O)[C@@H](OC(C)(C)C)c1c(C)nc2cc(C=CCc3ccc(F)cc3O)nn2c1N1CCC(C)(OCCCC[C@@H](C)O)CC1]

(S)-Ethyl 2-(tert-butoxy)-2-(2-(3-(4-fluoro-2-hydroxyphenyl)prop-1-en-1-yl)-7-(4-(((R)-5-hydroxyhexyl)oxy)-4-methylpiperidin-1-yl)-5-methylpyrazolo[1,5-a]pyrimidin-6-yl)acetate To a solution of (S)-ethyl 2-(tert-butoxy)-2-(7-(4-(((R)-5-((tert-butyldiphenylsilyl)oxy)hexyl)oxy)-4-methylpiperidin-1-yl)-2-(3-(4-fluoro-2-hydroxyphenyl)prop-1-en-1-yl)-5-methylpyrazolo[1,5-a]pyrimidin-6-yl)acetate (380 mg, 0.425 mmol) in THF (5 mL) was added TBAF 1M in THF (0.851 mL, 0.851 mmol) and the resulting mixture was stirred at room temp for 16 h. At this point LCMS indicated approx 70% conversion so another 1 equiv of TBAF was added and the mixture was stirred for another 5 h. At this point LCMS indicated completion of reaction. Mixture was then concentrated and purified by biotage (5-30% EtOAc/hexane) to afford (S)-ethyl 2-(tert-butoxy)-2-(2-(3-(4-fluoro-2-hydroxyphenyl)prop-1-en-1-yl)-7-(4-(((R)-5-hydroxyhexyl)oxy)-4-methylpiperidin-1-yl)-5-methylpyrazolo[1,5-a]pyrimidin-6-yl)acetate (240 mg, 0.367 mmol, 86% yield) as approx 2:1 mixture of isomers. LCMS (M+H)=655.3.

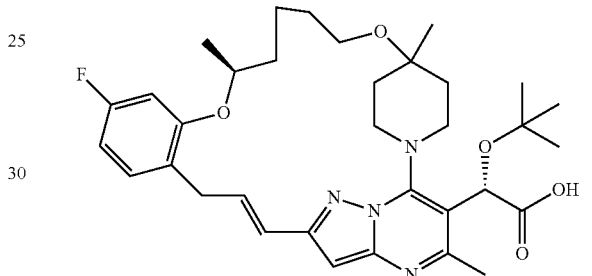

First eluting on HPLC

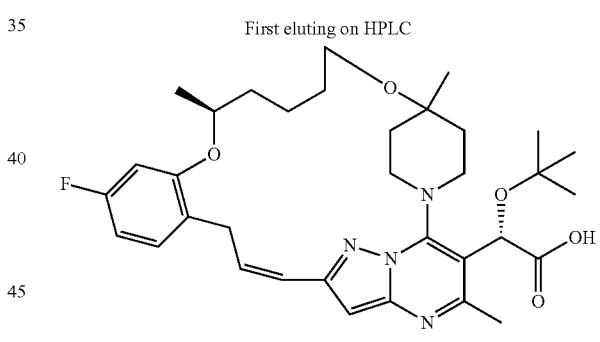

Second eluting on HPLC (2S)-2-(tert-Butoxy)-2-[(20S)-16-fluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,10,13(18),14,16-octaen-3-yl]acetic acid To a solution of (S)-ethyl 2-(tert-butoxy)-2-(2-(3-(4-fluoro-2-hydroxyphenyl)prop-1-en-1-yl)-7-(4-(((R)-5-hydroxyhexyl)oxy)-4-methylpiperidin-1-yl)-5-methylpyrazolo[1,5-a]pyrimidin-6-yl)acetate (240 mg, 0.367 mmol) in THF (50 mL) at 0° C. was added Ph$_3$P (144 mg, 0.550 mmol) followed by DEAD (0.087 mL, 0.550 mmol) and the resulting mixture was stirred at room temp for 3 h. At this point LCMS indicated completion of reaction and desired product as mixture of four isomers. Water (25 mL) was then added and the mixture was extracted with ether (50 mL), dried (Na$_2$SO$_4$), filtered and concentrated. The residue was then purified by Biotage (0-30% EtOAc/hexane) to afford to afford desired ester (165 mg, 0.259 mmol, 70.7% yield) as a inseparable mixture of two isomers which was used in the next step without further purification. LCMS (M+H)=637.3

A mixture of above crude ester and (0.754 mL, 0.754 mmol) in EtOH (4 mL) was heated at 80° C. for 3 h. Mixture was then cooled and purified by prep HPLC to afford two isomers First eluting major isomer: $^1$H NMR (400 MHz, CDCl$_3$) δ 7.13 (t, J=7.7 Hz, 1H), 6.65-6.54 (m, 2H), 6.50 (d, J=11.8 Hz, 1H), 6.45 (s, 1H), 5.96-5.76 (m, 2H), 4.51-4.36 (m, 2H), 4.29 (d, J=17.8 Hz, 1H), 4.12-3.96 (m, 1H), 3.73 (t, J=12.3 Hz, 1H), 3.61-3.51 (m, 1H), 3.33 (d, J=11.0 Hz, 2H), 3.01 (d, J=12.0 Hz, 1H), 2.58 (s, 3H), 2.06-1.96 (m, 1H), 1.87-1.78 (m, 5H), 1.66-1.50 (m, 4H), 1.38 (d, J=6.0 Hz, 3H), 1.27 (s, 9H), 1.22 (s, 3H). LCMS (M+H)=609.4.

Second eluting minor product: $^1$H NMR (400 MHz, CDCl$_3$) δ 7.17-7.07 (m, 1H), 6.99-6.86 (m, 1H), 6.66-6.49 (m, 3H), 6.37 (s, 1H), 5.97 (br. s., 1H), 4.58-4.45 (m, 2H), 3.87 (t, J=11.5 Hz, 1H), 3.74 (dd, J=13.4, 4.1 Hz, 1H), 3.53-3.38 (m, 2H), 3.31-3.17 (m, 2H), 2.69 (br. s., 1H), 2.59 (s, 3H), 2.05-1.87 (m, 5H), 1.80-1.51 (m, 5H), 1.30-1.27 (m, 12H), 1.25 (s, 3H). LCMS (M+H)=609.4.

Example 39 and 40

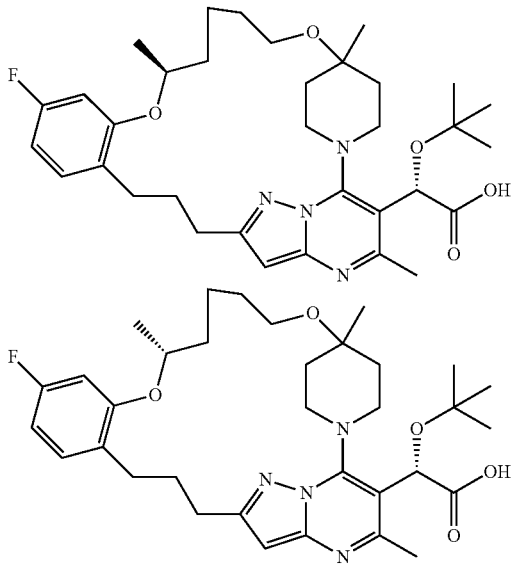

(2S)-2-(tert-Butoxy)-2-[(20S)-16-fluoro-4,20,26-trimethyl-19,25-dioxa-1,5,7,8-tetraazapentacyclo [24.2.2.1$^{6,9}$.0$^2$,$^7$.0$^{13,18}$]hentriaconta-2,4,6(31),8,13 (18),14,16-heptaen-3-yl]acetic acid To a mixture of (2S)-2-(tert-butoxy)-2-[(10E,20S)-16-fluoro-4,20,26-trimethyl-19,25-dioxa-1,5,7,8-tetraazapentacyclo[24.2.2.1$^{6,9}$.0$^2$,$^7$.0$^{13,18}$]hentriaconta-2,4,6(31),8,10,13 (18),14,16-octaen-3-yl]acetic acid (30 mg, 0.049 mmol) in ethyl acetate (1.5 mL) was added 10% Pd/C (5.24 mg, 4.93 μmol) and the resulting mixture was stirred under hydrogen balloon atmosphere for 16 h. At this point LCMS indicates completion of reaction. Mixture was then filtered and concentrated to afford (2S)-2-(tert-butoxy)-2-[(20S)-16-fluoro-4,20,26-trimethyl-19,25-dioxa-1,5,7,8-tetraazapentacyclo [24.2.2.1$^{6,9}$.0$^2$,$^7$.0$^{13,18}$]hentriaconta-2,4,6(31),8,13(18),14, 16-heptaen-3-yl]acetic acid (23 mg, 0.036 mmol, 72.6% yield) as white solid. $^1$H NMR (600 MHz, DMSO-d$_6$) δ 7.14 (t, J=7.5 Hz, 1H), 6.88 (d, J=11.4 Hz, 1H), 6.61 (t, J=7.7 Hz, 1H), 6.23 (s, 1H), 5.62 (br. s., 1H), 4.60 (br. s., 1H), 4.31 (t, J=12.1 Hz, 1H), 2.79-2.73 (m, 1H), 2.70 (t, J=8.1 Hz, 2H), 2.56 (d, J=11.4 Hz, 1H), 2.46 (s, 3H), 2.20 (br. s., 1H), 1.91 (s, 1H), 1.84-1.75 (m, 3H), 1.70-1.62 (m, 5H), 1.56-1.44 (m, 3H), 1.18 (d, J=5.5 Hz, 3H), 1.16 (s, 3H), 1.13 (s, 9H). 4 piperidine hydrogens are missing. LCMS (M+H)=611.4.

Second eluting diastereomer (Example 40), (7 mg, 0.011 mmol, 29.3% yield): $^1$H NMR (600 MHz, DMSO-d$_6$) δ 7.12 (t, J=7.7 Hz, 1H), 6.84 (d, J=11.7 Hz, 1H), 6.68-6.54 (m, 1H), 6.28 (s, 1H), 5.86 (br. s., 1H), 4.55 (d, J=8.8 Hz, 1H), 4.31 (t, J=11.7 Hz, 1H), 3.63 (t, J=11.0 Hz, 1H), 2.88-2.81 (m, 1H), 2.77 (dd, J=14.7, 5.5 Hz, 1H), 2.70-2.63 (m, 1H), 2.62-2.57 (m, 1H), 2.48 (s, 3H), 2.44-2.35 (m, 1H), 2.02 (dd, J=11.7, 5.5 Hz, 1H), 1.95-1.87 (m, 1H), 1.87-1.69 (m, 4H), 1.68-1.61 (m, 2H), 1.57-1.44 (m, 3H), 1.24 (d, J=5.5 Hz, 3H), 1.18 (br. s., 3H), 1.17 (s, 9H). 4 piperidine hydrogens are missing. LCMS (M+H)=611.4.

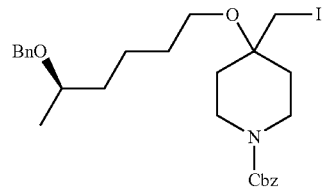 [SMILES: C[C@H](CCCCOC1(CI)CCN(C(=O)OCc2ccccc2)CC1)OCc1ccccc1]

To a solution of 5-benzyloxyhexan-1-ol (2.00 g, 9.03 mmol) and benzyl 4-methylenepiperidine-1-carboxylate (1.30 g, 5.40 mmol, 0.60 equiv) in dichloromethane (7.0 mL) was charged trimethylsilyl trifluoromethanesulfonate (0.133 mL, 0.720 mmol, 0.08 equiv) at 0-5° C. N-iodosuccinimide (1.24 g, 5.40 mmol, 0.60 equiv) was added slowly maintaining the temperature 0-5° C. The mixture was stirred at 0° C. for 3 h. Benzyl 4-methylenepiperidine-1-carboxylate (1.30 g, 5.40 mmol, 0.60 equiv) was added, followed by additional N-iodosuccinimide (1.24 g, 5.40 mmol, 0.60 equiv) at 0-5° C. After 3 h, the same routine was repeated and benzyl 4-methylenepiperidine-1-carboxylate (0.65 g, 2.70 mmol, 0.30 equiv) and N-iodosuccinimide (0.62 g, 2.70 mmol, 0.3 equiv) were added at 0-5° C. The mixture was then stirred at 0-5° C. for at least 12 h. Triethylamine (1.40 mL, 9.94 mmol, 1.1 equiv) was added into the reaction mixture at 0-5° C. After 10 min, the reaction mixture was warmed to room temperature, and stirred for ~1.5 hours. MTBE (60 mL) and water (40 mL) were added. The phases were allowed to split and the organic layer was washed with 10% aqueous KH$_2$PO$_4$ (30 mL), and concentrated. The residue was purified by flash chromatography (0-50% EtOAc in heptane), yielding the product as a pale yellow oil (4.20 g) in 78.6% corrected Yield. $^1$H NMR (400 MHz, CDCl$_3$) δ (ppm) 7.41-7.25 (m, 10H), 5.13 (s, 2H), 4.58 (d, J=11.7 Hz, 1H), 4.46 (d, J=11.7 Hz, 1H), 3.96-3.91 (m, 2H), 3.57-3.49 (m, 1H), 3.31-3.20 (m, 4H), 3.15-3.02 (m, 2H), 1.90-1.78 (m, 2H), 1.68-1.57 (m, 4H), 1.55-1.38 (m, 4H), 1.21 (d, J=6.1 Hz, 3H).

Triethylamine (0.65 mL, 4.7 mmol, 2 equiv) was added to a solution of the iodomethyl compound (1.35 g, 2.34 mmol, 1 equiv) in MeOH (15 mL). Pd/C (10 wt %, 100 mg) was then charged. The mixture was then subjected to hydrogenolysis conditions (45 psi, 40° C.). Upon reaction completion, the reaction mixture was filtered through celite and concentrated to dryness under reduced pressure. MTBE (35 mL) was added into the residue, and the resulting solution was sequentially washed with 1N NaOH (15 mL×2), then 20% NaCl (20 mL). The organic layer was dried over MgSO$_4$, and concentrated to provide 0.51 g of lightly yellow oil (AP 95) in 70% as-is yield. $^1$H NMR (400 MHz, CDCl$_3$) δ (ppm) 7.39-7.31 (m, 5H), 4.58 (d, J=11.6 Hz, 1H), 4.46 (d, J=11.6 Hz, 1H), 3.56-3.47 (m, 1H), 3.34-3.22 (m, 2H), 2.92 (t, J=11.0 Hz, 2H), 2.81-1.69 (m, 2H), 1.85 (s, br, 1H), 1.73-1.59 (m, 4H), 1.57-1.51 (m, 2H), 1.49-1.36 (m, 4H), 1.21 (d, J=4.1 Hz, 3H), 1.14 (s, 3H).

16 h to afford (R)-5-((tert-butyldiphenylsilyl)oxy)hexan-1-ol (8.9 g, 24.96 mmol, 99% yield) as a clear viscous oil. $^1$H NMR (500 MHz, CDCl$_3$) δ 7.72-7.67 (m, 4H), 7.50-7.36 (m, 6H), 3.92-3.84 (m, 1H), 3.61-3.50 (m, 2H), 1.55-1.41 (m, 4H), 1.37-1.31 (m, 2H), 1.21-1.15 (m, 1H), 1.11-1.09 (m, 3H), 1.08 (s, 9H).

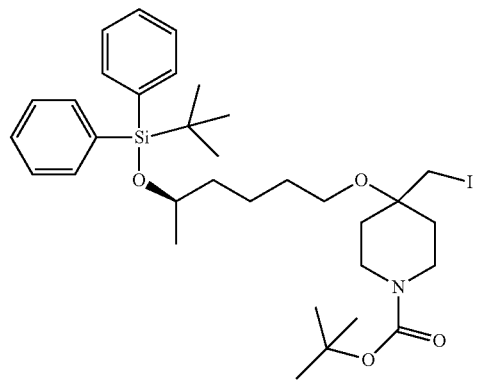

(R)-tert-Butyl 4-((5-((tert-butyldiphenylsilyl)oxy)hexyl)oxy)-4-(iodomethyl)piperidine-1-carboxylate

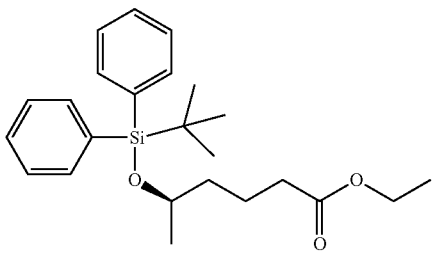 [SMILES: CCOC(=O)CCC[C@@H](C)O[Si](c1ccccc1)(c1ccccc1)C(C)(C)C]

(R)-Ethyl 5-((tert-Butyldiphenylsilyl)oxy)hexanoate

To a solution of (R)-ethyl 5-hydroxyhexanoate (5 g, 31.2 mmol) in DMF (100 mL) at 0° C. was added imidazole (3.19 g, 46.8 mmol) followed by tert-butylchlorodiphenylsilane (12.00 mL, 46.8 mmol) and the resulting mixture was stirred at room temp for 16 h. Water (30 mL) was then added and the mixture was extracted with ether (2×100 mL). Ether layer was then washed with brine (50 mL), dried (Na$_2$SO$_4$), filtered and concentrated. The residue was purified via Biotage (0-10% EtOAc/hexane) to afford (R)-ethyl 5-((tert-butyldiphenylsilyl)oxy)hexanoate (10 g, 25.09 mmol, 80% yield) as clear viscous liquid. $^1$H NMR (500 MHz, CDCl$_3$) δ 7.73-7.68 (m, 4H), 7.48-7.36 (m, 6H), 4.13 (q, J=7.2 Hz, 2H), 3.96-3.76 (m, 1H), 2.31-2.16 (m, 2H), 1.72-1.62 (m, 2H), 1.58-1.40 (m, 2H), 1.27 (t, J=7.1 Hz, 3H), 1.12-1.05 (m, 12H).

To a solution of (R)-5-((tert-butyldiphenylsilyl)oxy)hexan-1-ol (8.23 g, 23.08 mmol) and tert-butyl 4-methylenepiperidine-1-carboxylate (6.83 g, 34.6 mmol) in CH$_2$Cl$_2$ (40 mL) was added TMS-OTf (0.334 mL, 1.846 mmol), followed by CuSO$_4$ (1.842 g, 11.54 mmol) and the slurry was cooled to 0-5° C. N-iodosuccinimide (7.79 g, 34.6 mmol) was then added in one portion and the slurry was stirred for 0-5° C. for additional 16 h, then warmed to room temp over 2-3 h. Ether (200 mL) followed by aqueous solution of Na$_2$S$_2$O$_3$ (5% 100 mL) was added and the layers were separated. Organic layer was then washed with water (100 mL), dried (Na$_2$SO$_4$), filtered and concentrated. The residue was then purified by column chromatography (EtOAc/hexanes, 5-20%) to afford (R)-tert-butyl 4-((5-((tert-butyldiphenylsilyl)oxy)hexyl)oxy)-4-(iodomethyl)piperidine-1-carboxylate (13 g, 15.30 mmol, 66.3% yield) as yellow oil. $^1$H NMR (500 MHz, CDCl$_3$) δ 7.70 (dt, J=7.1, 1.7 Hz, 4H), 7.47-7.36 (m, 6H), 3.93 (s, 1H), 3.91-3.69 (m, 2H), 3.25 (br. s., 2H), 3.20 (t, J=6.4 Hz, 2H), 3.00 (br. s., 2H), 1.87 (d, J=13.1 Hz, 2H), 1.57-1.50 (m, 4H), 1.48 (s, 9H), 1.45-1.35 (m, 4H), 1.15-1.02 (m, 12H). LCMS (M-BOc)=580.6.

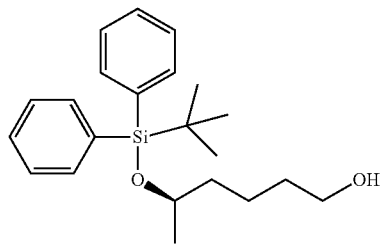 [SMILES: C[C@H](CCCCO)O[Si](c1ccccc1)(c1ccccc1)C(C)(C)C]

(R)-5-((tert-Butyldiphenylsilyl)oxy)hexan-1-ol

To a solution of (R)-ethyl 5-((tert-butyldiphenylsilyl)oxy)hexanoate (10 g, 25.09 mmol) in THF (150 mL) at 0° C. was added dropwise 1M LAH in THF (31.4 mL, 31.4 mmol) and the resulting mixture was stirred for 30 min. at 0° C. and then 2 h at room temp. The reaction was quenched with 1 mL of water (stir for 10 min), 1 mL of 15% NaOH/water (stir for 10 min), and then 2 mL of water. After stirring for 1 h, the mixture was filtered through celite. The filtrate was concentrated in vacuo. The residue was dried under high vacuum for

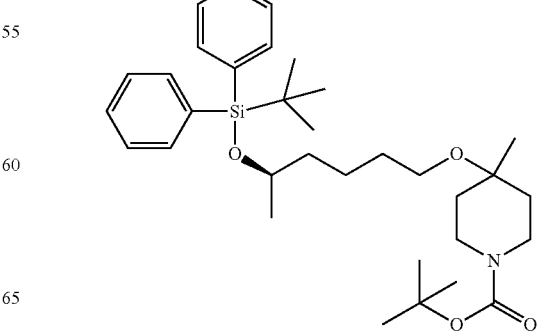

(R)-tert-Butyl 4-((5-((tert-butyldiphenylsilyl)oxy)hexyl)oxy)-4-methylpiperidine-1-carboxylate To a solution of (R)-tert-butyl 4-((5-((tert-butyldiphenylsilyl)oxy)hexyl)oxy)-4-(iodomethyl)piperidine-1-carboxylate (13 g, 19.12 mmol) in MeOH (100 mL) was added TEA (5.33 mL, 38.2 mmol) followed by 10% Pd—C (1.018 g, 0.956 mmol) and the resulting mixture was subjected to hydrogenolysis under PAR at 50 PSI. After 16 h, mixture was filtered through a pad of celite and the filtrate was concentrated. The residue was then purified by Biotage (0-15% EtOAc/hexane) to afford (R)-tert-butyl 4-((5-((tert-butyldiphenylsilyl)oxy)hexyl)oxy)-4-methylpiperidine-1-carboxylate (8.2 g, 14.81 mmol, 77% yield) as light yellow oil. $^1$H NMR (500 MHz, CDCl$_3$) δ 7.73-7.67 (m, 4H), 7.48-7.35 (m, 6H), 3.86 (sxt, J=5.8 Hz, 1H), 3.72 (br. s., 2H), 3.24 (t, J=6.3 Hz, 2H), 3.10 (br. s., 2H), 1.78-1.66 (m, 3H), 1.59-1.51 (m, 1H), 1.50-1.47 (m, 6H), 1.47 (s, 9H), 1.14 (s, 3H), 1.10-1.03 (m, 12H). LCMS (M+Na)=576.7.

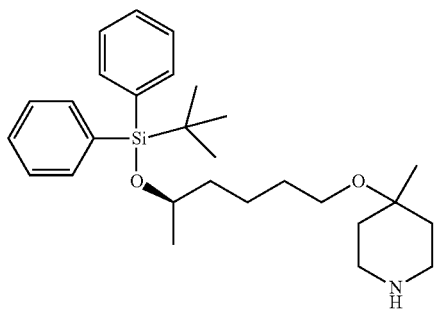 [SMILES: C[C@H](CCCCOC1(C)CCNCC1)O[Si](c1ccccc1)(c1ccccc1)C(C)(C)C]

(R)-4-((5-((tert-Butyldiphenylsilyl)oxy)hexyl)oxy)-4-methylpiperidine

A mixture of (R)-tert-butyl 4-((5-((tert-butyldiphenylsilyl)oxy)hexyl)oxy)-4-methylpiperidine-1-carboxylate (8.2 g, 14.81 mmol) and 4M HCl (22.21 mL, 89 mmol) in dioxane in 1,4-Dioxane (5 mL) was stirred at room temp for 2 h. Mixture was then concentrated, diluted with ethyl acetate (100 mL), washed with 1N NaOH, dried (Na$_2$SO$_4$), filtered and concentrated to afford (R)-4-((5-((tert-butyldiphenylsilyl)oxy)hexyl)oxy)-4-methylpiperidine (6.35 g, 14.00 mmol, 95% yield) as viscous oil. $^1$H NMR (500 MHz, CDCl$_3$) δ 7.72-7.65 (m, 4H), 7.47-7.34 (m, 6H), 3.87 (sxt, J=5.9 Hz, 1H), 3.24 (t, J=6.4 Hz, 2H), 2.94-2.86 (m, 2H), 2.77-2.69 (m, 2H), 1.74-1.68 (m, 4H), 1.48-1.32 (m, 6H), 1.14 (s, 3H), 1.10-1.05 (m, 12H). LCMS (M+H)=454.2.

Ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate A mixture of (S)-ethyl 6-(1-(tert-butoxy)-2-ethoxy-2-oxoethyl)-7-iodo-5-methylpyrazolo[1,5-a]pyrimidine-2-carboxylate (5.25 g, 10.73 mmol) in NMP (80 mL) was treated with (R)-4-((5-((tert-butyldiphenylsilyl)oxy)hexyl)oxy)-4-methylpiperidine (6.33 g, 13.95 mmol) and Hunig's Base (5.62 mL, 32.2 mmol), and the mixture was heated (70° C. oil bath) for 16 hrs. At this point LCMS indicates completion of reaction. Mixture was then cooled, diluted with Et$_2$O (200 mL) and washed with water (100 mL) and brine (50 mL), then dried (Na2SO4), filtered, and concentrated under reduced pressure. The residue was then purified by Biotage (5-15%) EtOAc Hexane to afford ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate (7, 8.59 mmol, 80% yield) as viscous oil. $^1$H NMR (400 MHz, CDCl$_3$) δ 7.69 (dd, J=8.0, 1.5 Hz, 4H), 7.47-7.28 (m, 6H), 7.01 (s, 1H), 5.82 (br. s., 1H), 4.50-4.38 (m, 2H), 4.31-4.07 (m, 2H), 3.94-3.77 (m, 1H), 3.41-3.24 (m, 3H), 2.61 (s, 3H), 1.88 (br. s., 2H), 1.67 (br. s., 1H), 1.54 (br. s., 1H), 1.51-1.39 (m, 5H), 1.30 (s, 3H), 1.26-1.23 (m, 6H), 1.22 (s, 9H), 1.08 (s, 3H), 1.06 (s, 9H). 4 missing piperidine hydrogens. LCMS (M+H)=816.4.

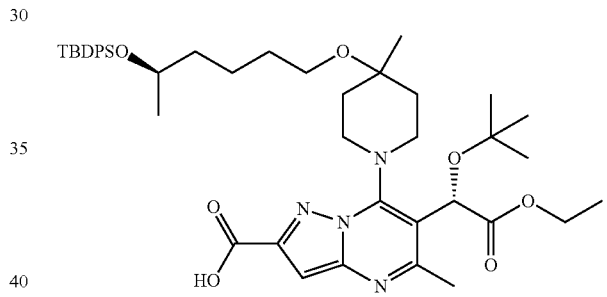

6-((S)-1-(tert-Butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid To a solution of ethyl 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylate (6.8 g, 8.34 mmol) in Ethanol (70 mL) was added 1N NaOH (9.18 mL, 9.18 mmol) and the resulting mixture was stirred at room temp for 5 h. Mixture was then concentrated and the residue was diluted with water (50 mL) acidified with 1N HCl and extracted with ether (200 mL), washed with brine (50 mL), dried (Na$_2$SO$_4$), filtered and concentrated to afford 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid (6.4 g, 8.13 mmol, 97% yield) as white solid. $^1$H NMR (500 MHz, CDCl$_3$) δ 7.73-7.68 (m, 4H), 7.47-7.35 (m, 6H), 7.13 (s, 1H), 5.85 (br.s, 1H), 4.30-4.16 (m, 2H), 3.94-3.84 (m, 1H), 3.35 (q, J=6.3 Hz, 2H), 2.65 (s, 3H), 1.92 (d, J=10.7 Hz, 2H), 1.67-1.39 (m, 12H), 1.30 (s, 3H), 1.28-1.25 (m, 3H), 1.24 (s, 9H), 1.11-1.08 (m, 3H), 1.07 (s, 9H). LCMS (M+H)=787.4.

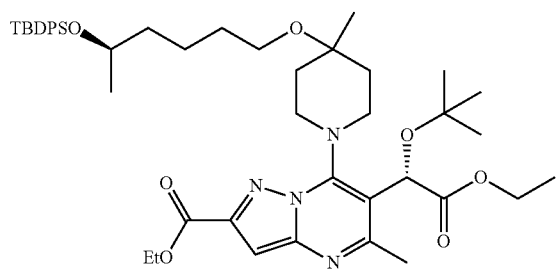

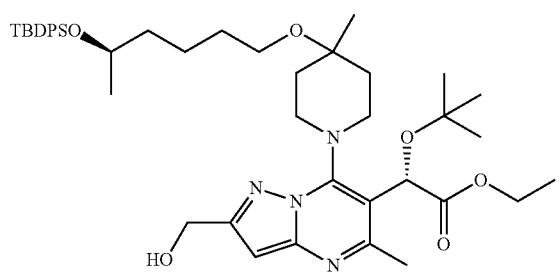

(S)-Ethyl 2-(tert-Butoxy)-2-(7-(4-(((R)-5-((tert-butyldiphenylsilyl)oxy)hexyl)oxy)-4-methylpiperidin-1-yl)-2-(hydroxymethyl)-5-methylpyrazolo[1,5-a]pyrimidin-6-yl)acetate To a stirred solution of 6-((S)-1-(tert-butoxy)-2-ethoxy-2-oxoethyl)-7-(4-(((R)-5-((tert-butyldiphenylsilyl)oxy)hexyl)oxy)-4-methylpiperidin-1-yl)-5-methylpyrazolo[1,5-a]pyrimidine-2-carboxylic acid (6.4 g, 8.13 mmol) and Et₃N (1.473 mL, 10.57 mmol) in THF (80 mL) was added ethyl carbonochloridate (1.011 mL, 10.57 mmol) at 0° C. After 1 h, a solution of NaBH₄ (1.538 g, 40.7 mmol) in cold water (80 mL) was added at once and stirred for additional 1 h at 0° C. Then the reaction was quenched with MeOH (5 mL), diluted with Et₂O (100 mL), washed with water (2×50 mL) and brine (25 mL). The organic layer dried (Na₂SO₄), filtered and concentrate. The residue was then purified by Biotage (5-30% EtOAc/hexane) to afford (S)-ethyl 2-(tert-butoxy)-2-(7-(4-(((R)-5-((tert-butyldiphenylsilyl)oxy)hexyl)oxy)-4-methylpiperidin-1-yl)-2-(hydroxymethyl)-5-methylpyrazolo[1,5-a]pyrimidin-6-yl)acetate (4.5 g, 5.82 mmol, 71.6% yield) as viscous oil. ¹H NMR (500 MHz, CDCl₃) δ 7.74-7.70 (m, 4H), 7.46-7.35 (m, 6H), 6.48 (s, 1H), 5.90 (br. s., 1H), 4.91-4.83 (m, 2H), 4.29-4.11 (m, 2H), 3.94-3.84 (m, 1H), 3.41-3.29 (m, 3H), 2.61 (s, 3H), 2.17 (q, J=5.8 Hz, 1H), 1.94-1.87 (m, 2H), 1.87 (br. s., 1H), 1.66 (br. s., 1H), 1.59 (s, 3H), 1.58-1.40 (m, 5H), 1.33-1.26 (m, 3H), 1.26-1.21 (m, 12H), 1.09 (d, J=6.1 Hz, 3H), 1.07 (s, 9H). LCMS (M+H)=773.4.

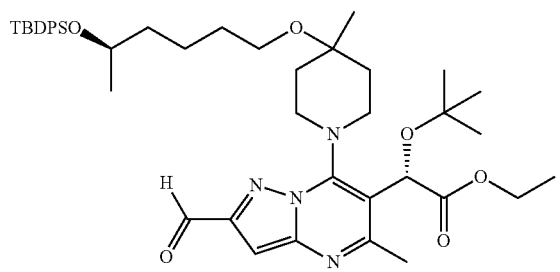

(S)-Ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate To a solution of (S)-ethyl 2-(tert-butoxy)-2-(7-(4-(((R)-5-((tert-butyldiphenylsilyl)oxy)hexyl)oxy)-4-methylpiperidin-1-yl)-2-(hydroxymethyl)-5-methylpyrazolo[1,5-a]pyrimidin-6-yl)acetate (2 g, 2.59 mmol) in CH₂Cl₂ (30 mL) was added Dess-Martin periodinane (1.317 g, 3.10 mmol) and the resulting mixture was stirred at room temp for 3 h. Sat. NaHCO₃ solution was then added and the mixture was extracted with dichloromethane (50 mL), dried (Na₂SO₄), filtered and concentrated. The residue was then purified by Biotage (5-30% EtOAc/hexane) to afford (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (1.9 g, 2.464 mmol, 95% yield) as viscous oil. ¹H NMR (500 MHz, CDCl₃) δ 10.15 (d, J=5.4 Hz, 1H), 7.74-7.66 (m, 4H), 7.47-7.34 (m, 6H), 7.02 (s, 1H), 5.88 (br. s., 1H), 4.30-4.18 (m, 2H), 3.94-3.81 (m, 1H), 3.40-3.28 (m, 3H), 2.64 (s, 3H), 2.02-1.85 (m, 3H), 1.68 (br. s., 1H), 1.57-1.52 (m, 2H), 1.50-1.39 (m, 3H), 1.31 (s, 3H), 1.28-1.25 (m, 3H), 1.25 (s, 9H), 1.09 (d, J=6.1 Hz, 3H), 1.07 (s, 9H). 4 missing piperidine hydrogens. LCMS (M+H)=772.3.

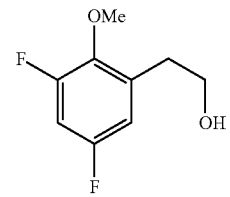

2-(3,5-Difluoro-2-methoxyphenyl)ethanol

To a solution of 2-(3,5-difluoro-2-methoxyphenyl)acetic acid (1 g, 4.95 mmol) in THF (20 mL) at 0° C. was added 1M LAH (9.89 mL, 9.89 mmol) in THF and the resulting mixture was heated at 60° C. for 3 h. Mixture was then cooled and quenched with dropwise addition of water (0.5 mL), 1N NaOH (0.5 mL), and then 1 mL H₂O. After stirring for 15 min. the mixture was filtered through celite. The filtrate was concentrated in vacuo. The residue was dried under high vacuum to afford 2-(3,5-difluoro-2-methoxyphenyl)ethanol (700 mg, 3.72 mmol, 75% yield) as a clear viscous oil. Used as is in the next step without further purification. ¹H NMR (500 MHz, CDCl₃) δ 6.83-6.72 (m, 2H), 3.90 (s, 3H), 3.87 (q, J=5.7 Hz, 2H), 2.92 (t, J=6.5 Hz, 2H), 1.73-1.64 (m, 1H).

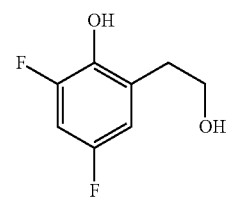

2,4-Difluoro-6-(2-hydroxyethyl)phenol

To a solution of 2-(3,5-difluoro-2-methoxyphenyl)ethanol (850 mg, 4.52 mmol) in DCM (30 mL) at 0° C. was added 1M BBr₃ (13.55 mL, 13.55 mmol) solution. The resulting mixture was slowly warmed to room temp and stir for 3 h. water (dropwise) was then added and after the bubbling stops mixture was diluted with DCM and washed with water, dried (Na₂SO₄), filtered and concentrated. The residue was then purified by Biotage (5-50%, EtOAc/hexane) to afford 2,4-difluoro-6-(2-hydroxyethyl)phenol (450 mg, 2.58 mmol, 57.2% yield) as clear viscous oil. $^1$H NMR (400 MHz, CDCl$_3$) δ 7.14 (br. s., 1H), 6.80-6.73 (m, 1H), 6.66 (dt, J=8.8, 2.4 Hz, 1H), 4.01-3.95 (m, 2H), 2.93 (t, J=5.5 Hz, 2H), 2.32 (br. s., 1H).

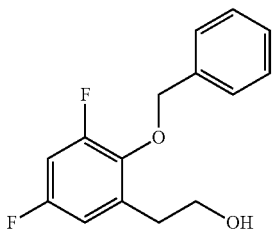 [SMILES: OCCc1cc(F)cc(F)c1OCc1ccccc1]

2-(2-(Benzyloxy)-3,5-difluorophenyl) ethanol

To a solution of 2,4-difluoro-6-(2-hydroxyethyl)phenol (450 mg, 2.58 mmol) in Acetone (10 mL) was added K$_2$CO$_3$ (714 mg, 5.17 mmol) followed by (bromomethyl)benzene (0.461 mL, 3.88 mmol) and the resulting mixture was stirred at room temp for 16 h. Water was then added and the mixture was extracted with ethyl acetate, dried (Na$_2$SO$_4$), filtered and concentrated. The residue was then purified by Biotage (5-30% EtOAc/hexane) to afford 2-(2-(benzyloxy)-3,5-difluorophenyl)ethanol (540 mg, 2.043 mmol, 79% yield) as viscous oil. $^1$H NMR (400 MHz, CDCl$_3$) δ 7.48-7.36 (m, 5H), 6.84-6.72 (m, 2H), 5.07 (s, 2H), 3.78 (q, J=6.3 Hz, 2H), 2.84 (t, J=6.4 Hz, 2H), 1.53 (t, J=5.5 Hz, 1H).

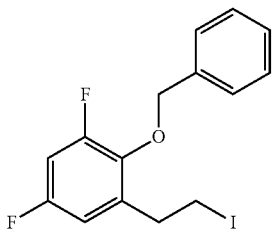 [SMILES: Fc1cc(F)c(OCc2ccccc2)c(CCI)c1]

2-(Benzyloxy)-1,5-difluoro-3-(2-iodoethyl)benzene

A solution of Ph$_3$P (750 mg, 2.86 mmol) and imidazole (195 mg, 2.86 mmol) in DCM (15 mL) was cooled to 0° C. Added to this was iodine (726 mg, 2.86 mmol) and the resulting mixture was stirred at 0° C. for 30 min. Then, 2-(2-(benzyloxy)-3,5-difluorophenyl)ethanol (630 mg, 2.384 mmol) was added portionwise over several minutes and the resulting mixture was stirred at room temp. After 5 h, the mixture was filtered washing the solids with DCM. The filtrate was washed with aq Na$_2$S$_2$O$_3$ and the organic phase was dried (Na$_2$SO$_4$), filtered and concentrated. The residue was purified by flash chromatography (5%-30% EtOAc/hexane) to give 2-(benzyloxy)-1,5-difluoro-3-(2-iodoethyl)benzene (630 mg, 1.684 mmol, 70.6% yield) as light yellow viscous oil. $^1$H NMR (500 MHz, CDCl$_3$) δ 7.46-7.34 (m, 5H), 6.83 (ddd, J=11.3, 8.2, 3.0 Hz, 1H), 6.69 (dt, J=8.6, 2.3 Hz, 1H), 5.10 (s, 2H), 3.21 (d, J=7.7 Hz, 2H), 3.13-3.00 (m, 2H).

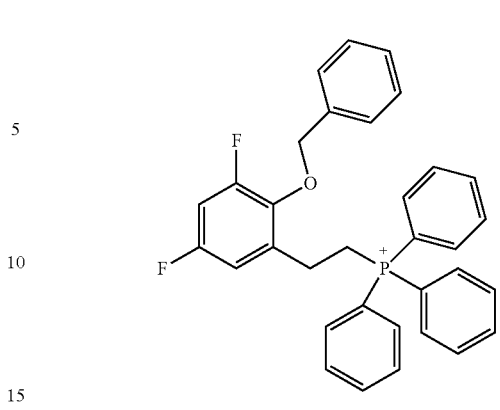

(2-(Benzyloxy)-3,5-difluorophenethyl)triphenylphosphonium, iodide salt

To a solution of 2-(benzyloxy)-1,5-difluoro-3-(2-iodoethyl)benzene (630 mg, 1.684 mmol) in toluene (8 ml) was added Ph$_3$P (442 mg, 1.684 mmol) and the mixture was heated at 100° C. for 16 h. The mixture was then cooled to rt and toluene was decanted via pipet and remaining residue was washed with ether and ethyl acetate, dried under high vac to afford (2-(benzyloxy)-3,5-difluorophenethyl)triphenylphosphonium, iodide salt (600 mg, 0.943 mmol, 56.0% yield) as white solid. Used as-is in the next step without further purification. $^1$H NMR (500 MHz, CDCl$_3$) δ 7.81-7.71 (m, 9H), 7.62 (td, J=7.8, 3.5 Hz, 5H), 7.39-7.33 (m, 2H), 7.31 (d, J=7.6 Hz, 1H), 7.25 (d, J=7.3 Hz, 2H), 7.22-7.14 (m, 2H), 6.75 (ddd, J=11.2, 8.2, 2.8 Hz, 1H), 5.01 (s, 2H), 3.92 (dt, J=12.4, 7.9 Hz, 2H), 3.02-2.94 (m, 2H).

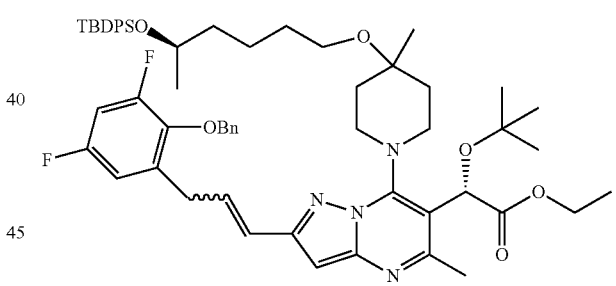

(S)-Ethyl 2-(2-(3-(2-(benzyloxy)-3,5-difluorophenyl) prop-1-en-1-yl)-7-(4-(((R)-5-((tert-butyldiphenylsilyl)oxy) hexyl)oxy)-4-methylpiperidin-1-yl)-5-methylpyrazolo[1,5-a]pyrimidin-6-yl)-2-(tert-butoxy) acetate To a suspension of (2-(benzyloxy)-3,5-difluorophenethyl) triphenylphosphonium, iodide salt (330 mg, 0.519 mmol) in THF (4 ml) at 0° C. was added NaH (21.27 mg, 0.532 mmol) and the resulting mixture was stirred at rt for 45 min. The mixture was cooled to 0° C. rd (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (200 mg, 0.259 mmol) dissolved in THF (4 ml) was added dropwise and the mixture was stirred at 0° C. for 1 h then warmed to rt and stirred 2 h. The reaction was quenched with water and the product was extracted with EtOAc. The organic phase was washed with brine, dried (Na2SO4), filtered and concentrated. The residue was purified by flash chromatography (Biotage; 0%-30% EtOAc/hexane) to afford (S)-ethyl 2-(2-(3-(2-(benzyloxy)-3,5-difluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (190 mg, 0.190 mmol, 73% yield) as mixture of E and Z isomers. LCMS (M+H)=1002.0.

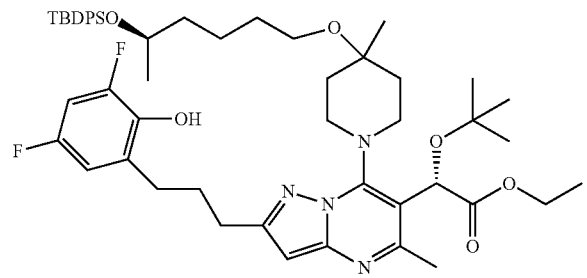

(S)-Ethyl 2-(tert-butoxy)-2-(7-(4-(((R)-5-((tert-butyldiphenylsilyl)oxy)hexyl)oxy)-4-methylpiperidin-1-yl)-2-(3-(3,5-difluoro-2-hydroxyphenyl)propyl)-5-methylpyrazolo[1,5-a]pyrimidin-6-yl)acetate To a solution of (S)-ethyl 2-(2-(3-(2-(benzyloxy)-3,5-difluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (190 mg, 0.190 mmol) in Ethanol (4 mL) was added 10% Pd—C (40.4 mg, 0.038 mmol) and the resulting mixture was stirred under balloon hydrogen atmosphere for 16 h. At this point LCMS indicates completion of reaction. Mixture was then filtered through a pad of celite, concentrated and dried under high vac to afford (S)-ethyl 2-(tert-butoxy)-2-(7-(4-(((R)-5-((tert-butyldiphenylsilyl)oxy)hexyl)oxy)-4-methylpiperidin-1-yl)-2-(3-(3,5-difluoro-2-hydroxyphenyl)propyl)-5-methylpyrazolo[1,5-a]pyrimidin-6-yl)acetate (140 mg, 0.153 mmol, 81% yield) as thick paste. Used as is in the next step without further purification. $^1$H NMR (500 MHz, CDCl$_3$) δ 7.70 (d, J=7.3 Hz, 4H), 7.45-7.34 (m, 6H), 6.75-6.63 (m, 2H), 6.34 (s, 1H), 5.90 (br. s., 1H), 4.33-4.10 (m, 3H), 3.95-3.79 (m, 1H), 3.35 (br. s., 2H), 2.92-2.76 (m, 3H), 2.73 (br. s., 1H), 2.61 (s, 3H), 2.16-2.04 (m, 3H), 1.92 (br. s., 1H), 1.87 (br. s., 1H), 1.53-1.46 (m, 3H), 1.45-1.26 (m, 9H), 1.24 (s, 9H), 1.07 (s, 9H). LCMS (M+H)=913.9.

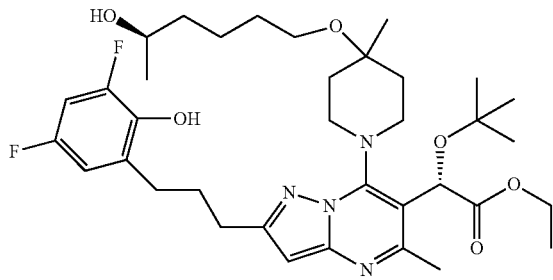 [SMILES: CCOC(=O)[C@@H](OC(C)(C)C)c1c(C)nc2cc(CCCc3cc(F)cc(F)c3O)nn2c1N1CCC(C)(OCCCC[C@@H](C)O)CC1]

(S)-Ethyl 2-(tert-butoxy)-2-(2-(3-(3,5-difluoro-2-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate To a solution of (S)-ethyl 2-(tert-butoxy)-2-(7-(4-(((R)-5-((tert-butyldiphenylsilyl)oxy)hexyl)oxy)-4-methylpiperidin-1-yl)-2-(3-(3,5-difluoro-2-hydroxyphenyl)propyl)-5-methylpyrazolo[1,5-a]pyrimidin-6-yl)acetate (130 mg, 0.142 mmol) in THF (3 mL) was added 1M solution of TBAF (0.712 mL, 0.712 mmol) and the resulting mixture was stirred at room temp for 16 h. Mixture was then concentrated and the residue was purified by Biotage (5-50% EtOAc/hexane) to afford (S)-ethyl 2-(tert-butoxy)-2-(2-(3-(3,5-difluoro-2-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate (70 mg, 0.104 mmol, 72.9% yield) as white solid. $^1$H NMR (500 MHz, CDCl$_3$) δ 6.79-6.61 (m, 2H), 6.34 (s, 1H), 5.94 (br. s., 1H), 4.29-4.09 (m, 2H), 3.87 (d, J=5.4 Hz, 1H), 3.49-3.36 (m, 2H), 2.92-2.79 (m, 3H), 2.76 (br. s., 1H), 2.62 (s, 3H), 2.16-2.07 (m, 2H), 1.98 (d, J=13.2 Hz, 2H), 1.64 (d, J=4.3 Hz, 3H), 1.56-1.41 (m, 4H), 1.33 (br. s., 2H), 1.27-1.20 (m, 15H). LCMS (M+H)=675.8.

Example 41

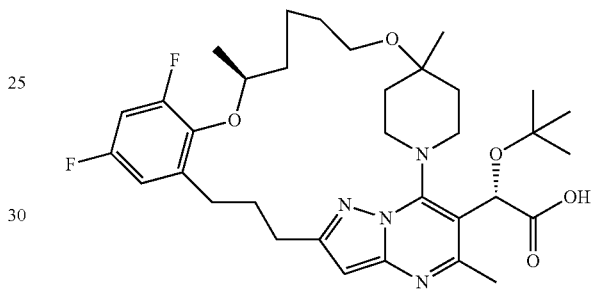

(2S)-2-(tert-Butoxy)-2-[(20S)-15,17-difluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid To a solution of (S)-ethyl 2-(tert-butoxy)-2-(2-(3-(3,5-difluoro-2-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate (65 mg, 0.096 mmol) in THF (15 mL) was added Ph$_3$P (37.9 mg, 0.144 mmol) followed by DEAD (0.023 mL, 0.144 mmol) and the resulting mixture was stirred at room temp for 3 h. At this point LCMS indicates completion of reaction. Water (25 mL) was then added and the mixture was extracted with ether (50 mL), dried (Na$_2$SO$_4$), filtered and concentrated. The residue was then purified by Biotage (0-30% EtOAc/hexane) to afford desired ester. LCMS (M+H)=657.7. Ester was then treated with 1N NaOH (0.482 mL, 0.482 mmol) in EtOH (2 mL) at 80° C. for 5 h. Mixture was then cooled, concentrated and purified by prep HPLC to afford (2S)-2-(tert-butoxy)-2-[(20S)-15,17-difluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid (24 mg, 0.036 mmol, 37.6% yield) as white solid. $^1$H NMR (500 MHz, METHANOL-d$_4$) δ 6.86-6.72 (m, 2H), 6.26 (s, 1H), 5.93 (s, 1H), 4.58 (t, J=11.3 Hz, 1H), 4.53-4.45 (m, 1H), 3.85 (t, J=10.9 Hz, 1H), 3.52 (t, J=5.0 Hz, 2H), 2.95-2.78 (m, 3H), 2.74 (d, J=11.2 Hz, 1H), 2.72-2.64 (m, 1H), 2.62-2.52 (m, 3H), 2.30-2.16 (m, 1H), 2.08-2.00 (m, 2H), 1.96-1.88 (m, 2H), 1.86-1.62 (m, 8H), 1.28 (s, 3H), 1.26 (s, 9H), 1.20 (d, J=6.0 Hz, 3H). LCMS (M+H) 629.6.

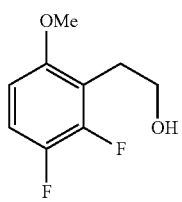 [SMILES: COc1ccc(F)c(F)c1CCO]

2-(2,3-Difluoro-6-methoxyphenyl) ethanol

To a solution of 2-(2,3-difluoro-6-methoxyphenyl)acetic acid (1 g, 4.95 mmol) in THF (20 mL) at 0° C. was added 1M LAH (9.89 mL, 9.89 mmol) in THF and the resulting mixture was heated at 60° C. for 3 h. Mixture was then cooled and quenched with dropwise addition of water (0.5 mL), 1N NaOH (0.5 mL), and then 1 mL H$_2$O. After stirring for 15 min, the mixture was filtered through celite. The filtrate was concentrated in vacuo. The residue was dried under high vacuum to afford 2-(2,3-difluoro-6-methoxyphenyl)ethanol (810 mg, 4.30 mmol, 87% yield) as a clear viscous oil. Used as is in the next step without further purification. $^1$H NMR (500 MHz, CDCl$_3$) δ 7.01 (q, J=9.2 Hz, 1H), 6.62-6.53 (m, 1H), 3.92-3.75 (m, 5H), 3.00 (td, J=6.6, 1.9 Hz, 2H), 1.65 (t, J=5.7 Hz, 1H).

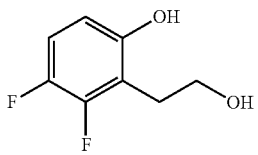 [SMILES: OCCc1c(O)ccc(F)c1F]

3,4-Difluoro-2-(2-hydroxyethyl)phenol

To a solution of 2-(2,3-difluoro-6-methoxyphenyl)ethanol (800 mg, 4.25 mmol) in DCM (25 mL) at 0° C. was added 1M BBR3 (17.01 mL, 17.01 mmol) solution and the resulting mixture was allowed to warm to room temp and stir for 4 h. Water (dropwise) was then added and after the bubbling stops mixture was diluted with DCM and washed with water, dried (Na$_2$SO$_4$), filtered and concentrated. The residue was then purified by Biotage (5-50%, EtOAc/hexane) to afford 3,4-difluoro-2-(2-hydroxyethyl)phenol (500 mg, 2.87 mmol, 67.5% yield) as clear viscous oil. $^1$H NMR (500 MHz, CDCl$_3$) δ 7.85 (br. s., 1H), 7.04-6.93 (m, 1H), 6.71-6.60 (m, 1H), 4.07-4.01 (m, 2H), 3.04-2.95 (m, 2H), 2.38 (br. s., 1H).

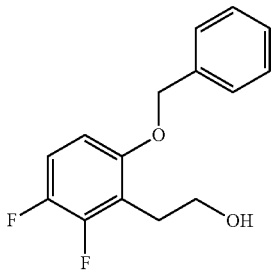 [SMILES: OCCc1c(OCc2ccccc2)ccc(F)c1F]

2-(6-(Benzyloxy)-2,3-difluorophenyl) ethanol

To a solution of 3,4-difluoro-2-(2-hydroxyethyl)phenol (460 mg, 2.64 mmol) in Acetone (10 mL) was added K$_2$CO$_3$ (730 mg, 5.28 mmol) followed by (bromomethyl)benzene (0.471 mL, 3.96 mmol) and the resulting mixture was stirred at room temp for 16 h. Water was then added and the mixture was extracted with ethyl acetate, dried (Na$_2$SO$_4$), filtered and concentrated. The residue was then purified by Biotage (5-30% EtOAc/hexane) to afford 2-(6-(benzyloxy)-2,3-difluorophenyl)ethanol (580 mg, 2.195 mmol, 83% yield) as viscous oil. $^1$H NMR (500 MHz, CDCl$_3$) δ 7.46-7.34 (m, 5H), 6.99 (q, J=9.1 Hz, 1H), 6.67-6.59 (m, 1H), 5.09 (s, 2H), 3.86 (q, J=6.4 Hz, 2H), 3.05 (td, J=6.5, 1.7 Hz, 2H).

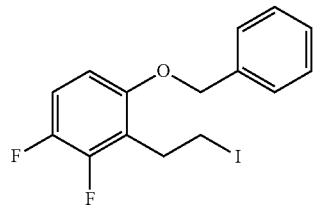 [SMILES: Fc1ccc(OCc2ccccc2)c(CCI)c1F]

1-(Benzyloxy)-3,4-difluoro-2-(2-iodoethyl)benzene

A solution of Ph$_3$P (697 mg, 2.66 mmol) and imidazole (181 mg, 2.66 mmol) in DCM (15 mL) was cooled to 0° C. Added to this was iodine (674 mg, 2.66 mmol) and the resulting mixture was stirred at 0° C. for 30 min. 2-(6-(benzyloxy)-2,3-difluorophenyl)ethanol (585 mg, 2.214 mmol) was added portionwise over several minutes and the resulting mixture was stirred at room temp. After 5 h, the mixture was filtered washing the solids with DCM. The filtrate was washed with aq Na$_2$S$_2$O$_3$ and the organic phase was dried (Na$_2$SO$_4$), filtered and concentrated. The residue was purified by flash chromatography (Biotage; 0%-100% EtOAc/hexane) to give 1-(benzyloxy)-3,4-difluoro-2-(2-iodoethyl)benzene (720 mg, 1.924 mmol, 87% yield) as colorless oil. $^1$H NMR (500 MHz, CDCl$_3$) δ 7.52-7.35 (m, 5H), 7.03 (q, J=9.3 Hz, 1H), 6.69-6.52 (m, 1H), 5.10 (s, 2H), 3.37-3.29 (m, 4H).

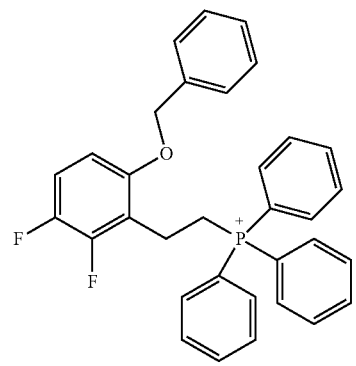

(6-(Benzyloxy)-2,3-difluorophenethyl)triphenylphosphonium, iodide salt

To a solution of 1-(benzyloxy)-3,4-difluoro-2-(2-iodoethyl)benzene (720 mg, 1.924 mmol) in Xylene (10 mL) was added Ph$_3$P (1514 mg, 5.77 mmol) and the mixture was heated at 140° C. for 16 h. The mixture was cooled to rt (The product solidified). Solids were then filtered off and washed with toluene and ether, dried under high vac to afford (6-(benzyloxy)-2,3-difluorophenethyl)triphenylphosphonium, iodide salt (600 mg, 0.943 mmol, 49.0% yield) as white solid. ¹H NMR (500 MHz, CDCl₃) δ 7.87-7.77 (m, 3H), 7.77-7.59 (m, 12H), 7.53-7.44 (m, 2H), 7.40-7.33 (m, 3H), 7.02 (q, J=9.3 Hz, 1H), 6.70 (d, J=9.1 Hz, 1H), 5.15 (s, 2H), 3.81-3.69 (m, 2H), 3.10-2.98 (m, 2H). LCMS (M+H)=510.2.

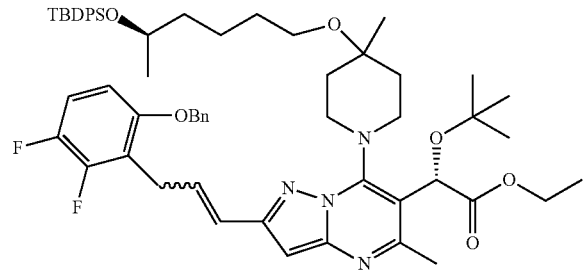

(S)-Ethyl 2-(2-(3-(6-(benzyloxy)-2,3-difluorophenyl) prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy) acetate To a suspension of (6-(benzyloxy)-2,3-difluorophenethyl)triphenylphosphonium, iodide salt (217 mg, 0.340 mmol) in THF (5 ml) at 0° C. was added n-BuLi (0.213 ml, 0.340 mmol) and the resulting mixture was heated at 60° C. for 1 h. The mixture was then cooled to rt and (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (175 mg, 0.227 mmol) dissolved in THF (5 ml) was added dropwise and the mixture was stirred rt for 5 h. The reaction was quenched with water and the product was extracted with EtOAc. The organic phase was washed with brine, dried (Na₂SO₄), filtered and concentrated. The residue was purified by flash chromatography (Biotage; 0%-30% EtOAc/hexane) to afford (S)-ethyl 2-(2-(3-(6-(benzyloxy)-2,3-difluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (114 mg, 0.114 mmol, 50% yield) as mixture of E and Z isomers. LCMS (M+H)=1001.8.

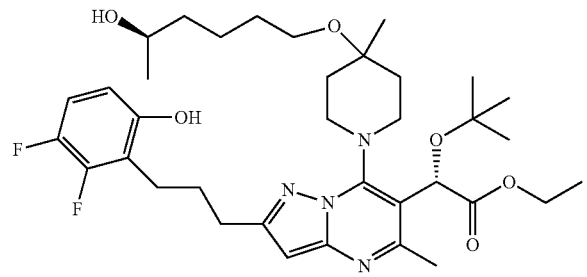 [SMILES: CCOC(=O)[C@@H](OC(C)(C)C)c1c(C)nc2cc(CCCc3c(O)ccc(F)c3F)nn2c1N1CCC(C)(OCCCC[C@@H](C)O)CC1]

(S)-Ethyl 2-(tert-butoxy)-2-(2-(3-(2,3-difluoro-6-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate To a solution of (S)-ethyl 2-(2-(3-(6-(benzyloxy)-2,3-difluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (114 mg, 0.114 mmol) in Ethanol (4 mL) was added 10% Pd—C (24 mg, 0.022 mmol) and the resulting mixture was stirred under balloon hydrogen atmosphere for 16 h. At this point LCMS indicates completion of reaction. Mixture was then filtered through a pad of celite, concentrated and dried under high vac. The residue was then treated with 1M TBAF (0.849 mL, 0.849 mmol) in THF (4 mL) for 16 h. Mixture was then concentrated and purified by Biotage (5-70% EtOAc/hexane) to afford (S)-ethyl 2-(tert-butoxy)-2-(2-(3-(2,3-difluoro-6-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate (35 mg, 0.052 mmol, 30% yield) as thick paste. ¹H NMR (400 MHz, CDCl₃) δ 6.90 (q, J=9.0 Hz, 1H), 6.59 (d, J=10.0 Hz, 1H), 6.36 (s, 1H), 5.91 (br. s., 1H), 4.32-4.15 (m, 2H), 3.85 (d, J=6.3 Hz, 2H), 3.44 (br. s., 3H), 2.94 (br. s., 1H), 2.89-2.71 (m, 4H), 2.63 (s, 3H), 2.15-2.04 (m, 2H), 2.04-1.94 (m, 2H), 1.90 (d, J=6.8 Hz, 2H), 1.75 (d, J=7.3 Hz, 1H), 1.57-1.44 (m, 6H), 1.38-1.27 (m, 12H), 0.94-0.87 (m, 6H). LCMS (M+H)=675.4.

Example 42

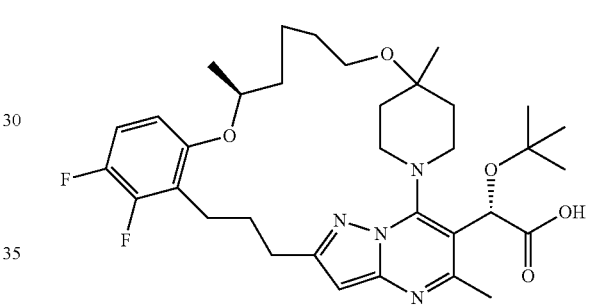

(2S)-2-(tert-Butoxy)-2-[(20S)-14,15-difluoro-4,20,26-trimethyl-19,25-dioxa-1,5,7,8-tetraazapentacyclo[24.2.2.1⁶,⁹.0²,⁷.0¹³,¹⁸]hentriaconta-2,4,6(31),8,13(18),14,16-heptaen-3-yl]acetic acid To a solution of (S)-ethyl 2-(tert-butoxy)-2-(2-(3-(2,3-difluoro-6-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate (35 mg, 0.052 mmol) in THF (10 mL) was added Ph₃P (40.8 mg, 0.156 mmol) followed by DEAD (0.025 mL, 0.156 mmol) and the resulting mixture was stirred at room temp for 3 h. At this point LCMS indicates completion of reaction. Water (25 mL) was then added and the mixture was extracted with ether (50 mL), dried (Na₂SO₄), filtered and concentrated. The residue was then purified by Biotage (0-30% EtOAc/hexane) to afford desired ester. LCMS (M+H)=657.7. Ester was then treated with 1N NaOH (0.259 mL, 0.259 mmol) in EtOH (2 mL) at 80° C. for 5 h. Mixture was then cooled, concentrated and purified by prep HPLC to afford (2S)-2-(tert-butoxy)-2-[(20S)-14,15-difluoro-4,20,26-trimethyl-19,25-dioxa-1,5,7,8-tetraazapentacyclo[24.2.2.1⁶,⁹.0²,⁷.0¹³,¹⁸]hentriaconta-2,4,6(31),8,13(18),14,16-heptaen-3-yl]acetic acid (7.7 mg, 0.012 mmol, 23.61% yield) as white solid. 1H NMR (500 MHz, DMSO-d₆) δ 7.18 (q, J=9.7 Hz, 1H), 6.82 (d, J=8.1 Hz, 1H), 6.28 (s, 1H), 5.70 (s, 1H), 4.58 (br. s., 1H), 4.30 (t, J=11.4 Hz, 1H), 3.65-3.56 (m, 1H), 3.35 (d, J=16.9 Hz, 2H), 2.80-2.62 (m, 4H), 2.55 (br. s., 1H), 2.47 (s, 3H), 2.19 (br. s., 1H), 1.87 (d, J=12.1 Hz, 2H), 1.83-1.74 (m, 2H), 1.73-1.57 (m, 6H), 1.56-1.44 (m, 2H), 1.20-1.15 (m, 6H), 1.14 (s, 9H). LCMS (M+H)=629.5.

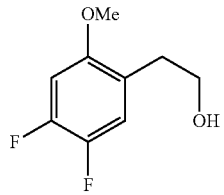 [SMILES: COc1cc(F)c(F)cc1CCO]

2-(4,5-Difluoro-2-methoxyphenyl)ethanol

To a solution of 2-(4,5-difluoro-2-methoxyphenyl)acetic acid (1 g, 4.95 mmol) in THF (20 mL) at 0° C. was added 1M LAH (9.89 mL, 9.89 mmol) in THF and the resulting mixture was heated at 60° C. for 3 h. Mixture was then cooled and quenched with dropwise addition of water (0.5 mL), 1N NaOH (0.5 mL), and then 1 mL H2O. After stirring for 15 min. the mixture was filtered through celite. The filtrate was concentrated in vacuo. The residue was dried under high vacuum to afford 2-(4,5-difluoro-2-methoxyphenyl)ethanol (800 mg, 4.25 mmol, 86% yield) as a clear viscous oil. Used as is in the next step without further purification. $^1$H NMR (500 MHz, CDCl$_3$) δ 7.02 (t, J=9.8 Hz, 1H), 6.71 (dd, J=12.1, 6.7 Hz, 1H), 3.87-3.82 (m, 2H), 3.81 (s, 3H), 2.85 (t, J=6.5 Hz, 2H), 1.56 (br. s., 1H).

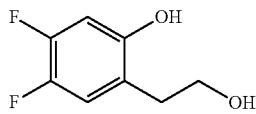

4,5-Difluoro-2-(2-hydroxyethyl)phenol

To a solution of 2-(4,5-difluoro-2-methoxyphenyl)ethanol (800 mg, 4.25 mmol) in DCM (25 mL) at 0° C. was added 1M BBr$_3$ (17.01 mL, 17.01 mmol) solution and the resulting mixture was allowed to warm to room temp and stir for 4 h. Then, water (dropwise) was added and after the bubbling stops mixture was diluted with DCM and washed with water, dried (Na$_2$SO$_4$), filtered and concentrated. The residue was then purified by Biotage (5-70%, EtOAc/hexane) to afford 4,5-difluoro-2-(2-hydroxyethyl)phenol (450 mg, 2.58 mmol, 60.8% yield) as clear viscous oil. $^1$H NMR (500 MHz, CDCl$_3$) δ 6.93-6.84 (m, 1H), 6.75 (dd, J=11.5, 7.1 Hz, 1H), 4.03-3.96 (m, 2H), 2.85 (t, J=5.2 Hz, 2H).

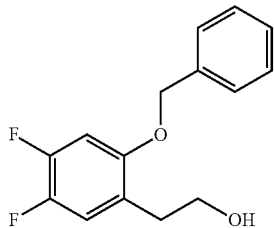 [SMILES: OCCc1cc(F)c(F)cc1OCc1ccccc1]

2-(2-(Benzyloxy)-4,5-difluorophenyl) ethanol

To a solution of 4,5-difluoro-2-(2-hydroxyethyl)phenol (450 mg, 2.58 mmol) in acetone (10 mL) was added K$_2$CO$_3$ (714 mg, 5.17 mmol) followed by (bromomethyl)benzene (0.461 mL, 3.88 mmol) and the resulting mixture was stirred at room temp for 16 h. Water was then added and the mixture was extracted with ethyl acetate, dried (Na$_2$SO$_4$), filtered and concentrated. The residue was then purified by Biotage (5-30% EtOAc/hexane) to afford 2-(2-(benzyloxy)-4,5-difluorophenyl)ethanol (580 mg, 2.195 mmol, 85% yield) as viscous oil. $^1$H NMR (500 MHz, CDCl$_3$) δ 7.48-7.33 (m, 5H), 7.10-7.01 (m, 1H), 6.78 (dd, J=12.1, 6.7 Hz, 1H), 5.05 (s, 2H), 3.85 (q, J=6.0 Hz, 2H), 2.90 (t, J=6.4 Hz, 2H), 1.52 (t, J=5.5 Hz, 1H).

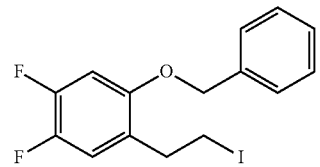 [SMILES: Fc1cc(CCI)c(OCc2ccccc2)cc1F]

1-(Benzyloxy)-4,5-difluoro-2-(2-iodoethyl)benzene

A solution of Ph$_3$P (691 mg, 2.63 mmol) and imidazole (179 mg, 2.63 mmol) in DCM (15 mL) was cooled to 0° C. Added to this was iodine (668 mg, 2.63 mmol) and the resulting mixture was stirred at 0° C. for 30 min. 2-(2-(Benzyloxy)-4,5-difluorophenyl)ethanol (580 mg, 2.195 mmol) was added portionwise over several minutes and the resulting mixture was stirred at room temperature. After 5 h, the mixture was filtered and washed the solids with DCM. The filtrate was washed with aq Na$_2$S$_2$O$_3$ and the organic phase was dried (Na$_2$SO$_4$), filtered and concentrated. The residue was purified by flash chromatography (Biotage; 0%-20% EtOAc/hexane) to give 1-(benzyloxy)-4,5-difluoro-2-(2-iodoethyl)benzene (630 mg, 1.684 mmol, 77% yield) as colorless viscous oil. $^1$H NMR (500 MHz, CDCl$_3$) δ 7.50-7.34 (m, 6H), 7.00 (dd, J=10.3, 9.2 Hz, 1H), 6.77 (dd, J=12.0, 6.6 Hz, 1H), 5.06 (s, 2H), 3.37 (t, J=7.5 Hz, 2H), 3.21-3.15 (m, 2H).

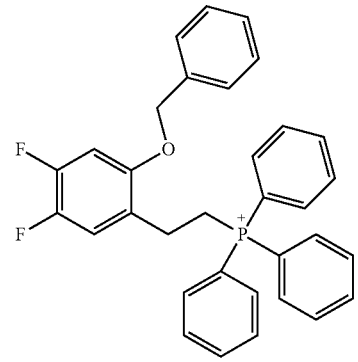

(2-(Benzyloxy)-4,5-difluorophenethyl)triphenylphosphonium, iodide salt

To a solution of 1-(benzyloxy)-4,5-difluoro-2-(2-iodoethyl)benzene (630 mg, 1.684 mmol) in xylene (10 mL) was added Ph$_3$P (883 mg, 3.37 mmol) and the mixture was heated at 140° C. for 16 h. The mixture was cooled to rt (The product solidified). Solids were then filtered off and washed with ether and hexane, dried under high vacuum to afford (2-

(benzyloxy)-4,5-difluorophenethyl)triphenylphosphonium iodide salt (850 mg, 1.336 mmol, 79% yield) as white solid. ¹H NMR (500 MHz, CDCl₃)) δ 7.87-7.61 (m, 15H), 7.44-7.33 (m, 6H), 6.74 (dd, J=11.6, 6.4 Hz, 1H), 5.00 (s, 2H), 3.94-3.83 (m, 2H), 3.06-2.91 (m, 2H). LCMS (M+H)=510.4.

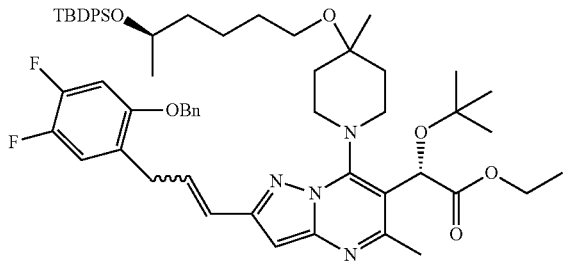

(S)-Ethyl 2-(2-(3-(2-(benzyloxy)-4,5-difluorophenyl) prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy) acetate To a suspension of (2-(benzyloxy)-4,5-difluorophenethyl) triphenylphosphonium iodide salt (289 mg, 0.454 mmol) in THF (4 ml) at 0° C. was added NaH (18.61 mg, 0.465 mmol) and the resulting mixture was stirred at rt for 45 min. The mixture was cooled to 0° C. and (S)-ethyl 2-(tert-butoxy)-2-(7-(4-(((R)-5-((tert-butyldiphenylsilyl)oxy)hexyl)oxy)-4-methylpiperidin-1-yl)-2-formyl-5-methylpyrazolo[1,5-a]pyrimidin-6-yl)acetate (175 mg, 0.227 mmol) dissolved in THF (4 ml) was added dropwise and the mixture was stirred at 0° C. for 1 h then warmed to rt and stirred 2 h. The reaction was quenched with water and the product was extracted with EtOAc. The organic phase was washed with brine, dried (Na₂SO₄), filtered and concentrated. The residue was purified by flash chromatography (Biotage; 0%-30% EtOAc/hexane) to afford (S)-ethyl 2-(2-(3-(2-(benzyloxy)-4,5-difluorophenyl)prop-1-en-1-yl)-7-(4-(((R)-5-((tert-butyldiphenylsilyl) oxy)hexyl)oxy)-4-methylpiperidin-1-yl)-5-methylpyrazolo [1,5-a]pyrimidin-6-yl)-2-(tert-butoxy)acetate (190 mg, 0.190 mmol, 84% yield) as mixture of E and Z isomers. LCMS (M+H)=1002.0.

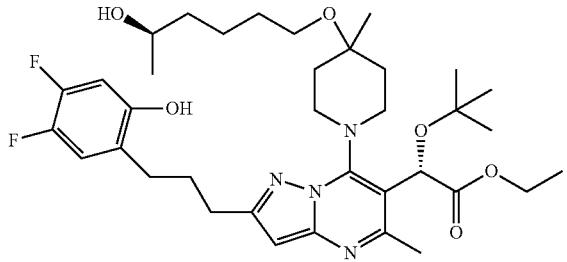 [SMILES: CCOC(=O)[C@@H](OC(C)(C)C)c1c(C)nc2cc(CCCc3cc(F)c(F)cc3O)nn2c1N1CCC(C)(OCCCC[C@@H](C)O)CC1]

(S)-Ethyl 2-(tert-butoxy)-2-(2-(3-(4,5-difluoro-2-hydroxyphenyl)propyl)-7-(4-(((R)-5-hydroxyhexyl) oxy)-4-methylpiperidin-1-yl)-5-methylpyrazolo[1,5-a]pyrimidin-6-yl)acetate To a solution of (S)-ethyl 2-(2-(3-(2-(benzyloxy)-4,5-difluorophenyl)prop-1-en-1-yl)-7-(4-(((R)-5-((tert-butyldiphenylsilyl)oxy)hexyl)oxy)-4-methylpiperidin-1-yl)-5-methylpyrazolo[1,5-a]pyrimidin-6-yl)-2-(tert-butoxy)acetate (190 mg, 0.190 mmol) in ethanol (4 mL) was added 10% Pd—C (60.6 mg, 0.057 mmol) and the resulting mixture was stirred under balloon hydrogen atmosphere for 16 h. At this point LCMS indicates completion of reaction. Mixture was then filtered through a pad of celite, concentrated and dried under high vacuum. The residue was then treated with 1M TBAF (0.949 mL, 0.949 mmol) in THF (4 mL) for 16 h. Mixture was then concentrated and purified by Biotage (5-70% EtOAc/hexane) to afford to afford (S)-ethyl 2-(tert-butoxy)-2-(2-(3-(4,5-difluoro-2-hydroxyphenyl)propyl)-7-(4-(((R)-5-hydroxyhexyl)oxy)-4-methylpiperidin-1-yl)-5-methylpyrazolo[1,5-a]pyrimidin-6-yl)acetate (85 mg, 0.126 mmol, 66.4% yield) as thick paste. ¹H NMR (500 MHz, CDCl₃) 6.96-6.89 (m, 1H), 6.68 (dd, J=11.7, 7.1 Hz, 1H), 6.34 (s, 1H), 5.90 (br. s., 1H), 4.31-4.09 (m, 2H), 3.93-3.81 (m, 1H), 3.44 (br. s., 2H), 2.88-2.70 (m, 4H), 2.63 (s, 4H), 2.12-1.94 (m, 4H), 1.90 (br. s., 2H), 1.57-1.42 (m, 6H), 1.41-1.31 (m, 3H), 1.27-1.18 (m, 18H). LCMS (M+H)=675.6.

Example 43

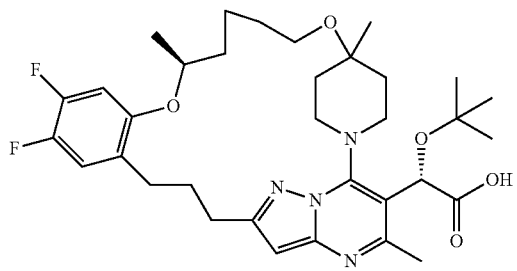 [SMILES: Cc1nc2cc3nn2c(c1[C@H](OC(C)(C)C)C(=O)O)N1CCC(C)(CC1)OCCCC[C@H](C)Oc1cc(F)c(F)cc1CCC3]

(2S)-2-(tert-Butoxy)-2-[(20S)-15,16-difluoro-4,20, 26-trimethyl-19,25-dioxa-1,5,7,8-tetraazapentacyclo [24.2.2.1⁶,⁹.0²,⁷.0¹³,¹⁸]hentriaconta-2,4,6(31),8,13 (18),14,16-heptaen-3-yl]acetic acid To a solution of (S)-ethyl 2-(tert-butoxy)-2-(2-(3-(4,5-difluoro-2-hydroxyphenyl)propyl)-7-(4-(((R)-5-hydroxyhexyl) oxy)-4-methylpiperidin-1-yl)-5-methylpyrazolo[1,5-a]pyrimidin-6-yl)acetate (85 mg, 0.126 mmol) in THF (12 mL) was added Ph3P (49.6 mg, 0.189 mmol) followed by DEAD (0.030 mL, 0.189 mmol) and the resulting mixture was stirred at room temp for 3 h. At this point LCMS indicates completion of reaction. Water (25 mL) was then added and the mixture was extracted with ether (50 mL), dried (Na₂SO₄), filtered and concentrated. The residue was then purified by Biotage (0-30% EtOAc/hexane) to afford desired ester. LCMS (M+H)=657.7. Ester was then treated with 1N NaOH (0.630 mL, 0.630 mmol) in EtOH (2 mL) at 80° C. for 5 h. Mixture was then cooled, concentrated and purified by prep HPLC to afford (2S)-2-(tert-butoxy)-2-[(20S)-15,16-difluoro-4,20,26-trimethyl-19,25-dioxa-1,5,7,8-tetraazapentacyclo[24.2.2.1⁶,⁹.0²,⁷.0¹³,¹⁸]hentriaconta-2,4,6(31),8,13 (18),14,16-heptaen-3-yl]acetic acid (16 mg, 0.024 mmol, 19.19% yield) as white solid. 1H NMR (500 MHz, METHANOL-d₄) δ 7.05 (br. s., 1H), 6.90 (br. s., 1H), 6.23 (s., 1H), 5.86 (s., 1H), 4.56-4.45 (m, 2H), 3.77 (br. s., 1H), 3.55-3.46 (m, 4H), 2.87-2.81 (m, 2H), 2.73 (br. s., 1H), 2.60 (br. s., 3H), 2.53 (br. s., 1H), 2.33 (br. s., 1H), 1.91-1.66 (m, 11H), 1.32-1.12 (m, 15H). LCMS (M+H)=629.5.

The following examples 44-53 were synthesised using appropriate reagents and using same methods as for Example 38.

Example 44

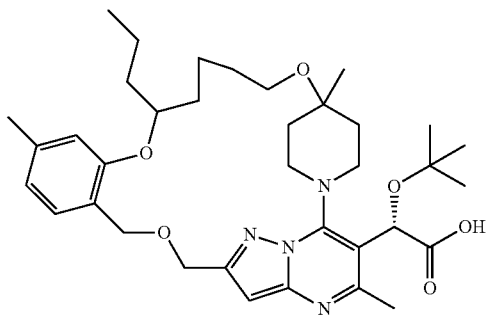 [SMILES: CCCC1CCCCOC2(C)CCN(CC2)c2c([C@H](OC(C)(C)C)C(=O)O)c(C)nc3cc(nn23)COCc2ccc(C)cc2O1]

(2S)-2-(tert-Butoxy)-2-{4,16,26-trimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-hepta en-3-yl}acetic acid The crude material was purified via preparative HPLC to yield 6.1 mg product and its estimated purity by LCMS analysis was 100%. $^1$H NMR (500 MHz, DMSO) δ 0.82 (t, 3H). 1.15 (s, 9H), 1.18 (s, 3H), 1.54-1.86 (overlapping m, 14H). 2.29 (s, 3H), 2.50 (s, 3H), 2.67 (m, 1H), 3.31 (m, 2H), 3.65 (t, 1H), 3.80 (m, 1H) 4.33 (m, 1H) 4.46 (m, 1H), 4.57 (overlapping m, 2H), 4.82 (d, 1H), 5.67 (s, 1H), 6.49 (s, 1H), 6.70 (d, 1H), 6.81 (s, 1H), 7.18 (d, 1H). LCMS (M+H)=637.6.

Example 45

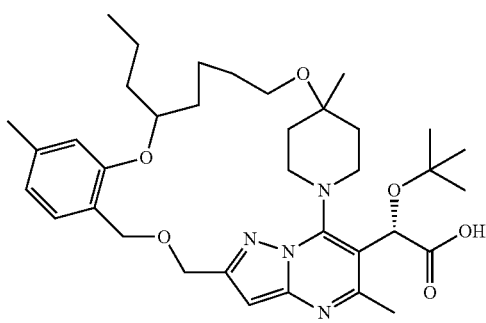 [SMILES: CCCC1CCCCOC2(C)CCN(CC2)c2c([C@H](OC(C)(C)C)C(=O)O)c(C)nc3cc(nn23)COCc2ccc(C)cc2O1]

(2S)-2-(tert-butoxy)-2-{4,16,26-trimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptane-3-yl}acetic acid The crude product was purified by preparative HPLC to yield 8.0 mg of product and its estimated purity by LCMS analysis was 97%. $^1$H NMR (500 MHz, DMSO) δ 0.88 (t, 3H). 1.16 (s, 9H), 1.18 (s, 3H), 1.36-1.76 (overlapping m, 14H), 2.26 (s, 3H), 2.50 (s 3H) 2.67 (m, 1H), 3.20 (m, 1H) 3.39 (overlapping m 2H), 3.62 (m, 1H), 4.38 (m, 1H), 4.45 (overlapping m, 2H), 4.56 (d, 1H), 4.71 (dd, 2H) 5.77 (s, 1H), 6.51 (s, 1H), 6.64 (d, 1H), 6.79 (d, 1H), 7.06 (d, 1H). LCMS (M+H)=636.6.

Example 46

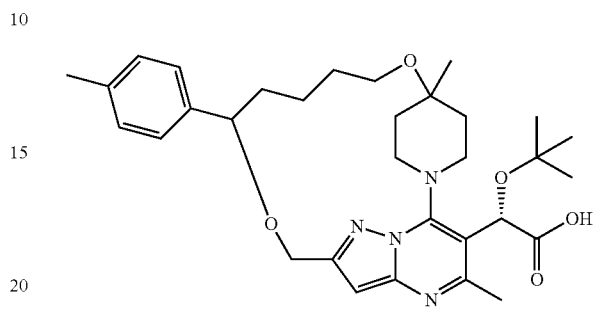

(2S)-2-(tert-butoxy)-2-[4,18-dimethyl-12-(4-methylphenyl)-11,17-dioxa-1,5,7,8-tetraazatetracyclo[16.2.2.1$^{6,9}$.0$^{2,7}$]tricosa-2,4,6(23),8-tetraen-3-yl]acetic acid $^1$H NMR (500 MHz, DMSO) δ 1.21 (overlapping s, 12H), 1.91-1.48 (overlapping m, 10H), 2.30 (s, 3H), 2.51 (s, 3H), 3.34-3.44 (overlapping m, 4H), 3.79 (m, 1H) 4.40 (m, 1H), 4.43 (d, 1H), 4.83 (overlapping, 2H), 5.91 (s, 1H), 6.25 (s, 1H), 7.16 (d, 2H), 7.22 (d, 2H). LCMS (M+H)=565.4.

Example 47

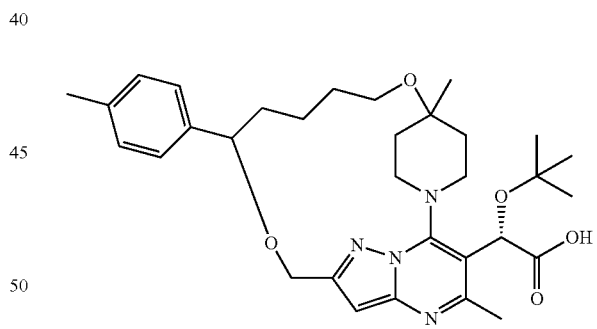

(2S)-2-(tert-butoxy)-2-[4,18-dimethyl-12-(4-methylphenyl)-11,17-dioxa-1,5,7,8-tetraazatetracyclo[16.2.2.1$^{6,9}$.0$^{2,7}$]tricosa-2,4,6(23),8-tetraen-3-yl]acetic acid $^1$H NMR (500 MHz, DMSO) δ 1.20 (s, 9H), 1.21 (s, 3H) 1.85-1.45 (overlapping m, 10H), 2.31 (s, 3H), 2.51 (s, 3H), 3.33-3.60 (overlapping m, 4H), 3.99 (m, 1H) 4.46 (m, 1H), 4.50 (overlapping, 1H), 4.52 (m, 1H) 4.78 (overlapping, 1H), 5.96 (s, 1H), 6.26 (s, 1H), 7.17 (d, 2H), 7.26 (d, 2H). LCMS (M+H)=565.4.

Example 48

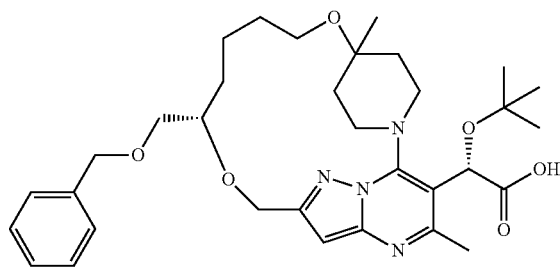 [SMILES: Cc1nc2cc3nn2c(c1[C@H](OC(C)(C)C)C(=O)O)N1CCC(C)(CC1)OCCCC[C@@H](COCc1ccccc1)OC3]

(2S)-2-[(12S)-12-[(benzyloxy)methyl]-4,18-dimethyl-11,17-dioxa-1,5,7,8-tetraazatetracyclo[16.2.2.1⁶,⁹.0²,⁷]tricosa-2,4,6(23),8-tetraen-3-yl]-2-(tert-butoxy)acetic acid $^1$H NMR (500 MHz, DMSO) δ 1.19 (s, 12H), 1.45-1.57 (overlapping m, 9H), 1.71 (m, 1H), 2.51 (s, 3H) 3.23-3.53 (overlapping m, 6H), 3.73 (m, 1H), 3.91 (m, 1H), 4.54 (s, 2H). 4.62 (m, 1H), 4.67 (d, 1H), 5.01 (d, 1H), 5.97 (s, 1H), 6.35 (s, 1H), 7.30 (m, 1H), 7.37 (overlapping m, 4H). LCMS (M+H)=595.3.

Example 49

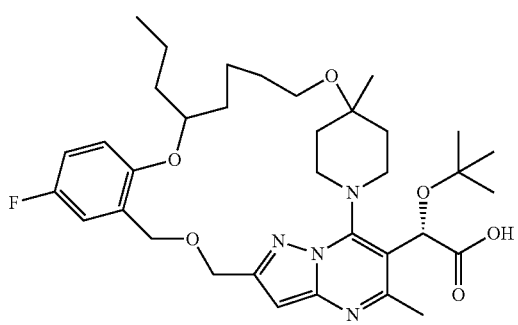 [SMILES: CCCC1CCCCOC2(C)CCN(CC2)c2c([C@H](OC(C)(C)C)C(=O)O)c(C)nc3cc(nn23)COCc2cc(F)ccc2O1]

(2S)-2-(tert-butoxy)-2-{15-fluoro-4,26-dimethyl-20-propyl-11,19,25-trioxa-1,5,7,8-tetraazapentacyclo[24.2.2.1⁶,⁹.0²,⁷.0¹³,¹⁸]hentriaconta-2,4,6(31),8,13(18),14,16-heptaen-3-yl}acetic acid $^1$H NMR (500 MHz, DMSO) δ 0.81 (m, 3H) 1.14 (s, 9H), 1.18 (s, 3H) 1.45-1.90 (overlapping m, 14H), 2.51 (s, 3H), 3.33-3.80 (overlapping m, 5H), 4.29 (m, 1H) 4.42 (m, 1H), 4.57 (overlapping, 2H), 4.6 (d, 1H) 4.87 (d, 1H), 5.59 (s, 1H), 6.49 (s, 1H), 6.97 (m, 1H), 7.02 (m, 1H) 7.12 (d, 1H). LCMS (M+H)=641.4.

Example 50

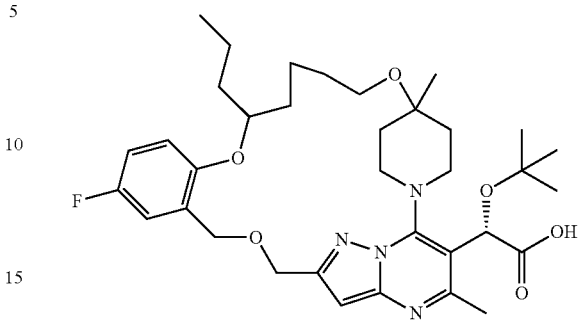

(2S)-2-(tert-butoxy)-2-{15-fluoro-4,26-dimethyl-20-propyl-11,19,25-trioxa-1,5,7,8-tetraazapentacyclo[24.2.2.1⁶,⁹.0²,⁷.0¹³,¹⁸]hentriaconta-2,4,6(31),8,13(18),14,16-heptaen-3-yl}acetic acid $^1$H NMR (500 MHz, DMSO) δ 0.85 (m, 3H) 1.15 (s, 9H), 1.18 (s, 3H) 1.34-1.90 (overlapping m, 14H), 2.51 (s, 3H), 2.72 (m, 1H), 3.11 (m, 1H), 3.31-3.80 (overlapping m, 3H), 4.55 (overlapping m, 2H) 4.61 (overlapping m, 3H), 4.60 (d, 1H) 5.73 (s, 1H), 6.54 (s, 1H), 7.00 (overlapping m, 3H). LCMS (M+H)=641.4.

Example 51

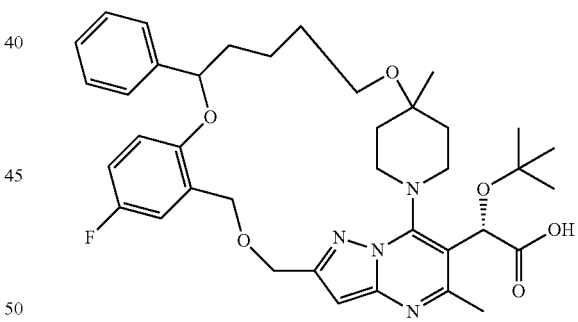

(2S)-2-(tert-butoxy)-2-{15-fluoro-4,26-dimethyl-20-phenyl-11,19,25-trioxa-1,5,7,8-tetraazapentacyclo[24.2.2.1⁶,⁹.0²,⁷.0¹³,¹⁸]hentriaconta-2,4,6(31),8,13(18),14,16-heptaen-3-yl}acetic acid $^1$H NMR (500 MHz, DMSO) δ 1.15 (s, 9H), 1.16 (s, 3H), 1.48-1.91 (overlapping m, 10H), 2.52 (s, 3H), 2.81 (m, 1H), 3.32-3.59 (overlapping m, 5H), 4.38 (m, 1H), 4.70 (overlapping m, 2H), 4.80 (d, 1H), 4.94 (d, 1H), 5.41 (m, 1H), 5.48 (s, 1H), 6.53 (s, 1H), 6.67 (m, 1H), 6.86 (m, 1H), 7.10 (dd, 1H), 7.18 (overlapping m, 2H), 7.29 (d, 2H). LCMS (M+H)=675.2.

Example 52

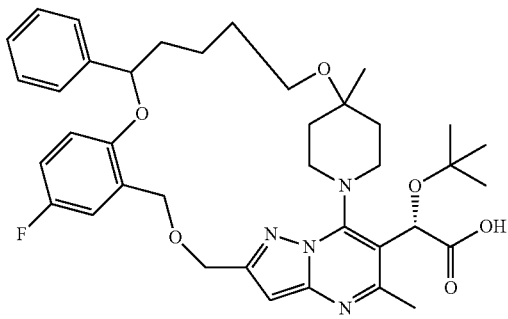 [SMILES: Cc1nc2cc3nn2c(c1[C@H](OC(C)(C)C)C(=O)O)N1CCC(C)(CC1)OCCCCC(c1ccccc1)Oc1ccc(F)cc1COC3]

(2S)-2-(tert-butoxy)-2-{15-fluoro-4,26-dimethyl-20-phenyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid $^1$H NMR (500 MHz, DMSO) δ 1.13 (s, 9H), 1.18 (s, 3H), 1.56 (overlapping m, 5H), 1.83-1.97 (overlapping m, 5H), 2.51 (s, 3H), 2.81 (m, 1H), 3.32-3.54 (overlapping m, 5H), 4.40 (m, 1H), 4.70 (d. 1H), 4.79 (m, 2H), 4.93 (d, 1H), 5.29 (m, 1H), 5.47 (s, 1H), 6.52 (s, 1H), 6.57 (m, 1H), 6.78 (m, 1H), 7.00 (d, 1H), 7.24 (m, 1H), 7.35 (overlapping m, 3H). LCMS (M+H)=675.2.

Example 53

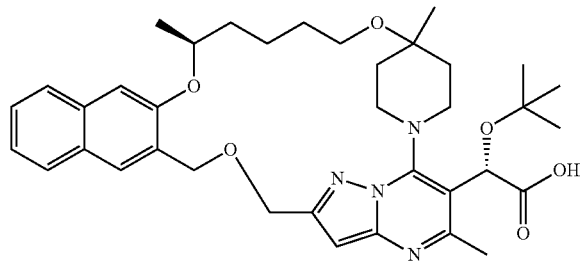 [SMILES: Cc1nc2cc3nn2c(c1[C@H](OC(C)(C)C)C(=O)O)N1CCC(C)(CC1)OCCCC[C@H](C)Oc1cc2ccccc2cc1COC3]

(2S)-2-(tert-butoxy)-2-[(24S)-4,24,30-trimethyl-11,23,29-trioxa-1,5,7,8-tetraazahexacyclo[28.2.2.1$^{6,9}$.0$^{2,7}$.0$^{13,22}$.0$^{15,20}$]pentatriaconta-2,4,6(35),8,13,15,17,19,21-nonaen-3-yl]acetic acid $^1$H NMR (500 MHz, DMSO) δ 1.13 (s, 9H), 1.18 (s, 3H), 1.27 (d, 3H), 1.53-1.88 (overlapping m 10H) 2.51 (s, 3H), 3.39-3.62 (overlapping m, 5H), 4.33 (m, 1H), 4.74 (overlapping m, 4H), 4.96 (d, 1H), 5.54 (s, 1H), 6.51 (s, 1H), 7.31 (overlapping m, 2H), 7.41 (m, 1H), 7.79 (dd, 2H), 7.84 (s, 1H). LCMS (M+H)=645.5.

Methyl 4 fluoro-2-[(1,1,1-trifluoropent-4-en-2-yl)oxy]benzoate

Methyl 2,4-difluorobenzoate (1.72 g, 9.99 mmol) was dissolved in dioxane. To this was added 1,1,1-trifluoropent-4-en-2-ol (1.40 g, 9.99 mmol) followed by 60% (mineral oil) NaH (0.40 g, 9.99 mmol). The resulting mixture was heated to 90° C. and stirred overnight. After cooling to RT, 1N HCl was added and the mixture transferred to separatory funnel. The mixture was extracted with ethyl acetate after which the organic solution was washed with 1N NaOH (2 times) and sat'd NaCl. The solution was dried over Na$_2$SO$_4$, filtered and the solvent removed to yield the title compound as an oil which was used in the next step without further purification.

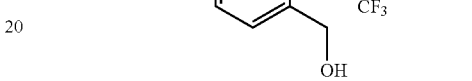

{4-Fluoro-2-[(1,1,1-trifluoropent-4-en-2-yl)oxy]phenyl}methanol

Methyl 4-fluoro-2-[(1,1,1-trifluoropent-4-en-2-yl)oxy]benzoate (2.92 g, 10 mmol) was dissolved in 20 mL of THF and cooled to 0° C. 1M (THF) LiAlH$_4$ (10 mL, 10 mmol) was added and the mixture stirred for 3 hours. Ethyl acetate (10 mL) was added and the mixture stirred 5 min, after which sat'd NaHCO$_3$ was added and stirring continued for 15 min. The mixture was transferred to a separatory funnel and extracted with ethylacetate. The organic layers were combined and dried over Na$_2$SO$_4$, filtered and the solvent removed under vacuum. The crude product was purified by column chromatography on a Biotage instrument using hexanes/ethyl acetate as eluent. 1H NMR (400 MHz, CDCl$_3$) δ 2.70 (m, 2H), 4.64 (overlapping m, 3H), 5.23 (d, 1H), 5.27 (d, 1H), 5.84 (m, 1H), 6.68 (dd, 1H), 6.77 (td, 1H), 7.35 (m, 1H).

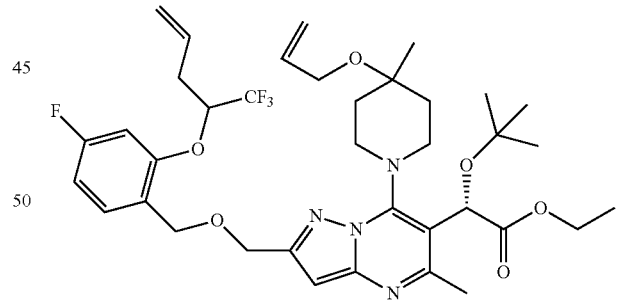

Ethyl (2S)-2-(tert-butoxy)-2-{2-[({4-fluoro-2-[(1,1,1-trifluoropent-4-en-2-yl)oxy]phenyl}methoxy)methyl]-5-methyl-7-[4-methyl-4-(prop-2-en-1-yloxy)piperidin-1-yl]pyrazolo[1,5-a]pyrimidin-6-yl}acetate (4-Fluoro-2-((1,1,1-trifluoropent-4-en-2-yl)oxy)phenyl)methanol (66 mg, 0.25 mmol) and (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (145 mg, 0.25 mmol) were dissolved in 1 mL of DMF at 0° C. and 60% (mineral oil) NaH (10 mg, 0.25 mmol) added. The resulting mixture was stirred at 0° C. for 3 hours then quenched with 1N HCl. The mixture was extracted with ethyl acetate. The organic fractions were combined and dried over Na$_2$SO$_4$, filtered and the solvent removed to yield the crude product which was used in the next reaction without further purification.

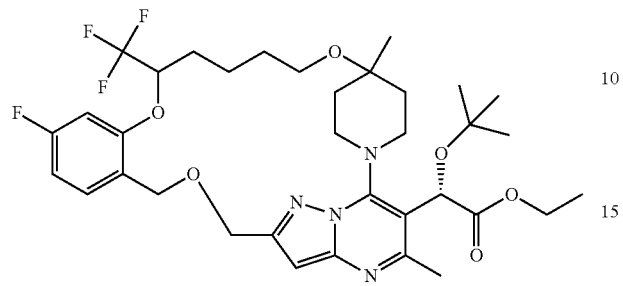

Ethyl (2S)-2-(tert-butoxy)-2-[(21E)-16-fluoro-4,26-dimethyl-20-(trifluoromethyl)-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,21-octaen-3-yl]acetate Ethyl (2S)-2-(tert-butoxy)-2-{2-[({4-fluoro-2-[(1,1,1-trifluoropent-4-en-2-yl)oxy]phenyl}m ethoxy)methyl]-5-methyl-7-[4-methyl-4-(prop-2-en-1-yloxy)piperidin-1-yl]pyrazolo[1,5-a]pyrimidin-6-yl}acetate (90 mg, 0.125 mmol) was dissolved in 70 mL of CH$_2$Cl$_2$. To this was added [1,3-bis-(2,4,6-trimethylphenyl)-2-imidazolidinylidene]dichloro(phenylmethylene)(tricyclohexylphosphine)ruthenium (21 mg, 0.025 mmol) and the resulting mixture stirred at reflux for 4 hours. The solvent was removed under vacuum and the residue dissolved in 1 mL of methanol. [1,3-bis-(2,4,6-trimethylphenyl)-2-imidazolidinylidene]dichloro(phenylmethylene)(tricyclohexylphosphine)ruthenium (21 mg, 0.025 mmol) was added followed by NaBH$_4$ (26 mg, 0.624 mmol). After stirring for 15 min the solvent was removed under vacuum and the crude product purified by chromatography on a Biotage instrument eluting with hexanes/ethyl acetate to provide 61 mg of product. LCMS (M+H)=695.5.

Example 54

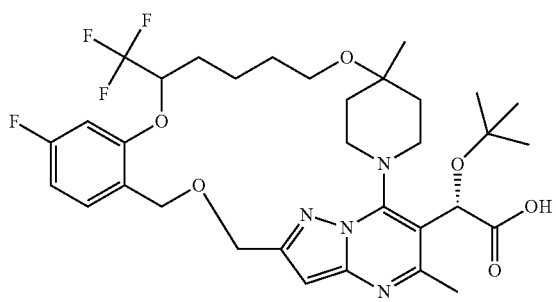 [SMILES: Cc1nc2cc3nn2c(c1[C@H](OC(C)(C)C)C(=O)O)N1CCC(C)(CC1)OCCCCC(C(F)(F)F)Oc1cc(F)ccc1COC3]

(2S)-2-(tert-butoxy)-2-[16-fluoro-4,26-dimethyl-20-(trifluoromethyl)-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid $^1$H NMR (500 MHz, DMSO) δ 1.13 (s, 9H), 1.17 (s, 3H), 1.52-1.85 (overlapping m, 10H), 2.51 (s, 3H), 3.34-3.9 (overlapping m, 5H), 4.26 (m, 1H), 4.57 (m, 2H), 4.90 (d, 1H), 4.78 (d, 1H), 5.38 (br s, 1H), 5.54 (s, 1H), 6.45 (s, 1H), 6.85 (m, 1H), 7.29 (d, 1H), 7.40 (t, 1H). LCMS (M+H)=667.5.

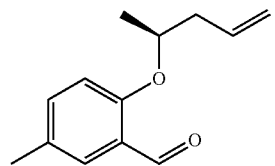

(S)-5-Methyl-2-(pent-4-en-2-yloxy)benzaldehyde

A mixture (S)-(4-methyl-2-(pent-4-en-2-yloxy)phenyl)methanol (100 mg, 0.485 mmol), Dess-Martin periodinane (247 mg, 0.582 mmol) in DCM (5 mL) was stirred at rt for 1 h. It was then diluted with EtOAc and washed with sat. NaHCO$_3$ and water. The organic layer was dried over MgSO$_4$, filtered and concentrated to obtain an oil, which was then purified by biotage, eluting with 10% EtOAc/hexane to isolate (S)-5-methyl-2-(pent-4-en-2-yloxy)benzaldehyde (90 mg, 91%) as an oil. $^1$H NMR (400 MHz, CDCl$_3$) δ 10.44 (s, 1H), 7.75 (d, J=8.1 Hz, 1H), 6.87-6.78 (m, 2H), 5.88 (ddt, J=17.1, 10.1, 7.1 Hz, 1H), 5.21-5.10 (m, 2H), 4.59 (sxt, J=6.1 Hz, 1H), 2.63-2.51 (m, 1H), 2.51-2.42 (m, 1H), 2.40 (s, 3H), 1.40 (d, J=6.1 Hz, 3H).

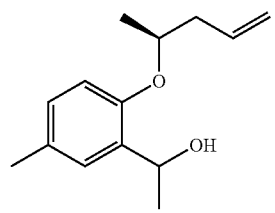 [SMILES: C=CC[C@H](C)Oc1ccc(C)cc1C(C)O]

1-(4-Methyl-2-((S)-pent-4-en-2-yloxy)phenyl)ethanol

To a mixture of (S)-4-methyl-2-(pent-4-en-2-yloxy)benzaldehyde (50 mg, 0.245 mmol) in diethyl ether (2 mL) was added methylmagnesium iodide (0.245 mL, 0.734 mmol) and the mixture was stirred at rt for 1 h. It was then diluted with water, extracted with EtOAc. The organic layer was dried over MgSO$_4$, filtered and concentrated. The residue was purified by biotage, eluting with 25% EtOAc/hexane to obtain 1-(4-methyl-2-((S)-pent-4-en-2-yloxy)phenyl)ethanol (50 mg, 93%) as an oil. $^1$H NMR (400 MHz, CDCl3) δ 7.19 (dd, J=7.7, 3.8 Hz, 1H), 6.76 (d, J=7.8 Hz, 1H), 6.71 (s, 1H), 5.88 (ddtd, J=17.2, 10.3, 7.0, 3.5 Hz, 1H), 5.22-5.10 (m, 2H), 5.10-4.96 (m, 1H), 4.62-4.47 (m, 1H), 2.94 (dd, J=18.8, 5.4 Hz, 1H), 2.64-2.38 (m, 2H), 2.34 (s, 3H), 1.51 (d, J=6.6 Hz, 3H), 1.37 (dd, J=6.0, 4.0 Hz, 3H).

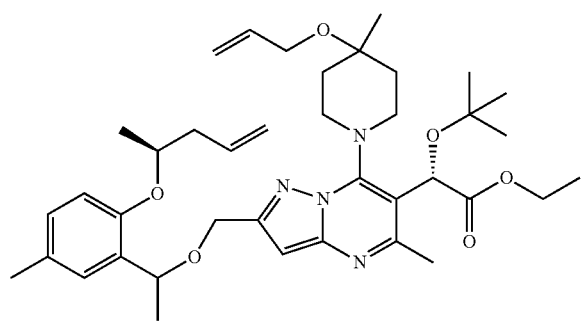 [SMILES: C=CCOC1(C)CCN(c2c([C@H](OC(C)(C)C)C(=O)OCC)c(C)nc3cc(COC(C)c4cc(C)ccc4O[C@@H](C)CC=C)nn23)CC1]

(2S)-Ethyl 2-(7-(4-(allyloxy)-4-methylpiperidin-1-yl)-5-methyl-2-((1-(5-methyl-2-((S)-pent-4-en-2-yloxy)phenyl)ethoxy)methyl)pyrazolo[1,5-a]pyrimidin-6-yl)-2-(tert-butoxy)acetate A mixture of 1-(4-methyl-2-((S)-pent-4-en-2-yloxy)phenyl)ethanol (41.5 mg, 0.188 mmol) and (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (100 mg, 0.171 mmol) in DMF (5 mL) was added sodium hydride (7.53 mg, 0.188 mmol) at 0° C. It was then stirred at 0° C. for 4 h and then quenched with NH$_4$Cl, extracted with EtOAc. The organic layer was dried over MgSO$_4$, filtered and concentrated. The residue was then purified by biotage, eluting with 25% EtOAc/hexane to isolate (2S)-ethyl 2-(7-(4-(allyloxy)-4-methylpiperidin-1-yl)-5-methyl-2-((1-(4-methyl-2-((S)-pent-4-en-2-yloxy)phenyl)ethoxy)methyl)pyrazolo[1,5-a]pyrimidin-6-yl)-2-(tert-butoxy)acetate (20 mg, 0.030 mmol, 17.27% yield) as an oil. LCMS (M+1)=677.5.

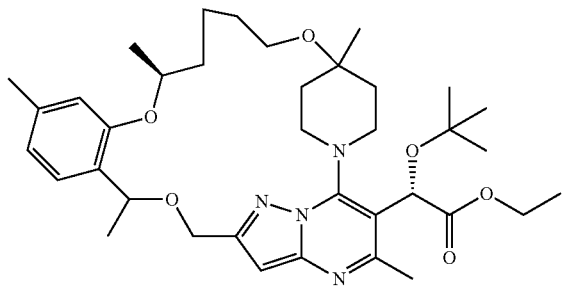 [SMILES: CCOC(=O)[C@@H](OC(C)(C)C)c1c(C)nc2cc3nn2c1N1CCC(C)(CC1)OCCCC[C@H](C)Oc1cc(C)ccc1C(C)OC3]

Ethyl (2S)-2-(tert-butoxy)-2-[(20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetate A mixture of (2S)-ethyl 2-(7-(4-(allyloxy)-4-methylpiperidin-1-yl)-5-methyl-2-((1-(4-methyl-2-((S)-pent-4-en-2-yloxy)phenyl)ethoxy)methyl)pyrazolo[1,5-a]pyrimidin-6-yl)-2-(tert-butoxy)acetate (20 mg, 0.030 mmol) and (1,3-dimesitylimidazolidin-2-ylidene)(2-isopropoxybenzylidene)ruthenium(VI) chloride (1.851 mg, 2.95 μmol) in ClCH$_2$CH$_2$Cl (25 mL) was refluxed for 2 h. It was then concentrated and the residue was diluted in MeOH (2 mL). Sodium borohydride (1.118 mg, 0.030 mmol) was added and the reaction was stirred at rt for 0.5 h. It was then quenched with water, extracted with EtOAc. The organic layer was dried over MgSO$_4$, filtered and concentrated to obtain 20 mg oil, which was then purified by biotage, eluting with 20% EtOAc/hexane to isolate ethyl (2S)-2-(tert-butoxy)-2-[(20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetate (10 mg, 52%) as an oil. LCMS (M+1)=651.4, two peaks on HPLC.

Example 55

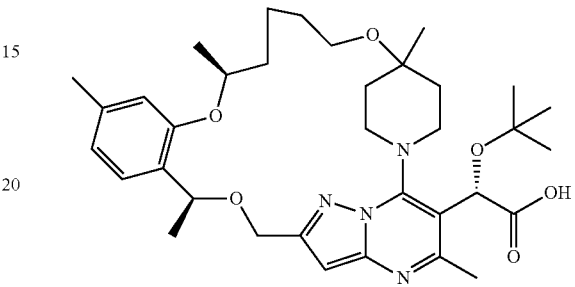

(2S)-2-(tert-Butoxy)-2-[(12S,20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid A mixture of ethyl (2S)-2-(tert-butoxy)-2-[(20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetate (10 mg, 0.015 mmol) and sodium hydroxide (0.077 mL, 0.077 mmol) in EtOH (2 mL) was refluxed for 2 h. It was then cooled to rt and purified by preparative HPLC to isolate the first eluting isomer (2S)-2-(tert-butoxy)-2-[(12S,20S)-4,12,16,20,26pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid (4.0 mg, 41.8%) as a white solid. $^1$H NMR (500 MHz, DMSO-d$_6$) δ 7.24 (d, J=7.7 Hz, 1H), 6.82 (s, 1H), 6.74 (d, J=7.7 Hz, 1H), 6.31 (s, 1H), 5.56-5.43 (m, 2H), 4.63-4.39 (m, 4H), 3.66-3.51 (m, 4H), 2.85 (d, J=11.0 Hz, 1H), 2.48 (s, 3H), 2.28 (s, 3H), 1.94-1.86 (m, 2H), 1.75-1.48 (m, 8H), 1.28 (d, J=6.2 Hz, 3H), 1.19 (d, J=8.4 Hz, 6H), 1.14 (s, 9H). LCMS (M+1)=623.3.

Example 56

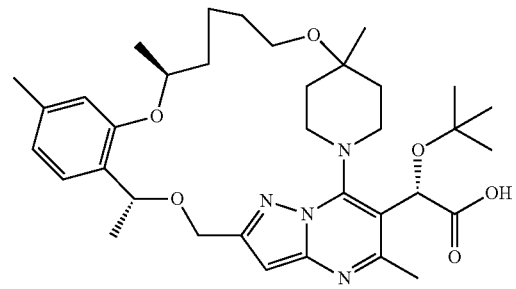 [SMILES: Cc1ccc2c(c1)O[C@@H](C)CCCCOC1(C)CCN(CC1)c1c([C@H](OC(C)(C)C)C(=O)O)c(C)nc3cc(nn13)CO[C@@H]2C]

(2S)-2-(tert-Butoxy)-2-[(12R,20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid The second eluting isomer from the above reaction. $^1$H NMR (500 MHz, DMSO-d$_6$) δ 7.28 (d, J=7.3 Hz, 1H), 6.82 (s, 1H), 6.75 (d, J=7.3 Hz, 1H), 6.46 (s, 1H), 5.44 (br. s., 1H), 4.88 (d, J=6.6 Hz, 1H), 4.64 (d, J=12.8 Hz, 1H), 4.56 (br. s., 1H), 4.25 (t, J=12.5 Hz, 1H), 4.14 (d, J=12.8 Hz, 1H), 3.81-3.37 (m, 4H), 2.85 (m, 1H), 2.48 (s, 3H), 2.29 (s, 3H), 1.85-1.43 (m, 10H), 1.19-1.07 (m, 18H). LCMS (M+1)=623.3.

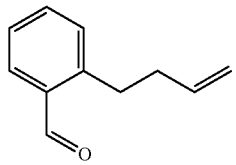

2-(But-3-en-1-yl)benzaldehyde

To a mixture of 1-bromo-2-(but-3-en-1-yl)benzene (1 g, 4.74 mmol) in THF (10 mL) at −78° C. was added BuLi (2.274 mL, 5.68 mmol) dropwise. It was then stirred at this temperature for 1 h, then N,N-dimethylformamide (0.416 g, 5.68 mmol) was added. The reaction was stirred at 78° C. for 30 min, then warmed to rt and stirred at rt for 1 h. It was then quenched with NH$_4$Cl, extracted with ether. The organic layer was then dried over MgSO$_4$, filtered and concentrated. The residue was purified by biotage, eluting with 10% EtOAc/hexane to obtain 2-(but-3-en-1-yl)benzaldehyde (0.7 g, 92%) as an oil. $^1$H NMR (400 MHz, CDCl$_3$) δ 10.35-10.26 (m, 1H), 7.86 (dd, J=7.6, 1.5 Hz, 1H), 7.54 (td, J=7.5, 1.6 Hz, 1H), 7.44-7.38 (m, 1H), 7.30 (d, J=8.1 Hz, 1H), 5.95-5.83 (m, 1H), 5.09-5.00 (m, 2H),), 3.20-3.12 (m, 2H), 2.44-2.36 (m, 2H).

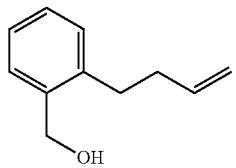

(2-(But-3-en-1-yl)phenyl)methanol

A mixture of 2-(but-3-en-1-yl)benzaldehyde (500 mg, 3.12 mmol) in MeOH (10 mL) was added NaBH$_4$(118 mg, 3.12 mmol) and the mixture was stirred at rt for 1 h. It was then added water, extracted with EtOAc. The organic was dried over MgSO$_4$, filtered and concentrated to obtain an oil, which was then purified by biotage, eluting with 10% EtOAc/hexane to obtain (2-(but-3-en-1-yl)phenyl)methanol (320 mg, 1.973 mmol, 63.2% yield) as a clear oil. $^1$H NMR (400 MHz, CDCl$_3$) δ 7.44-7.37 (m, 1H), 7.33-7.21 (m, 3H), 5.91 (ddt, J=16.9, 10.2, 6.6 Hz, 1H), 5.13-4.99 (m, 2H), 4.76 (d, J=5.9 Hz, 2H), 2.86-2.77 (m, 2H), 2.44-2.35 (m, 2H).

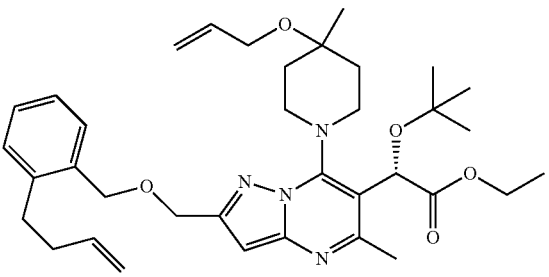 [SMILES: C=CCCc1ccccc1COCc1cc2nc(C)c([C@H](OC(C)(C)C)C(=O)OCC)c(N3CCC(C)(OCC=C)CC3)n2n1]

(S)-Ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate To a mixture of (2-(but-3-en-1-yl)phenyl)methanol (35.1 mg, 0.216 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (115 mg, 0.197 mmol) and NaH (7.87 mg, 0.197 mmol). It was stirred at 0° C. for 4 h, then quenched with water, extracted with EtOAc. The organic layer was dried over MgSO$_4$, filtered and concentrated. The residue was purified by biotage, eluting with 20% EtOac/hexane to obtain (S)-ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate (55 mg, 0.089 mmol, 45.2% yield) as an oil. LCMS (M+1)=619.4.

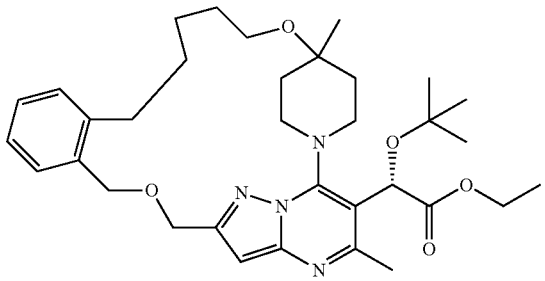 [SMILES: CCOC(=O)[C@@H](OC(C)(C)C)c1c(C)nc2cc3nn2c1N1CCC(C)(CC1)OCCCCCc1ccccc1COC3]

Ethyl (2S)-2-(tert-butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate (S)-ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate (55 mg, 0.089 mmol) and (1,3-dimesitylimidazolidin-2-ylidene)(2-isopropoxybenzylidene)ruthenium(VI) chloride (5.57 mg, 8.89 μmol) in ClCH$_2$CH$_2$Cl (60 mL) was refluxed for 2 h. It was then concentrated and the residue was dissolved in MeOH (5 mL). Sodium borohydride (3.36 mg, 0.089 mmol) was added and the reaction was stirred at rt for 1 h. It was then quenched with water, extracted with EtOAc. The organic layer was dried over MgSO$_4$, filtered and concentrated to obtain an oil, which was then purify by biotage to obtain ethyl (2S)-2-(tert-butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate (37 mg, 70.2%) as a white solid.

¹H NMR (400 MHz, CDCl₃) δ 7.38-7.15 (m, 4H), 6.57 (s, 1H), 6.07 (s, 1H), 4.82-4.69 (m, 4H), 4.59 (t, J=11.2 Hz, 1H), 4.28-4.12 (m, 2H), 3.91 (t, J=10.9 Hz, 1H), 3.44 (d, J=7.3 Hz, 2H), 3.05 (d, J=11.3 Hz, 1H), 2.89 (dd, J=14.2, 6.4 Hz, 1H), 2.78 (dd, J=13.8, 8.3 Hz, 2H), 2.63 (s, 3H), 2.03-1.89 (m, 2H), 1.88-1.64 (m, 8H), 1.28 (s, 3H), 1.25 (s, 9H), 1.24-1.19 (m, 3H). LCMS (M+1)=593.4.

Example 57

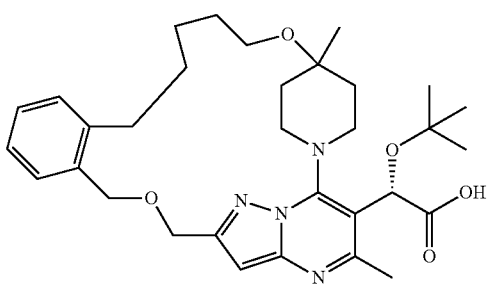 [SMILES: Cc1nc2cc3nn2c(c1[C@H](OC(C)(C)C)C(=O)O)N1CCC(C)(CC1)OCCCCCc1ccccc1COC3]

(2S)-2-(tert-Butoxy)-2-{4,25-dimethyl-11,24-dioxa-1,5,7,8-tetraazapentacyclo[23.2.2.1⁶,⁹.0²,⁷.0¹³,¹⁸]triaconta-2,4,6(30),8,13(18),14,16-heptaen-3-yl}acetic acid A mixture of ethyl (2S)-2-(tert-butoxy)-2-{4,25-dimethyl-11,24-dioxa-1,5,7,8-tetraazapentacyclo[23.2.2.1⁶,⁹.0²,⁷.0¹³,¹⁸]triaconta-2,4,6(30),8,13(18),14,16-heptaen-3-yl}acetate (37 mg, 0.062 mmol) and NaOH (0.312 mL, 0.312 mmol) in EtOH (2 mL) was refluxed for 2 h. It was then filtered and purified by preparative HPLC to obtain (2S)-2-(tert-butoxy)-2-{4,25-dimethyl-11,24-dioxa-1,5,7,8-tetraazapentacyclo[23.2.2.1⁶,⁹.0²,⁷.0¹³,¹⁸]triaconta-2,4,6(30),8,13(18),14,16-heptaen-3-yl}acetic acid (21 mg, 0.037 mmol, 59.6% yield) as a white solid. ¹H NMR (500 MHz, DMSO) δ 7.29 (d, J=7.7 Hz, 1H), 7.26-7.19 (m, 2H), 7.17-7.11 (m, 1H), 6.53 (s, 1H), 5.71 (s, 1H), 4.74-4.58 (m, 4H), 4.50-4.42 (m, 1H), 3.68-3.20 (m, 4H), 2.82-2.75 (m, 1H), 2.66 (d, J=8.4 Hz, 2H), 2.51 (s, 3H), 1.90-1.81 (m, 2H), 1.71-1.51 (m, 8H), 1.19 (s, 3H), 1.15 (s, 9H). LCMS (M+1)=565.3.

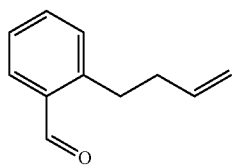

2-(But-3-en-1-yl)benzaldehyde

To a mixture of 1-bromo-2-(but-3-en-1-yl)benzene (1 g, 4.74 mmol) in THF (15 mL) at −78° C. was added BuLi (2.274 mL, 5.68 mmol) dropwise. It was stirred at this temperature for 1 h, then N,N-dimethylformamide (0.416 g, 5.68 mmol) was added and stirred at −78° C. for 30 min. then warmed up to rt and stirred at rt for 1 h. It was then quenched with NH₄Cl, extracted with ether. The organic layer was then dried over MgSO₄, filtered and concentrated to obtain 2-(but-3-en-1-yl)benzaldehyde (0.7 g, 92%) as an oil. 1H NMR (400 MHz, CDCl₃) δ 10.35-10.26 (m, 1H), 7.86 (dd, J=7.6, 1.5 Hz, 1H), 7.54 (td, J=7.5, 1.6 Hz, 1H), 7.44-7.38 (m, 1H), 7.30 (d, J=8.1 Hz, 1H), 5.95-5.83 (m, 1H), 5.09-5.00 (m, 2H),), 3.20-3.12 (m, 2H), 2.44-2.36 (m, 2H).

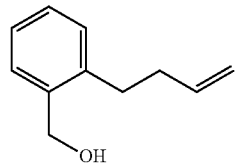

(2-(But-3-en-1-yl)phenyl)methanol

A mixture of 2-(but-3-en-1-yl)benzaldehyde (500 mg, 3.12 mmol) in MeOH (10 mL) was added NaBH₄ (118 mg, 3.12 mmol) and the mixture was stirred at rt for 1 h. It was then added water, extracted with EtOAc. The organic layer was dried over MgSO₄, filtered and concentrated to obtain an oil, which was then purified by biotage, eluting with 10% EtOAc/hexane to obtain (2-(but-3-en-1-yl)phenyl)methanol (320 mg, 1.973 mmol, 63.2% yield) as an oil. ¹H NMR (400 MHz, CDCl₃) δ 7.44-7.37 (m, 1H), 7.33-7.21 (m, 3H), 5.91 (ddt, J=16.9, 10.2, 6.6 Hz, 1H), 5.13-4.99 (m, 2H), 4.76 (d, J=5.9 Hz, 2H), 2.86-2.77 (m, 2H), 2.44-2.35 (m, 2H).

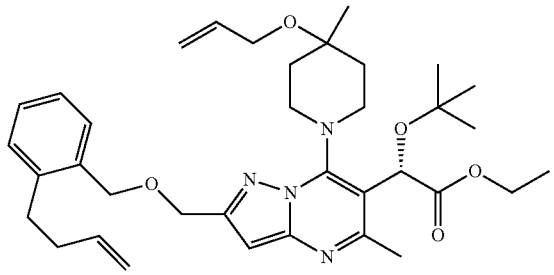 [SMILES: C=CCCc1ccccc1COCc1cc2nc(C)c([C@H](OC(C)(C)C)C(=O)OCC)c(N3CCC(C)(OCC=C)CC3)n2n1]

(S)-Ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate To a mixture of (2-(but-3-en-1-yl)phenyl)methanol (35.1 mg, 0.216 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (115 mg, 0.197 mmol) and NaH (7.87 mg, 0.197 mmol). It was then stirred at 0° C. for 4 h. The reaction mixture was quenched with water, extracted with EtOAc. The organic layer was dried over MgSO₄, filtered and concentrated. The residue was purified by biotage, eluting with 20% EtOAc/hexane to obtain (S)-ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate (55 mg, 0.089 mmol, 45.2% yield) as an oil. LCMS (M+1)=619.4.

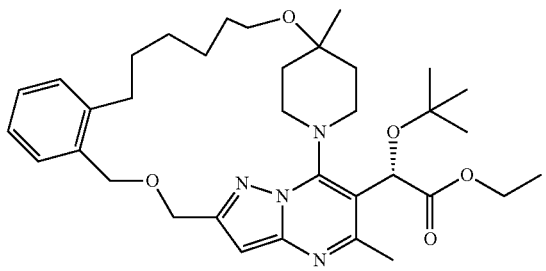 [SMILES: CCOC(=O)[C@@H](OC(C)(C)C)c1c(C)nc2cc3nn2c1N1CCC(C)(CC1)OCCCCCCc1ccccc1COC3]

Ethyl (2S)-2-(tert-butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate A mixture of (S)-ethyl 2-(7-(4-(allyloxy)-4-methylpiperidin-1-yl)-2-(((2-(but-3-en-1-yl)benzyl)oxy)methyl)-5-methylpyrazolo[1,5-a]pyrimidin-6-yl)-2-(tert-butoxy)acetate (55 mg, 0.089 mmol) and (1,3-dimesitylimidazolidin-2-ylidene)(2-isopropoxybenzylidene)ruthenium(VI) chloride (5.57 mg, 8.89 μmol) in ClCH$_2$CH$_2$Cl (60 mL) was refluxed for 2 h. It was then concentrated and the residue was dissolved in MeOH (5 mL). Sodium borohydride (3.36 mg, 0.089 mmol) was added and the reaction was stirred at rt for 1 h. It was then quenched with water, extracted with EtOAc. The organic layer was dried over MgSO$_4$, filtered and concentrated to obtain an oil, which was then purify by biotage, eluting with 20% EtOAc/hexane to obtain ethyl (2S)-2-(tert-butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate (37 mg, 70%) as a white solid. $^1$H NMR (400 MHz, CDCl$_3$) δ 7.38-7.15 (m, 4H), 6.57 (s, 1H), 6.07 (s, 1H), 4.82-4.69 (m, 4H), 4.59 (t, J=11.2 Hz, 1H), 4.28-4.12 (m, 2H), 3.91 (t, J=10.9 Hz, 1H), 3.44 (d, J=7.3 Hz, 2H), 3.05 (d, J=11.3 Hz, 1H), 2.89 (dd, J=14.2, 6.4 Hz, 1H), 2.78 (dd, J=13.8, 8.3 Hz, 2H), 2.63 (s, 3H), 2.03-1.89 (m, 2H), 1.88-1.64 (m, 8H), 1.28 (s, 3H), 1.25 (s, 9H), 1.24-1.19 (m, 3H). LCMS (M+1)=593.4.

Example 58

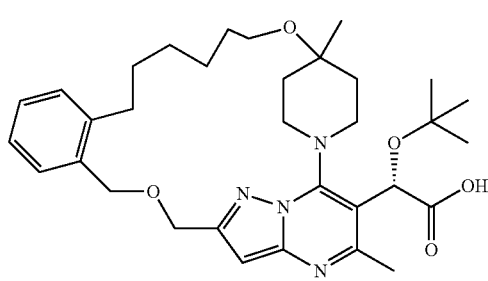 [SMILES: Cc1nc2cc3nn2c(c1[C@H](OC(C)(C)C)C(=O)O)N1CCC(C)(CC1)OCCCCCCc1ccccc1COC3]

(2S)-2-(tert-Butoxy)-2-{4,26-dimethyl-11,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid A mixture of ethyl (2S)-2-(tert-butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate (37 mg, 0.062 mmol) and NaOH (0.312 mL, 0.312 mmol) in EtOH (2 mL) was refluxed for 2 h. It was then filtered and purified by preparative HPLC to obtain (2S)-2-(tert-butoxy)-2-{4,26-dimethyl-11,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid (21 mg, 0.037 mmol, 59.6% yield) as a white solid. $^1$H NMR (500 MHz, DMSO-d$_6$) δ 7.29 (d, J=7.7 Hz, 1H), 7.26-7.19 (m, 2H), 7.17-7.11 (m, 1H), 6.53 (s, 1H), 5.71 (s, 1H), 4.74-4.58 (m, 4H), 4.50-4.42 (m, 1H), 3.68-3.20 (m, 4H), 2.82-2.75 (m, 1H), 2.66 (d, J=8.4 Hz, 2H), 2.51 (s, 3H), 1.90-1.81 (m, 2H), 1.71-1.51 (m, 8H), 1.19 (s, 3H), 1.15 (s, 9H). LCMS (M+1)=565.3.

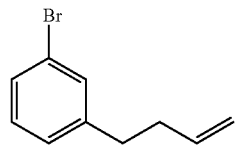

1-Bromo-3-(but-3-en-1-yl)benzene

A mixture of 1-bromo-3-(bromomethyl)benzene (1 g, 4.00 mmol) in THF (15 mL) was added allylmagnesium bromide (4.80 mL, 4.80 mmol) and stirred at rt for 1 h, then refluxed for 2 h. It was then quenched with NH$_4$Cl, extracted with EtOAc. The organic layer was dried over MgSO$_4$, filtered and concentrated to obtain an oil. It was then purified by 5% EtOAc/hexane to isolate 1-bromo-3-(but-3-en-1-yl)benzene (0.7 g, 3.32 mmol, 83% yield) as an oil. $^1$H NMR (400 MHz, CDCl$_3$) δ 7.41-7.31 (m, 2H), 7.21-7.12 (m, 2H), 5.85 (ddt, J=17.1, 10.3, 6.6 Hz, 1H), 5.14-4.94 (m, 2H), 2.75-2.64 (m, 2H), 2.45-2.31 (m, 2H).

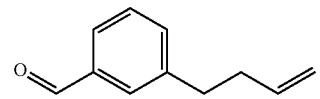

3-(But-3-en-1-yl)benzaldehyde

To a mixture of 1-bromo-3-(but-3-en-1-yl)benzene (0.5 g, 2.369 mmol) in tetrahydrofuran (10 mL) at −78° C. was added BuLi (1.137 mL, 2.84 mmol) dropwise. It was then stirred at this temperature for 1 h, then N,N-dimethylformamide (0.208 g, 2.84 mmol) was added. The reaction mixture was stirred at −78° C. for 30 min, then rt for 3 h. It was then quenched with NH$_4$Cl, extracted with ether. The organic layer was dried over MgSO$_4$, filtered and concentrated to obtain 3-(but-3-en-1-yl)benzaldehyde (0.3 g, 79%) as an oil. $^1$H NMR (400 MHz, CDCl$_3$) δ 10.03 (s, 1H), 7.77-7.72 (m, 2H), 7.51-7.46 (m, 2H), 5.86 (ddt, J=17.1, 10.3, 6.6 Hz, 1H), 5.10-5.00 (m, 2H), 2.86-2.79 (m, 2H), 2.48-2.39 (m, 2H).

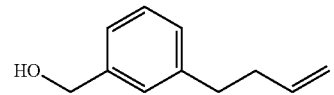

(3-(But-3-en-1-yl)phenyl)methanol

A mixture of 3-(but-3-en-1-yl)benzaldehyde (300 mg, 1.873 mmol) in MeOH (5 mL) was added sodium borohydride (142 mg, 3.75 mmol) and the mixture was stirred at rt for 1 h. It was then added water, extracted with EtOAc. The organic layer was dried over MgSO$_4$, filtered and concentrated to obtain an oil, which was then purified by biotage, eluting with 10% EtOAc/hexane to obtain (3-(but-3-en-1-yl)phenyl)methanol (167 mg, 1.029 mmol, 55.0% yield) as an oil. $^1$H NMR (400 MHz, CDCl$_3$) δ 7.45-7.10 (m, 4H), 5.88 (ddt, J=17.0, 10.4, 6.5 Hz, 1H), 5.15-4.94 (m, 2H), 4.70 (br. s., 2H), 2.84-2.71 (m, 2H), 2.48-2.34 (m, 2H).

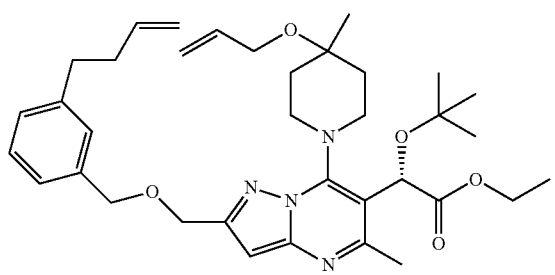 [SMILES: C=CCCc1cccc(COCc2cc3nc(C)c([C@H](OC(C)(C)C)C(=O)OCC)c(N4CCC(C)(OCC=C)CC4)n3n2)c1]

(S)-Ethyl 2-(7-(4-(allyloxy)-4-methylpiperidin-1-yl)-2-(((3-(but-3-en-1-yl)benzyl)oxy)methyl)-5-methylpyrazolo[1,5-a]pyrimidin-6-yl)-2-(tert-butoxy)acetate To a mixture of (3-(but-3-en-1-yl)phenyl)methanol (40.2 mg, 0.248 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (145 mg, 0.248 mmol) and NaH (9.92 mg, 0.248 mmol). The mixture was stirred at 0° C. for 3 h. It was then quenched with NH$_4$Cl, extracted with EtOAc. The organic layer was dried over MgSO$_4$, filtered and concentrated. The residue was purified by biotage, eluting with 20% EtOAc/hexane to obtain (S)-ethyl 2-(7-(4-(allyloxy)-4-methylpiperidin-1-yl)-2-(((3-(but-3-en-1-yl)benzyl)oxy)methyl)-5-methylpyrazolo[1,5-a]pyrimidin-6-yl)-2-(tert-butoxy)acetate (50 mg, 0.081 mmol, 32.6% yield) as an oil. LCMS (M+1)=619.5.

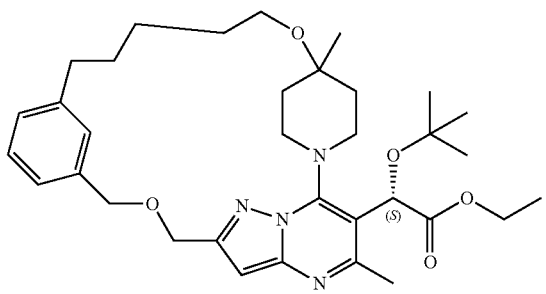

Ethyl (2S)-2-(tert-butoxy)-2-{4,24-dimethyl-11,23-dioxa-1,5,7,8-tetraazapentacyclo[22.2.2.1$^{6,9}$.1$^{13,17}$]triaconta-2,4,6(30),8,13(29),14,16-heptaen-3-yl}acetate A mixture of (S)-ethyl 2-(7-(4-(allyloxy)-4-methylpiperidin-1-yl)-2-(((3-(but-3-en-1-yl)benzyl)oxy)methyl)-5-methylpyrazolo[1,5-a]pyrimidin-6-yl)-2-(tert-butoxy)acetate (50 mg, 0.081 mmol) and Grubbs II catalyst (6.86 mg, 8.08 µmol) in DCM (50 mL) was refluxed for 2 h. It was then concentrated and the residue was dissolved in MeOH (3 mL). NaBH$_4$ (15.28 mg, 0.404 mmol) was added and the reaction mixture was stirred at rt for 1 h. It was then quenched with water, extracted with EtOAc. The organic layer was dried over MgSO$_4$, filtered and concentrated. The residue was then purified by biotage, eluting with 25% EtOAc/hexane to isolate ethyl (2S)-2-(tert-butoxy)-2-{4,24-dimethyl-11,23-dioxa-1,5,7,8-tetraazapentacyclo[22.2.2.1$^{6,9}$.1$^{13,17}$.0$^{2,7}$]triaconta-2,4,6(30),8,13(29),14,16-heptaen-3-yl}acetate (20 mg, 0.034 mmol, 41.8% yield) as a white solid. LCMS (M+1)=593.4. $^1$H NMR (400 MHz, CDCl$_3$) δ 7.36-7.32 (m, 2H), 7.23-7.16 (m, 2H), 6.61 (s, 1H), 5.93 (s, 1H), 4.66 (s, 2H), 4.61-4.52 (m, 2H), 4.34 (td, J=12.3, 2.2 Hz, 1H), 4.27-4.16 (m, 2H), 3.85 (td, J=12.0, 2.2 Hz, 1H), 3.42-3.36 (m, 2H), 3.17 (d, J=11.7 Hz, 1H), 2.81 (dt, J=13.1, 6.3 Hz, 2H), 2.65-2.60 (m, 4H), 2.00 (dd, J=13.7, 2.2 Hz, 1H), 1.89 (dd, J=13.6, 2.1 Hz, 1H), 1.85-1.70 (m, 4H), 1.61-1.43 (m, 4H), 1.26-1.21 (m, 15H).

Example 59

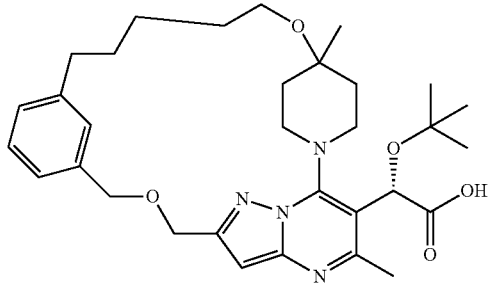 [SMILES: Cc1nc2cc3nn2c(c1[C@H](OC(C)(C)C)C(=O)O)N1CCC(C)(CC1)OCCCCCc1cccc(c1)COC3]

(2S)-2-(tert-Butoxy)-2-{4,24-dimethyl-11,23-dioxa-1,5,7,8-tetraazapentacyclo[22.2.2.1$^{6,9}$.1$^{13,17}$.0$^{2,7}$]triaconta-2,4,6(30),8,13(29),14,16-heptaen-3-yl}acetic acid A mixture of ethyl (2S)-2-(tert-butoxy)-2-{4,24-dimethyl-11,23-dioxa-1,5,7,8-tetraazapentacyclo[22.2.2.1$^{6,9}$.1$^{13,17}$.0$^{2,7}$]triaconta-2,4,6(30),8,13(29),14,16-heptaen-3-yl}acetate (20 mg, 0.034 mmol) and NaOH (0.169 mL, 0.169 mmol) in EtOH (2 mL) was refluxed for 2 h. It was then filtered and purified by preparative HPLC to isolate (2S)-2-(tert-butoxy)-2-{4,24-dimethyl-11,23-dioxa-1,5,7,8-tetraazapentacyclo[22.2.2.1$^{6,9}$.1$^{13,17}$.0$^{2,7}$]triaconta-2,4,6(30),8,13(29),14,16-heptaen-3-yl}acetic acid (10 mg, 0.017 mmol, 51.4% yield) as a white solid. $^1$H NMR (500 MHz, DMSO-d$_6$) δ 7.34-7.27 (m, 1H), 7.22 (s, 1H), 7.16 (d, J=7.3 Hz, 2H), 6.50 (s, 1H), 5.62 (s, 1H), 4.62-4.40 (m, 4H), 4.17 (t, J=12.5 Hz, 1H), 3.65-3.56 (m, 1H), 3.38-3.23 (m, 2H), 2.77 (d, J=11.4 Hz, 1H), 2.74-2.66 (m, 1H), 2.59-2.53 (m, 1H), 2.50 (br. s., 4H), 1.91 (d, J=12.5 Hz, 1H), 1.84-1.75 (m, 1H), 1.75-1.62 (m, 3H), 1.58-1.44 (m, 3H), 1.43-1.33 (m, 2H), 1.17 (s, 3H), 1.14 (s, 9H). LCMS (M+1)=565.3.

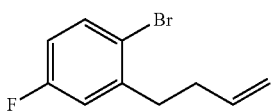

1-Bromo-2-(but-3-en-1-yl)-4-fluorobenzene

To a solution of 2-bromo-5-fluorobenzyl bromide (1 g, 3.73 mmol) in THF (15 mL) was added allylmagnesium bromide (5.60 mL, 5.60 mmol) at 0° C. It was warmed to rt and then refluxed for 5 h. The reaction mixture was quenched with NH$_4$Cl, extracted with EtOAc. The organic layer was dried over MgSO$_4$, filtered and concentrated to obtain an oil. It was then purified by 5% EtOAc/hexane to isolate 1-bromo-2-(but-3-en-1-yl)-4-fluorobenzene (0.7 g, 3.06 mmol, 82% yield) as an oil. $^1$H NMR (400 MHz, CDCl$_3$) δ 7.53-7.45 (m, 1H), 6.99-6.94 (m, 1H), 6.82 (td, J=8.3, 2.9 Hz, 1H), 5.89 (ddt, J=16.9, 10.2, 6.6 Hz, 1H), 5.14-4.98 (m, 2H), 2.89-2.76 (m, 2H), 2.45-2.33 (m, 2H).

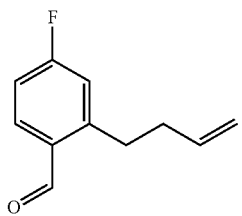

2-(But-3-en-1-yl)-4-fluorobenzaldehyde

To a mixture of 1-bromo-2-(but-3-en-1-yl)-4-fluorobenzene (0.5 g, 2.183 mmol) in tetrahydrofuran (10 mL) at −78° C. was added BuLi (1.048 mL, 2.62 mmol) dropwise. It was then stirred at this temperature for 1 h, then N,N-dimethylformamide (0.204 mL, 2.62 mmol) was added. The reaction mixture was stirred at −78° C. for 30 min, then warmed up to rt and stirred at rt for 1 h. It was then quenched with NH$_4$Cl, extracted with ether. The organic layer was dried over MgSO4, filtered and concentrated. The residue was purified by biotage, eluting with 10% EtOAc/hexane to obtain 2-(but-3-en-1-yl)-4-fluorobenzaldehyde (0.35 g, 90%) as an oil. $^1$H NMR (400 MHz, CDCl$_3$) δ 10.22 (s, 1H), 7.88 (dd, J=8.6, 6.1 Hz, 1H), 7.08 (td, J=8.3, 2.6 Hz, 1H), 7.05-6.96 (m, 1H), 6.00-5.73 (m, 1H), 5.12-4.99 (m, 2H), 3.22-3.09 (m, 2H), 2.49-2.34 (m, 2H).

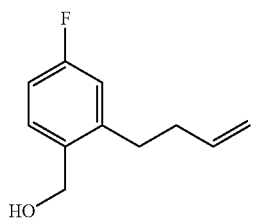

(2-(But-3-en-1-yl)-4-fluorophenyl)methanol

A mixture of 3-(but-3-en-1-yl)benzaldehyde (300 mg, 1.873 mmol) in MeOH (10 mL) was added sodium borohydride (142 mg, 3.75 mmol) and the mixture was stirred at rt for 1 h. It was then added water, extracted with EtOAc. The organic layer was dried over MgSO$_4$, filtered and concentrated to obtain an oil, which was then purified by biotage, eluting with 10% EtOAc/hexane to obtain (2-(but-3-en-1-yl)-4-fluorophenyl)methanol (160 mg, 0.888 mmol, 79% yield) as an oil. $^1$H NMR (400 MHz, CDCl$_3$) δ 7.35 (dd, J=8.2, 6.0 Hz, 1H), 7.01-6.87 (m, 2H), 5.88 (ddt, J=17.1, 10.3, 6.6 Hz, 1H), 5.16-4.95 (m, 2H), 4.71 (d, J=4.9 Hz, 2H), 2.86-2.72 (m, 2H), 2.39 (td, J=7.8, 6.6 Hz, 2H), 1.54 (t, J=5.5 Hz, 1H).

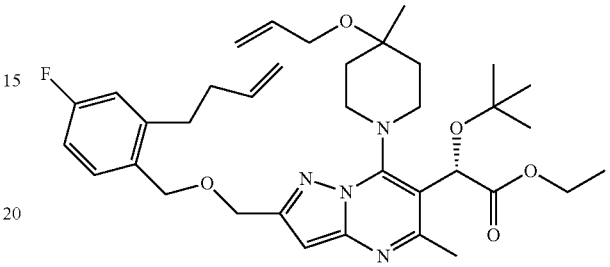

(S)-Ethyl 2-(7-(4-(allyloxy)-4-methylpiperidin-1-yl)-2-(((2-(but-3-en-1-yl)-4-fluorobenzyl)oxy)methyl)-5-methylpyrazolo[1,5-a]pyrimidin-6-yl)-2-(tert-butoxy)acetate A mixture of (2-(but-3-en-1-yl)-4-fluorophenyl)methanol (43.8 mg, 0.243 mmol) and (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (142 mg, 0.243 mmol) in DMF (5 mL) at 0° C. was added NaH (9.72 mg, 0.243 mmol) and the reaction was stirred at 0° C. for 3 h. It was then quenched with water, extracted with EtOAc. The organic layer was dried over MgSO$_4$, filtered and concentrated to obtain an oil, which was then purified by biotage, eluting with 20% EtOAc/hexane to isolate (S)-ethyl 2-(7-(4-(allyloxy)-4-methylpiperidin-1-yl)-2-(((2-(but-3-en-1-yl)-4-fluorobenzyl)oxy)methyl)-5-methylpyrazolo[1,5-a]pyrimidin-6-yl)-2-(tert-butoxy)acetate (50 mg, 0.079 mmol, 32.3% yield) as an oil. LCMS (M+1)=637.3.

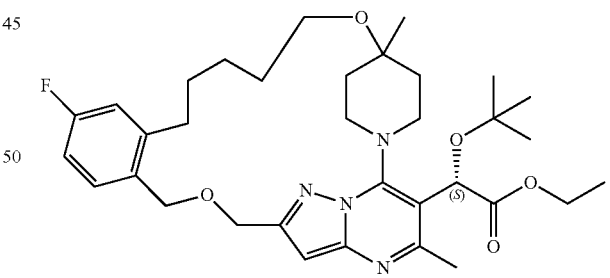

Ethyl (2S)-2-(tert-butoxy)-2-{16-fluoro-4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetate A mixture of (S)-ethyl 2-(7-(4-(allyloxy)-4-methylpiperidin-1-yl)-2-(((2-(but-3-en-1-yl)-4-fluorobenzyl)oxy)methyl)-5-methylpyrazolo[1,5-a]pyrimidin-6-yl)-2-(tert-butoxy)acetate (50 mg, 0.079 mmol) and Grubb's II catalyst (66.7 mg, 0.079 mmol) in DCM (50 mL) was refluxed for 2 h. It was then concentrated and the residue was dissolved in MeOH (2 mL). NaBH$_4$ (2.97 mg, 0.079 mmol) was added and the reaction mixture was stirred at rt for 1 h. It was then diluted with water, extracted with EtOAc. The organic layer was dried over MgSO$_4$, filtered and concentrated to obtain an oil, which was then purified by biotage, eluting with 20% EtOAc/hexane to obtain ethyl (2S)-2-(tert-butoxy)-2-{16-fluoro-4,25-dimethyl-11,24-dioxa-1,5,7,8-tetraazapentacyclo[23.2.2.1$^{6,9}$.0$^2$,$^7$.0$^{13,18}$]triaconta-2,4,6(30),8,13(18),14,16-heptaen-3-yl}acetate (36 mg, 0.059 mmol, 75% yield) as a white solid. $^1$H NMR (400 MHz, CDCl$_3$) δ 7.33-7.27 (m, 1H), 6.95 (dd, J=10.3, 2.7 Hz, 1H), 6.85 (td, J=8.3, 2.7 Hz, 1H), 6.56 (s, 1H), 6.07 (s, 1H), 4.78-4.64 (m, 4H), 4.58 (t, J=11.2 Hz, 1H), 4.18-4.11 (m, 2H), 3.90 (t, J=11.0 Hz, 1H), 3.44 (d, J=5.1 Hz, 2H), 3.05 (d, J=11.5 Hz, 1H), 2.95-2.85 (m, 1H), 2.83-2.72 (m, 2H), 2.63 (s, 3H), 2.03-1.88 (m, 2H), 1.84-1.62 (m, 8H), 1.31-1.24 (m, 15H). LCMS (M+1)=611.4.

Example 60

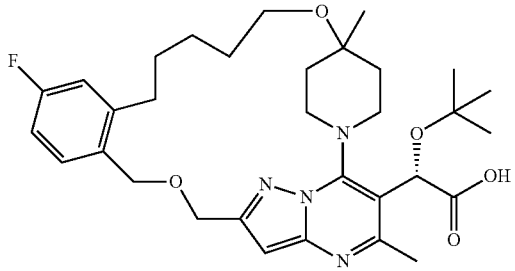 [SMILES: Cc1nc2cc3nn2c(c1[C@H](OC(C)(C)C)C(=O)O)N1CCC(C)(CC1)OCCCCCc1cc(F)ccc1COC3]

(2S)-2-(tert-Butoxy)-2-{16-fluoro-4,25-dimethyl-1,24-dioxa-1,5,7,8-tetraazapentacyclo[23.2.2.1$^{6,9}$.0$^2$,$^7$.0$^{13,18}$]triaconta-2,4,6(30),8,13(18),14,16-heptaen-3-yl}acetic acid A mixture of ethyl (2S)-2-(tert-butoxy)-2-{16-fluoro-4,25-dimethyl-11,24-dioxa-1,5,7,8-tetraazapentacyclo[23.2.2.1$^{6,9}$.0$^2$,$^7$.0$^{13,18}$]triaconta-2,4,6(30),8,13(18),14,16-heptaen-3-yl}acetate (36 mg, 0.059 mmol) and NaOH (0.295 mL, 0.295 mmol) in EtOH (2 mL) was refluxed for 2 h. It was then filtered and purified by preparative HPLC to obtain (2S)-2-(tert-butoxy)-2-{16-fluoro-4,25-dimethyl-11,24-dioxa-1,5,7,8-tetraazapentacyclo[23.2.2.1$^{6,9}$.0$^2$,$^7$.0$^{13,18}$]triaconta-2,4,6(30),8,13(18),14,16-heptaen-3-yl}acetic acid (23.3 mg, 0.040 mmol, 67.8% yield) as a white solid. $^1$H NMR (500 MHz, DMSO-d$_6$) δ 7.37-7.29 (m, 1H), 7.04 (d, J=9.9 Hz, 1H), 6.95 (t, J=8.3 Hz, 1H), 6.49 (s, 1H), 5.59 (s, 1H), 4.72-4.66 (m, 1H), 4.65-4.57 (m, 3H), 4.45 (t, J=11.7 Hz, 1H), 3.58-3.30 (m, 4H), 2.84-2.75 (m, 1H), 2.66 (d, J=12.8 Hz, 2H), 2.50 (br. s., 3H), 1.93-1.88 (m, 1H), 1.83 (d, J=13.9 Hz, 1H), 1.70-1.49 (m, 8H), 1.19 (s, 3H), 1.14 (s, 9H). LCMS (M+1)=583.7.

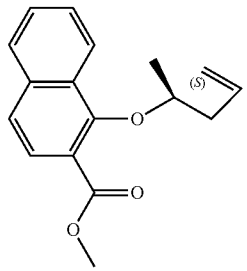

(S)-Methyl 1-(pent-4-en-2-yloxy)-2-naphthoate

A mixture of methyl 1-hydroxy-2-naphthoate (500 mg, 2.473 mmol), (R)-pent-4-en-2-ol (0.382 mL, 3.71 mmol), triphenylphosphine (1297 mg, 4.95 mmol) and (Z)-diethyl diazene-1,2-dicarboxylate (0.836 mL, 4.95 mmol) in THF (20 mL) was stirred at rt for 3 h. It was then concentrated and the residue was purified by biotage, eluting with 10% EtOAc/hexane to isolate (S)-methyl 1-(pent-4-en-2-yloxy)-2-naphthoate (500 mg, 74.8%) as an oil. $^1$H NMR (400 MHz, CDCl$_3$) δ 8.41-8.27 (m, 1H), 7.96-7.81 (m, 2H), 7.69-7.45 (m, 3H), 5.89 (ddt, J=17.2, 10.1, 7.1 Hz, 1H), 5.22-5.04 (m, 2H), 4.49-4.29 (m, 1H), 3.99 (s, 3H), 2.66-2.57 (m, 1H), 2.55-2.46 (m, 1H), 1.28 (d, J=6.4 Hz, 3H).

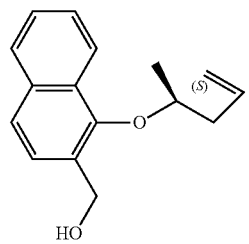

(S)-(1-(Pent-4-en-2-yloxy)naphthalen-2-yl)methanol

To a mixture of (S)-methyl 1-(pent-4-en-2-yloxy)-2-naphthoate (300 mg, 1.110 mmol) in THF (10 mL) was added 1 N LAH (2.220 mL, 2.220 mmol) and the reaction was stirred at rt for 1 h. It was then quenched with NH$_4$Cl and extracted with EtOAc. The organic layer was dried over MgSO$_4$, filtered and concentrated to obtain an oil, which was then purified by biotage, eluting with 10% EtOAc/hexane to isolate (S)-(1-(pent-4-en-2-yloxy)naphthalen-2-yl)methanol (200 mg, 0.825 mmol, 74.4% yield) as an oil. $^1$H NMR (400 MHz, CDCl$_3$) δ 8.19-8.08 (m, 1H), 7.90-7.80 (m, 1H), 7.65 (d, J=8.3 Hz, 1H), 7.58-7.45 (m, 3H), 5.96 (ddt, J=17.1, 10.1, 7.2 Hz, 1H), 5.25-5.11 (m, 2H), 4.93 (qd, J=12.6, 5.9 Hz, 2H), 4.54-4.34 (m, 1H), 2.65 (qd, J=6.8, 5.5 Hz, 1H), 2.59-2.48 (m, 1H), 2.18 (t, J=6.0 Hz, 1H), 1.31 (d, J=6.4 Hz, 3H).

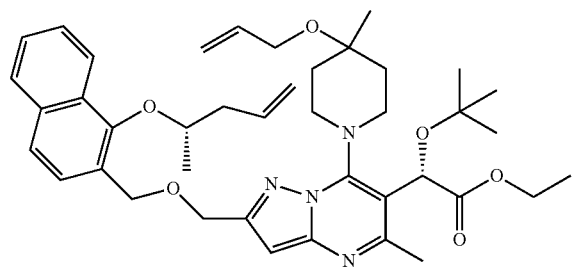 [SMILES: C=CCOC1(C)CCN(c2c([C@H](OC(C)(C)C)C(=O)OCC)c(C)nc3cc(COCc4ccc5ccccc5c4O[C@@H](C)CC=C)nn23)CC1]

(S)-Ethyl 2-(7-(4-(allyloxy)-4-methylpiperin-1yl)-5-methyl-2-(((1-((S)-pent-4-en-2-yloxy)naphthalen-2-yl)methoxy)methyl)pyrazolo[1,5-a]pyrimidin-6-yl)-2-(tert-butoxy)acetate To a mixture of (S)-(1-(pent-4-en-2-yloxy)naphthalen-2-yl)methanol (60.9 mg, 0.252 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (147 mg, 0.252 mmol) and NaH (10.06 mg, 0.252 mmol). The reaction was stirred at 0° C. for 3 h. It was then quenched with water, extracted with EtOAc. The organic layer was dried over MgSO$_4$, filtered and concentrated to obtain an oil, which was then purified by biotage, eluting with 20% EtOAc/hexane to isolate (S)-ethyl 2-(7-(4-(allyloxy)-4-methylpiperidin-1-yl)-5-methyl-2-(((1-((S)-pent-4-en-2-yloxy)naphthalen-2-yl)methoxy)methyl)pyrazolo[yl],5-a]pyrimidin-6-yl)-2-(tert-butoxy)acetate (62 mg, 0.089 mmol, 35.3% yield) as an oil. LCMS (M+1)=699.5.

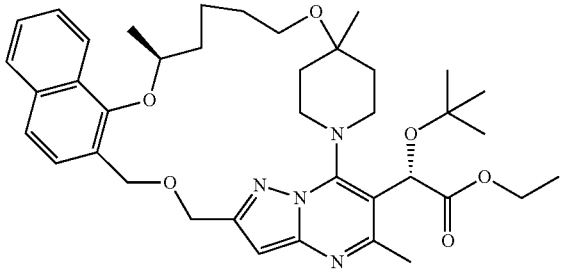 [SMILES: CCOC(=O)[C@@H](OC(C)(C)C)c1c(C)nc2cc3nn2c1N1CCC(C)(CC1)OCCCC[C@H](C)Oc1c(ccc2ccccc12)COC3]

Ethyl (2S)-2-(tert-butoxy)-2-[(24S)-4,24,30-trimethyl-11,23,29-trioxa-1,5,7,8-tetraazahexacyclo [28.2.2.1⁶,⁹.0²,⁷.0¹³,²².0¹⁶,²¹]pentatriaconta-2,4,6 (35),8,13(22),14,16(21),17,19-nonaen-3-yl]acetate A mixture of (S)-ethyl 2-(7-(4-(allyloxy)-4-methylpiperidin-1-yl)-5-methyl-2-(((1-((S)-pent-4-en-2-yloxy)naphthalen-2-yl)methoxy)methyl)pyrazolo[1,5-a]pyrimidin-6-yl)-2-(tert-butoxy)acetate (100 mg, 0.114 mmol) and Grubb's II catalyst (9.72 mg, 0.011 mmol) in DCM (80 mL) was refluxed for 2 h. It was then concentrated and the residue was dissolved in MeOH (3 mL). NaBH₄ (8.66 mg, 0.229 mmol) was added and the reaction was stirred at rt for 1 h. It was then quenched with NH₄Cl, extracted with EtOAc. The organic layer was dried over MgSO4, filtered and concentrated to obtain an oil, which was then purified by biotage, eluting with 25% EtOAc/hexane to obtain ethyl (2S)-2-(tert-butoxy)-2-[(24S)-4,24, 30-trimethyl-11,23,29-trioxa-1,5,7,8-tetraazahexacyclo [28.2.2.1⁶,⁹.0²,⁷.0¹³,²².0¹⁶,¹²]pentatriaconta-2,4,6(35),8,13 (22),14,16(21),17,19-nonaen-3-yl]acetate (47 mg, 61%) as an white solid. ¹H NMR (400 MHz, CDCl₃) δ 8.25-8.18 (m, 1H), 7.82-7.78 (m, 1H), 7.61-7.58 (m, 1H), 7.54-7.50 (m, 1H), 7.49-7.45 (m, 2H), 6.64 (s, 1H), 6.14 (s, 1H), 4.92-4.87 (m, 2H), 4.86-4.80 (m, 1H), 4.63-4.49 (m, 3H), 4.24-4.10 (m, 2H), 4.01 (t, J=10.8 Hz, 1H), 3.54-3.46 (m, 1H), 2.95 (d, J=11.0 Hz, 1H), 2.70 (d, J=11.2 Hz, 1H), 2.66-2.59 (m, 4H), 2.12 (dd, J=9.5, 5.1 Hz, 1H), 2.05-1.61 (m, 9H), 1.30-1.17 (m, 18H). LCMS (M+1)=673.6.

Example 61

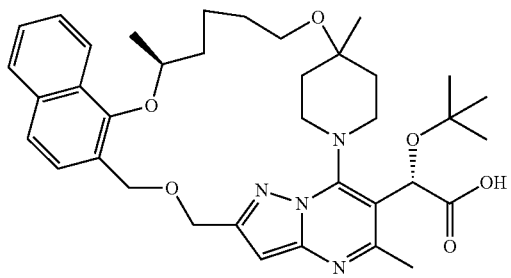 [SMILES: Cc1nc2cc3nn2c(c1[C@H](OC(C)(C)C)C(=O)O)N1CCC(C)(CC1)OCCCC[C@H](C)Oc1c(ccc2ccccc12)COC3]

(2S)-2-(tert-butoxy)-2-[(24S)-4,24,30-trimethyl-11,23,29-trioxa-1,5,7,8-tetraazahexacyclo[28.2.2. 1⁶,⁹.0²,⁷.0¹³,²².0¹⁶,²¹]pentatriaconta-2,4,6(35),8,13 (22),14,16(21),17,19-nonaen-3-yl]acetic acid A mixture of ethyl (2S)-2-(tert-butoxy)-2-[(24S)-4,24,30-trimethyl-11,23,29-trioxa-1,5,7,8-tetraazahexacyclo [28.2.2.1⁶,⁹.0²,⁷.0¹³,²².0¹⁶,²¹]pentatriaconta-2,4,6(35),8,13 (22),14,16(21),17,19-nonaen-3-yl]acetate (47 mg, 0.070 mmol) and NaOH (0.070 mL, 0.070 mmol) in EtOH (2 mL) was refluxed for 2 h. It was then cooled to rt and purified by preparative HPLC to obtain (2S)-2-(tert-butoxy)-2-[(24S)-4, 24,30-trimethyl-11,23,29-trioxa-1,5,7,8-tetraazahexacyclo [28.2.2.1⁶,⁹.0²,⁷.0¹³,²².0¹⁶,²¹]pentatriaconta-2,4,6(35),8,13 (22),14,16(21),17,19-nonaen-3-yl]acetic acid (31.3 mg, 0.046 mmol, 66.0% yield) as a white solid. ¹H NMR (500 MHz, DMSO-d₆) δ 8.12 (d, J=8.4 Hz, 1H), 7.87 (d, J=8.8 Hz, 1H), 7.63 (d, J=8.4 Hz, 1H), 7.53-7.43 (m, 3H), 6.58 (s, 1H), 5.82 (s, 1H), 4.83-4.75 (m, 2H), 4.75-4.67 (m, 1H), 4.58 (d, J=10.6 Hz, 1H), 4.49-4.35 (m, 2H), 3.74 (t, J=10.8 Hz, 1H), 3.37-3.53 (m, 2H), 3.06 (d, J=9.2 Hz, 1H), 2.64 (d, J=11.7 Hz, 1H), 2.50 (s, 3H), 1.95 (d, J=13.2 Hz, 2H), 1.88-1.45 (m, 8H), 1.20 (s, 3H), 1.16 (s, 9H), 1.07 (d, J=5.9 Hz, 3H). LCMS (M+1)=645.3.

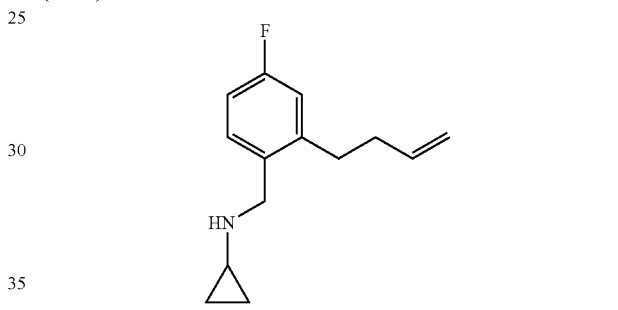

N-(2-(But-3-en-1-yl)-4-fluorobenzyl)cyclopropanamine

A mixture of 2-(but-3-en-1-yl)-4-fluorobenzaldehyde (50 mg, 0.281 mmol) and cyclopropanamine (16.02 mg, 0.281 mmol) in MeOH (2 mL) was stirred at rt for 30 min. Sodium borohydride (5.31 mg, 0.140 mmol) was added and stirred at rt for 1 h. It was then quenched with NH₄Cl, extracted with EtOAc. The organic layer was dried over MgSO₄, filtered and concentrated. The residue was purified by biotage, eluting with 25% EtOAc/hexane to isolate N-(2-(but-3-en-1-yl)-4-fluorobenzyl)cyclopropanamine (20 mg, 0.091 mmol, 32.5% yield) as an oil. ¹H NMR (400 MHz, CDCl₃) δ 7.26 (dd, J=8.3, 6.1 Hz, 1H), 6.93-6.82 (m, 2H), 5.95-5.84 (m, 1H), 5.13-5.00 (m, 2H), 3.83 (s, 2H), 2.81-2.75 (m, 2H), 2.41-2.33 (m, 2H), 2.18 (tt, J=6.6, 3.5 Hz, 1H), 0.51-0.44 (m, 2H), 0.43-0.35 (m, 2H).

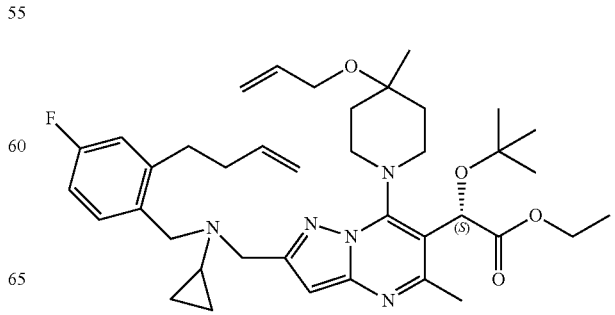

(S)-Ethyl 2-(7-(4-(allyloxy)-4-methylpiperidin-1-yl)-2-(((2-(but-3-en-1-yl)-4-fluorobenzyl)(cyclopropyl)amino)methyl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (53.3 mg, 0.091 mmol) in acetonitrile (2 mL) at 0° C. was added Hunig's Base (0.016 mL, 0.091 mmol) and N-(2-(but-3-en-1-yl)-4-fluorobenzyl)cyclopropanamine (20 mg, 0.091 mmol). It was stirred at 0° C. for 2 h and then quenched with water, extracted with EtOAc. The organic layer was dried over MgSO$_4$, filtered and concentrated. The residue was purified by biotage, eluting with 20% EtOAc/hexane to obtain (S)-ethyl 2-(7-(4-(allyloxy)-4-methylpiperidin-1-yl)-2-(((2-(but-3-en-1-yl)-4-fluorobenzyl)(cyclopropyl)amino)methyl)-5-methylpyrazolo[1,5-a]pyrimidin-6-yl)-2-(tert-butoxy)acetate (45 mg, 0.067 mmol, 73.0% yield) as an oil. $^1$H NMR (400 MHz, CDCl$_3$) δ 7.36 (dd, J=8.3, 6.1 Hz, 1H), 6.89-6.78 (m, 2H), 6.41 (s, 1H), 6.06-5.95 (m, 2H), 5.80 (ddt, J=17.1, 10.3, 6.6 Hz, 1H), 5.41 (d, J=17.1 Hz, 1H), 5.17 (d, J=11.0 Hz, 1H), 5.03-4.92 (m, 2H), 4.30-4.13 (m, 2H), 4.01 (d, J=4.9 Hz, 2H), 3.88 (s, 2H), 3.80 (s, 2H), 2.76-2.69 (m, 2H), 2.63 (s, 3H), 2.33-2.22 (m, 2H), 2.10-1.87 (m, 4H), 1.72 (br. s., 1H), 1.36 (br. s., 3H), 1.27-1.21 (m, 12H), 0.48-0.31 (m, 4H), 4 protons from piperidine were missing. LCMS (M+1)=676.5.

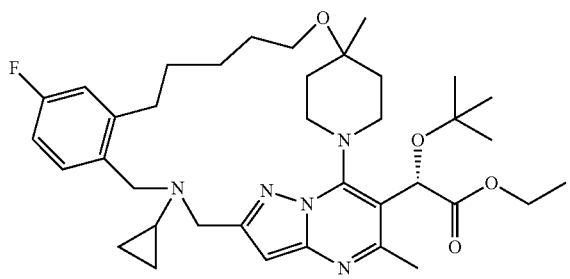 [SMILES: CCOC(=O)[C@@H](OC(C)(C)C)c1c(C)nc2cc3nn2c1N1CCC(C)(CC1)OCCCCCc1cc(F)ccc1CN(C1CC1)C3]

Ethyl (2S)-2-(tert-butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetate A mixture of (S)-ethyl 2-(7-(4-(allyloxy)-4-methylpiperidin-1-yl)-2-(((2-(but-3-en-1-yl)-4-fluorobenzyl)(cyclopropyl)amino)methyl)-5-methylpyrazolo[1,5-a]pyrimidin-6-yl)-2-(tert-butoxy)acetate (45 mg, 0.067 mmol) and Grubb's II catalyst (5.65 mg, 6.66 μmol) in DCM (45 mL) was refluxed for 2 h. It was then concentrated and the residue was dissolved in MeOH (2 mL). NaBH$_4$ (2.52 mg, 0.067 mmol) was added and the reaction mixture was stirred at rt for 1 h. It was then diluted with water, extracted with EtOAc. The organic layer was dried over MgSO$_4$, filtered and concentrated to obtain an oil. It was then purified by biotage, eluting with 25% EtOac/hexane to obtain ethyl (2S)-2-(tert-butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetate (35 mg, 0.054 mmol, 81% yield) as a white solid. $^1$H NMR (400 MHz, CDCl$_3$) δ 7.14 (dd, J=8.4, 6.1 Hz, 1H), 6.90 (dd, J=10.3, 2.8 Hz, 1H), 6.77 (td, J=8.4, 2.8 Hz, 1H), 6.48 (s, 1H), 6.10 (s, 1H), 4.58-4.48 (m, 1H), 4.28-4.21 (m, 1H), 4.18-4.12 (m, 1H), 4.04 (d, J=1.0 Hz, 2H), 3.96-3.83 (m, 2H), 3.62 (d, J=13.8 Hz, 1H), 3.44-3.33 (m, 2H), 3.06-2.98 (m, 1H), 2.90-2.72 (m, 3H), 2.68-2.60 (m, 3H), 2.03-1.85 (m, 3H), 1.79-1.62 (m, 8H), 1.30-1.21 (m, 19H). LCMS (M+1)=650.3.

Example 62

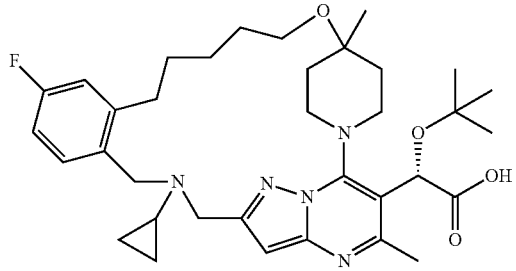 [SMILES: Cc1nc2cc3nn2c(c1[C@H](OC(C)(C)C)C(=O)O)N1CCC(C)(CC1)OCCCCCc1cc(F)ccc1CN(C1CC1)C3]

(2S)-2-(tert-Butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetic acid A mixture of ethyl (2S)-2-(tert-butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetate (35 mg, 0.054 mmol) and NaOH (2.154 mg, 0.054 mmol) in EtOH (3 mL) was refluxed for 2 h. It was then cooled to rt and purified by preparative HPLC to isolate (2S)-2-(tert-butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetic acid (25.2 mg, 0.040 mmol, 73.7% yield) as a white solid. $^1$H NMR (500 MHz, DMSO-d$_6$) δ 7.18 (t, J=7.2 Hz, 1H), 6.98 (d, J=9.9 Hz, 1H), 6.85 (t, J=7.7 Hz, 1H), 6.43 (s, 1H), 5.75 (s, 1H), 4.39 (t, J=11.9 Hz, 1H), 3.89 (d, J=9.9 Hz, 1H), 3.65-3.54 (m, 2H), 3.30 (d, J=15.0 Hz, 2H), 3.17 (s, 2H), 2.87-2.77 (m, 1H), 2.73-2.63 (m, 2H), 2.51-2.45 (m, 4H), 1.89-1.42 (m, 11H), 1.16 (br. s., 12H), 0.33 (br. s., 1H), 0.24 (br. s., 1H), 0.13 (br. s., 1H), −0.06 (br. s., 1H). LCMS (M+1)=622.3.

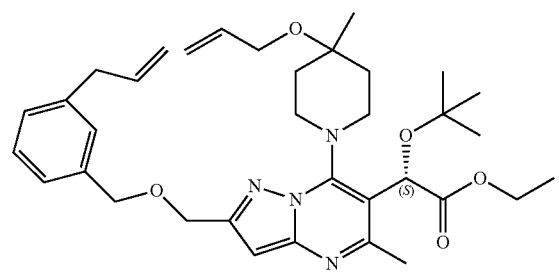

(S)-Ethyl 2-(2-(((3-allylbenzyl)oxy)methyl)-7-(4-(allyloxy)-4-methylpiperidin-1-yl)-5-methylpyrazolo[1,5-a]pyrimidin-6-yl)-2-(tert-butoxy)acetate To a mixture of (3-allylphenyl)methanol (33.0 mg, 0.222 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (130 mg, 0.222 mmol) and NaH (8.90 mg, 0.222 mmol). The reaction mixture was stirred at 0° C. for 2 h. It was then diluted with water, extracted with EtOAc. The organic layer was dried over MgSO$_4$, filtered and concentrated to obtain an oil, which was then purified by biotage, eluting with 25% EtOAc/hexane to obtain (S)-ethyl 2-(2-(((3-allylbenzyl)oxy)methyl)-7-(4-(allyloxy)-4-methylpiperidin-1-yl)-5-methylpyrazolo[1,5-a]pyrimidin-6-yl)-2-(tert-butoxy)acetate (50 mg, 0.083 mmol, 37.2% yield) as an oil. LCMS (M+1)=605.4.

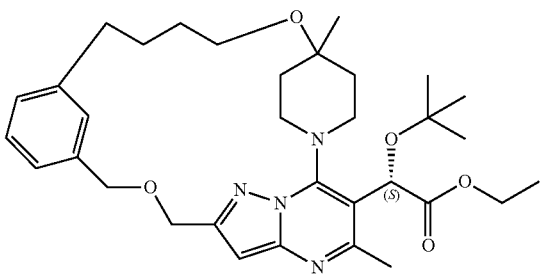

Ethyl (2S)-2-(tert-butoxy)-2-{4,23-dimethyl-1,22-dioxa-1,5,7,8-tetraazapentacyclo[21.2.2.1$^{6,9}$.0$^{13,17}$.0$^{2,7}$]nonacosa-2,4,6(29),8,13(28),14,16-heptaen-3-yl}acetate A mixture of (S)-ethyl 2-(2-(((3-allylbenzyl)oxy)methyl)-7-(4-(allyloxy)-4-methylpiperidin-1-yl)-5-methylpyrazolo[1,5-a]pyrimidin-6-yl)-2-(tert-butoxy)acetate (50 mg, 0.083 mmol) and Grubb's II catalyst (70.2 mg, 0.083 mmol) in DCM (50 mL) was refluxed for 2 h. It was then concentrated. The residue was dissolved in MeOH (2 mL). Sodium borohydride (3.13 mg, 0.083 mmol) was added and the reaction was stirred at rt for 2 h. It was then diluted with NH$_4$Cl, extracted with EtOAc. The organic layer was dried over MgSO$_4$, filtered and concentrated to obtain an oil, which was then purified by biotage, eluting with 20% EtOAc/hexane to isolate ethyl (2S)-2-(tert-butoxy)-2-{4,23-dimethyl-11,22-dioxa-1,5,7,8-tetraazapentacyclo[21.2.2.1$^{6,9}$.1$^{13,17}$.0$^{2,7}$]nonacosa-2,4,6(29),8,13(28),14,16-heptaen-3-yl}acetate (20 mg, 0.035 mmol, 41.8% yield) as a white solid. LCMS (M+1)=579.7.

Example 63

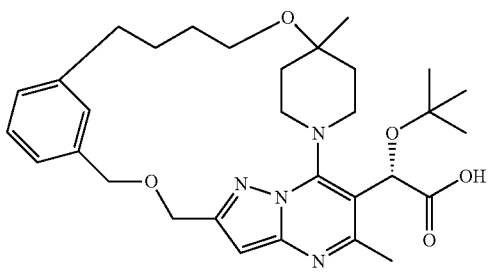 [SMILES: Cc1nc2cc3nn2c(c1[C@H](OC(C)(C)C)C(=O)O)N1CCC(C)(CC1)OCCCCc1cccc(c1)COC3]

(2S)-2-(tert-Butoxy)-2-{4,23-dimethyl-11,22-dioxa-1,5,7,8-tetraazapentacyclo[21.2.2.1$^{6,9}$.1$^{13,17}$.0$^{2,7}$]nonacosa-2,4,6(29),8,13(28),14,16-heptaen-3-yl}acetic acid A mixture of ethyl (2S)-2-(tert-butoxy)-2-{4,23-dimethyl-11,22-dioxa-1,5,7,8-tetraazapentacyclo[21.2.2.1$^{6,9}$.1$^{13,17}$.0$^{2,7}$]nonacosa-2,4,6(29),8,13(28),14,16-heptaen-3-yl}acetate (20 mg, 0.035 mmol) and NaOH (0.035 mL, 0.035 mmol) in EtOH (2 mL) was refluxed for 2 h. It was then cooled to rt, filtered and purified by preparative HPLC to obtain (2S)-2-(tert-butoxy)-2-{4,23-dimethyl-1,5,7,8-tetraazapentacyclo[21.2.2.1$^{6,9}$.1$^{13,17}$.0$^{2,7}$]nonacosa-2,4,6(29),8,13(28),14,16-heptaen-3-yl}acetic acid (17 mg, 0.031 mmol, 89% yield) as a white solid. $^1$H NMR (500 MHz, DMSO-d$_6$) δ 7.41 (s, 1H), 7.33-7.24 (m, 1H), 7.16 (d, J=7.0 Hz, 2H), 6.51 (s, 1H), 5.64 (s, 1H), 4.50-4.29 (m, 5H), 3.65-3.58 (m, 1H), 3.57-3.38 (m, 3H), 2.76 (d, J=11.4 Hz, 1H), 2.51 (s, 3H), 2.66 (t, J=8.1 Hz, 2H), 1.97 (d, J=13.6 Hz, 1H), 1.89-1.51 (m, 7H), 1.22 (s, 3H), 1.15 (s, 9H). LCMS (M+1)=551.6.

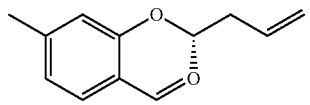

(S)-4-Methyl-2-(pent-4-en-2-yloxy)benzaldehyde

A mixture (S)-(4-methyl-2-(pent-4-en-2-yloxy)phenyl)methanol (260 mg, 1.260 mmol), Dess-Martin periodinane (642 mg, 1.513 mmol) in DCM (10 mL) was stirred at rt for 1 h. It was then diluted with EtOAc, washed with sat. NaHCO$_3$ and water. The organic layer was dried over MgSO$_4$, filtered and concentrated to obtain an oil, which was then purified by biotage, eluting with 10% EtOAc/hexane to isolate (S)-4-methyl-2-(pent-4-en-2-yloxy)benzaldehyde (90 mg, 35%) as an oil. $^1$H NMR (400 MHz, CDCl$_3$) δ 10.44 (s, 1H), 7.75 (d, J=8.1 Hz, 1H), 6.87-6.78 (m, 2H), 5.88 (ddt, J=17.1, 10.1, 7.1 Hz, 1H), 5.21-5.10 (m, 2H), 4.59 (sxt, J=6.1 Hz, 1H), 2.63-2.51 (m, 1H), 2.51-2.42 (m, 1H), 2.40 (s, 3H), 1.40 (d, J=6.1 Hz, 3H).

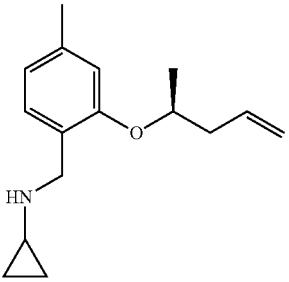 [SMILES: C=CC[C@H](C)Oc1cc(C)ccc1CNC1CC1]

(S)—N-(4-Methyl-2-(pent-4-en-2-yloxy)benzyl)cyclopropanamine

A mixture of cyclopropanamine (40.0 mg, 0.700 mmol), (S)-4-methyl-2-(pent-4-en-2-yloxy)benzaldehyde (130 mg, 0.636 mmol) in MeOH (5 mL) was stirred at rt for 0.5 h. Sodium borohydride (12.04 mg, 0.318 mmol) was then added and the reaction was stirred at rt for 2 h. It was then quenched with water, extracted with EtOAc. The organic layer was dried over MgSO$_4$, filtered and concentrated. The residue was purified by biotage, eluting with 20% EtOAc/hexane to isolate (S)—N-(4-methyl-2-(pent-4-en-2-yloxy)benzyl)cyclopropanamine (20 mg, 0.082 mmol, 12.81% yield) as an oil. $^1$H NMR (400 MHz, CDCl$_3$) δ 7.12 (d, J=7.8 Hz, 1H), 6.77-6.67 (m, 2H), 5.90 (ddt, J=17.2, 10.2, 7.1 Hz, 1H), 5.20-5.07

(m, 2H), 4.51 (sxt, J=6.0 Hz, 1H), 3.86-3.69 (m, 2H), 2.60-2.39 (m, 2H), 2.34 (s, 3H), 2.12-2.02 (m, 1H), 1.36 (d, J=6.1 Hz, 3H), 0.48-0.32 (m, 4H).

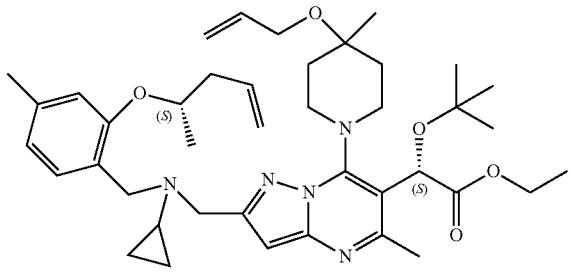

(S)-Ethyl 2-(7-(4-(allyloxy)-4-methylpiperidin-1-yl)-2-((cyclopropyl(4-methyl-2-((S)-pent-4-en-2-yloxy)benzyl)amino)methyl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (95 mg, 0.163 mmol) in acetonitrile (3 mL) at 0° C. was added (S)—N-(4-Methyl-2-(pent-4-en-2-yloxy)benzyl)cyclopropanamine (40 mg, 0.163 mmol) and Hunig's Base (0.028 mL, 0.163 mmol). It was stirred at 0° C. for 2 h and then quenched with water, extracted with EtOAc. The organic layer was dried over MgSO$_4$, filtered and concentrated. The residue was then purify by 20% EtOAc/hexane to obtain (S)-ethyl 2-(7-(4-(allyloxy)-4-methylpiperidin-1-yl)-2-((cyclopropyl(4-methyl-2-((S)-pent-4-en-2-yloxy)benzyl)amino)methyl)-5-methylpyrazolo[1,5-a]pyrimidin-6-yl)-2-(tert-butoxy)acetate (90 mg, 0.128 mmol, 79% yield) as an oil. LCMS (M+1)=702.5.

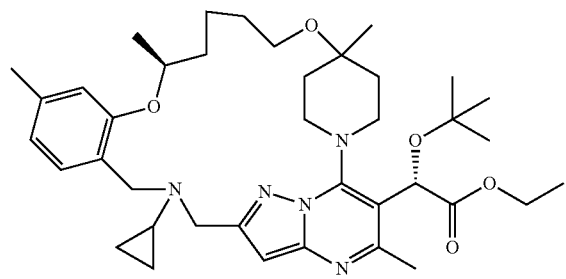 [SMILES: CCOC(=O)[C@@H](OC(C)(C)C)c1c(C)nc2cc3nn2c1N1CCC(C)(CC1)OCCCC[C@H](C)Oc1cc(C)ccc1CN(C1CC1)C3]

Ethyl (2S)-2-(tert-butoxy)-2-[(20S)-1-cyclopropyl-4,16,20,26-tetramethyl-19,25-dioxa-1,5,7,8,1-pentaazapentacyclo[24.2.2.1$^{6,9}$.0$^{2,7}$.0$^{13,18}$]hentriaconta-2,4,6(31),8,13(18),14,16-heptaen-3-yl]acetate A mixture of (S)-ethyl 2-(7-(4-(allyloxy)-4-methylpiperidin-1-yl)-2-((cyclopropyl(4-methyl-2-((S)-pent-4-en-2-yloxy)benzyl)amino)methyl)-5-methylpyrazolo[1,5-a]pyrimidin-6-yl)-2-(tert-butoxy)acetate (90 mg, 0.128 mmol) and Grubb's II catalyst (10.89 mg, 0.013 mmol) in DCM (80 mL) was refluxed for 2 h. It was then concentrated and the residue was dissolved in MeOH (2 mL). NaBH$_4$ (4.85 mg, 0.128 mmol) was added and the reaction was stirred at rt for 1 h. It was then diluted with water, extracted with EtOAc. The organic layer was dried over MgSO$_4$, filtered and concentrated to obtain an oil, which was then purified by biotage, eluting with 25% EtOac/hexane to obtain ethyl (2S)-2-(tert-butoxy)-2-[(20S)-11-cyclopropyl-4,16,20,26-tetramethyl-19,25-dioxa-1,5,7,8,11-pentaazapentacyclo[24.2.2.1$^{6,9}$.0$^{2,7}$.0$^{13,18}$]hentriaconta-2,4,6(31),8,13(18),14,16-heptaen-3-yl]acetate (90 mg, 0.107 mmol, 83% yield) as a white solid. LCMS (M+1)=676.4.

Example 64

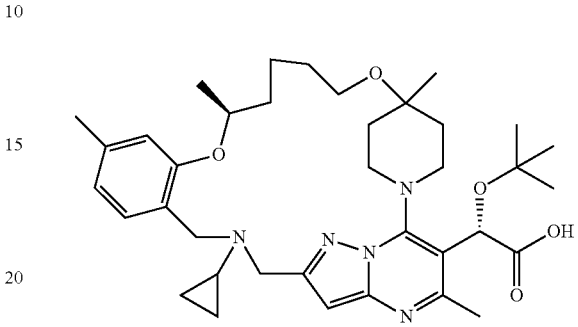

(2S)-2-(tert-Butoxy)-2-[(20S)-11-cyclopropyl-4,16,20,26-tetramethyl-19,25-dioxa-1,5,7,8,11-pentaazapentacyclo[24.2.2.1$^{6,9}$.0$^{2,7}$.0$^{13,18}$]hentriaconta-2,4,6(31),8,13(18),14,16-heptaen-3-yl]acetic acid A mixture of ethyl (2S)-2-(tert-butoxy)-2-[(20S)-11-cyclopropyl-4,16,20,26-tetramethyl-19,25-dioxa-1,5,7,8,11-pentaazapentacyclo[24.2.2.1$^{6,9}$.0$^{2,7}$.0$^{13,18}$]hentriaconta-2,4,6(31),8,13(18),14,16-heptaen-3-yl]acetate (70 mg, 0.104 mmol) and NaOH (0.311 mL, 0.311 mmol) in EtOH (2 mL) was refluxed for 2 h. It was then cooled to rt, purified by preparative HPLC to obtain (2S)-2-(tert-butoxy)-2-[(20S)-11-cyclopropyl-4,16,20,26-tetramethyl-19,25-dioxa-1,5,7,8,11-pentaazapentacyclo[24.2.2.1$^{6,9}$.0$^{2,7}$.0$^{13,18}$]hentriaconta-2,4,6(31),8,13(18),14,16-heptaen-3-yl]acetic acid (42 mg, 0.065 mmol, 62.6% yield) as a white solid. $^1$H NMR (500 MHz, DMSO-d$_6$) δ 7.12 (d, J=7.3 Hz, 1H), 6.76 (s, 1H), 6.64 (d, J=7.7 Hz, 1H), 6.37 (s, 1H), 5.61 (s, 1H), 4.52 (br. s., 1H), 4.34 (t, J=12.3 Hz, 1H), 4.04 (d, J=14.3 Hz, 1H), 3.92 (d, J=15.0 Hz, 1H), 3.81 (d, J=14.3 Hz, 1H), 3.72 (d, J=15.0 Hz, 1H), 3.68-3.59 (m, 1H), 3.50-3.29 (m, 3H), 2.79-2.71 (m, 1H), 2.48 (s, 3H), 2.27 (s, 3H), 1.97 (br. s., 1H), 1.91 (s, 1H), 1.83 (d, J=12.8 Hz, 1H), 1.78-1.43 (m, 8H), 1.20 (d, J=5.9 Hz, 3H), 1.17 (s, 3H), 1.14 (s, 9H), 0.45 (d, J=5.5 Hz, 1H), 0.35 (d, J=4.8 Hz, 2H), 0.27 (br. s., 1H). LCMS (M+1)=648.5.

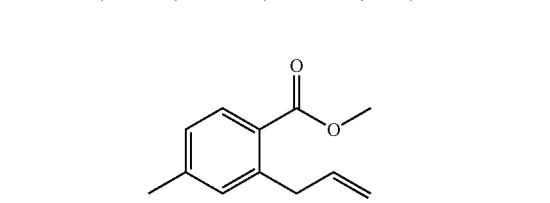

Methyl 2-allyl-4-methylbenzoate

A mixture of methyl 2-bromo-4-methylbenzoate (500 mg, 2.183 mmol), allyltributylstannane (0.744 mL, 2.401 mmol), lithium chloride (185 mg, 4.37 mmol) in DMF (1 mL), acetonitrile (10 mL) was added bis(triphenylphosphine)palladium (ii) dichloride (77 mg, 0.109 mmol). It was then degassed for 2 min, then filled with N$_2$. After heating at 90° C. for 16 h, it was quenched with NH₄Cl, extracted with EtOAc. The organic layer was washed with KF solution, dried over MgSO₄, filtered and concentrated to obtain an oil, which was then purified by biotage, eluting with 10% EtOAc/hexane to isolate methyl 2-allyl-4-methylbenzoate (330 mg, 1.735 mmol, 79% yield) as an oil. ¹H NMR (400 MHz, CDCl₃) δ 7.95-7.77 (m, 1H), 7.21-6.99 (m, 2H), 6.19-5.85 (m, 1H), 5.22-4.91 (m, 2H), 3.89 (s, 3H), 3.76 (d, J=6.6 Hz, 2H), 2.39 (s, 3H).

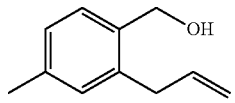

(2-Allyl-4-methylphenyl)methanol

To a mixture of methyl 2-allyl-4-methylbenzoate (220 mg, 1.156 mmol) in THF (2 mL) was added LAH (2.313 mL, 2.313 mmol) and the reaction mixture was stirred at rt for 1 h. It was then added NH₄Cl and extracted with EtOAc. The organic layer was dried over MgSO₄, filtered and concentrated to obtain an oil, which was then purified by biotage, eluting with 10% EtOAc/hexane to isolate (2-allyl-4-methylphenyl)methanol (150 mg, 0.925 mmol, 80% yield) as an oil. ¹H NMR (500 MHz, CDCl₃) δ 7.31-7.25 (m, 1H), 7.10-7.03 (m, 2H), 6.03 (ddt, J=16.9, 10.4, 6.3 Hz, 1H), 5.13-5.00 (m, 2H), 4.69 (d, J=5.2 Hz, 2H), 3.48 (d, J=6.3 Hz, 2H), 2.36 (s, 3H), 1.53 (t, J=5.7 Hz, 1H).

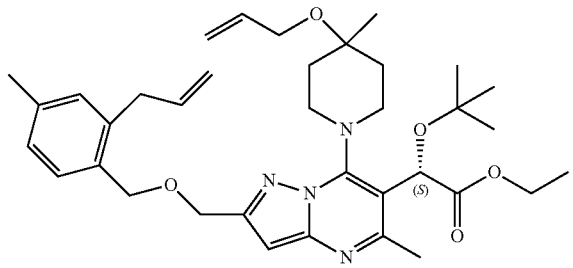

(S)-Ethyl 2-(2-(((2-allyl-4-methylbenzyl)oxy)methyl)-7-(4-(allyloxy)-4-methylpiperidin-1-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (144 mg, 0.247 mmol) and (2-allyl-4-methylphenyl)methanol (40 mg, 0.247 mmol) in DMF (5 mL) at 0° C. was added NaH (9.86 mg, 0.247 mmol). The reaction mixture was stirred h at 0° C. for 2 h. It was then quenched with water, extracted with EtOAc. The organic layer was dried over MgSO₄, filtered and concentrated. The residue was purified by biotage, eluting with 20% EtOAc/hexane to obtain (S)-ethyl 2-(2-(((2-allyl-4-methylbenzyl)oxy)methyl)-7-(4-(allyloxy)-4-methylpiperidin-1-yl)-5-methylpyrazolo[1,5-a]pyrimidin-6-yl)-2-(tert-butoxy) acetate (50 mg, 0.081 mmol, 32.8% yield) as an oil. LCMS (M+1)=619.4.

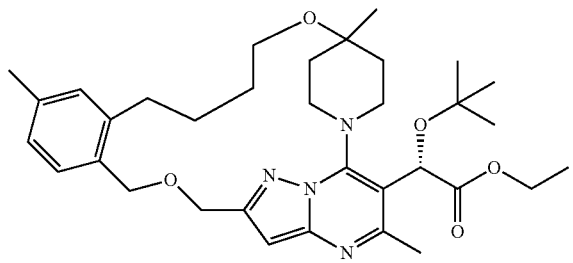 [SMILES: CCOC(=O)[C@@H](OC(C)(C)C)c1c(C)nc2cc3nn2c1N1CCC(C)(CC1)OCCCCc1cc(C)ccc1COC3]

Ethyl (2S)-2-(tert-butoxy)-2-{4,16,24-trimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetate A mixture of (S)-ethyl 2-(2-(((2-allyl-4-methylbenzyl)oxy)methyl)-7-(4-(allyloxy)-4-methylpiperidin-1-yl)-5-methylpyrazolo[1,5-a]pyrimidin-6-yl)-2-(tert-butoxy)acetate (50 mg, 0.081 mmol) and Grubbs II catalyst (68.6 mg, 0.081 mmol) in DCM (50 mL) was refluxed for 2 h. It was then concentrated and the residue was dissolved in MeOH (2 mL). NaBH₄ (3.06 mg, 0.081 mmol) was then added and the reaction was stirred at rt for 1 h. It was then diluted with water, extracted with EtOAc. The organic layer was dried over MgSO₄, filtered and concentrated. The residue was purified by biotage, eluting with 20% EtOAc/hexane to isolate ethyl (2S)-2-(tert-butoxy)-2-{4,16,24-trimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetate (30 mg, 0.051 mmol, 62.6% yield) as a white solid. ¹H NMR (400 MHz, CDCl₃) δ 7.36-7.25 (m, 1H), 7.08-6.97 (m, 2H), 6.50 (s, 1H), 6.16 (s, 1H), 4.88 (s, 2H), 4.76-4.59 (m, 3H), 4.24-4.08 (m, 2H), 3.96 (t, J=11.0 Hz, 1H), 3.57-3.40 (m, 2H), 2.92 (d, J=11.0 Hz, 1H), 2.80-2.72 (m, 2H), 2.69-2.59 (m, 4H), 2.34 (s, 3H), 2.11-2.01 (m, 1H), 1.98-1.86 (m, 3H), 1.86-1.74 (m, 2H), 1.76-1.60 (m, 2H), 1.29-1.22 (m, 12H), 1.19 (t, J=7.2 Hz, 3H). LCMS (M+1)=593.5.

Example 65

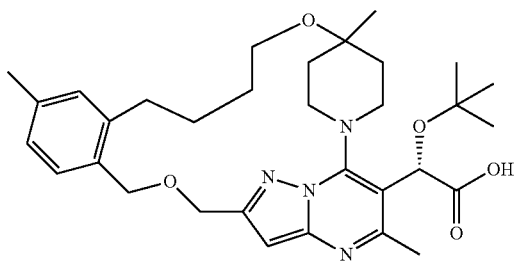 [SMILES: Cc1ccc2c(c1)CCCCOC1(C)CCN(CC1)c1c([C@H](OC(C)(C)C)C(=O)O)c(C)nc3cc(nn13)COC2]

(2S)-2-(tert-Butoxy)-2-{4,16,24-trimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetic acid A mixture of ethyl (2S)-2-(tert-butoxy)-2-{4,16,24-trimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetate (30 mg, 0.051 mmol) and NaOH (0.152 mL, 0.152 mmol) in EtOH (2 mL) was refluxed for 2 h. It was then cooled to rt and purified by preparative HPLC to obtain (2S)-2-(tert-butoxy)-2-{4,16,24-trimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid (24 mg, 0.042 mmol, 84% yield) as a white solid. $^1$H NMR (500 MHz, DMSO-d$_6$) δ 7.25 (d, J=7.3 Hz, 1H), 7.03-6.96 (m, 2H), 6.49 (s, 1H), 5.76 (br. s., 1H), 4.87-4.76 (m, 2H), 4.72 (d, J=12.1 Hz, 1H), 4.58 (d, J=12.1 Hz, 1H), 4.54-4.46 (m, 1H), 3.66-3.58 (m, 2H), 3.39 (m, 1H), 3.12 (br. s., 1H), 2.69-2.60 (m, 2H), 2.55 (br. s., 4H), 2.27 (s, 3H), 1.92-1.50 (m, 8H), 1.18 (s, 3H), 1.15 (s, 9H). LCMS (M+1)=565.4.

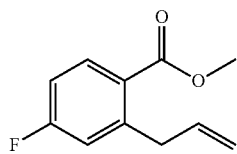

Methyl 2-allyl-4-fluorobenzoate

A mixture of methyl 2-bromo-4-fluorobenzoate (1 g, 4.29 mmol), allyltributylstannane (1.464 mL, 4.72 mmol), lithium chloride (0.364 g, 8.58 mmol) in DMF (1 mL), acetonitrile (10 mL) was added bis(triphenylphosphine)palladium(ii) dichloride (0.151 g, 0.215 mmol). It was then degassed for 2 min, then filled with N$_2$. After heating at 90° C. for 16 h, it was quenched with NH$_4$Cl, extracted with EtOAc. The organic layer was washed with KF solution, dried over MgSO$_4$, filtered and concentrated. The residue was purified by biotage, eluting with 10% EtOAc/hexane to isolate methyl 2-allyl-4-fluorobenzoate (330 mg, 1.699 mmol, 39.6% yield) as an white solid. $^1$H NMR (400 MHz, CDCl$_3$) δ 7.96 (dd, J=8.6, 6.1 Hz, 1H), 7.09-6.87 (m, 2H), 6.01 (ddt, J=16.9, 10.3, 6.6 Hz, 1H), 5.19-4.96 (m, 2H), 3.90 (s, 3H), 3.80 (d, J=6.6 Hz, 2H).

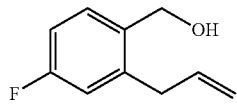

(2-Allyl-4-fluorophenyl)methanol

To a mixture of methyl 2-allyl-4-fluorobenzoate (400 mg, 2.060 mmol) in THF (5 mL) was added LAH (4.12 mL, 4.12 mmol) and the reaction was stirred at rt for 1 h. It was then added NH$_4$Cl and extracted with EtOAc. The organic layer was dried over MgSO$_4$, filtered and concentrated to obtain an oil, which was then purified by biotage, eluting with 10% EtOAc/hexane to isolate (2-allyl-4-fluorophenyl)methanol (300 mg, 1.805 mmol, 88% yield) as an oil. $^1$H NMR (400 MHz, CDCl$_3$) δ 7.37 (dd, J=8.9, 6.0 Hz, 1H), 7.06-6.84 (m, 2H), 6.08-5.88 (m, 1H), 5.24-5.03 (m, 2H), 4.76-4.68 (m, 2H), 3.58-3.39 (m, 2H).

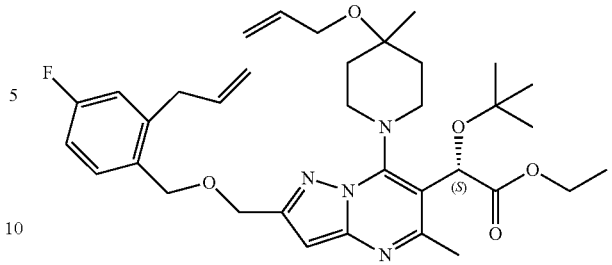

(S)-Ethyl 2-(2-(((2-allyl-4-fluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (150 mg, 0.257 mmol) and (2-allyl-4-fluorophenyl)methanol (42.7 mg, 0.257 mmol) in DMF (5 mL) at 0° C. was added NaH (10.26 mg, 0.257 mmol). The reaction was stirred at 0° C. for 2 h. It was then quenched with water, extracted with EtOAc. The organic layer was dried over MgSO$_4$, filtered and concentrated to obtain an oil, which was purified by biotage, eluting with 20% EtOAc/hexane to obtain (S)-ethyl 2-(2-(((2-allyl-4-fluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate (70 mg, 0.112 mmol, 43.8% yield) as an oil. LCMS (M+1)=623.3.

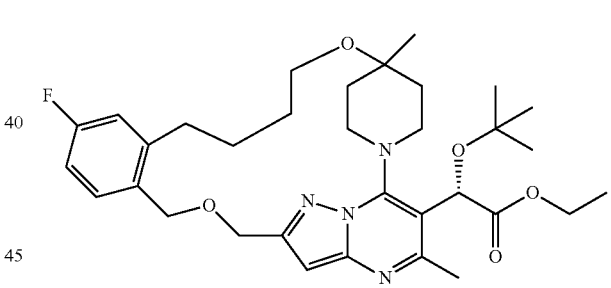

Ethyl (2S)-2-(tert-butoxy)-2-{16-fluoro-4,24-dimethyl-11,23-dioxa-1,5,7,8-tetraazapentacyclo [22.2.2.1$^{6,9}$.0$^{2,7}$.0$^{13,18}$]nonacosa-2,4,6(29),8,13(18),14,16-heptaen-3-yl}acetate A mixture of (S)-ethyl 2-(2-(((2-allyl-4-fluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate (70 mg, 0.112 mmol) and Grubbs II catalyst (95 mg, 0.112 mmol) in DCM (70 mL) was refluxed for 2 h. It was then concentrated and the residue was dissolved in MeOH (2 mL). Sodium borohydride (4.25 mg, 0.112 mmol) was added and the reaction mixture was stirred at rt for 1 h. It was then extracted with EtOAc, washed with water. The organic layer was dried over MgSO$_4$, filtered and concentrated. The residue was purified by biotage, eluting with 20% EtOac/hexane to isolate ethyl (2S)-2-(tert-butoxy)-2-{16-fluoro-4,24-dimethyl-11,23-dioxa-1,5,7,8-tetraazapentacyclo[22.2.2.

1⁶,⁹.0²,⁷.0¹³,¹⁸]nonacosa-2,4,6(29),8,13(18),14,16-heptaen-3-yl}acetate (30 mg, 0.050 mmol, 44.7% yield) as a white solid. LCMS (M+1)=597.3.

Example 66

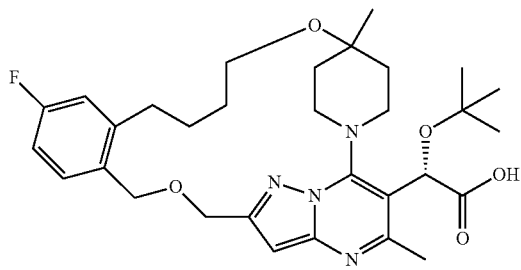 [SMILES: Cc1nc2cc3nn2c(c1[C@H](OC(C)(C)C)C(=O)O)N1CCC(C)(CC1)OCCCCc1cc(F)ccc1COC3]

(2S)-2-(tert-Butoxy)-2-{16-fluoro-4,24-dimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetic acid A mixture of ethyl (2S)-2-(tert-butoxy)-2-{16-fluoro-4,24-dimethyl-11,23-dioxa-1,5,7,8-tetraazapentacyclo [22.2.2.1⁶,⁹.0²,⁷.0¹³,¹⁸]nonacosa-2,4,6(29),8,13(18),14,16-heptaen-3-yl}acetate (28 mg, 0.047 mmol) and NaOH (1.877 mg, 0.047 mmol) in EtOH (2 mL) was refluxed for 2 h. It was then cooler to rt and purified by preparative HPLC to obtain (2S)-2-(tert-butoxy)-2-{16-fluoro-4,24-dimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetic acid (20 mg, 0.035 mmol, 75.0% yield) as a white solid. $^1$H NMR (500 MHz, DMSO-d$_6$) δ 7.46-7.32 (m, 1H), 7.08-6.91 (m, 2H), 6.50 (s, 1H), 5.79 (s, 1H), 4.83 (q, J=12.1 Hz, 2H), 4.75 (d, J=12.5 Hz, 1H), 4.61 (d, J=12.5 Hz, 1H), 4.49 (t, J=11.7 Hz, 1H), 3.69-3.32 (m, 3H), 3.07 (br. s., 1H), 2.69 (br. s., 2H), 2.56 (d, J=9.5 Hz, 1H), 2.51 (br. s., 3H), 1.87-1.50 (m, 8H), 1.18 (s, 3H), 1.16 (s, 9H). LCMS (M+1)=569.2.

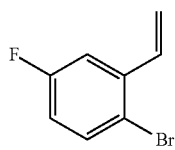

1-Bromo-4-fluoro-2-vinylbenzene

A mixture of methyltriphenylphosphonium iodide (1.195 g, 2.96 mmol) in tetrahydrofuran (25 mL) was added BuLi (1.182 mL, 2.96 mmol) at 0° C. and stirred at 0° C. for 0.5 h. It was then added 2-bromo-5-fluorobenzaldehyde (0.5 g, 2.463 mmol) and stirred at rt for 16 h. The reaction was then diluted with water, extracted with EtOAc. The organic layer was dried over MgSO4, filtered and concentrated to obtain an oil, which was then purified by biotage, eluting with 5% EtOAc/hexane to obtain 1-bromo-4-fluoro-2-vinylbenzene (320 mg, 1.592 mmol, 64.6% yield) as an oil. $^1$H NMR (400 MHz, CDCl$_3$) δ 7.56-7.48 (m, 1H), 7.33-7.23 (m, 1H), 7.09-6.96 (m, 1H), 6.89 (td, J=8.3, 3.1 Hz, 1H), 5.73 (d, J=17.4 Hz, 1H), 5.45 (d, J=11.0 Hz, 1H).

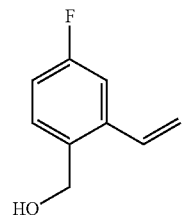

(4-Fluoro-2-vinylphenyl)methanol

To a mixture of 1-bromo-4-fluoro-2-vinylbenzene (0.32 g, 1.592 mmol) in tetrahydrofuran (5 mL) at −78° C. was added BuLi (0.764 mL, 1.910 mmol) dropwise. It was then stirred at this temperature for 1 h, then N,N-dimethylformamide (0.185 mL, 2.388 mmol) was added. The reaction mixture was stirred at −78° C. for 30 min, then warmed to rt and stirred at rt for 3 h. It was then quenched with NH4Cl, extracted with ether. The organic layer was dried over MgSO4, filtered and concentrated to obtain 4-fluoro-2-vinylbenzaldehyde (0.2 g) as an oil, which was used in the next step without purification. A mixture of 4-fluoro-2-vinylbenzaldehyde (200 mg, 1.332 mmol) and NaBH4 (50.4 mg, 1.332 mmol) in MeOH (2 mL) was stirred at rt for 1 h. It was then diluted with water, extracted with EtOAc. The organic layer was dried over MgSO4, filtered and concentrated. The residue was purified by biotage, eluting with 20% EtOac/hexane to obtain (4-fluoro-2-vinylphenyl)methanol (150 mg, 0.986 mmol, 74.0% yield) as an oil. $^1$H NMR (400 MHz, CDCl$_3$) δ 7.35 (dd, J=8.3, 5.9 Hz, 1H), 7.25 (dd, J=10.0, 2.7 Hz, 1H), 7.09-7.02 (m, 1H), 7.02-6.95 (m, 1H), 5.73 (d, J=17.4 Hz, 1H), 5.44 (d, J=11.0 Hz, 1H), 4.75 (d, J=4.9 Hz, 2H).

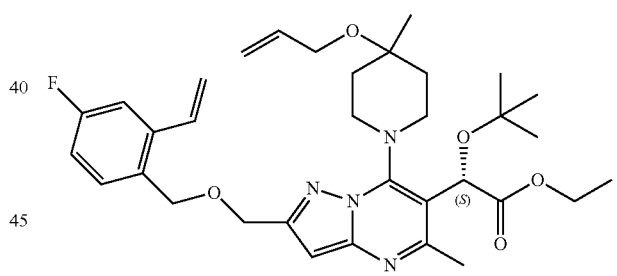

(S)-Ethyl 2-(7-(4-(allyloxy)-4-methylpiperidin-1-yl)-2-(((4-fluoro-2-vinylbenzyl)oxy)methyl)-5-methylpyrazolo[1,5-a]pyrimidin-6-yl)-2-(tert-butoxy)acetate To a mixture of (4-fluoro-2-vinylphenyl)methanol (39.1 mg, 0.257 mmol) in DMF (3 mL) at 0° C. was added (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (150 mg, 0.257 mmol) and NaH (10.26 mg, 0.257 mmol). It was then quenched with sat. NH4Cl, extracted with EtOAc. The organic layer was dried over MgSO4, filtered and concentrated to obtain an oil, which was then purified by biotage, eluting with 25% EtOAc/hexane to isolate (S)-ethyl 2-(7-(4-(allyloxy)-4-methylpiperidin-1-yl)-2-(((4-fluoro-2-vinylbenzyl)oxy)methyl)-5-methylpyrazolo[1,5-a]pyrimidin-6-yl)-2-(tert-butoxy)acetate (70 mg, 0.115 mmol, 44.8% yield) as an oil. LCMS (M+1)=609.3.

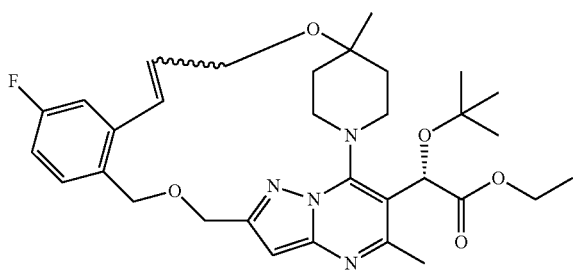 [SMILES: CCOC(=O)[C@@H](OC(C)(C)C)c1c(C)nc2cc3nn2c1N1CCC(C)(CC1)OCC=Cc1cc(F)ccc1COC3]

Ethyl (2S)-2-(tert-butoxy)-2-[(19E/Z)-16-fluoro-4,
23-dimethyl-11,22-dioxa-1,5,7,8-tetraazapentacyclo
[21.2.2.1$^{6,9}$.0$^{2,7}$.0$^{13,18}$]octacosa-2,4,6(28),8,13(18),
14,16,19-octaen-3-yl]acetate A mixture of (S)-ethyl 2-(7-(4-(allyloxy)-4-methylpiperidin-1-yl)-2-(((4-fluoro-2-vinylbenzyl)oxy)methyl)-5-methylpyrazolo[1,5-a]pyrimidin-6-yl)-2-(tert-butoxy)acetate (70 mg, 0.115 mmol), (1,3-dimesitylimidazolidin-2-ylidene)(2-isopropoxybenzylidene)ruthenium(VI) chloride (7.21 mg, 0.011 mmol) and TsOH.H$_2$O (23.92 mg, 0.115 mmol) in ClCH$_2$CH$_2$Cl (70 mL) was refluxed for 6 h. It was then cooled to rt, washed with NaHCO$_3$ and water. The organic layer was dried over MgSO$_4$, filtered and concentrated. The residue was purified by biotage, eluting with 20% EtOAc/hexane to isolate ethyl (2S)-2-(tert-butoxy)-2-[(19E/Z)-16-fluoro-4,23-dimethyl-11,22-dioxa-1,5,7,8-tetraazapentacyclo
[21.2.2.1$^{6,9}$.0$^{2,7}$.0$^{13,18}$]octacosa-2,4,6(28),8,13(18),14,16,19-octaen-3-yl]acetate (40 mg, 0.069 mmol, 59.9% yield) as a white solid. LCMS (M+1)=581.4.

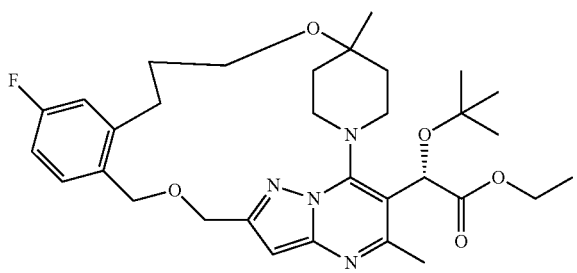 [SMILES: CCOC(=O)[C@@H](OC(C)(C)C)c1c(C)nc2cc3nn2c1N1CCC(C)(CC1)OCCCc1cc(F)ccc1COC3]

Ethyl (2S)-2-(tert-butoxy)-2-{16-fluoro-4,23-dimethyl-11,22-dioxa-1,5,7,8-tetraazapentacyclo
[21.2.2.1$^{6,9}$.0$^{2,7}$.0$^{13,18}$]octacosa-2,4,6(28),8,13(18),
14,16-heptaen-3-yl}acetate A mixture of ethyl (2S)-2-(tert-butoxy)-2-[(19E/Z)-16-fluoro-4,23-dimethyl-11,22-dioxa-1,5,7,8-tetraazapentacyclo[21.2.2.1$^{6,9}$.0$^{2,7}$.0$^{13,18}$]octacosa-2,4,6(28),8,13(18),14,16,19-octaen-3-yl]acetate (40 mg, 0.069 mmol) and sodium borohydride (7.82 mg, 0.207 mmol) in MeOH (2 mL) was stirred at rt for 1 h. It was then diluted with water, extracted with EtOAc. The organic layer was dried over MgSO$_4$, filtered and concentrated to obtain an oil, which was then purified by biotage, eluting with 20% EtOAc/hexane to obtain ethyl (2S)-2-(tert-butoxy)-2-{16-fluoro-4,23-dimethyl-11,22-dioxa-1,5,7,8-tetraazapentacyclo[21.2.2.1$^{6,9}$.0$^{2,7}$.0$^{13,18}$] octacosa-2,4,6(28),8,13(18),14,16-heptaen-3-yl}acetate (32 mg, 0.055 mmol, 80% yield) as a white solid. LCMS (M+1)=583.3.

Example 67

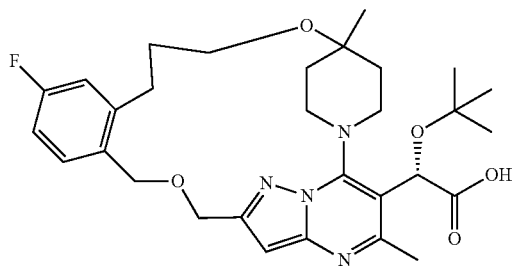 [SMILES: Cc1nc2cc3nn2c(c1[C@H](OC(C)(C)C)C(=O)O)N1CCC(C)(CC1)OCCCc1cc(F)ccc1COC3]

(2S)-2-(tert-Butoxy)-2-{16-fluoro-4,23-dimethyl-
11,22-dioxa-1,5,7,8tetraazapentacyclo[21.2.2.
1$^{6,9}$.0$^{2,7}$.0$^{13,18}$]octacosa-2,4,6(28),8,13(18),14,16-
heptaen-3-yl}acetic acid A mixture of ethyl (2S)-2-(tert-butoxy)-2-{16-fluoro-4,23-dimethyl-11,22-dioxa-1,5,7,8-tetraazapentacyclo [21.2.2.1$^{6,9}$.0$^{2,7}$.0$^{13,18}$]octacosa-2,4,6(28),8,13(18),14,16-heptaen-3-yl}acetate (32 mg, 0.055 mmol) and NaOH (2.196 mg, 0.055 mmol) in EtOH (2 mL) was refluxed for 2 h. It was then cooled to rt and purified by preparative HPLC to isolate (2S)-2-(tert-butoxy)-2-{16-fluoro-4,23-dimethyl-11,22-dioxa-1,5,7,8tetraazapentacyclo[21.2.2.1$^{6,9}$.0$^{2,7}$.0$^{13,18}$]octacosa-2,4,6(28),8,13(18),14,16-heptaen-3-yl}acetic acid (13.9 mg, 0.025 mmol, 44.7% yield) as a white solid. $^1$H NMR (500 MHz, DMSO-d$_6$) δ 7.49-7.41 (m, 1H), 7.11-7.00 (m, 2H), 6.47 (s, 1H), 5.91 (s, 1H), 4.92 (d, J=11.7 Hz, 1H), 4.75 (d, J=12.1 Hz, 1H), 4.71-4.55 (m, 3H), 3.84 (t, J=10.6 Hz, 1H), 3.50 (m, 2H), 3.16-3.01 (m, 3H), 2.59 (d, J=11.7 Hz, 1H), 2.53 (s, 3H), 1.99-1.79 (m, 4H), 1.77-1.54 (m, 2H), 1.24 (s, 3H), 1.19 (s, 9H). LCMS (M+1)=555.2.

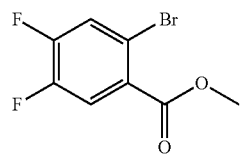

Methyl 2-bromo-4,5-difluorobenzoate

To a mixture of 2-bromo-4,5-difluorobenzoic acid (1 g, 4.22 mmol) in dichloromethane (10 mL) and MeOH (1 mL) was added trimethylsilyl)diazomethane (2.110 mL, 4.22 mmol) and the reaction was stirred at rt for 1 h. It was then concentrated to obtain methyl 2-bromo-4,5-difluorobenzoate (1 g, 3.98 mmol, 94% yield) as an oil. $^1$H NMR (400 MHz, CDCl3) δ 7.76 (dd, J=10.5, 8.3 Hz, 1H), 7.57-7.49 (m, 1H), 3.96 (s, 3H).

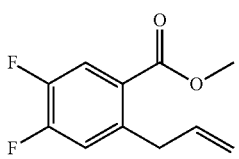

Methyl 2-allyl-4,5-difluorobenzoate

A mixture of methyl 2-bromo-4,5-difluorobenzoate (0.5 g, 1.992 mmol), allyltributylstannane (0.679 mL, 2.191 mmol), lithium chloride (0.169 g, 3.98 mmol) in DMF (1 mL), acetonitrile (10 mL) was added bis(triphenylphosphine)palladium (ii) dichloride (0.070 g, 0.100 mmol). It was then degassed for 2 min, then filled with $N_2$. After heating at 90° C. for 16 h, it was quenched with $NH_4Cl$, extracted with EtOAc. The organic layer was washed with KF solution for 5 times, then dried over $MgSO_4$, filtered and concentrated to obtain an oil, which was then purified by biotage, eluting with 10% EtOAc/hexane to isolate methyl 2-allyl-4,5-difluorobenzoate (330 mg, 1.555 mmol, 78% yield) as an oil. $^1$H NMR (400 MHz, $CDCl_3$) 7.78 (dd, J=11.1, 8.2 Hz, 1H), 7.11 (dd, J=11.1, 7.7 Hz, 1H), 5.98 (ddt, J=16.9, 10.2, 6.5 Hz, 1H), 5.16-5.02 (m, 2H), 3.91 (s, 3H), 3.76 (d, J=6.6 Hz, 2H).

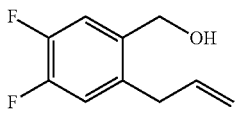

(2-Allyl-4,5-difluorophenyl)methanol

To a mixture of methyl 2-allyl-4,5-difluorobenzoate (360 mg, 1.697 mmol) in THF (4 mL) was added LAH (3.39 mL, 3.39 mmol) and the reaction was stirred at rt for 1 h. It was then quenched with $NH_4Cl$ and extracted with EtOAc. The organic layer was dried over $MgSO_4$, filtered and concentrated to obtain an oil, which was then purified by biotage, eluting with 10% EtOAc/hexane to isolate (2-allyl-4,5-difluorophenyl)methanol (150 mg, 0.814 mmol, 48.0% yield) as an oil. $^1$H NMR (400 MHz, $CDCl_3$) δ 7.34-7.24 (m, 1H), 7.08-6.97 (m, 1H), 5.96 (ddt, J=16.8, 10.4, 6.2 Hz, 1H), 5.14 (d, J=10.0 Hz, 1H), 5.03 (d, J=17.1 Hz, 1H), 4.67 (d, J=5.1 Hz, 2H), 3.40 (d, J=6.1 Hz, 2H).

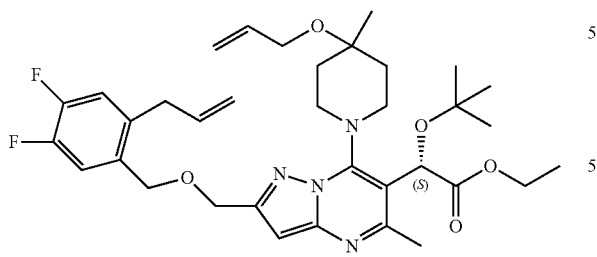

(S)-Ethyl 2-(2-(((2-allyl-4,5-difluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate To a mixture of (S)-ethyl 2-(7-(4-(allyloxy)-4-methylpiperidin-1-yl)-2-(iodomethyl)-5-methylpyrazolo[1,5-a]pyrimidin-6-yl)-2-(tert-butoxy)acetate (200 mg, 0.342 mmol) and (2-allyl-4,5-difluorophenyl)methanol (63.0 mg, 0.342 mmol) in DMF (2 mL) at 0° C. was added NaH (13.69 mg, 0.342 mmol). It was stirred at 0° C. for 2 h, then quenched with water, extracted with EtOAc. The organic layer was dried over $MgSO_4$, filtered and concentrated to obtain an oil, which was then purified by biotage, eluting with 25% EtOAc/hexane to obtain (S)-ethyl 2-(2-(((2-allyl-4,5-difluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate (100 mg, 43.6%) as an oil. LCMS (M+1)=641.5.

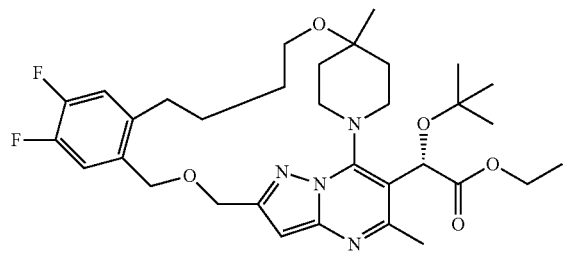 [SMILES: CCOC(=O)[C@@H](OC(C)(C)C)c1c(C)nc2cc3nn2c1N1CCC(C)(CC1)OCCCCc1cc(F)c(F)cc1COC3]

Ethyl (2S)-2-(tert-butoxy)-2-{15,16-difluoro-4,24-dimethyl-11,23-dioxa-1,5,7,8-tetraazapentacyclo [22.2.2.1$^{6,9}$.0$^{2,7}$.0$^{13,18}$]nonacosa-2,4,6(29),8,13(18), 14,16-heptaen-3-yl}acetate A mixture of (S)-ethyl 2-(2-(((2-allyl-4,5-difluorobenzyl)oxy)methyl)-7-(4-(allyloxy)-4-methylpiperidin-1-yl)-5-methylpyrazolo[1,5-a]pyrimidin-6-yl)-2-(tert-butoxy)acetate (100 mg, 0.156 mmol) and Grubbs II catalyst (13.25 mg, 0.016 mmol) in DCM (100 mL) was refluxed for 2 h. It was then concentrated and the residue was dissolved in MeOH (2 mL). Sodium borohydride (5.90 mg, 0.156 mmol) was added and stirred at rt for 1 h. It was then quenched with $NH_4Cl$, extracted with EtOAc. The organic layer was washed with water, dried over $MgSO_4$, filtered and concentrated. The residue was purified by biotage, eluting with 20% EtOAc/hexane to isolate ethyl (2S)-2-(tert-butoxy)-2-{15,16-difluoro-4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14, 16-heptaen-3-yl}acetate (60 mg, 0.098 mmol, 62.5% yield) as a white solid. LCMS (M+1)=615.3.

Example 68

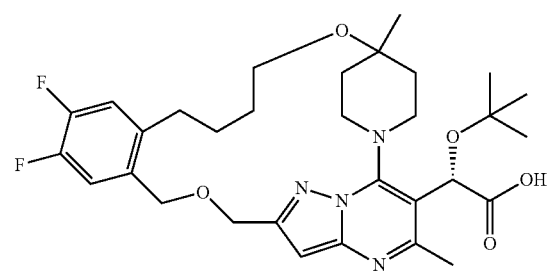 [SMILES: Cc1nc2cc3nn2c(c1[C@H](OC(C)(C)C)C(=O)O)N1CCC(C)(CC1)OCCCCc1cc(F)c(F)cc1COC3]

(2S)-2-(tert-Butoxy)-2-{15,16-difluoro-4,24-dimethyl-11,23-dioxa-1,5,7,8-tetraazapentacyclo [22.2.2.1$^{6,9}$.0$^{2,7}$.0$^{13,18}$]nonacosa-2,4,6(29),8,13(18), 14,16-heptaen-3-yl}acetic acid A mixture of ethyl (2S)-2-(tert-butoxy)-2-{15,16-difluoro-4,24-dimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetate (60 mg, 0.098 mmol) and NaOH (3.90 mg, 0.098 mmol) in EtOH (2 mL) was refluxed for 2 h. It was then cooled to rt and purified by preparative HPLC to isolate (2S)-2-(tert-butoxy)-2-{15,16-difluoro-4,24-dimethyl-11,23-dioxa-1,5,7,8-tetraazapentacyclo[22.2.2.1⁶,⁹.0²,⁷.0¹³,¹⁸]nonacosa-2,4,6(29),8,13(18),14,16-heptaen-3-yl}acetic acid (32.5 mg, 55.6%) as a white solid. $^1$H NMR (500 MHz, DMSO-$d_6$) δ 7.44-7.31 (m, 1H), 7.27 (dd, J=11.6, 8.6 Hz, 1H), 6.51 (s, 1H), 5.71 (s, 1H), 4.97-4.76 (m, 3H), 4.62 (d, J=12.5 Hz, 1H), 4.49 (t, J=11.2 Hz, 1H), 3.63-3.53 (m, 2H), 3.21-3.19 (m, 2H), 2.68-2.56 (m, 3H), 2.50 (br. s., 3H), 1.83 (d, J=12.8 Hz, 3H), 1.71-1.50 (m, 5H), 1.18 (s, 3H), 1.15 (s, 9H). LCMS (M+1)=587.3.

The Examples 69 and 70 were synthesized by using methods similar to the Example 35.

Example 69

(2S)-2-(tert-Butoxy)-2-[(20S)-15-chloro-4,16,20,26-tetramethyl-11,19,25-trioxa-1,5,7,8-tetraazapentacyclo[24.2.2.1⁶,⁹.0²,⁷.0¹³,¹⁸]hentriaconta-2,4,6(31),8,13,15,17-heptaen-3-yl]acetic acid $^1$H NMR (500 MHz, DMSO-$d_6$) δ 7.28 (s, 1H), 7.00 (s, 1H), 6.41 (s, 1H), 5.35 (s, 1H), 4.84 (d, J=12.5 Hz, 1H), 4.62-4.49 (m, 4H), 4.31 (t, J=11.7 Hz, 1H), 3.66-3.43 (m, 3H), 3.38 (br. s., 2H), 2.91-2.72 (m, 3H), 2.30 (s, 3H), 1.74-1.40 (m, 10H), 1.18 (s, 6H), 1.14-1.05 (m, 9H). LCMS (M+H)=643.3.

Example 70

(2S)-2-(tert-Butoxy)-2-[(20S)-15-chloro-4,16,20,27-tetramethyl-11,19,26-trioxa-1,5,7,8-tetraazapentacyclo[25.2.2.1⁶,⁹.0²,⁷.0¹³,¹⁸]dotriaconta-2,4,6(32),8,13,15,17-heptaen-3-yl]acetic acid $^1$H NMR (500 MHz, DMSO-$d_6$) δ 7.29 (s, 1H), 7.06 (s, 1H), 6.44 (br. s., 1H), 5.72 (s, 1H), 4.75-4.41 (m, 6H), 4.29 (d, J=4.4 Hz, 1H), 3.83-3.45 (m, 4H), 2.5 (s, 3H), 2.35-2.18 (m, 3H), 1.95-1.37 (m, 10H), 1.33-0.94 (m, 17H). LCMS (M+H)=657.5.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I where:
$R^1$ is alkyl or haloalkyl;
$R^2$ is hydrogen or alkyl;
$R^3$ is hydrogen, halo, or alkyl;
$R^4$ is hydrogen, alkyl, or cycloalkyl;
$R^5$ is hydrogen, alkyl, or ($Ar^4$)alkyl;
$Ar^1$ is phenyl or naphthyl and is substituted with 0-3 substituents selected from cyano, halo, alkyl, haloalkyl, alkoxy, and haloalkoxy;
$Ar^2$ is pyrrolyl, pyrazolyl, or triazolyl substituted with 0-2 alkyl substituents;
$Ar^3$ is phenyl substituted with 0-3 substituents selected from cyano, halo, alkyl, haloalkyl, alkoxy, and haloalkoxy;
$Ar^4$ is phenyl substituted with 0-3 substituents selected from cyano, halo, alkyl, haloalkyl, alkoxy, and haloalkoxy;
$X^1$ is alkylene, alkenylene, —CH$_2$O—, —CH$_2$OCH$_2$—, —CH$_2$N(R$^4$)CH$_2$—, or —CH$_2$CON(R$^4$)—;
$X^2$ is —O—, —Ar$^1$—, —Ar$^2$—, —CON(R$^5$)—, —(Ar$^3$)CH—, -((benzyloxy)CH$_2$)CH—,)—, —O(Ar$^3$)CH—, —CH$_2$CON(R$^5$)—, or —N(R$^5$)COCON(R$^5$)—;
$X^3$ is absent, —O—, alkyloxy, cycloalkyloxy, cycloalkyl, Ar$^3$, (Ar$^3$)O—, or ((Ar$^3$)alkyl)O—;
$X^4$ is alkylene, alkenylene, alkyleneoxy, or alkenyleneoxy;
$X^5$ is absent or —O—; and
$X^6$ is azetidinyl, pyirolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

2. A compound of claim 1 where $R^1$ is alkyl or haloalkyl; $R^2$ is hydrogen or alkyl; $R^3$ is hydrogen, halo, or alkyl; $R^4$ is hydrogen, alkyl, or cycloalkyl; $R^5$ is hydrogen, alkyl, or (Ar$^4$)alkyl; $Ar^1$ is phenyl substituted with 0-3 substituents selected from cyano, halo, alkyl, haloalkyl, alkoxy, and haloalkoxy; $Ar^3$ is phenyl substituted with 0-3 substituents selected from cyano, halo, alkyl, haloalkyl, alkoxy, and haloalkoxy; $Ar^4$ is phenyl substituted with 0-3 substituents selected from cyano, halo, alkyl, haloalkyl, alkoxy, and haloalkoxy; $X^1$ is alkylene, alkenylene, —CH$_2$O—, —CH$_2$OCH$_2$—, —CH$_2$N(R$^4$)CH$_2$—, or —CH$_2$CON(R$^4$)—; $X^2$ is —O—, —Ar$^1$—, —CON(R$^5$)—, —(Ar$^3$)CH—, -((benzyloxy)CH$_2$)CH—,)—, —O(Ar$^3$)CH—, —CH$_2$CON(R$^5$)—, or —N(R$^5$)COCON(R$^5$)—; $X^3$ is absent, —O—, alkyloxy; cycloalkyloxy, cycloalkyl, Ar$^3$, (Ar$^3$)O—, or ((Ar$^3$)alkyl)O—; $X^4$ is alkylene, alkenylene, alkyleneoxy, or alkenyleneoxy; $X^5$ is absent or —O—; and $X^6$ is piperidinyl substituted with 0-3 halo or alkyl substituents; or a pharmaceutically acceptable salt thereof.

3. A compound of claim 1 where $X^2$ is Ar$^1$.

4. A compound of claim 1 where $X^3$ is absent or —O—; $X^4$ is alkylene or alkenylene; and $X^5$ is —O—.

5. A compound of claim 1 where R$^1$ is alkyl, R$^2$ is alkyl, and R$^3$ is hydrogen.

6. A compound of claim 1 where Ar$^1$ is phenyl substituted with 0-3 substituents selected from cyano, halo, alkyl, haloalkyl, alkoxy, and haloalkoxy.

7. A compound of claim 1 where $X^6$ is piperidinyl substituted with 0-3 halo or alkyl substituents.

8. A compound of claim 1 selected from the group consisting of (2S)-2-(tert-Butoxy)-2-[4,22-dimethyl-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27),18-heptaen-3-yl]acetic acid;

(2S)-2-(tert-Butoxy)-2-{4,22-dimethyl-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27)-hexaen-3-yl}acetic acid;

(2S)-2-(tert-Butoxy)-2-[4,15,15,22-tetramethyl-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27),19-heptaen-3-yl]acetic acid;

(2S)-2-(tert-Butoxy)-2-[4,15,15,22-tetramethyl-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27),17-heptaen-3-yl]acetic acid;

(2S)-2-(tert-Butoxy)-2-{4,28-dimethyl-22,27-dioxa-1,5,7,8,11,12,13-heptaazahexacyclo[26.2.2.1$^{6,9}$.1$^{11,14}$.0$^{2,7}$.0$^{15,20}$]tetratriaconta-2,4,6(34),8,12,14(33),15(20),16,18-nonaen-3-yl}acetic acid;

(2S)-2-(tert-Butoxy)-2-{4,26-dimethyl-20,25-dioxa-1,5,7,8,11,12,13-heptaazahexacyclo[24.2.2.1$^{6,9}$.1$^{11,14}$.1$^{15,19}$.0$^{2,7}$]tritriaconta-2,4,6(33),8,12,14(32),15(31),16,18-nonaen-3-yl}acetic acid;

(2S)-2-(tert-Butoxy)-2-[4',22'-dimethyl-16',21'-dioxa-1',5',7',8',11',12',13'-heptaazaspiro[cyclohexane-1,15'-pentacyclo[20.2.2.1$^{6,9}$.1$^{11,14}$.0$^{2,7}$]octacosane]-2',4',6'(28'),8',12',14'(27'),19'-heptaen-3'-yl]acetic acid;

(2S)-2-(tert-Butoxy)-2-{4',22'-dimethyl-16',21'-dioxa-1',5',7',8',11',12',13'-heptaazaspiro[cyclohexane-1,15'-pentacyclo[20.2.2.1$^{6,9}$.1$^{11,14}$.0$^{2,7}$]octacosane]-2',4',6'(28'),8',12',14'(27')-hexaen-3'-yl}acetic acid;

(2S)-2-(tert-Butoxy)-2-[4,22-dimethyl-15-(propan-2-yl)-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27),19-heptaen-3-yl]acetic acid;

(2S)-2-(tert-Butoxy)-2-[4,22-dimethyl-15-(propan-2-yl)-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27)-hexaen-3-yl]acetic acid;

(2S)-2-(tert-Butoxy)-2-[4,22-dimethyl-15-(2-methylpropyl)-16,21-dioxa-1,5,7,8,11,12,13-heptaazapentacyclo[20.2.2.1$^{6,9}$.1$^{11,14}$.0$^{2,7}$]octacosa-2,4,6(28),8,12,14(27)-hexaen-3-yl]acetic acid;

(2S)-2-(tert-Butoxy)-2-[4,24-dimethyl-12-oxo-23-oxa-1,5,7,8,11-pentaazapentacyclo[22.2.2.1$^{6,9}$.0$^{2,7}$.0$^{13,18}$]nonacosa-2,4,6(29),8,13(18),14,16,20-octaen-3-yl]acetic acid;

(2S)-2-(tert-Butoxy)-2-{4,24-dimethyl-12-oxo-23-oxa-1,5,7,8,11-pentaazapentacyclo[22.2.2.1$^{6,9}$.0$^{2,7}$.0$^{13,18}$]nonacosa-2,4,6(29),8,13(18),14,16-heptaen-3-yl}acetic acid;

(2S)-2-(tert-Butoxy)-2-[4,26-dimethyl-12-oxo-20,25-dioxa-1,5,7,8,11-pentaazapentacyclo[24.2.2.1$^{6,9}$.0$^{2,7}$.0$^{14,19}$]hentriaconta-2,4,6(31),8,14(19),15,17,23-octaen-3-yl]acetic acid;

(2S)-2-(tert-Butoxy)-2-{4,26-dimethyl-12-oxo-20,25-dioxa-1,5,7,8,11-pentaazapentacyclo[24.2.2.1$^{6,9}$.0$^{2,7}$.0$^{14,19}$]hentriaconta-2,4,6(31),8,14(19),15,17-heptaen-3-yl}acetic acid;

(2S)-2-(tert-Butoxy)-2-[14-[(4-fluoro-3-methylphenyl)methyl]-4,20-dimethyl-12,13-dioxo-19-oxa-1,5,7,8,11,14-hexaazatetracyclo[18.2.2.1$^{6,9}$.0$^{2,7}$]pentacosa-2,4,6(25),8,16-pentaen-3-yl]acetic acid;

(2S)-2-(tert-Butoxy)-2-{14-[(4-fluoro-3-methylphenyl)methyl]-4,20-dimethyl-12,13-dioxo-19-oxa-1,5,7,8,11,14-hexaazatetracyclo[18.2.2.1$^{6,9}$.0$^{2,7}$]pentacosa-2,4,6(25),8-tetraen-3-yl}acetic acid;

(2S)-2-(tert-Butoxy)-2-[(18Z)-4,23-dimethyl-11,22-dioxa-1,5,7,8-tetraazapentacyclo[21.2.2.1$^{6,9}$.0$^{2,7}$.0$^{12,17}$]octacosa-2,4,6(28),8,12(17),13,15,18-octaen-3-yl]acetic acid;

(2S)-2-(tert-Butoxy)-2-[(20Z)-4,23-dimethyl-11,22-dioxa-1,5,7,8-tetraazapentacyclo[21.2.2.1$^{6,9}$.0$^{2,7}$.0$^{12,17}$]octacosa-2,4,6(28),8,12(17),13,15,20-octaen-3-yl]acetic acid;

(2S)-2-(tert-Butoxy)-2-[(19Z)-4,23-dimethyl-11,22-dioxa-1,5,7,8-tetraazapentacyclo[21.2.2.1$^{6,9}$.0$^{2,7}$.0$^{12,17}$]octacosa-2,4,6(28),8,12(17),13,15,19-octaen-3-yl]acetic acid;

(2S)-2-(tert-Butoxy)-2-{4,23-dimethyl-11,22-dioxa-1,5,7,8-tetraazapentacyclo[21.2.2.1$^{6,9}$.0$^{2,7}$.0$^{13,18}$]octacosa-2,4,6(28),8,13(18),14,16-heptaen-3-yl}acetic acid;

(2S)-2-(tert-Butoxy)-2-{4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid;

(2S)-2-(tert-Butoxy)-2-{4,23-dimethyl-22-oxa-1,5,7,8-tetraazapentacyclo[21.2.2.1$^{6,9}$.0$^{2,7}$.0$^{13,18}$]octacosa-2,4,6(28),8,13(18),14,16-heptaen-3-yl}acetic acid;

(2S)-2-(tert-Butoxy)-2-[4,23-dimethyl-16-(trifluoromethyl)-11,22-dioxa-1,5,7,8-tetraazapentacyclo[21.2.2.1$^{6,9}$.0$^{2,7}$.0$^{13,18}$]octacosa-2,4,6(28),8,13(18),14,16,19-octaen-3-yl]acetic acid;

(2S)-2-(tert-Butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid;

(2S)-2-(tert-Butoxy)-2-[(20S)-15-fluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid;

(2S)-2-(tert-Butoxy)-2-[(20S)-4,15,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid;

(2S)-2-(tert-Butoxy)-2-[(20S)-4,15,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic;

(2S)-2-(tert-Butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid;

(2S)-2-(tert-Butoxy)-2-[(20S)-14,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid;

(2S)-2-(tert-Butoxy)-2-[(20S)-15,16-difluoro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid;

(2S)-2-(tert-Butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17,22-octaen-3-yl]acetic acid;

(2S)-2-(tert-Butoxy)-2-[(20S)-16-chloro-4,20,26-trimethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid;

(2S)-2-(tert-Butoxy)-2-[(20S,22Z)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid;

(2S)-2-(tert-Butoxy)-2-[(20S,22E)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16,22-octaen-3-yl]acetic acid;

(2S)-2-(tert-Butoxy)-2-[(20S)-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(20S)-16-fluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(20R)-16-fluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(20S)-15,17-difluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(20S)-14,15-difluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(20S)-15,16-difluoro-4,20,26-trimethyl-19,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-{4,16,26-trimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

(2S)-2-(tert-Butoxy)-2-{4,16,26-trimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

(2S)-2-(tert-Butoxy)-2-[4,18-dimethyl-12-(4-methylphenyl)-11,17-dioxa-1,5,7,8-tetraazatetracyclo[16.2.2.1$^{6,9}$.0$^{2,7}$]tricosa-2,4,6(23),8-tetraen-3-yl]acetic acid;

(2S)-2-(tert-Butoxy)-2-[4,18-dimethyl-12-(4-methylphenyl)-11,17-dioxa-1,5,7,8-tetraazatetracyclo[16.2.2.1$^{6,9}$.0$^{2,7}$]tricosa-2,4,6(23),8-tetraen-3-yl]acetic acid;

(2S)-2-[(12S)-12-[(Benzyloxy)methyl]-4,18-dimethyl-11,17-dioxa-1,5,7,8-tetraazatetracyclo[16.2.2.1$^{6,9}$.0$^{2,7}$]tricosa-2,4,6(23),8-tetraen-3-yl]-2-(tert-butoxy)acetic acid;

(2S)-2-(tert-Butoxy)-2-{15-fluoro-4,26-dimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

2S)-2-(tert-Butoxy)-2-{15-fluoro-4,26-dimethyl-20-propyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

(2S)-2-(tert-Butoxy)-2-{15-fluoro-4,26-dimethyl-20-phenyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

(2S)-2-(tert-Butoxy)-2-{15-fluoro-4,26-dimethyl-20-phenyl-11,19,25-trioxa-1,5,7,8-tetraazapentacyclo[24.2.2.1$^{6,9}$.0$^{2,7}$.0$^{13,8}$]hentriaconta-2,4,6(31),8,13(18),14,16-heptaen-3-yl}acetic acid;

(2S)-2-(tert-Butoxy)-2-[(24S)-4,24,30-trimethyl-11,23,29-trioxa-1,5,7,8-tetraazahexacyclo[28.2.2.1$^{6,9}$.0$^{2,7}$.0$^{13,22}$.0$^{15,20}$]pentatriaconta-2,4,6(35),8,13,15,17,19,21-nonaen-3-yl]acetic acid;

(2S)-2-(tert-Butoxy)-2-[16-fluoro-4,26-dimethyl-20-(trifluoromethyl)-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid;

(2S)-2-(tert-Butoxy)-2-[(12S,20S)-4,12,16,20,26pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-[(12R,20S)-4,12,16,20,26-pentamethyl-11,19,25-trioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-{4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetic acid;

(2S)-2-(tert-Butoxy)-2-{4,26-dimethyl-11,25-dioxa-1,5,7,8-tetraazapentacyclo[24.2.2.1$^{6,9}$.0$^{2,7}$.0$^{13,18}$]hentriaconta-2,4,6(31),8,13(18),14,16-heptaen-3-yl}acetic acid;

(2S)-2-(tert-Butoxy)-2-{4,24-dimethyl-11,23-dioxa-1,5,7,8-tetraazapentacyclo[22.2.2.1$^{6,9}$.1$^{13,17}$.0$^{2,7}$]triaconta-2,4,6(30),8,13(29),14,16-heptaen-3-yl}acetic acid;

(2S)-2-(tert-Butoxy)-2-{16-fluoro-4,25-dimethyl-11,24-dioxa-1,5,7,8-tetraazapentacyclo[23.2.2.1$^{6,9}$.0$^{2,7}$.0$^{13,18}$]triaconta-2,4,6(30),8,13(18),14,16-heptaen-3-yl}acetic acid;

(2S)-2-(tert-Butoxy)-2-[(24S)-4,24,30-trimethyl-11,23,29-trioxa-1,5,7,8-tetraazahexacyclo[28.2.2.1$^{6,9}$.0$^{2,7}$.0$^{13,22}$.0$^{16,21}$]pentatriaconta-2,4,6(35),8,13(22),14,16(21),17,19-nonaen-3-yl]acetic acid;

(2S)-2-(tert-Butoxy)-2-{11-cyclopropyl-16-fluoro-4,25-dimethyl-24-oxa-1,5,7,8,11-pentaazapentacyclo[23.2.2.1$^{6,9}$.0$^{2,7}$.0$^{13,18}$]triaconta-2,4,6(30),8,13(18),14,16-heptaen-3-yl}acetic acid;

(2S)-2-(tert-Butoxy)-2-{4,23-dimethyl-11,22-dioxa-1,5,7,8-tetraazapentacyclo[21.2.2.1$^{6,9}$.1$^{13,17}$.0$^{2,7}$]nonacosa-2,4,6(29),8,13(28),14,16-heptaen-3-yl}acetic acid;

(2S)-2-(tert-Butoxy)-2-[(20S)-11-cyclopropyl-4,16,20,26-tetramethyl-19,25-dioxa-1,5,7,8,11-pentaazapentacyclo[24.2.2.1$^{6,9}$.0$^{2,7}$.0$^{13,18}$]hentriaconta-2,4,6(31),8,13(18),14,16-heptaen-3-yl]acetic acid;

(2S)-2-(tert-Butoxy)-2-{4,16,24-trimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid;

(2S)-2-(tert-Butoxy)-2-{16-fluoro-4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid;

(2S)-2-(tert-Butoxy)-2-{16-fluoro-4,23-dimethyl-11,22-dioxa-1,5,7,8tetraazapentacyclo[21.2.2.1$^{6,9}$.0$^{2,7}$.0$^{13,18}$]octacosa-2,4,6(28),8,13(18),14,16-heptaen-3-yl}acetic acid;

(2S)-2-(tert-Butoxy)-2-{15,16-difluoro-4,24-dimethyl-11,23-dioxa-1,5,7,8-tetraazapentacyclo[22.2.2.1$^{6,9}$.0$^{2,7}$.0$^{13,18}$]nonacosa-2,4,6(29),8,13(18),14,16-heptaen-3-yl}acetic acid;

(2S)-2-(tert-butoxy)-2-[(20S)-15-chloro-4,16,20,26-tetramethyl-11,19,25-trioxa-1,5,7,8-tetraazapentacyclo[24.2.2.1$^{6,9}$.0$^{2,7}$.0$^{13,18}$]hentriaconta-2,4,6(31),8,13,15,17-heptaen-3-yl]acetic acid; and (2S)-2-(tert-Butoxy)-2-[(20S)-15-chloro-4,16,20,27-tetramethyl-11,19,26-trioxa-1,5,7,8-tetraazapentacyclo[25.2.2.1$^{6,9}$.0$^{2,7}$.0$^{13,18}$]dotriaconta-2,4,6(32),8,13,15,17-heptaen-3-yl]acetic acid;

or a pharmaceutically acceptable salt thereof.

9. A compound of Formula II where R$^1$ is hydrogen or alkyl; R$^2$ is hydrogen, arylalkyl, allyloxycarbonyl, alkoxycarbonyl, aryloxycarbonyl, arylalkoxycarbonyl, trialkylsilyl, alkyl(aryl)$_2$silyl, or (alkyl)$_2$arylsilyl; R$^3$ is alkyl or haloalkyl; R$^4$ is hydrogen, alkyl, arylalkyl, alkoxycarbonyl, aryloxycarbonyl, or arylalkoxycarbonyl:

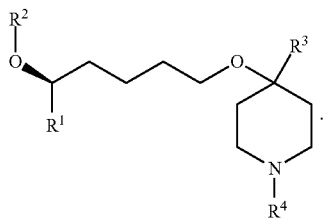

II

10. A compound of claim 9 where R$^1$ is alkyl; R$^2$ is hydrogen, benzyl, or t-butyldiphenylsilyl; R$^3$ is methyl or iodomethyl; R$^4$ is hydrogen, t-butoxycarbonyl, or benzyloxycarbonyl.

11. A method for a preparing a compound of formula II where R$^1$ is alkyl, R$^2$ is hydrogen, R$^3$ is methyl, and R$^4$ is hydrogen; comprising the hydrogenolysis of a compound of formula II where R$^1$ is alkyl, R$^2$ is benzyl, R$^3$ is iodomethyl, and R$^4$ is benzyloxycarbonyl

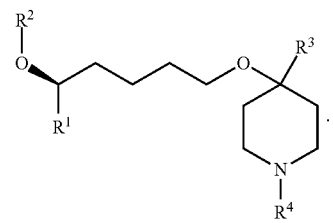

II

12. The method of claim 11 further comprising where the compound of formula II where R$^1$ is alkyl, R$^2$ is benzyl, R$^3$ is iodomethyl, and R$^4$ is benzyloxycarbonyl is prepared from N-benzyloxycarbonyl-4-methylenepiperidine and 5-alkyl-5-benzyloxypentane-1-ol.

13. A method for preparing a compound of formula II where R$^1$ is alkyl, R$^2$ is trialkylsilyl, alkyl(aryl)$_2$silyl, or (alkyl)$_2$arylsilyl, R$^3$ is methyl, and R$^4$ is hydrogen; comprising protonolysis of a compound of formula II where R$^1$ is alkyl, R$^2$ is trialkylsilyl, alkyl(aryl)$_2$silyl, or (alkyl)$_2$arylsilyl, R$^3$ is methyl, and R$^4$ is t-butoxycarbonyl

II

14. The method of claim 13 further comprising where the compound of formula II where R$^1$ is alkyl, R$^2$ is trialkylsilyl, alkyl(aryl)$_2$silyl, or (alkyl)$_2$arylsilyl, R$^3$ is methyl, and R$^4$ is t-butoxycarbonyl is hydrogenolyzed from compound of formula II where R$^1$ is alkyl, R$^2$ is trialkylsilyl, alkyl(aryl)$_2$silyl, or (alkyl)$_2$arylsilyl, R$^3$ is iodomethyl, and R$^4$ is t-butoxycarbonyl.

15. The method of 14 further comprising where the compound of formula II where R$^1$ is alkyl, R$^2$ is trialkylsilyl, alkyl(aryl)$_2$silyl, or (alkyl)$_2$arylsilyl, R$^3$ is iodomethyl, and R$^4$ is t-butoxycarbonyl is prepared from N-benzyloxycarbonyl-4-methylenepiperidine and 5-alkyl-5-(trialkylsilyloxy, alkyl (aryl)$_2$silyloxy, or (alkyl)$_2$arylsilyloxy)pentane-1-ol.

16. A composition useful for treating HIV infection comprising a therapeutic amount of a compound of claim 1 and a pharmaceutically acceptable carrier.

17. A method for treating HIV infection comprising administering a therapeutically effective amount of a compound of claim 1, or a pharmaceutically acceptable salt thereof, to a patient in need thereof.

* * * * *